US008314101B2

(12) United States Patent
Kadoma et al.

(10) Patent No.: US 8,314,101 B2
(45) Date of Patent: Nov. 20, 2012

(54) QUINOXALINE DERIVATIVE, AND LIGHT-EMITTING ELEMENT, LIGHT-EMITTING DEVICE, AND ELECTRONIC DEVICE USING QUINOXALINE DERIVATIVE

(75) Inventors: Hiroshi Kadoma, Kanagawa (JP); Sachiko Kawakami, Kanagawa (JP); Satoko Shitagaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 385 days.

(21) Appl. No.: 12/277,421

(22) Filed: Nov. 25, 2008

(65) Prior Publication Data

US 2009/0203704 A1  Aug. 13, 2009

(30) Foreign Application Priority Data

Nov. 30, 2007  (JP) ................................. 2007-310286

(51) Int. Cl.
*A61K 31/495* (2006.01)
(52) U.S. Cl. ....................................... 514/249; 544/353
(58) Field of Classification Search .................. 514/249; 544/353
See application file for complete search history.

(56) References Cited

U.S. PATENT DOCUMENTS

| | | | |
|---|---|---|---|
| 5,077,142 A | 12/1991 | Sakon et al. | |
| 7,227,313 B2 | 6/2007 | Huiberts et al. | |
| 2005/0118454 A1 | 6/2005 | Nakaya et al. | |
| 2005/0186446 A1 | 8/2005 | Shitagaki et al. | |
| 2006/0051613 A1 | 3/2006 | Tomita et al. | |
| 2006/0194076 A1 | 8/2006 | Nariyuki | |
| 2008/0036369 A1 | 2/2008 | Tokuda et al. | |
| 2008/0091012 A1 | 4/2008 | Egawa et al. | |
| 2009/0140641 A1 | 6/2009 | Nomura et al. | |
| 2009/0140642 A1 | 6/2009 | Kadoma et al. | |
| 2009/0184633 A1 | 7/2009 | Kadoma et al. | |
| 2010/0120778 A1 * | 5/2010 | Hu et al. ....................... 514/249 |

FOREIGN PATENT DOCUMENTS

| | | |
|---|---|---|
| EP | 1 616 864 A1 | 1/2006 |
| JP | 7-142169 | 6/1995 |
| JP | 2003-40873 | 2/2003 |
| JP | 2004-200162 | 7/2004 |
| JP | 2006-16384 | 1/2006 |
| JP | 2006-89728 | 4/2006 |
| WO | WO 2004/094389 A1 | 11/2004 |
| WO | WO 2006/022193 A1 | 3/2006 |

OTHER PUBLICATIONS

Krueger.H et al., "Some New Electron-Affine Polymers for Organic Photovoltaics,", Proceedings of SPIE, 2004, vol. 5215, pp. 141-152.
Tao, Y.T. et al, "Sharp Green Electroluminescence from 1 H-pyrazolo[3,4-b] Quinoline-Based Light-Emitting Diodes," Applied Physics Letters, vol. 77, No. 11, Sep. 11, 2000, pp. 1575-1577.
Thomas, K.R.J. et al, "Quinoxalines Incorporating Triarylamines: Potential Electroluminescent Materials with Tunable Emission Characteristics," Chemistry of Materials, vol. 14, No. 6, Jun. 2002, pp. 2796-2802.
Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID Digest 04: SID International Symposium Digest of Technical Papers, 2004, pp. 900-903.
Thomas, K.R.J. et al, "Chromophore-Labeled Quinoxaline Derivatives as Efficient Electroluminescent Materials," Chemistry of Materials, vol. 17, No. 7, Apr. 5, 2005, pp. 1860-1866.
Dorwald, F.Z., *Side Reactions in Organic Synthesis, A Guide to Successful Synthesis Design*, Wiley-VCH Verlag GmbH & Co. KGaA, 2005, preface, p. IX.
Chen, S. et al, "New Organic Light-Emitting Materials: Synthesis, Thermal, Photophysical, Electrochemical and Electroluminescent Properties," Database Caplus on STN, AN 2006:1296274, DN 146:260905, Journal of Physical Chemistry, vol. 111, No. 2, 2007, pp. 1029-1034.
Xiao, L. et al, "Highly Efficient Electron-Transporting Phenanthroline Derivatives for Electroluminescent Devices," Chemistry Letters, vol. 36, No. 6, 2007, pp. 802-803.

* cited by examiner

*Primary Examiner* — Douglas M Willis
(74) *Attorney, Agent, or Firm* — Husch Blackwell LLP

(57) ABSTRACT

An object is to provide a novel quinoxaline derivative. Another object is to provide a light-emitting element with low driving voltage. Still another object is to provide a light-emitting element with low power consumption. Yet another object is to provide a light-emitting device and an electronic device each having low power consumption by using such a light-emitting element. A quinoxaline derivative is provided which has a structure in which at least one of carbon at a 2-position and carbon at a 3-position of quinoxaline, and carbon of a pyridine ring are bound via an arylene group.

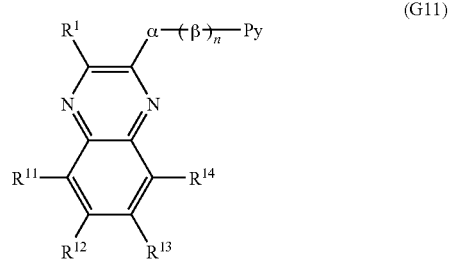

15 Claims, 55 Drawing Sheets

QUINOXALINE DERIVATIVE, AND LIGHT-EMITTING ELEMENT, LIGHT-EMITTING DEVICE, AND ELECTRONIC DEVICE USING QUINOXALINE DERIVATIVE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to quinoxaline derivatives. The present invention also relates to light-emitting elements, light-emitting devices, and electronic devices using the quinoxaline derivatives.

(2) Description of Related Art

An organic compound can have various structures in comparison with an inorganic compound, and it is possible to synthesize materials having various functions by appropriate molecular design. Owing to these advantages, photo electronics and electronics which utilize functional organic materials have been attracting attention in recent years.

For example, a solar cell, a light-emitting element, an organic transistor, and the like can be given as examples of electronic devices utilizing an organic compound as a functional material. These devices take advantage of electrical properties and optical properties of the organic compound. Among them, in particular, a light-emitting element has been making remarkable progress.

It is considered that a light-emitting mechanism of a light-emitting element is as follows: when a voltage is applied to a pair of electrodes between which a light-emitting layer is interposed, electrons injected from a cathode and holes injected from an anode are recombined at luminescent centers in the light-emitting layer to form molecular excitons, and the molecular excitons release energy to cause light emission when relaxing to the ground state. Singlet excitation and triplet excitation are known as excitation states, and it is considered that luminescence can be conducted through either one of those excitation states.

In an attempt to improve performance of such a light-emitting element, there are many problems which depend on the material, and in order to solve these problems, improvement of element structure, development of a material, and the like have been carried out.

For example, as a material with an electron-transporting property for a light-emitting element, tris(8-quinolinolato)aluminum(III) (abbr.: Alq) is widely used (see Reference 1: Taishi TSUJI et al., SID 04 DIGEST, 35, PP. 900-903 (2004)).

However, development of a material with more superior characteristics such as further higher mobility has been demanded. In particular, in view of commercialization, reduction in power consumption is an important object, and developments of material and light-emitting element with more superior characteristics have been desired.

BRIEF SUMMARY OF THE INVENTION

In view of the foregoing problems, it is an object of the present invention to provide a novel quinoxaline derivative.

In addition, it is also an object of the present invention to provide a light-emitting element with low driving voltage. Further, it is also an object of the present invention to provide a light-emitting element with low power consumption. Furthermore, it is also an object of the present invention to provide a light-emitting device and an electronic device each having low power consumption by using such a light-emitting element.

As a result of diligent studies, the present inventors have synthesized a quinoxaline derivative in which at least one of carbon at a 2-position and carbon at a 3-position of quinoxaline, and carbon of a pyridine ring are bound via an arylene group, and have found that the quinoxaline derivative can be suitably used for a light-emitting element.

That is, as a result of diligent studies, the present inventors have synthesized a quinoxaline derivative in which one of or both carbon at a 2-position and carbon at a 3-position of quinoxaline, and carbon of a pyridine ring are bound via an arylene group, and have found that the quinoxaline derivative can be suitably used for a light-emitting element.

The present invention is broadly divided into two modes, i.e., a case of quinoxaline derivative in which one of carbon at a 2-position and carbon at a 3-position of quinoxaline, and carbon of a pyridine ring are bound via an arylene group, and a case of quinoxaline derivative in which both carbon at a 2-position and carbon at a 3-position of quinoxaline, and carbon of a pyridine ring are bound via an arylene group.

Therefore, one aspect of the present invention is a quinoxaline derivative represented by a general formula (G11), which is a quinoxaline derivative of mode in which one of carbon at a 2-position and carbon at a 3-position of quinoxaline, and carbon of a pyridine ring are bound via an arylene group.

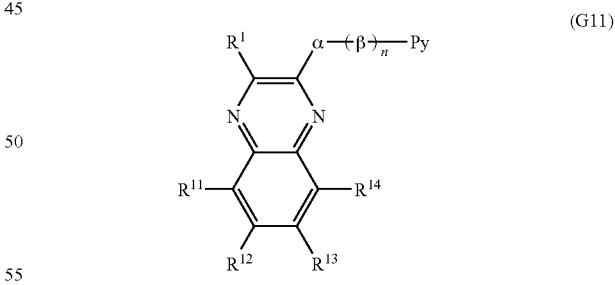

(G11)

In the formula, α represents a substituted or unsubstituted arylene group having 6 to 13 carbon atoms; β represents a substituted or unsubstituted arylene group having 6 to 13 carbon atoms; n represents an integer of 0 or 1; Py represents a substituted or unsubstituted pyridyl group; $R^1$ represents any of an alkyl group having 1 to 4 carbon atoms and a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, and an aryl group having 6 to 13 carbon atoms.

Another aspect of the present invention is a quinoxaline derivative represented by a general formula (G12).

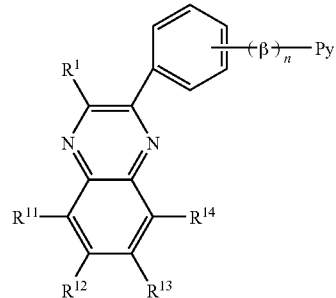

(G12)

In the formula, β represents a substituted or unsubstituted arylene group having 6 to 13 carbon atoms; n represents an integer of 0 or 1; Py represents a substituted or unsubstituted pyridyl group; $R^1$ represents any of an alkyl group having 1 to 4 carbon atoms and a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, and a substituted or unsubstituted aryl group having 6 to 13 carbon atoms.

In the above structure, β is preferably any of a phenylene group, a naphthalene-diyl group, and a biphenyl-diyl group.

Another aspect of the present invention is a quinoxaline derivative represented by a general formula (G13).

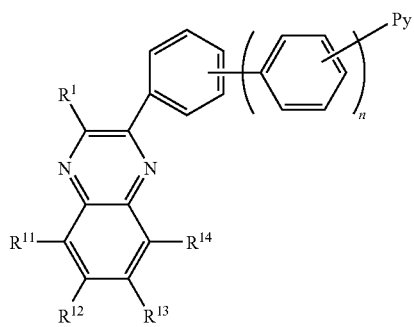

(G13)

In the formula, n represents an integer of 0 or 1; Py represents a substituted or unsubstituted pyridyl group; $R^1$ represents any of an alkyl group having 1 to 4 carbon atoms and a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, and a substituted or unsubstituted aryl group having 6 to 13 carbon atoms.

Another aspect of the present invention is a quinoxaline derivative represented by a general formula (G14).

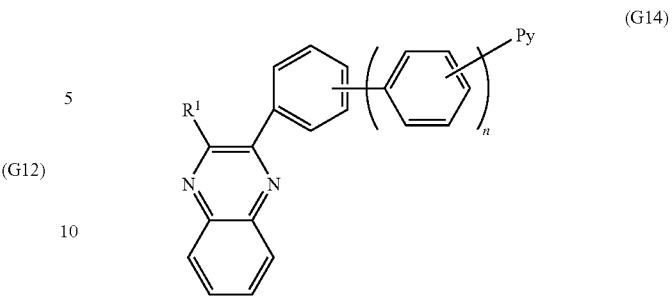

(G14)

In the formula, n represents an integer of 0 or 1; Py represents a substituted or unsubstituted pyridyl group; and $R^1$ represents any of an alkyl group having 1 to 4 carbon atoms and a substituted or unsubstituted aryl group having 6 to 13 carbon atoms.

Another aspect of the present invention is a quinoxaline derivative represented by a general formula (G15).

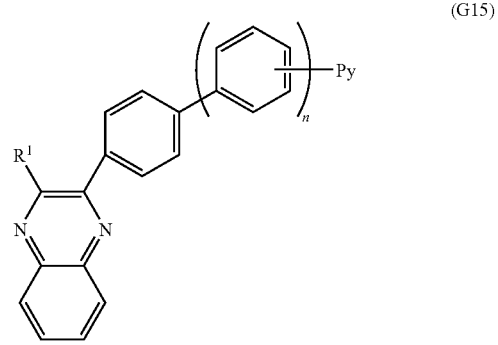

(G15)

In the formula, n represents an integer of 0 or 1; Py represents a substituted or unsubstituted pyridyl group; and $R^1$ represents any of an alkyl group having 1 to 4 carbon atoms and a substituted or unsubstituted aryl group having 6 to 13 carbon atoms.

Another aspect of the present invention is a quinoxaline derivative represented by a general formula (G16).

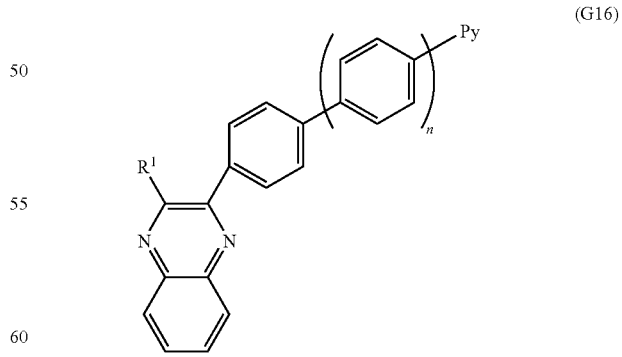

(G16)

In the formula, n represents an integer of 0 or 1; Py represents a substituted or unsubstituted pyridyl group; and $R^1$ represents any of an alkyl group having 1 to 4 carbon atoms and a substituted or unsubstituted aryl group having 6 to 13 carbon atoms.

In the above structure, $R^1$ is preferably a phenyl group or a biphenyl group.

Further, one aspect of the present invention is a quinoxaline derivative represented by a general formula (G21), which is a quinoxaline derivative of mode in which both carbon at a 2-position and carbon at a 3-position of quinoxaline, and carbon of a pyridine ring are bound via an arylene group.

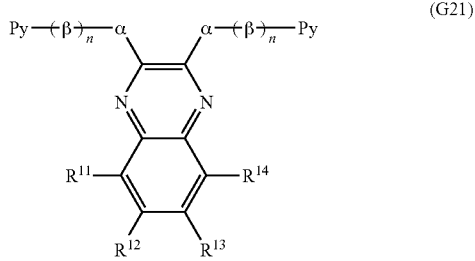

(G21)

In the formula, α represents a substituted or unsubstituted arylene group having 6 to 13 carbon atoms; β represents a substituted or unsubstituted arylene group having 6 to 13 carbon atoms; n represents an integer of 0 or 1; Py represents a substituted or unsubstituted pyridyl group; and $R^{11}$ to $R^{14}$ may be the same or different from each other and each represents any of hydrogen, an alkyl group having 1 to 4 carbon atoms, and a substituted or unsubstituted aryl group having 6 to 13 carbon atoms.

Another aspect of the present invention is a quinoxaline derivative represented by a general formula (G22).

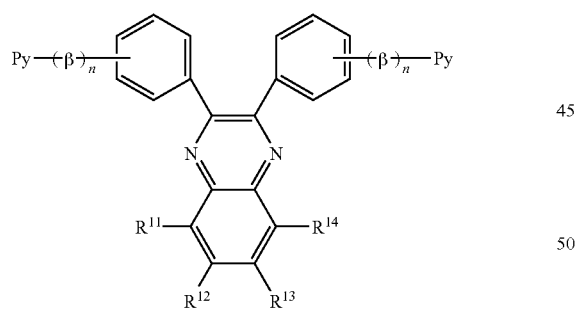

(G22)

In the formula, β represents a substituted or unsubstituted arylene group having 6 to 13 carbon atoms; n represents an integer of 0 or 1; Py represents a substituted or unsubstituted pyridyl group; and $R^{11}$ to $R^{14}$ may be the same or different from each other and each represents any of hydrogen, an alkyl group having 1 to 4 carbon atoms, and a substituted or unsubstituted aryl group having 6 to 13 carbon atoms.

In the above structure, β is preferably any of a phenylene group, a naphthalene-diyl group, and a biphenyl-diyl group.

Another aspect of the present invention is a quinoxaline derivative represented by a general formula (G23).

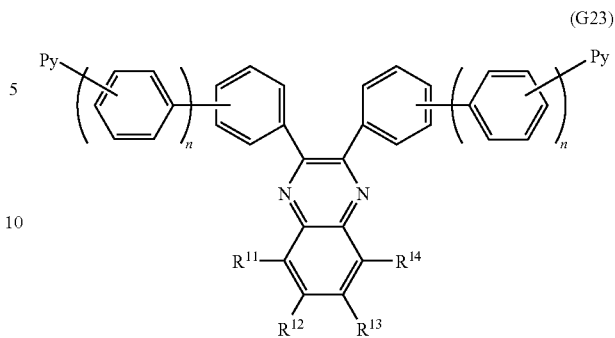

(G23)

In the formula, n represents an integer of 0 or 1; Py represents a substituted or unsubstituted pyridyl group; and $R^{11}$ to $R^{14}$ may be the same or different from each other and each represent any of hydrogen, an alkyl group having 1 to 4 carbon atoms, and an aryl group having 6 to 13 carbon atoms.

Another aspect of the present invention is a quinoxaline derivative represented by a general formula (G24).

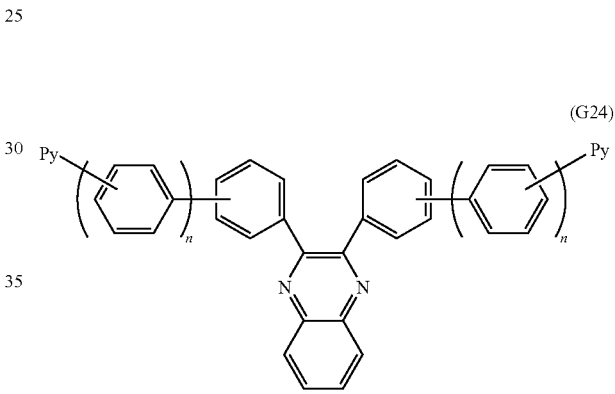

(G24)

In the formula, n represents an integer of 0 or 1 and Py represents a substituted or unsubstituted pyridyl group.

Another aspect of the present invention is a quinoxaline derivative represented by a general formula (G25).

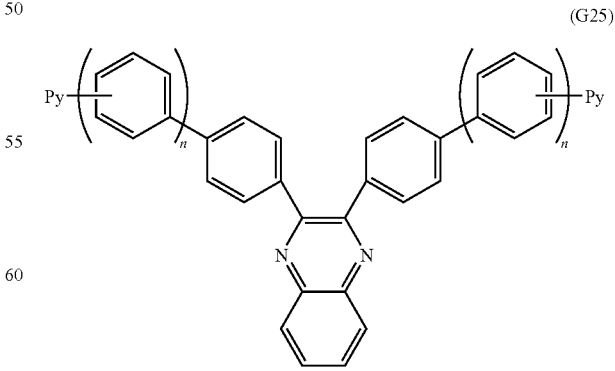

(G25)

In the formula, n represents an integer of 0 or 1 and Py represents a substituted or unsubstituted pyridyl group.

Another aspect of the present invention is a quinoxaline derivative represented by a general formula (G26).

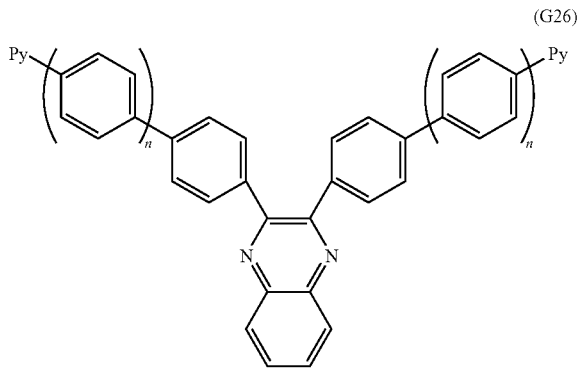

(G26)

In the formula, n represents an integer of 0 or 1 and Py represents a substituted or unsubstituted pyridyl group.

In addition, the quinoxaline derivatives described above can be suitably used for a light-emitting element.

Thus, one aspect of the present invention is a light-emitting element including any of the quinoxaline derivatives described above between a pair of electrodes.

Further, one aspect of the present invention is a light-emitting element having a light-emitting layer and a layer including any of the quinoxaline derivatives described above between an anode and a cathode, in which the layer including the quinoxaline derivative is provided between the light-emitting layer and the cathode.

In that case, the quinoxaline derivatives described above are superior in an electron-transporting property, so the quinoxaline derivatives are particularly preferably used for an electron-transporting layer.

Furthermore, the present invention also includes a light-emitting device having the above-described light-emitting element.

Thus, one aspect of the present invention includes a light-emitting element including any of the quinoxaline derivatives described above and a control circuit which controls light emission of the light-emitting element.

Note that the light-emitting device in this specification includes image display devices, light-emitting devices, and light sources (including lighting devices). Further, the light-emitting device includes all of the following modules: modules in which a connector such as a flexible printed circuit (FPC), a tape automated bonding (TAB) tape, or a tape carrier package (TCP) is attached to a panel in which a light-emitting element is formed; modules having a TAB tape or a TCP provided with a printed wiring board at the end thereof; and modules having an integrated circuit (IC) directly mounted on a light-emitting device by a chip-on-glass (COG) method.

Further, the present invention also includes an electronic device using a light-emitting element of the present invention in a display portion. Thus, an electronic device of the present invention includes a display portion which is provided with the light-emitting element and the control circuit which controls light emission of the light-emitting element described above.

A quinoxaline derivative of the present invention is superior in an electron-transporting property, so the quinoxaline derivative is suitably used for a light-emitting element. In addition, by using a quinoxaline derivative of the present invention for a light-emitting element, a light-emitting element with low driving voltage can be obtained. In addition, a light-emitting element with low power consumption can be obtained.

Further, by applying a light-emitting element of the present invention to a light-emitting device and an electronic device, a light-emitting device and an electronic device each having low power consumption can be obtained.

DETAILED DESCRIPTION OF THE INVENTION

Figure 1:
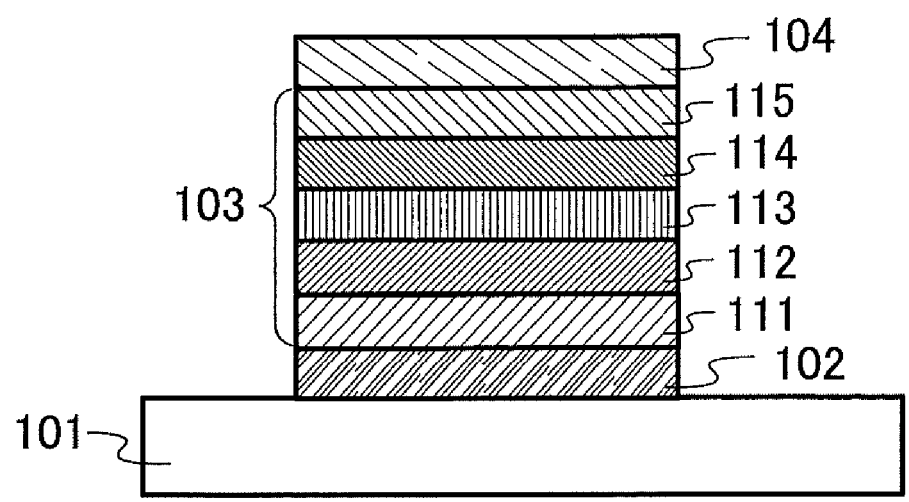
FIG. 1 is a diagram illustrating a light-emitting element of the present invention.

Hereinafter, embodiment modes and embodiments of the present invention are described in detail with reference to the drawings. However, the present invention is not limited to the following description, and it is easily understood by those skilled in the art that the mode and detail of the present invention can be variously changed without departing from the scope and spirit thereof. Therefore, the present invention is not interpreted as being limited to the following description in the embodiment modes and embodiments.

Embodiment Mode 1

In this embodiment mode, a quinoxaline derivative of the present invention is described.

A quinoxaline derivative of the present invention has a structure in which at least one of carbon at a 2-position and carbon at a 3-position of quinoxaline, and carbon of a pyridine ring are bound via an arylene group so that a quinoxaline derivative which is superior in an electron-transporting property can be obtained.

Specifically, a quinoxaline derivative according to the present invention is broadly divided into a monosubstituted quinoxaline derivative and a disubstituted quinoxaline derivative. That is, a quinoxaline derivative according to the present invention can be broadly divided into two mode, i.e., a case of quinoxaline derivative in which one of carbon at a 2-position and carbon at a 3-position of quinoxaline, and carbon of a pyridine ring are bound via an arylene group, and a case of quinoxaline derivative in which both carbon at a 2-position and carbon at a 3-position of quinoxaline, and carbon of a pyridine ring are bound via an arylene group. Further, the former monosubstituted quinoxaline derivative is a quinoxaline derivative represented by the general formula (G11).

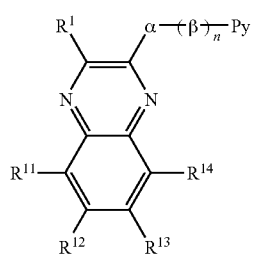

(G11)

In the formula, α represents a substituted or unsubstituted arylene group having 6 to 13 carbon atoms; β represents a substituted or unsubstituted arylene group having 6 to 13 carbon atoms; n represents an integer of 0 or 1; Py represents a substituted or unsubstituted pyridyl group; $R^1$ represents any of an alkyl group having 1 to 4 carbon atoms and a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, and a substituted or unsubstituted aryl group having 6 to 13 carbon atoms. Further, the number of substituents of aryl group may be either one or more than one, more than one substituent may be bound to each other to form a ring, and a ring structure may be a spiro ring structure.

On the other hand, the latter disubstituted quinoxaline derivative is a quinoxaline derivative represented by the general formula (G21).

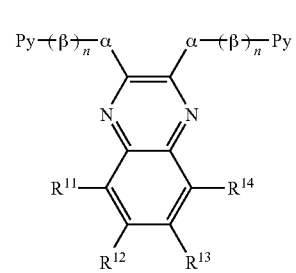

(G21)

In the formula, α represents a substituted or unsubstituted arylene group having 6 to 13 carbon atoms; β represents a substituted or unsubstituted arylene group having 6 to 13 carbon atoms; n represents an integer of 0 or 1; Py represents a substituted or unsubstituted pyridyl group; and $R^{11}$ to $R^{14}$ may be the same or different from each other and each represent any of hydrogen, an alkyl group having 1 to 4 carbon atoms, and a substituted or unsubstituted aryl group having 6 to 13 carbon atoms.

The quinoxaline derivative represented by the general formula (G21) has a structure in which carbon at a 2-position and carbon at a 3-position of quinoxaline, and carbon of a pyridine ring are bound via an arylene group. Thus, the molecular weight of the quinoxaline derivative represented by the general formula (G21) is larger than that of the quinoxaline derivative represented by the general formula (G11), and the thermophysical property of the quinoxaline derivative represented by the general formula (G21) is higher. In addition, since the thermophysical property is higher, improvement in stability of a film quality (suppression of crystallization) can be expected.

In the general formulas (G11) and (G21), examples of the pyridyl group represented by Py include pyridyl groups represented by structural formulas (11-1) to (11-4). As shown in the structural formula (11-4), the pyridyl group represented by Py may include a substituent.

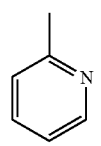

(11-1)

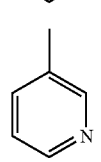

(11-2)

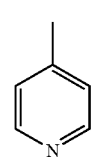

(11-3)

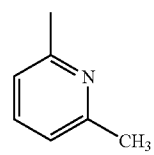

(11-4)

Further, in the general formulas (G11) and (G21), examples of the substituent represented by α include arylene groups represented by structural formulas (12-1) to (12-10). As shown in the structural formulas (12-4), (12-8) to (12-10), and the like, the arylene group represented by α may include a substituent. Note that the carbon atoms of aryl group or arylene group shown in this specification represent carbon atoms which form a ring of the main skeleton, and carbon atoms of a substituent bound thereto are not included therein. Note that the number of substituents of aryl group or arylene group may be either one or more than one. In particular, more than one substituent may be bound to each other to form a ring. For example, in the case where an arylene group is a fluorene-diyl group, carbon at a 9-position may include two phenyl groups, and the two phenyl groups may be bound to each other to form a spiro ring structure. The structural formula (12-9) is an example in which a spiro ring structure is formed.

(12-1)
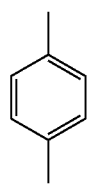

(12-2)
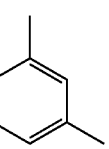

(12-3)
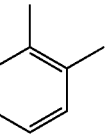

(12-4)
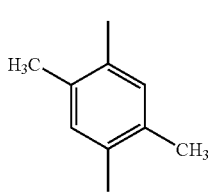

(12-5)
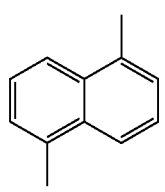

(12-6)
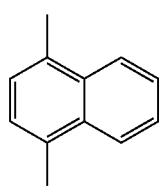

(12-7)
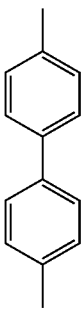

(12-8)
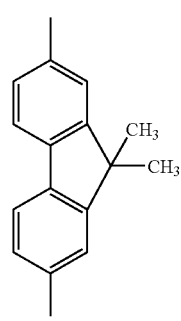

(12-9)
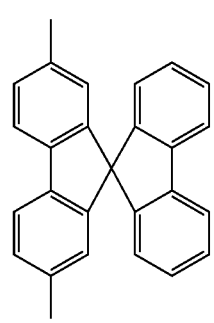

(12-10)
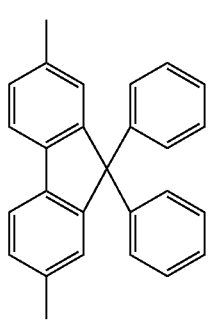

Further, in the general formulas (G11) and (G21), examples of the substituent represented by β include arylene groups represented by structural formulas (13-1) to (13-10). As shown in the structural formulas (13-4), (13-8) to (13-10), and the like, the arylene group represented by β may include a substituent.

(13-1) 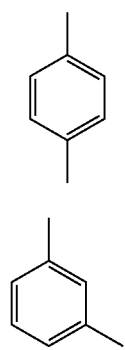
(13-2) 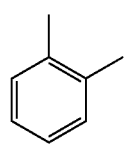
(13-3) 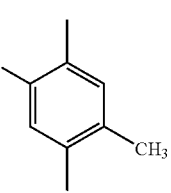
(13-4) 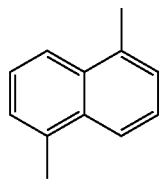
(13-5) 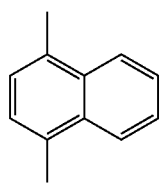
(13-6) 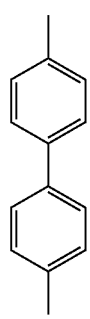
(13-7) 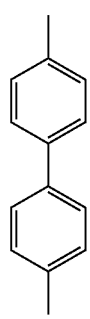
(13-8) 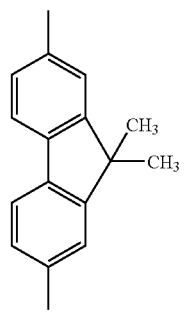
(13-9) 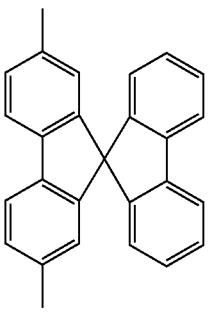
(13-10) 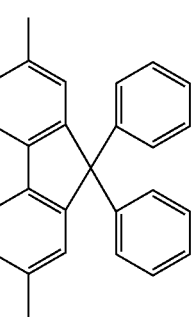
Further, in the general formulas (G11) and (G21), examples of the substituents represented by $R^{11}$ to $R^{14}$ include hydrogen, alkyl groups, and aryl groups, which are represented by structural formulas (14-1) to (14-22), and the like. As shown in the structural formulas (14-16) to (14-22) and the like, the aryl groups represented by $R^{11}$ to $R^{14}$ may each include a substituent.
(14-1) 
(14-2) 
(14-3) 
(14-4) 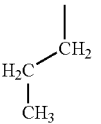

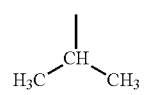 (14-5)
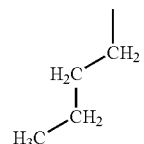 (14-6)
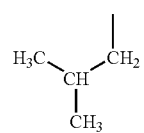 (14-7)
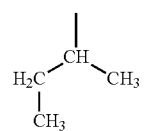 (14-8)
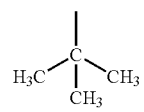 (14-9)
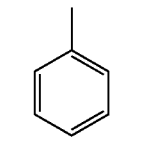 (14-10)
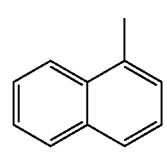 (14-11)
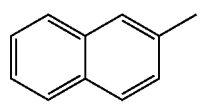 (14-12)
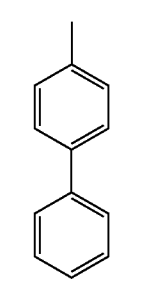 (14-13)
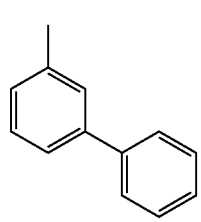 (14-14)
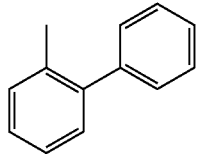 (14-15)
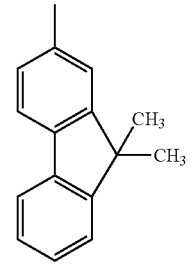 (14-16)
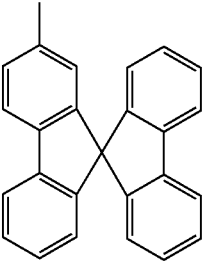 (14-17)
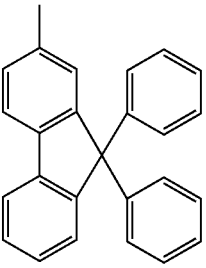 (14-18)
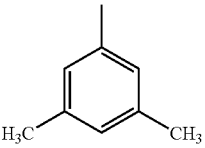 (14-19)
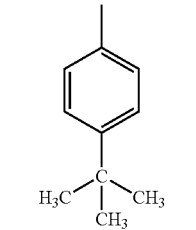 (14-20)
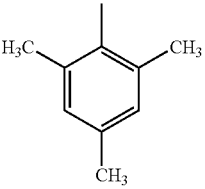 (14-21)

(14-22)
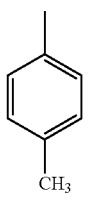
In addition, in the general formula (G11), examples of the substituent represented by $R^1$ include alkyl groups and aryl groups represented by structural formulas (15-1) to (15-21). As shown in the structural formulas (15-15) to (15-21) and the like, the aryl group represented by $R^1$ may include a substituent.
(15-1)
(15-2)
(15-3)
(15-4)
(15-5)
(15-6)
(15-7)
(15-8)
(15-9)
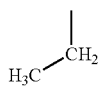
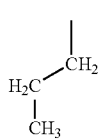
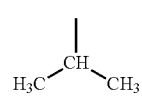
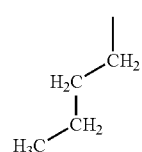
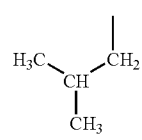
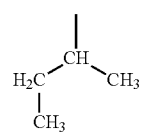
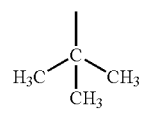
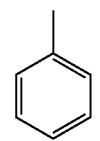
(15-10)
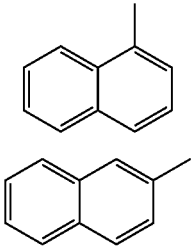
(15-11)
(15-12)
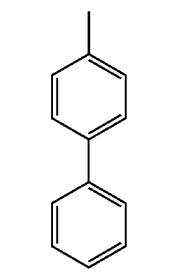
(15-13)
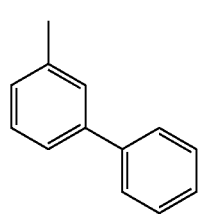
(15-14)
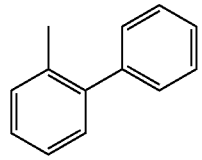
(15-15)
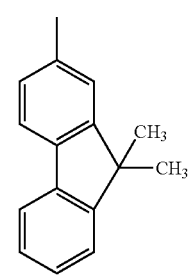
(15-16)
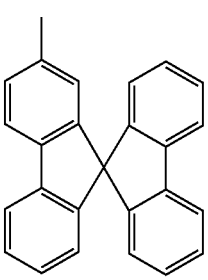

(15-17)
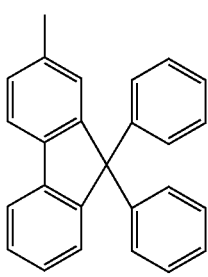

(15-18)
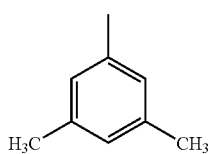

(15-19)
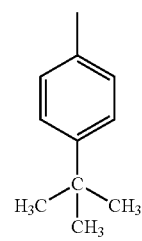

(15-20)
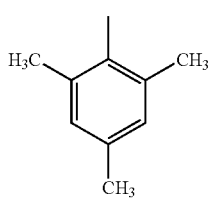

(15-21)
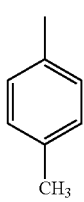

In the quinoxaline derivative represented by the general formula (G11), α is preferably a phenylene group for ease of synthesis. In that case, two phenylene groups may be bound at any of an ortho position, a meta position, and a para position. That is, the quinoxaline derivative represented by the general formula (G12) is preferable.

In the formula, β represents a substituted or unsubstituted arylene group having 6 to 13 carbon atoms; n represents an integer of 0 or 1; Py represents a substituted or unsubstituted pyridyl group; $R^1$ represents any of an alkyl group having 1 to 4 carbon atoms and a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, and a substituted or unsubstituted aryl group having 6 to 13 carbon atoms.

Similarly, in the quinoxaline derivative represented by the general formula (G21), α is preferably a phenylene group for ease of synthesis. In that case, two phenylene groups may be bound at any of an ortho position, a meta position, and a para position. That is, the quinoxaline derivative represented by the general formula (G22) is preferable.

(G22)
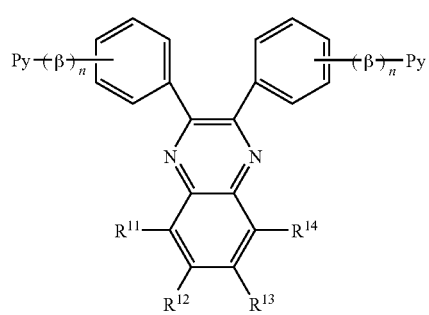

In the formula, β represents a substituted or unsubstituted arylene group having 6 to 13 carbon atoms; n represents an integer of 0 or 1; Py represents a substituted or unsubstituted pyridyl group; and $R^{11}$ to $R^{14}$ may be the same or different from each other and each represent any of hydrogen, an alkyl group having 1 to 4 carbon atoms, and a substituted or unsubstituted aryl group having 6 to 13 carbon atoms.

In each of the quinoxaline derivatives described above, β is preferably any of a phenylene group, a naphthalene-diyl group, and a biphenyl-diyl group for ease of synthesis.

Moreover, in the quinoxaline derivative represented by the general formula (G11), β is preferably a phenylene group for ease of synthesis and purification (purity improvement). That is, the quinoxaline derivative represented by the general formula (G13) is preferable.

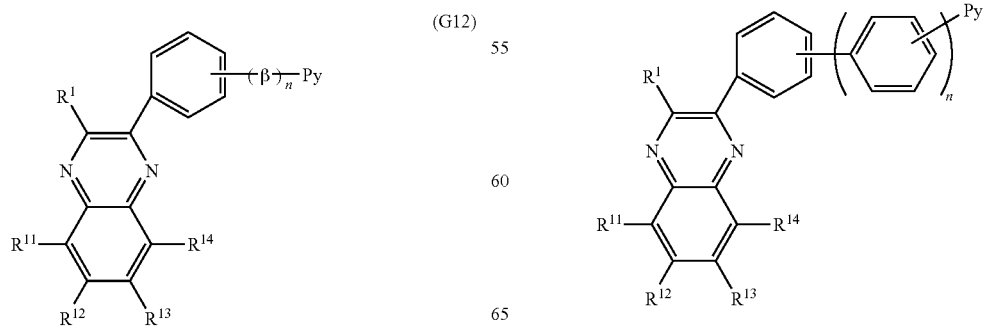

In the formula, n represents an integer of 0 or 1; Py represents a substituted or unsubstituted pyridyl group; R¹ represents any of an alkyl group having 1 to 4 carbon atoms and a substituted or unsubstituted aryl group having 6 to 13 carbon atoms; and R¹¹ to R¹⁴ may be the same or different from each other and each represent any of hydrogen, an alkyl group having 1 to 4 carbon atoms, and a substituted or unsubstituted aryl group having 6 to 13 carbon atoms.

Similarly, in the quinoxaline derivative represented by the general formula (G21), β is preferably a phenylene group for ease of synthesis and purification (purity improvement). That is, the quinoxaline derivative represented by the general formula (G23) is preferable.

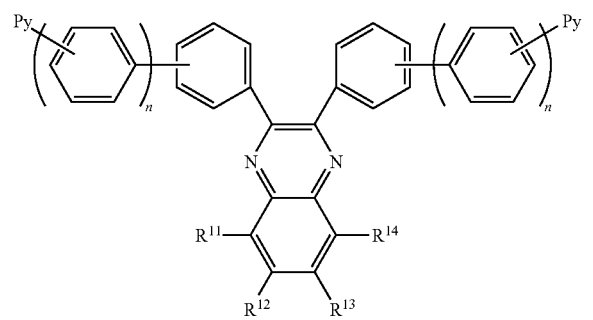
(G23)

In the formula, n represents an integer of 0 or 1; Py represents a substituted or unsubstituted pyridyl group; and R¹¹ to R¹⁴ may be the same or different from each other and each represent any of hydrogen, an alkyl group having 1 to 4 carbon atoms, and a substituted or unsubstituted aryl group having 6 to 13 carbon atoms.

Furthermore, in the quinoxaline derivative represented by the general formula (G11), R¹¹ to R¹⁴ are each preferably hydrogen for ease of synthesis and purification (purity improvement). That is, the quinoxaline derivative represented by the general formula (G14) is preferable.

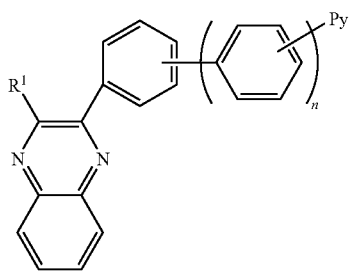
(G14)

In the formula, n represents an integer of 0 or 1; Py represents a substituted or unsubstituted pyridyl group; and R¹ represents any of an alkyl group having 1 to 4 carbon atoms and a substituted or unsubstituted aryl group having 6 to 13 carbon atoms.

Similarly, in the quinoxaline derivative represented by the general formula (G21), to R¹⁴ are each preferably hydrogen for ease of synthesis and purification (purity improvement). That is, the quinoxaline derivative represented by the general formula (G24) is preferable.

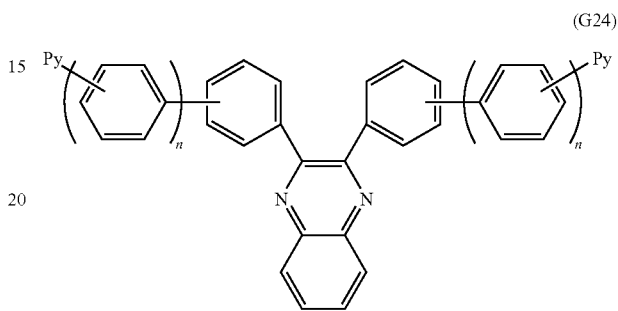
(G24)

In the formula, n represents an integer of 0 or 1 and Py represents a substituted or unsubstituted pyridyl group.

Moreover, in the quinoxaline derivative represented by the general formula (G11), in the case where α is a phenylene group, β which is bound to the phenylene group bound to the quinoxaline skeleton is preferably bound at a para position for reduction of steric hindrance and ease of synthesis. That is, the quinoxaline derivative represented by the general formula (G15) is preferable.

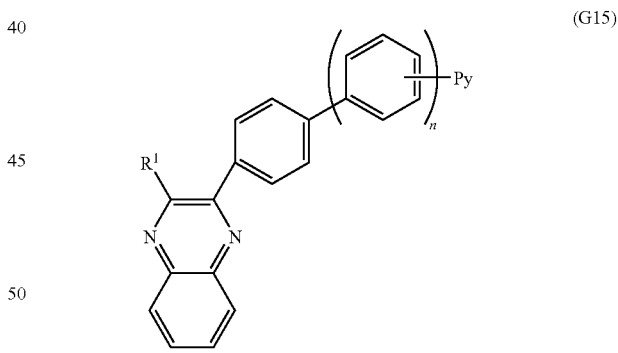
(G15)

In the formula, n represents an integer of 0 or 1; Py represents a substituted or unsubstituted pyridyl group; and R¹ represents any of an alkyl group having 1 to 4 carbon atoms and a substituted or unsubstituted aryl group having 6 to 13 carbon atoms.

Similarly, in the quinoxaline derivative represented by the general formula (G21), in the case where α is a phenylene group, β which is bound to the phenylene group bound to the quinoxaline skeleton is preferably bound at a para position for reduction of steric hindrance and ease of synthesis. That is, the quinoxaline derivative represented by the general formula (G25) is preferable.

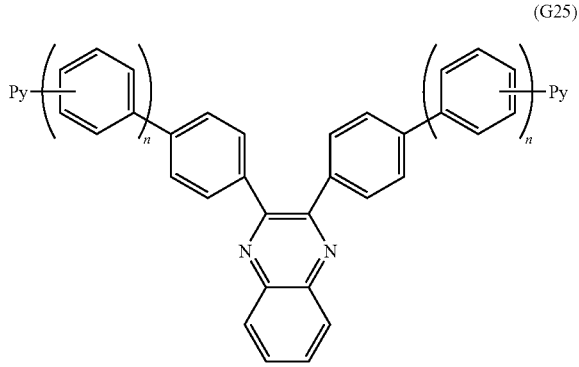

(G25)

In the formula, n represents an integer of 0 or 1 and Py represents a substituted or unsubstituted pyridyl group.

Moreover, in the quinoxaline derivative represented by the general formula (G11), in the case where α is a phenylene group and β is also a phenylene group, both phenylene groups are preferably bound to each other at a para position. With such a structure, steric hindrance is reduced, and synthesis is easier. That is, the quinoxaline derivative represented by the general formula (G16) is preferable.

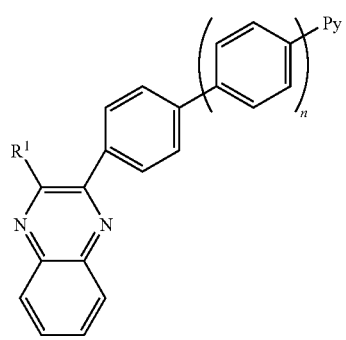

(G16)

In the formula, n represents an integer of 0 or 1; Py represents a substituted or unsubstituted pyridyl group; and $R^1$ represents any of an alkyl group having 1 to 4 carbon atoms and a substituted or unsubstituted aryl group having 6 to 13 carbon atoms.

Similarly, in the quinoxaline derivative represented by the general formula (G21), in the case where α is a phenylene group and β is also a phenylene group, both phenylene groups are preferably bound to each other at a para position. With such a structure, steric hindrance is reduced, and synthesis is easier. That is, the quinoxaline derivative represented by the general formula (G26) is preferable.

(G26)

In the formula, n represents an integer of 0 or 1 and Py represents a substituted or unsubstituted pyridyl group.

Furthermore, in the quinoxaline derivative represented by the general formula (G11), $R^1$ is preferably a phenyl group or a biphenyl group for ease of synthesis and purification (purity improvement).

Examples of the quinoxaline derivative represented by the general formula (G11) include quinoxaline derivatives represented by structural formulas (101) to (301). Further, examples of the quinoxaline derivative represented by the general formula (G21) include quinoxaline derivatives represented by structural formulas (401) to (427). However, the present invention is not limited to these examples.

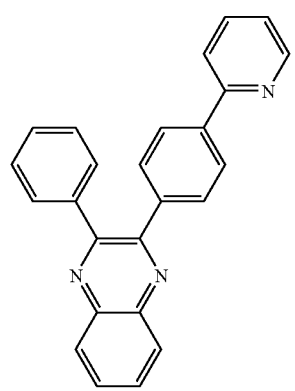

(101)

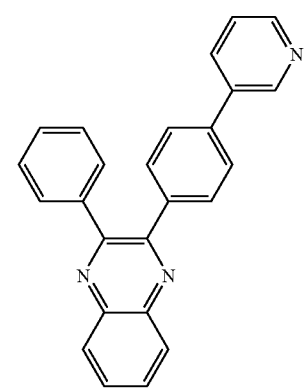

(102)

-continued
(103)
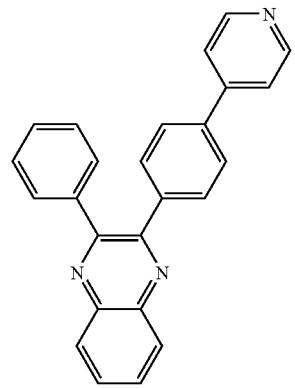
(104)
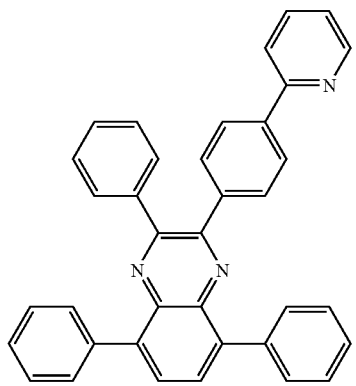
(105)
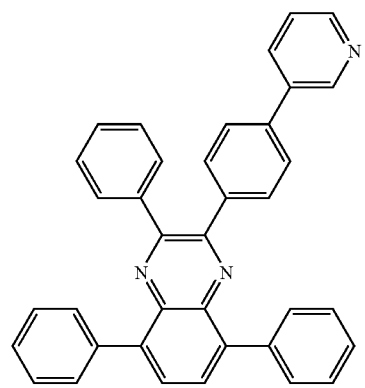
(106)
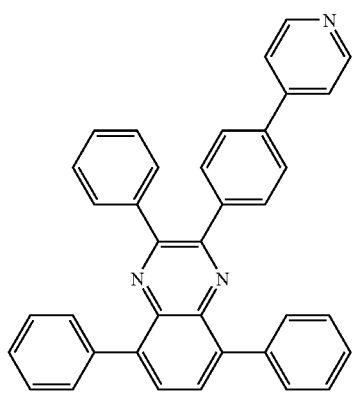
(107)
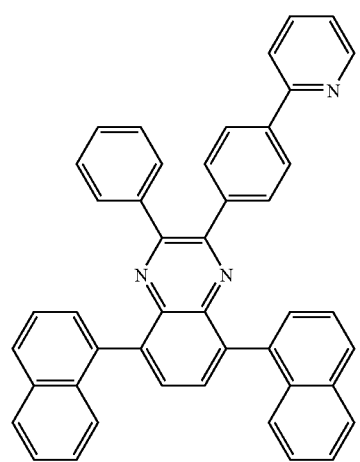
(108)
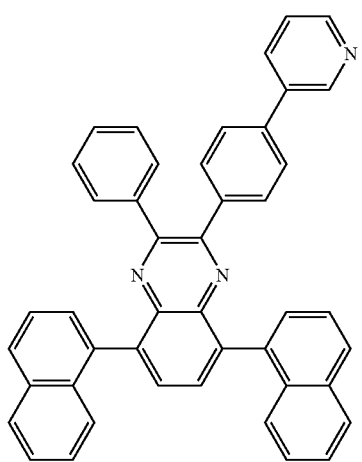

-continued
(109)
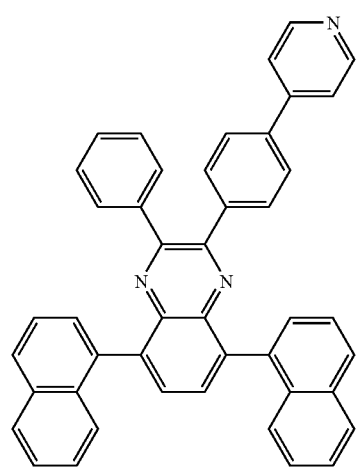
(110)
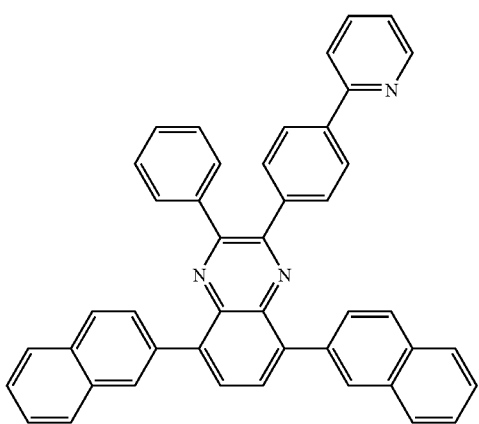
(111)
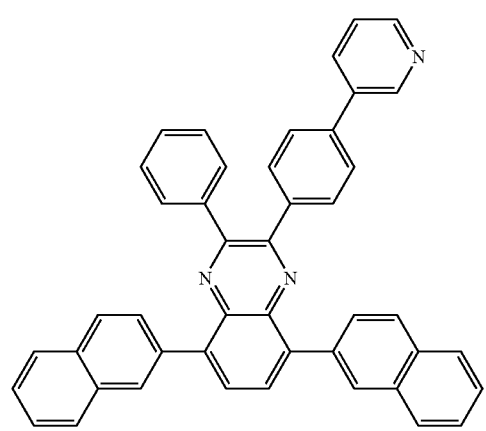
(112)
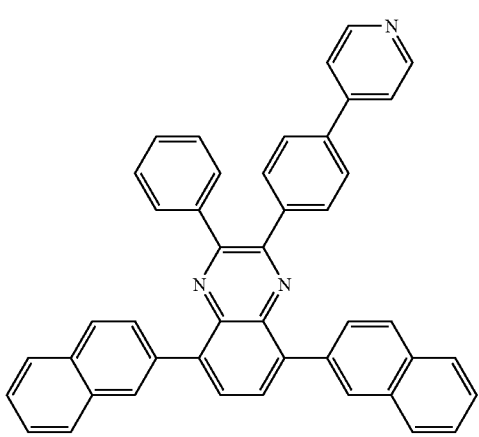
(113)
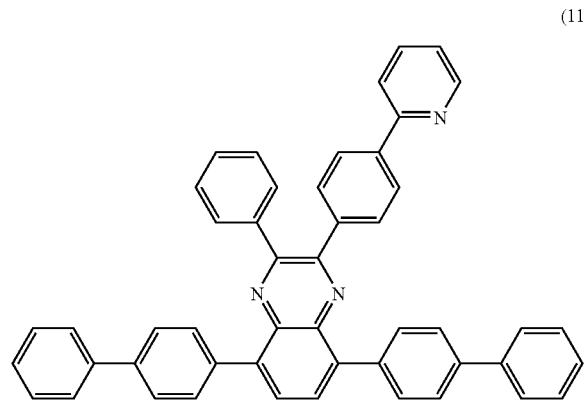
(114)
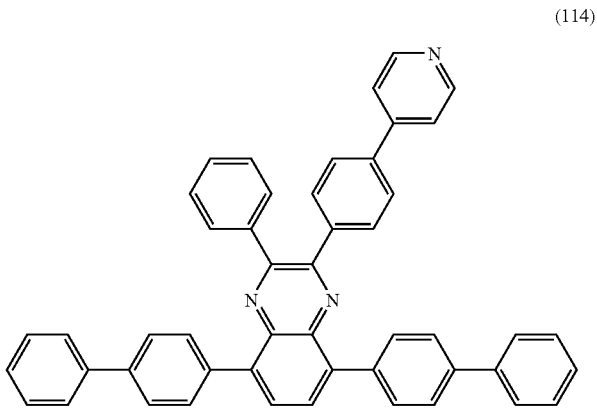

(115)
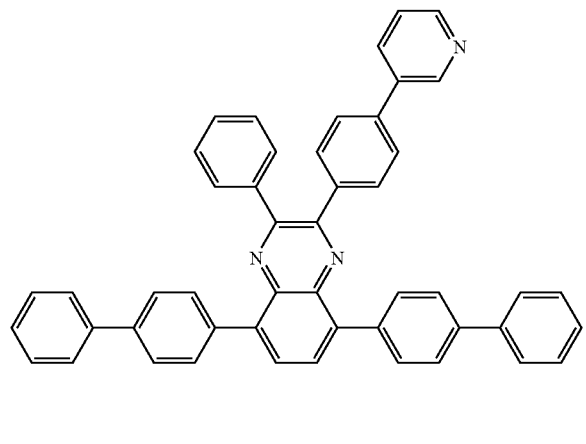
(116)
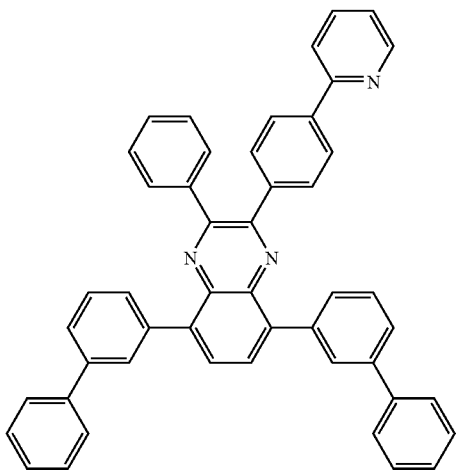
(117)
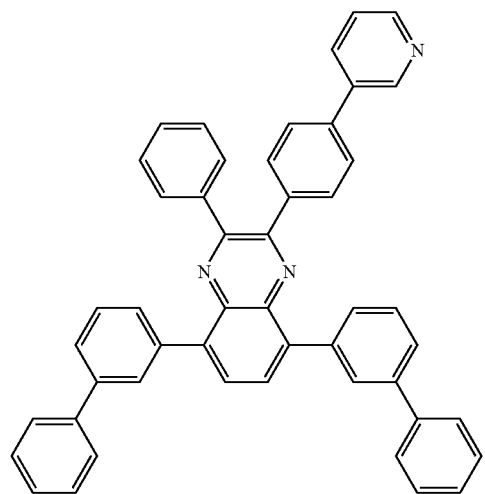
(118)
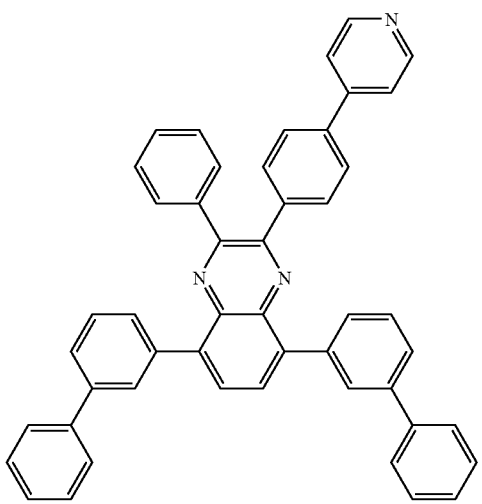
(119)
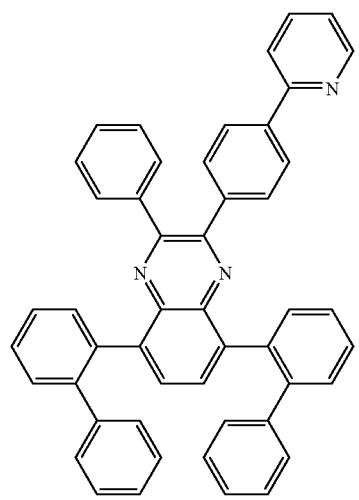
(120)
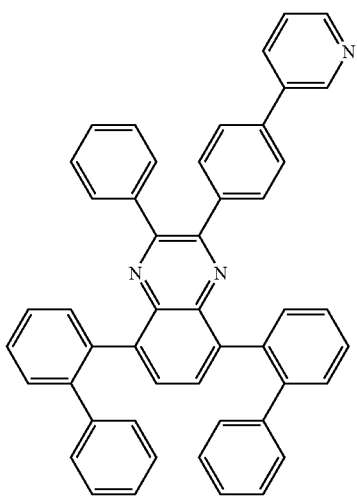

-continued
(121)
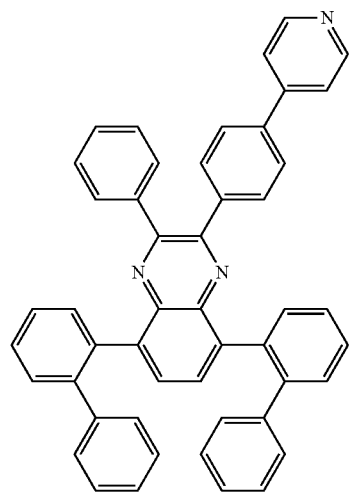
(122)
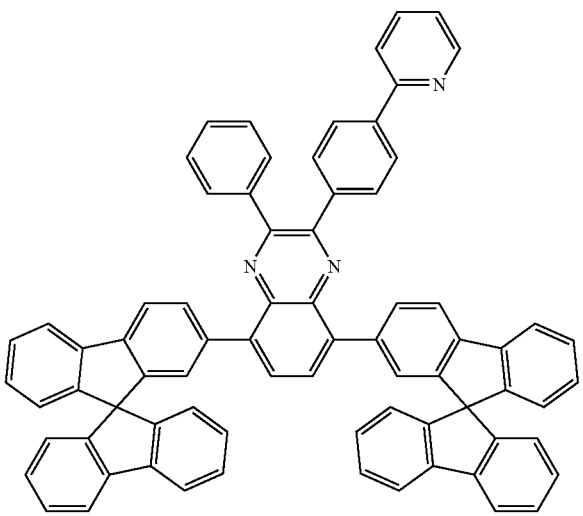
(123)
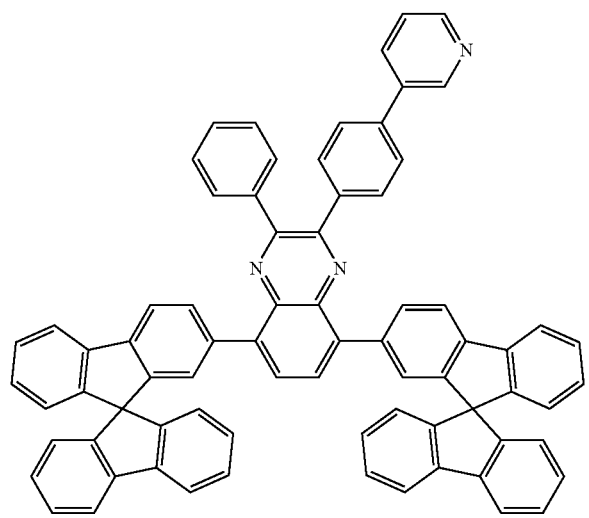
(124)
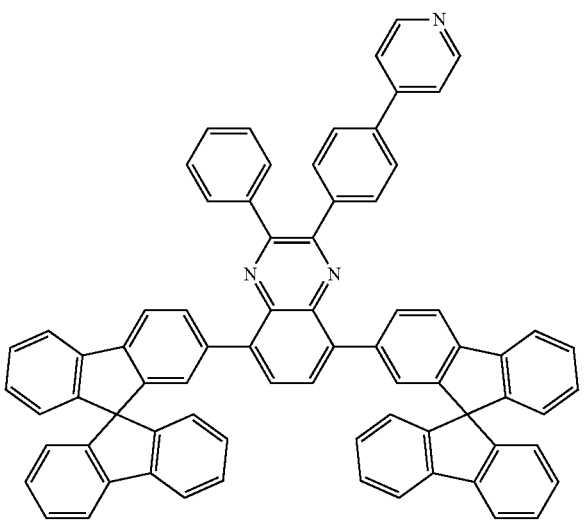
(125)
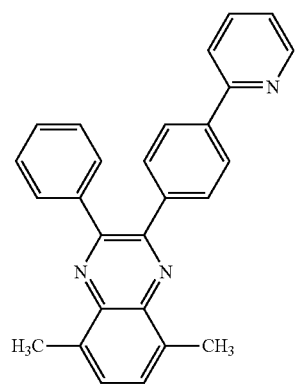
(126)
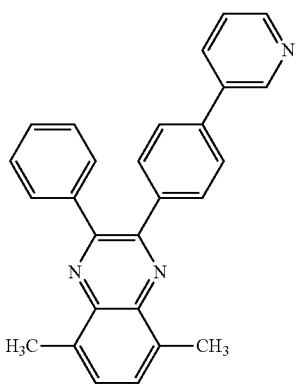

-continued
(127)
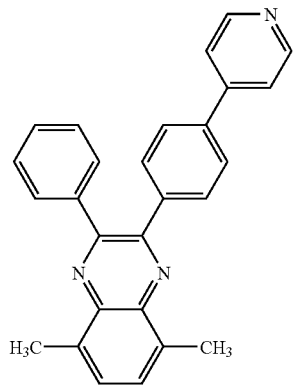
(128)
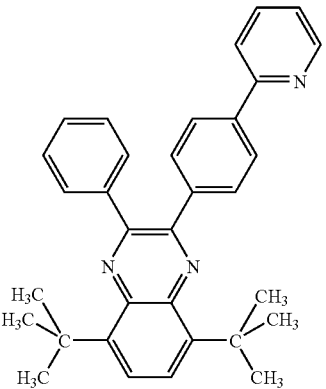
(129)
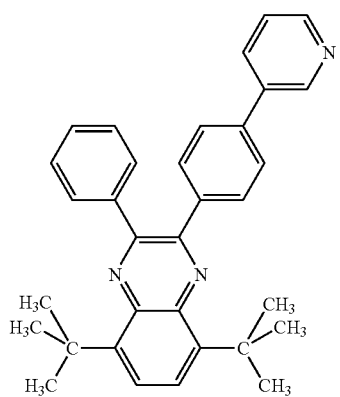
(130)
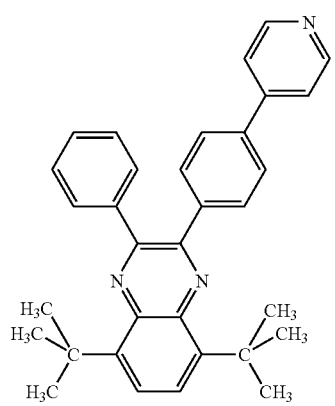
(131)
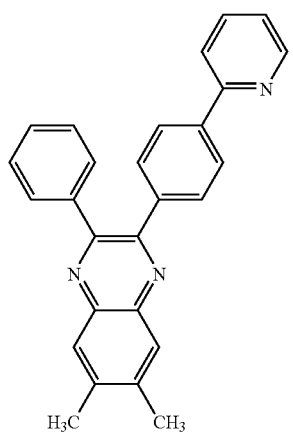
(132)
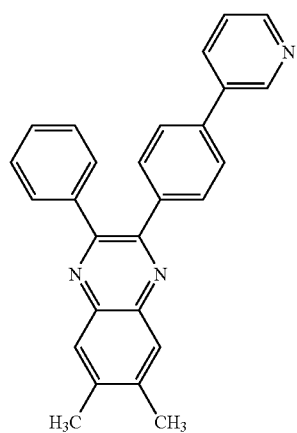

-continued
(133)
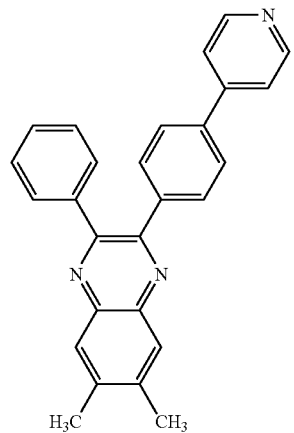
(134)
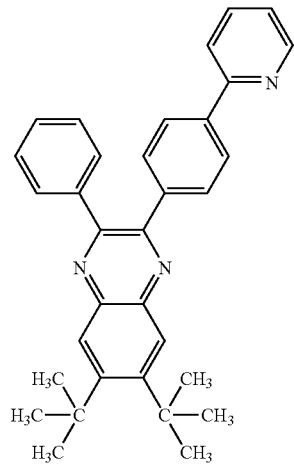
(135)
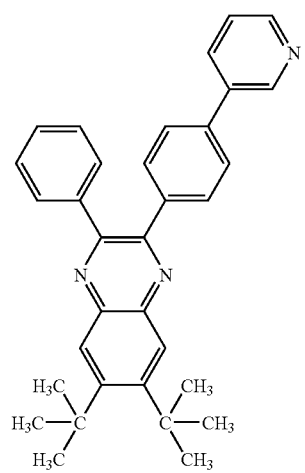
(136)
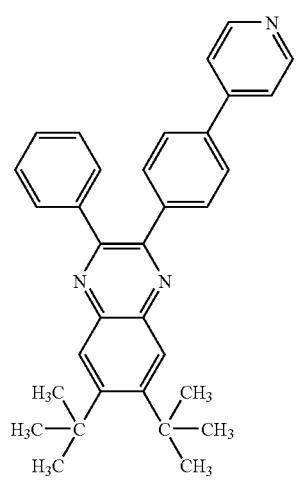
(137)
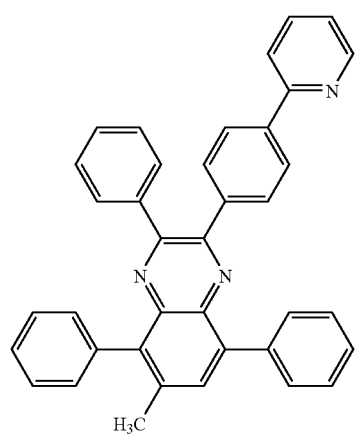
(138)
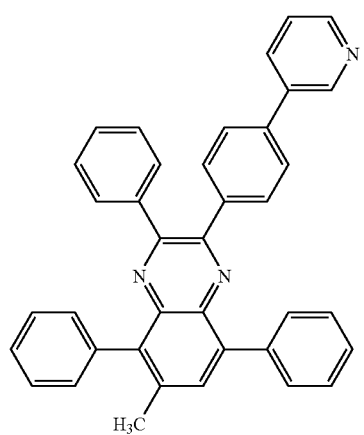

-continued
(139)
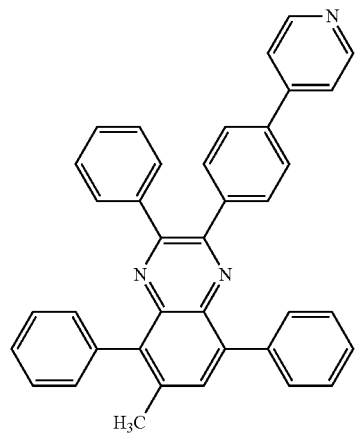
(140)
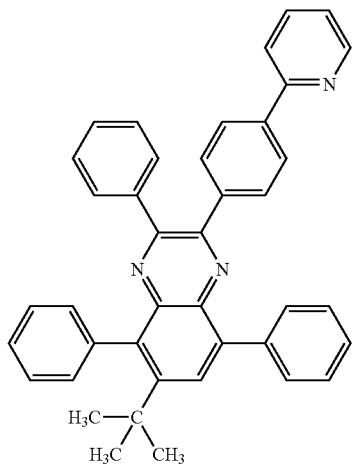
(141)
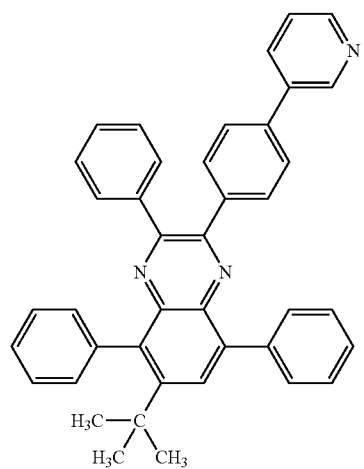
(142)
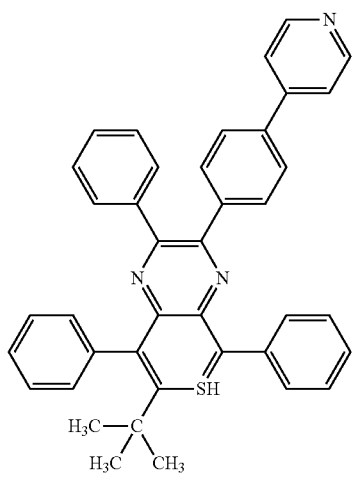
(143)
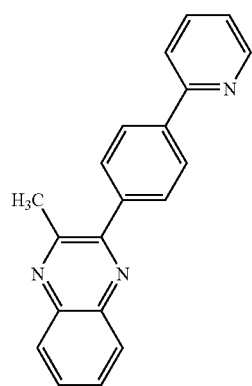
(144)
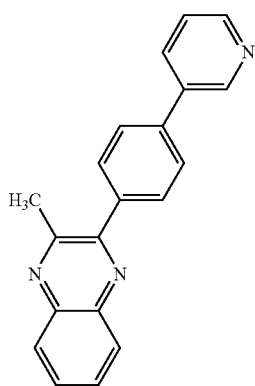

-continued
(145)
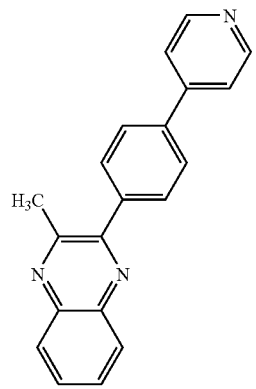
(146)
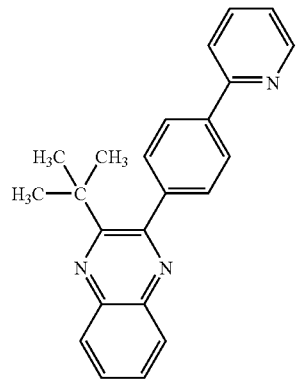
(147)
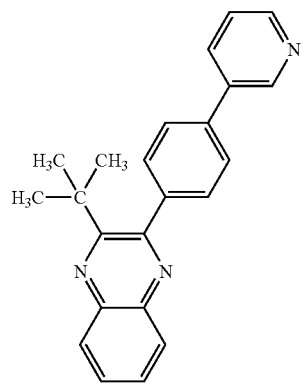
(148)
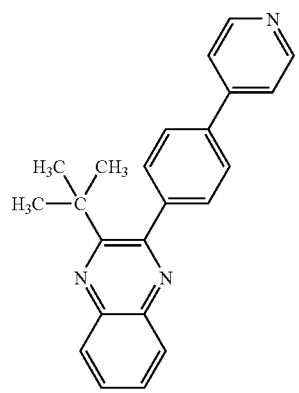
(149)
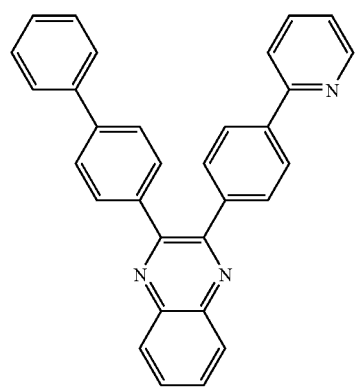
(150)
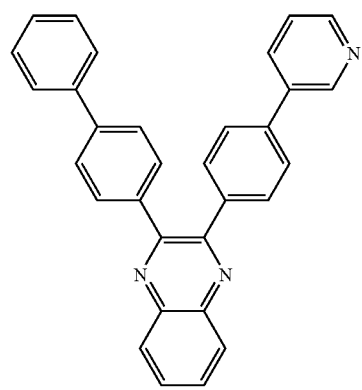
(151)
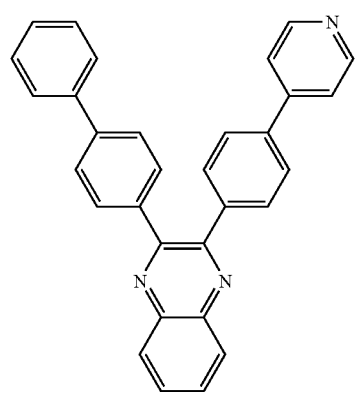
(152)
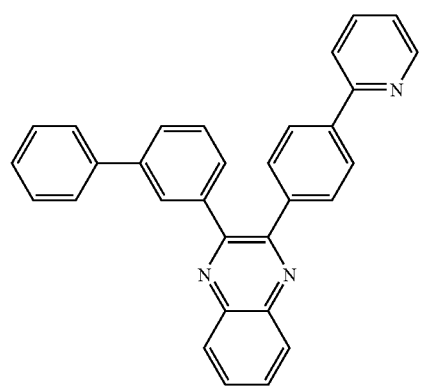

-continued
(153)
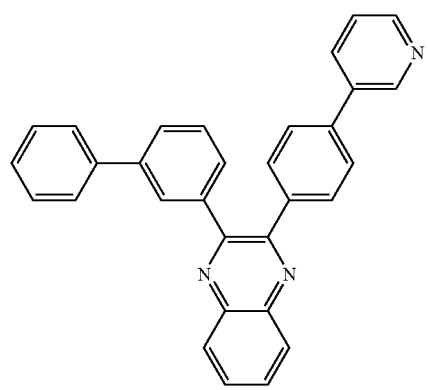
(154)
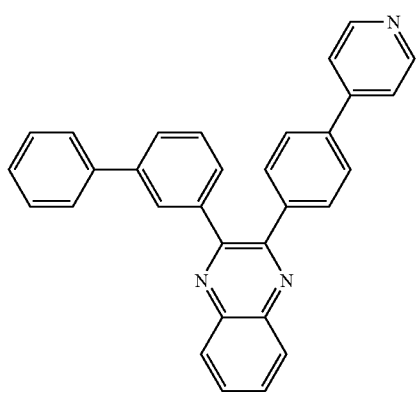
(155)
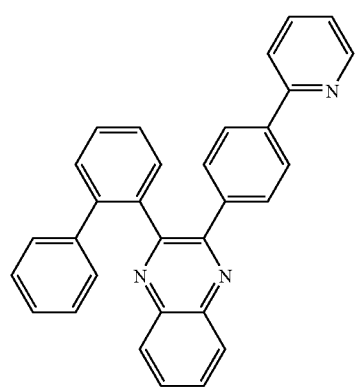
(156)
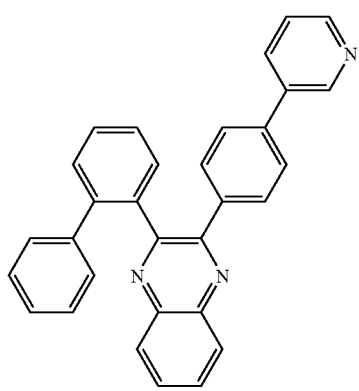
(157)
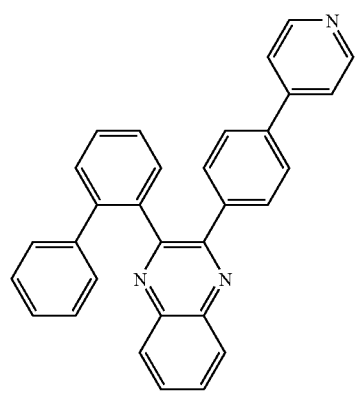
(158)
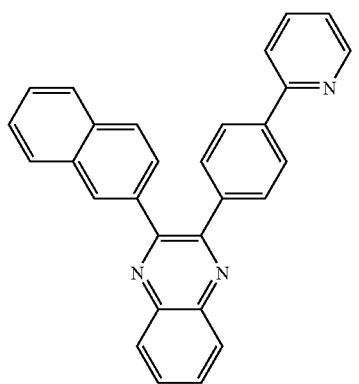
(159)
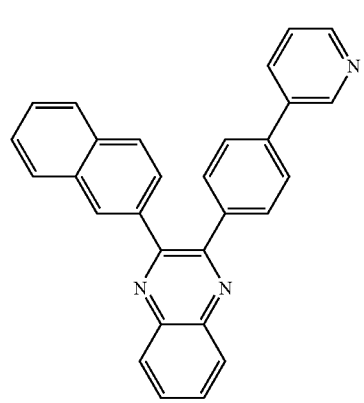
(160)
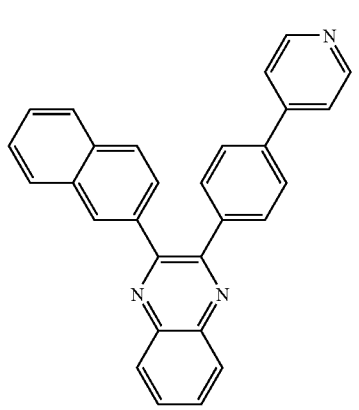

-continued
(161) 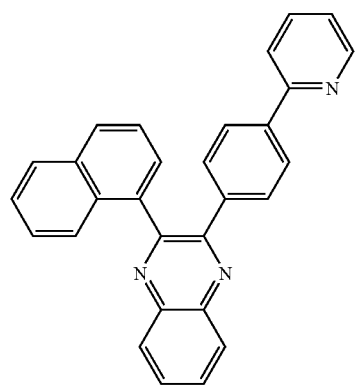
(162) 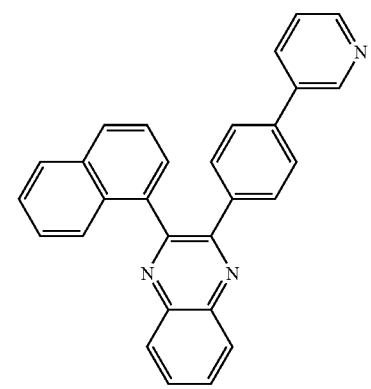
(163) 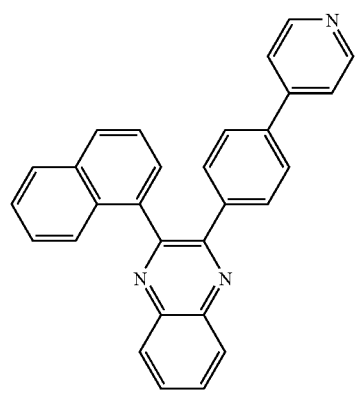
(164) 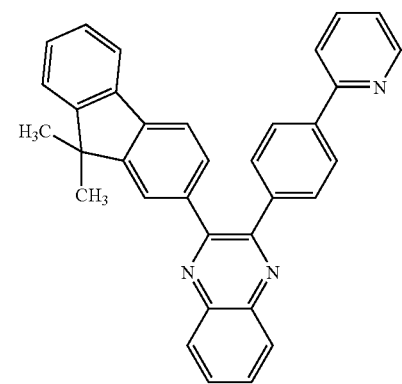
(165) 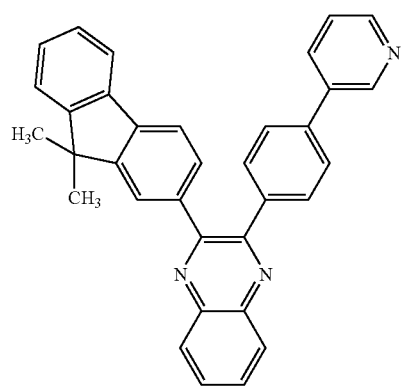
(166) 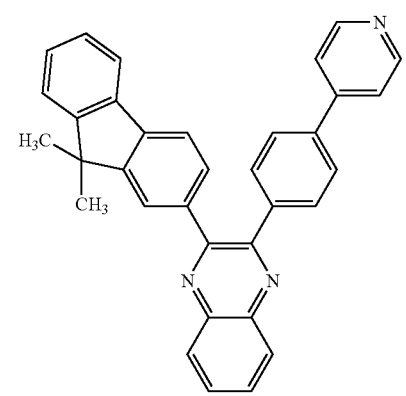
(167) 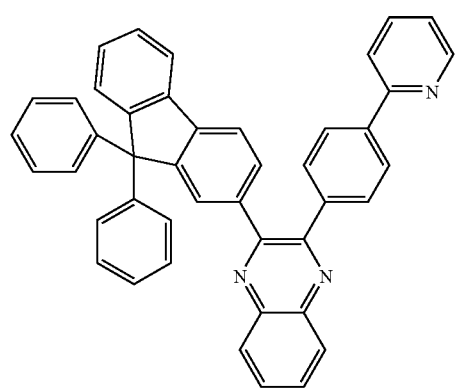
(168) 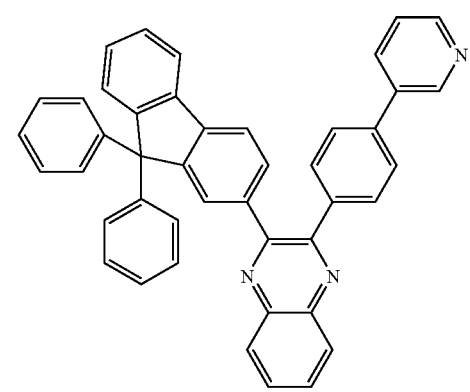

-continued
(169) 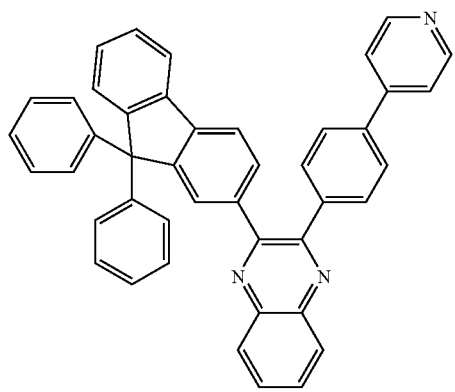
(170) 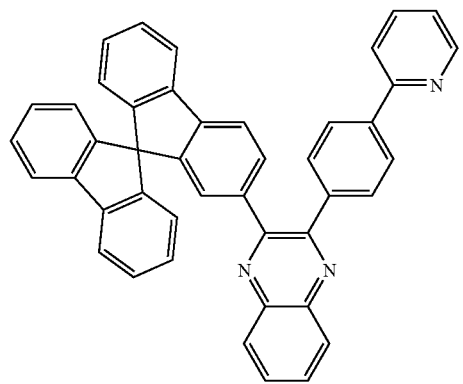
(171) 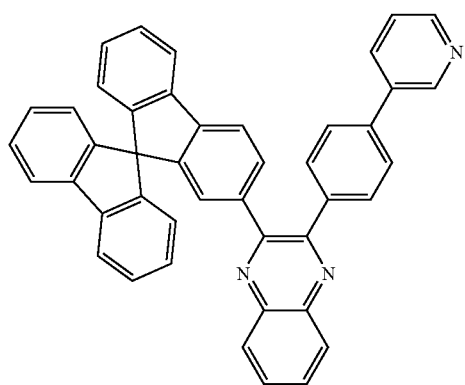
(172) 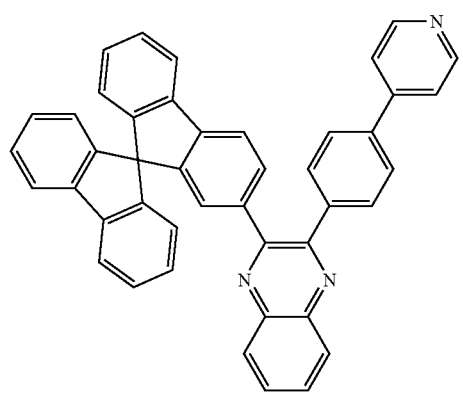
(173) 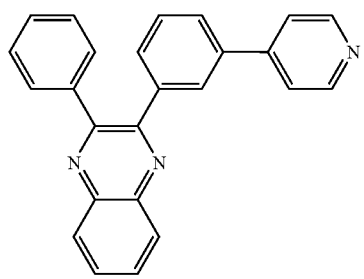
(174) 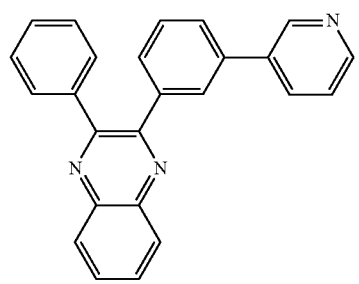
(175) 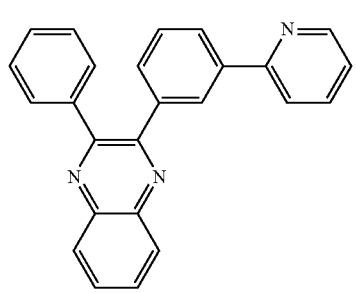
(176) 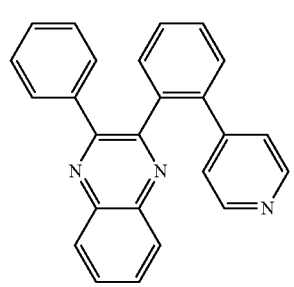
(177) 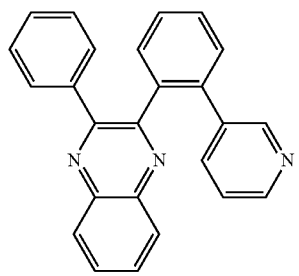
(178) 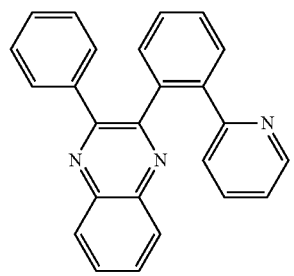

-continued
(179) 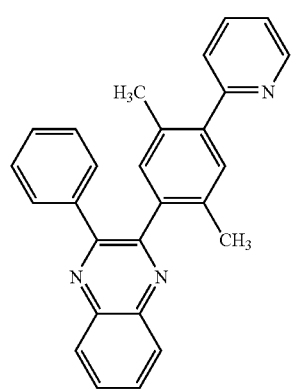
(180) 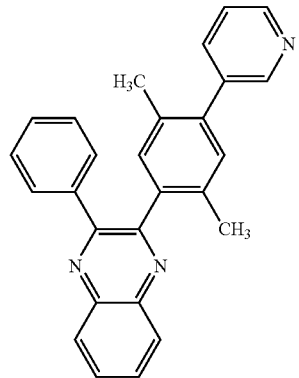
(181) 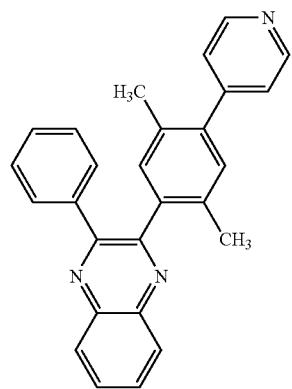
(182) 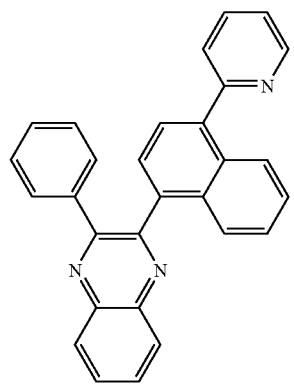
(183) 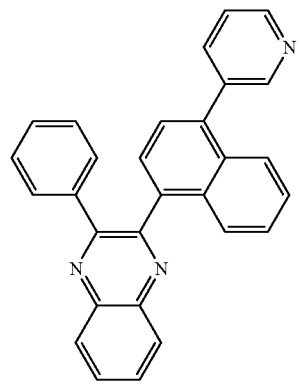
(184) 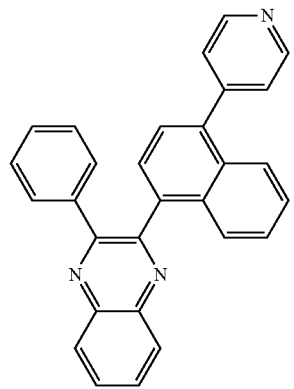
(185) 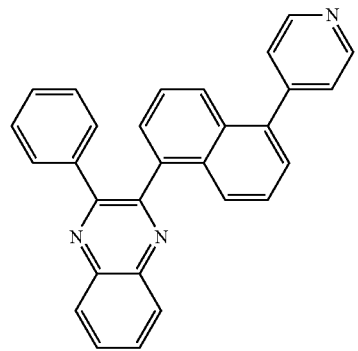
(186) 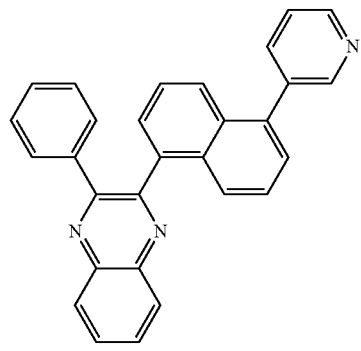

-continued
(187)
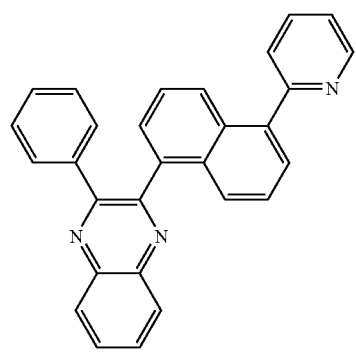
(188)
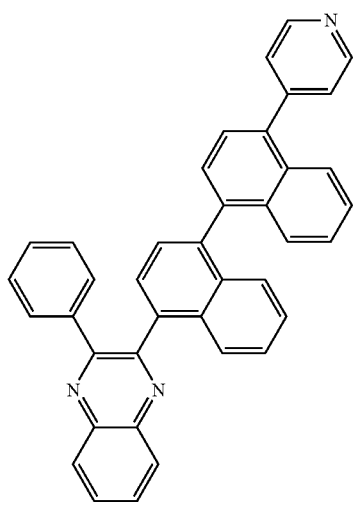
(189)
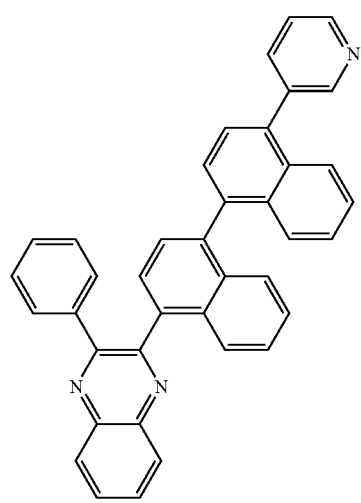
(190)
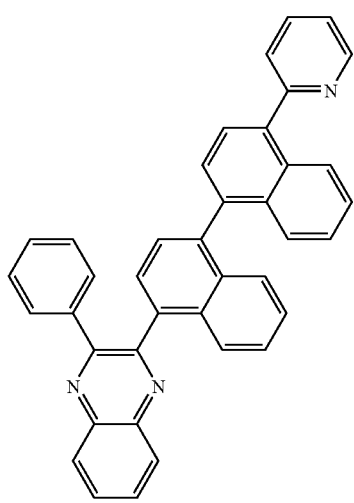
(191)
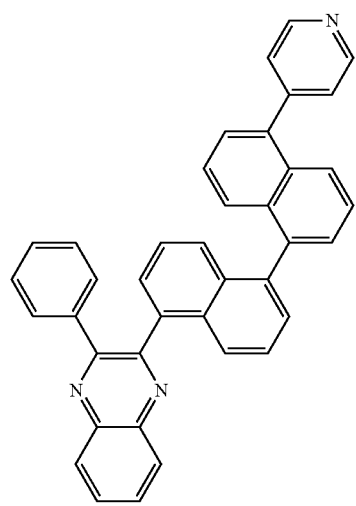
(192)
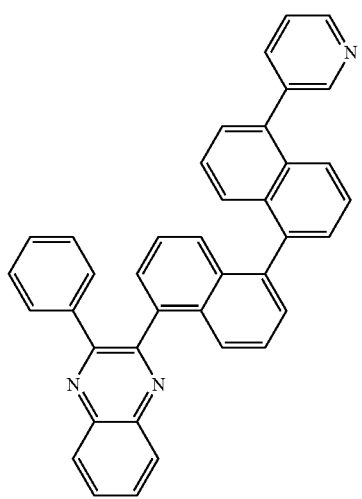

(193)
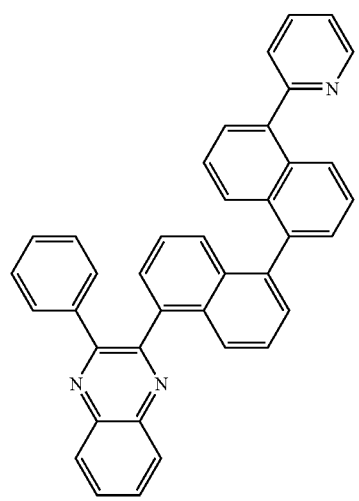
(194)
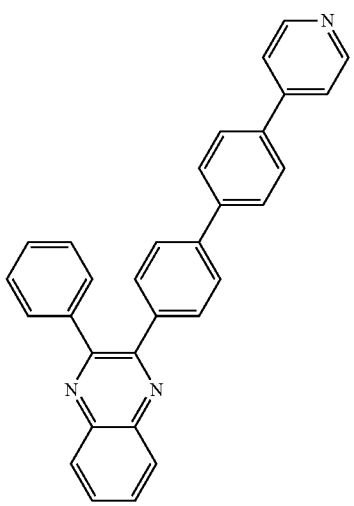
(195)
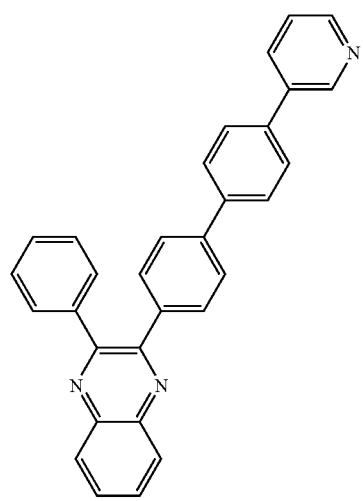
(196)
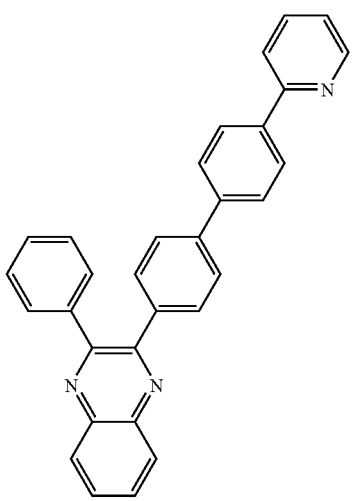
(197)
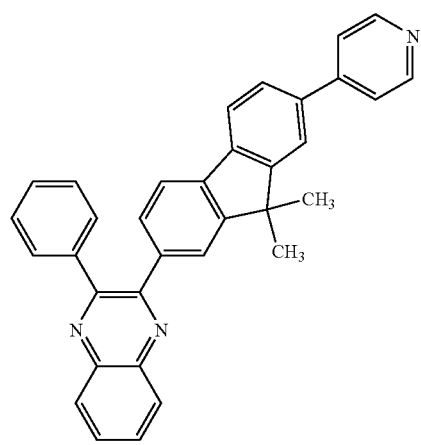
(198)
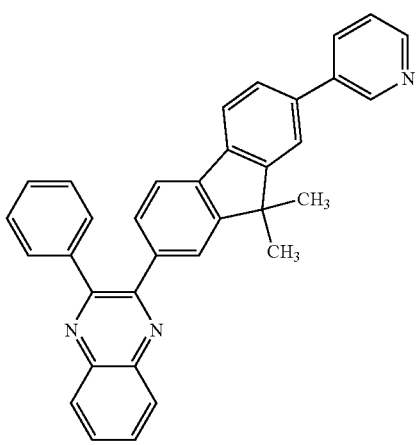

-continued
(199)
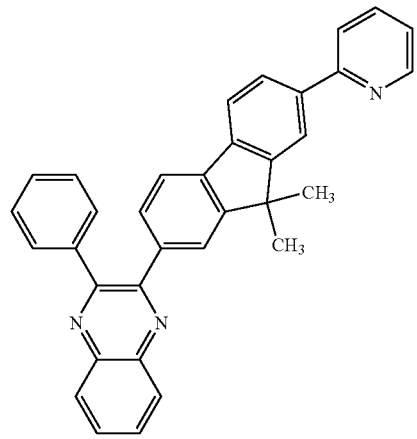
(200)
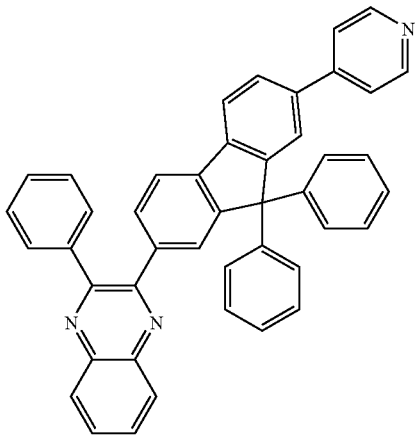
(201)
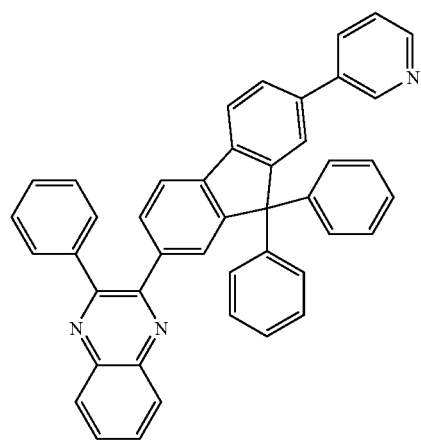
(202)
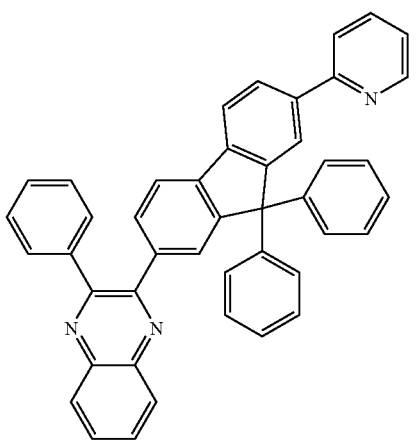
(203)
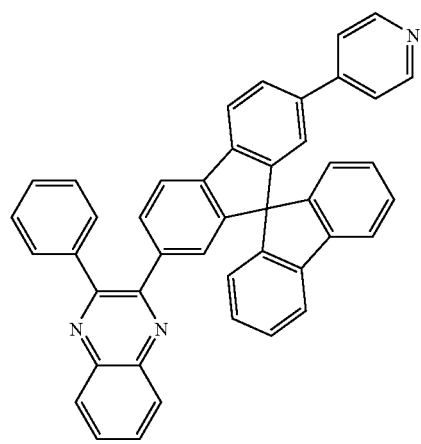
(204)
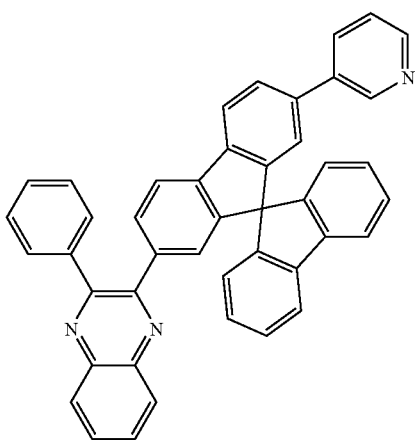

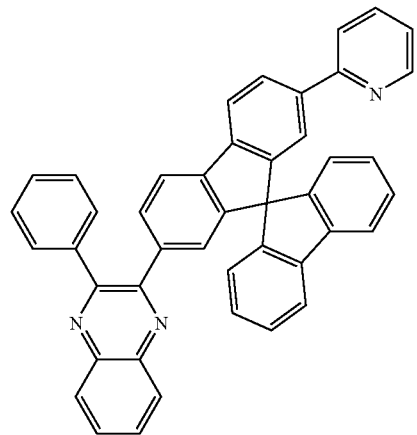
(205)
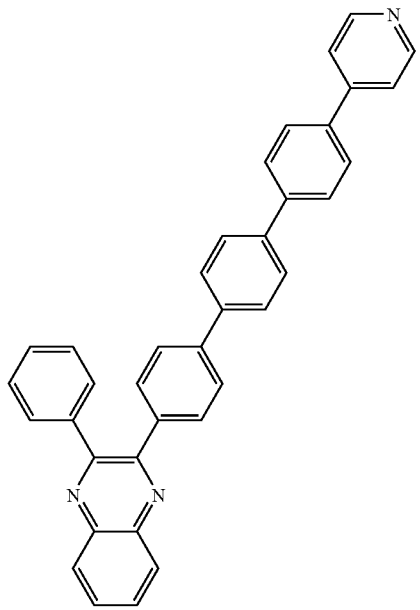
(206)
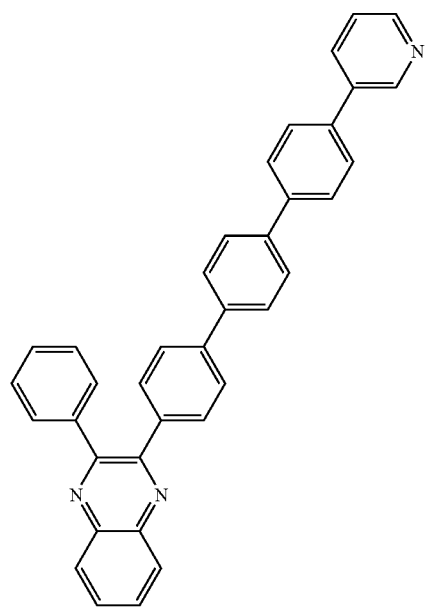
(207)
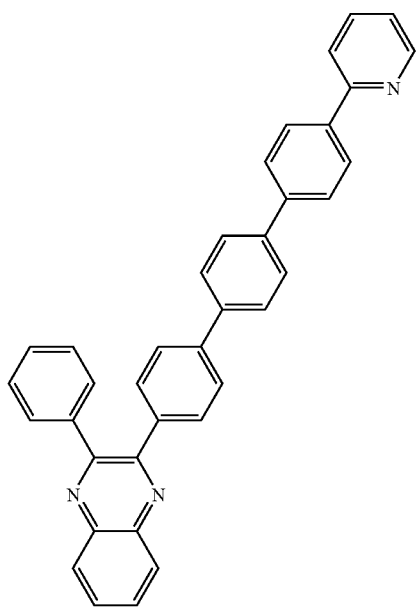
(208)

-continued
(209)
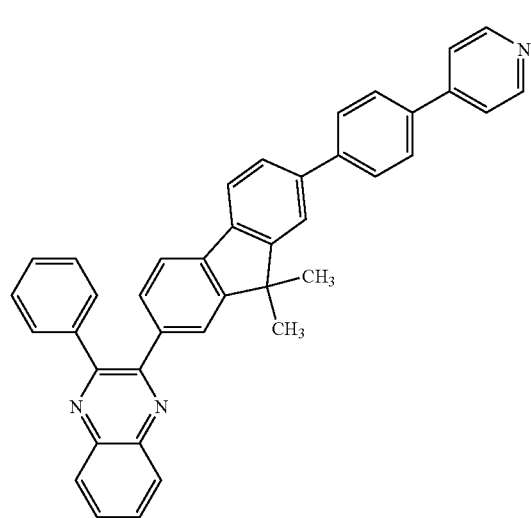
(210)
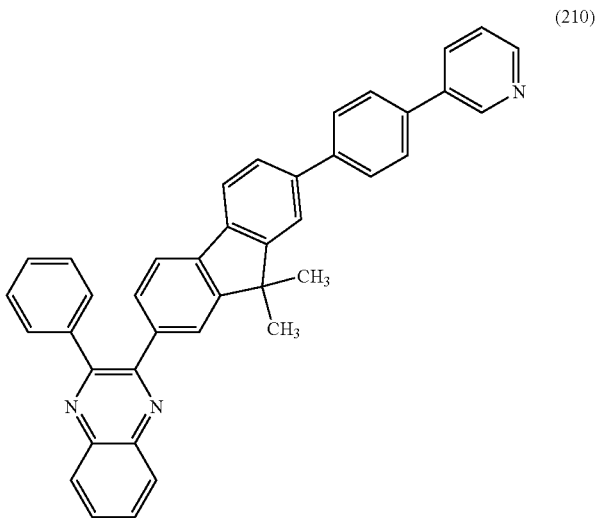
(211)
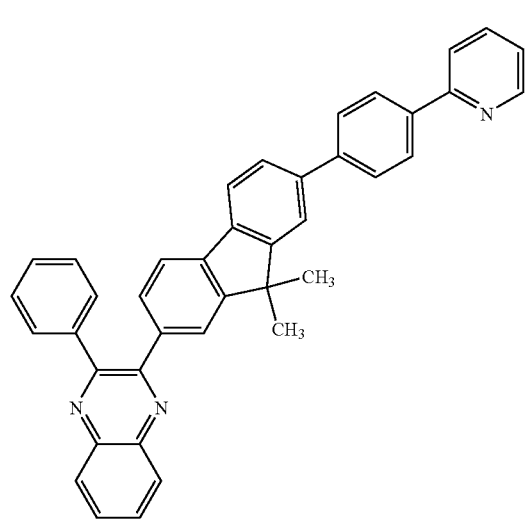
(212)
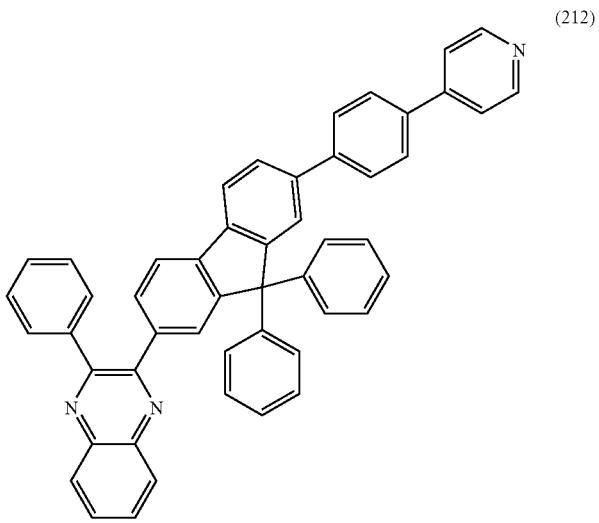
(213)
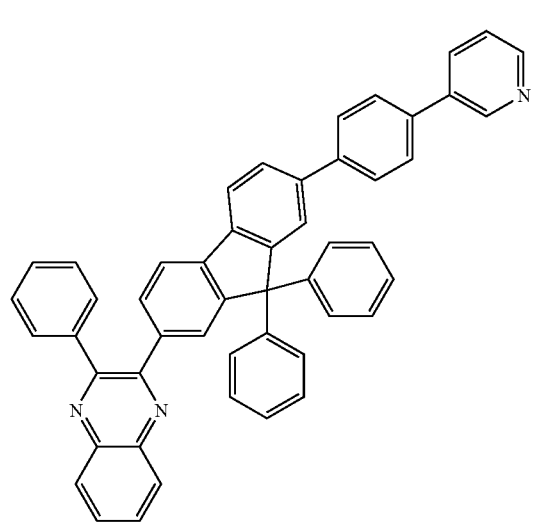
(214)
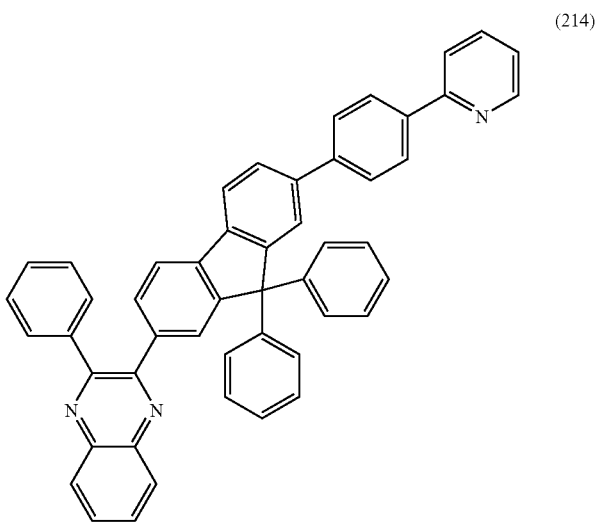

-continued
(215)
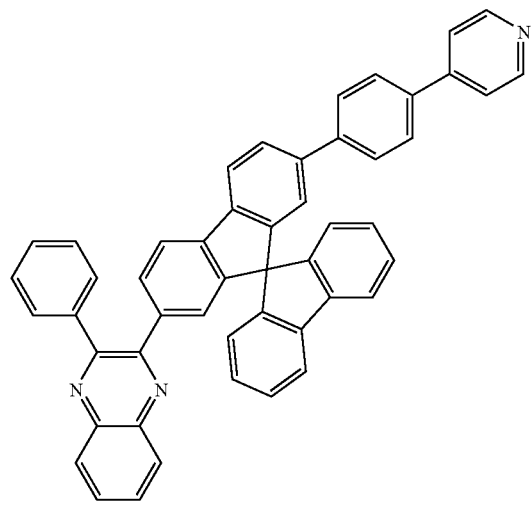
(216)
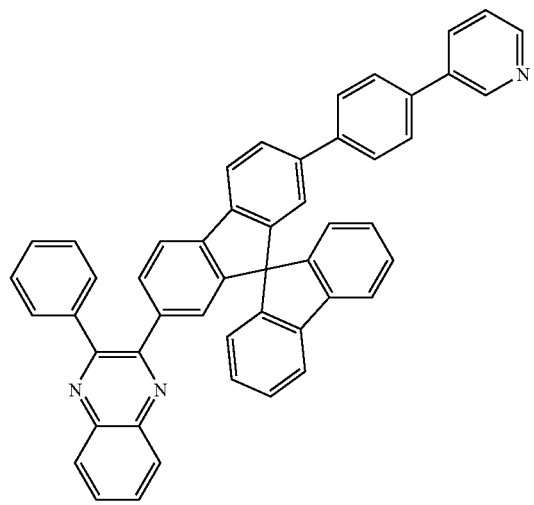
(217)
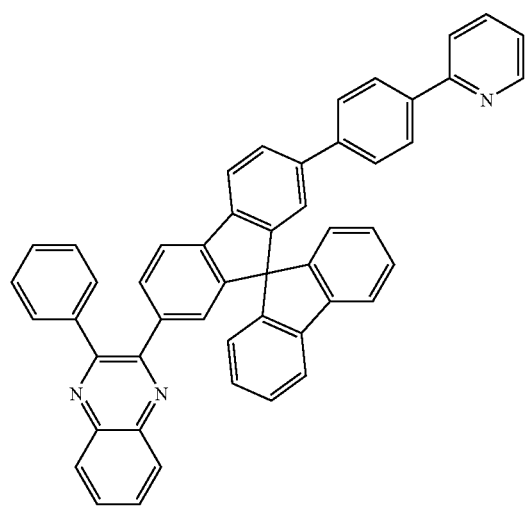
(218)
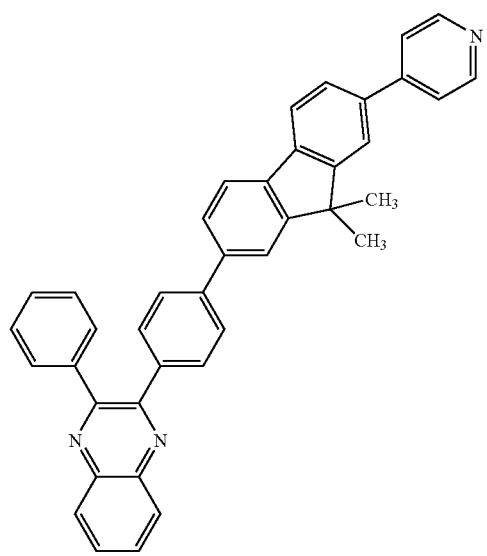
(219)
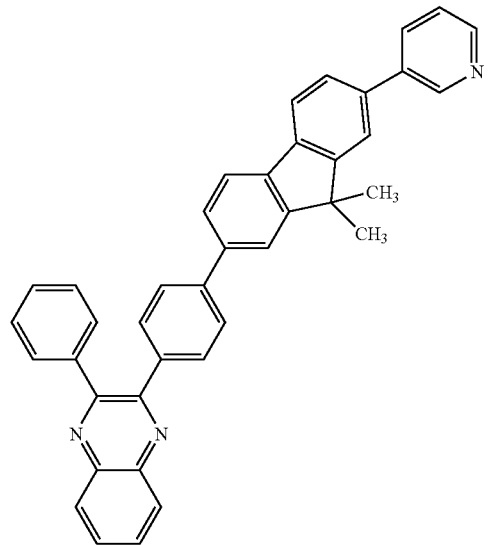
(220)
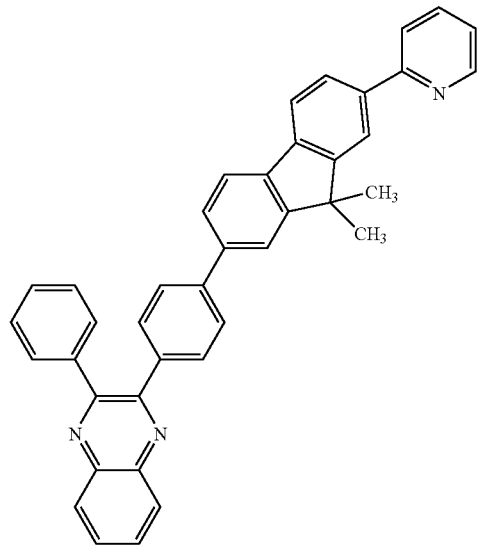

-continued
(221)
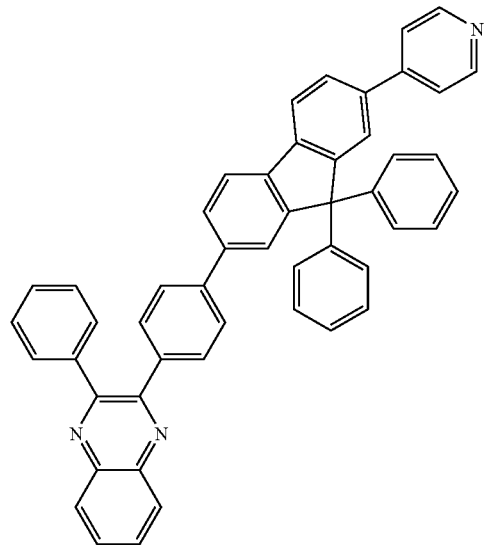
(222)
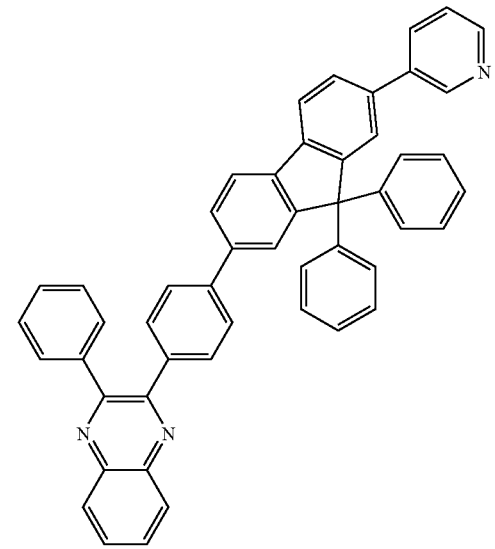
(223)
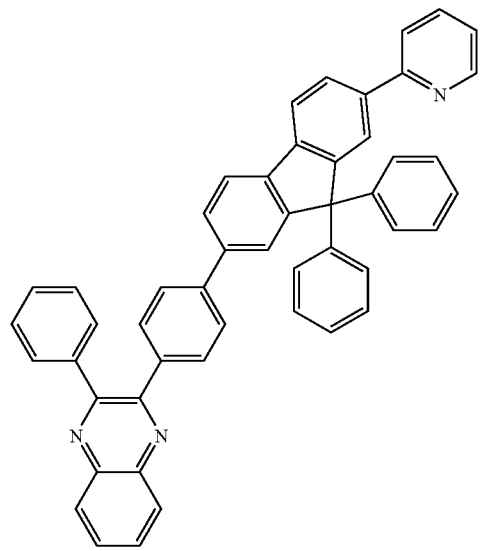
(224)
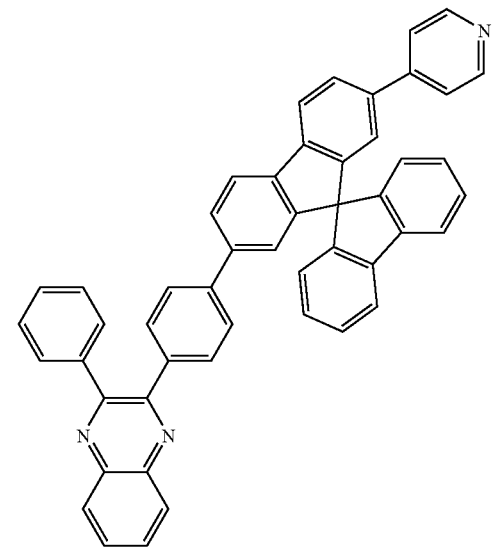
(225)
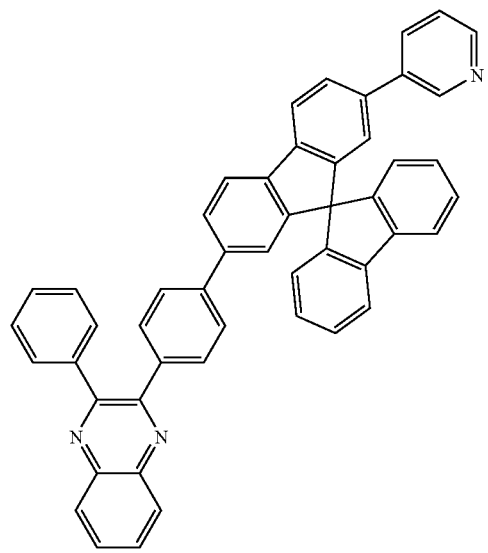
(226)
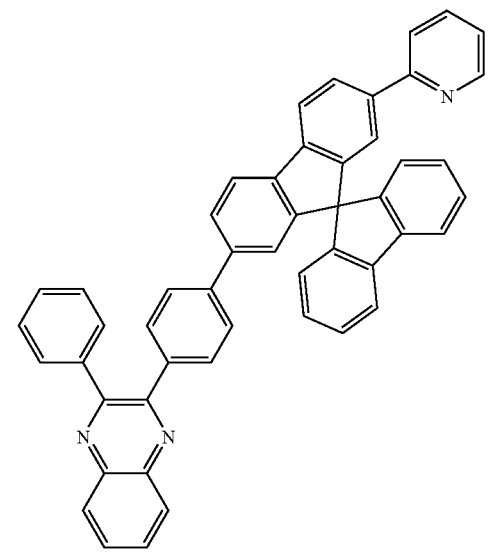

(227)
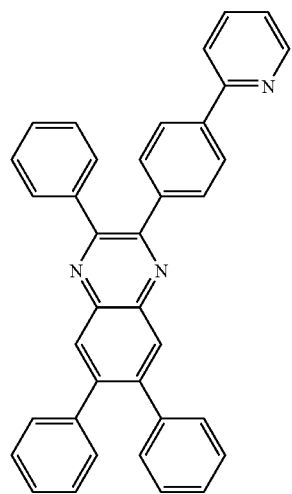
(228)
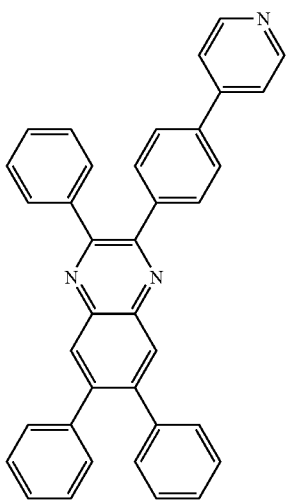
(229)
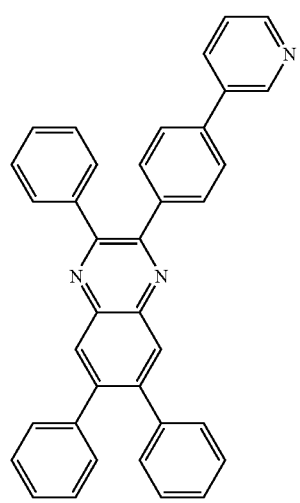
(230)
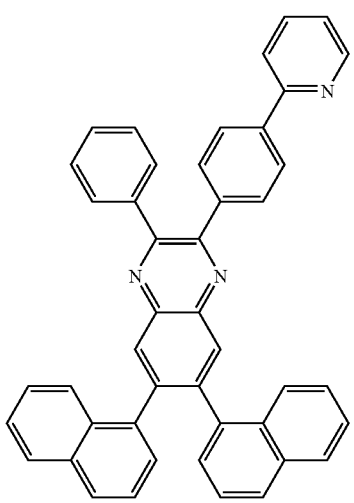
(231)
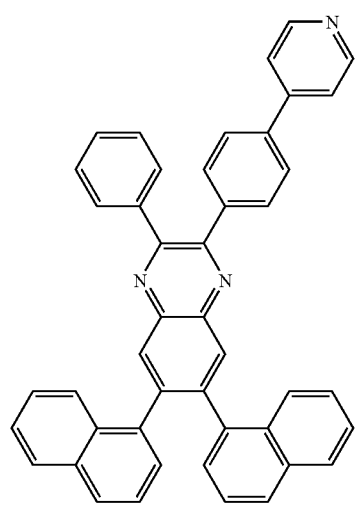
(232)
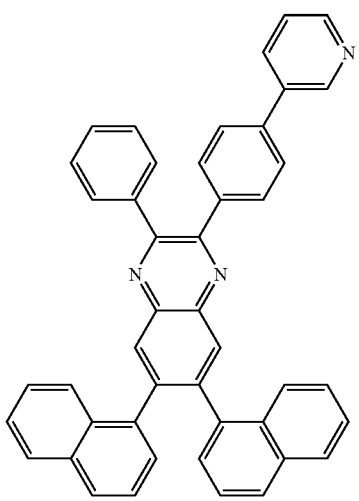

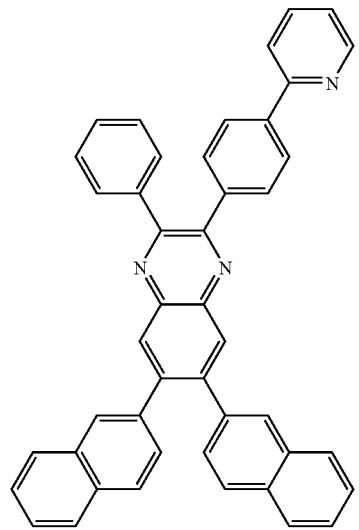
(233)
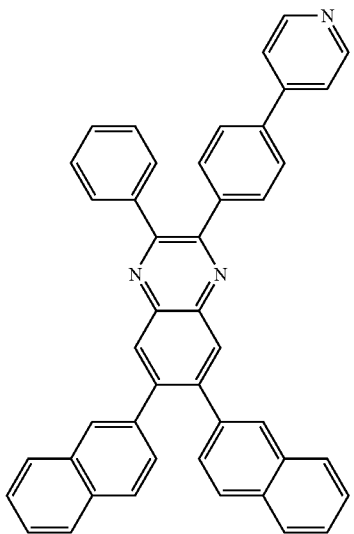
(234)
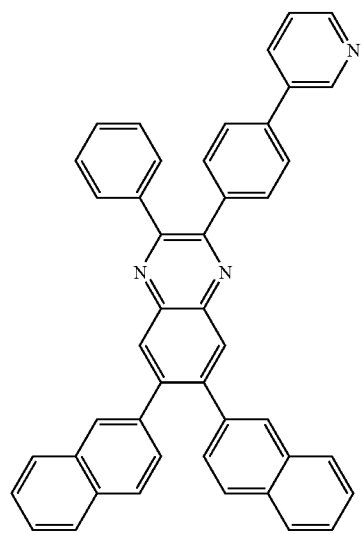
(235)
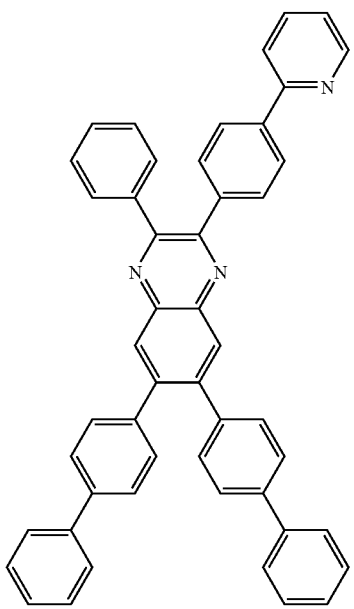
(236)

-continued
(237)
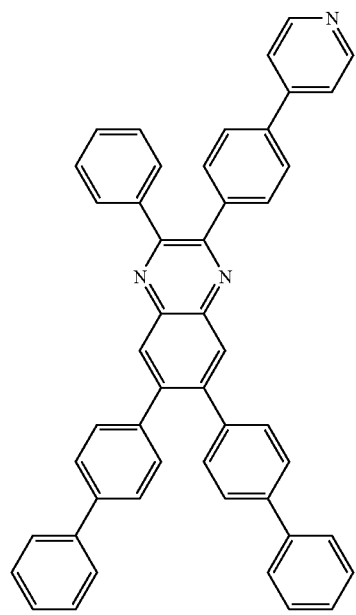
(238)
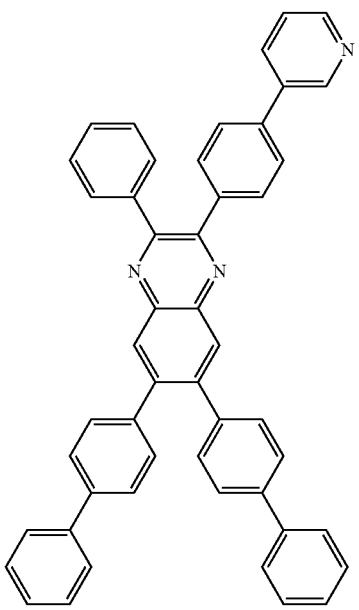
(245)
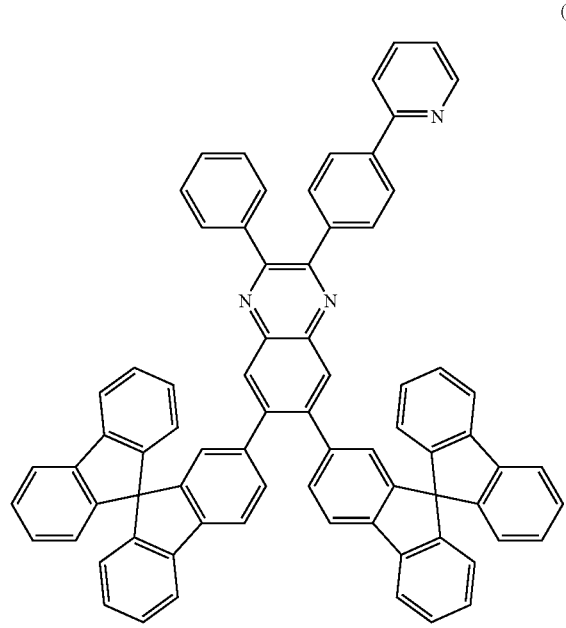
(246)
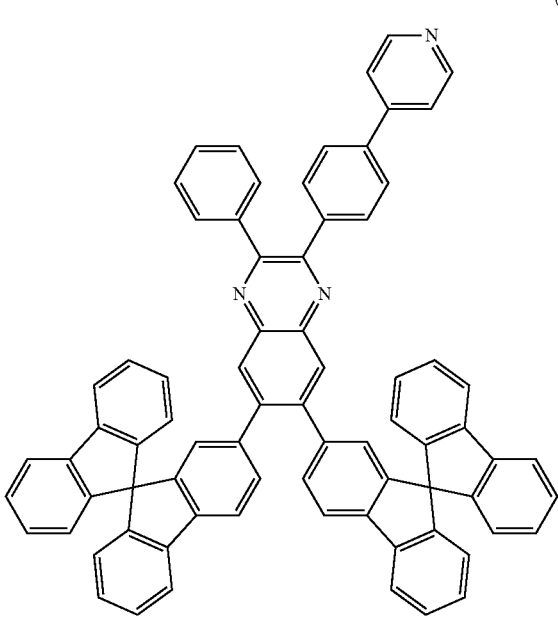

-continued
(247)
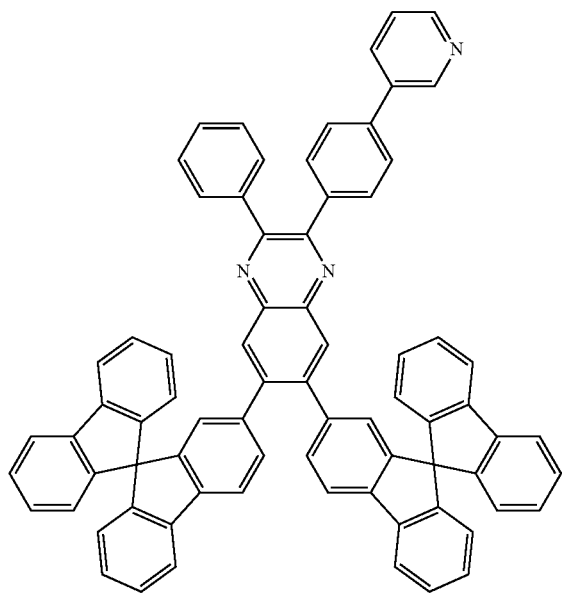
(248)
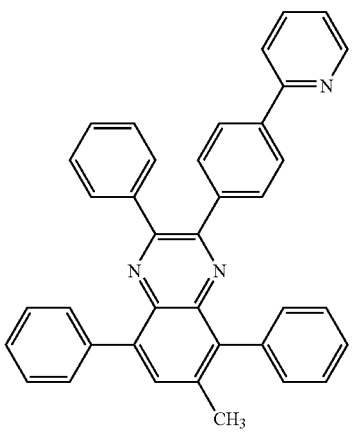
(249)
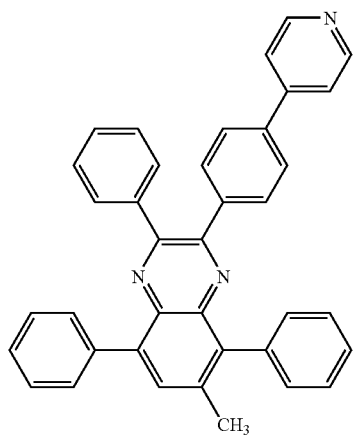
(250)
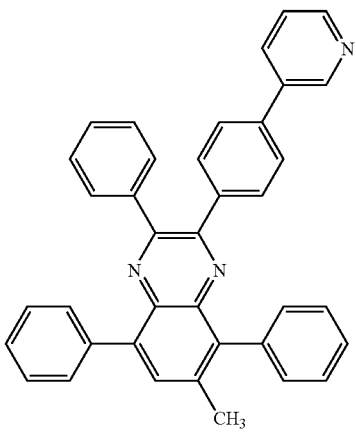
(251)
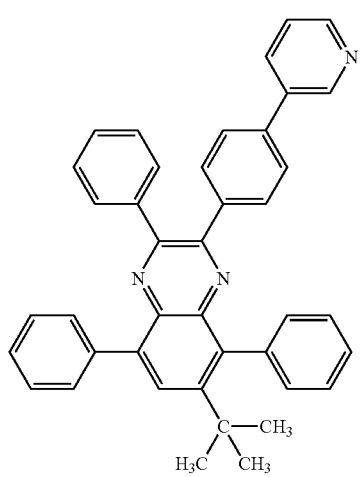
(252)
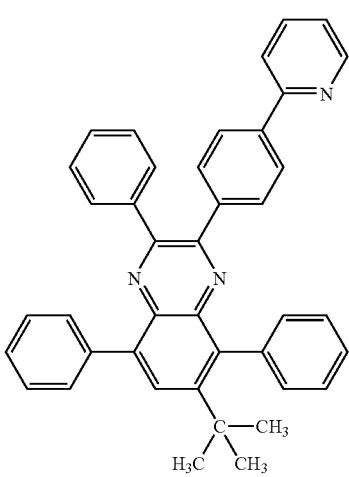

-continued
(253)
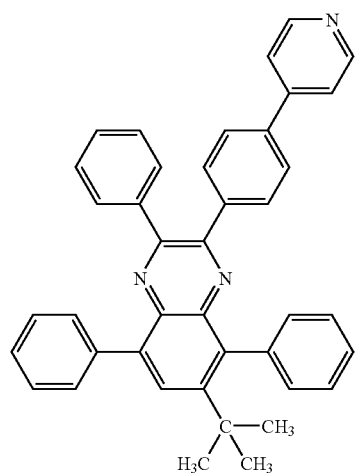
(254)
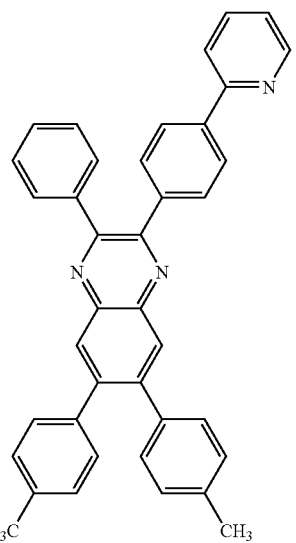
(255)
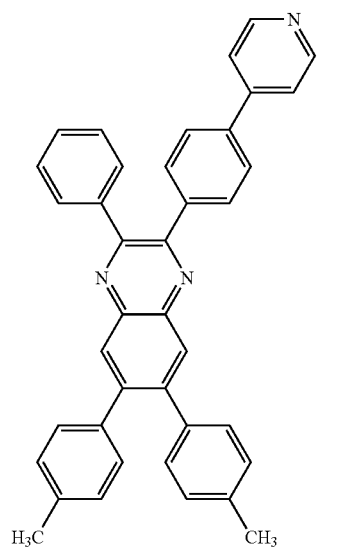
(256)
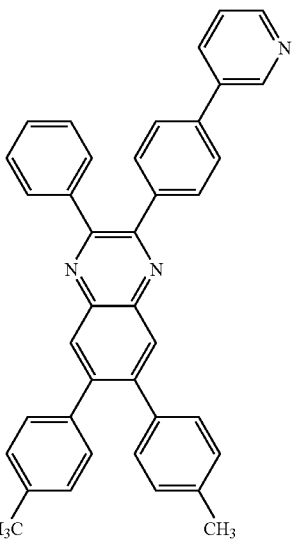
(257)
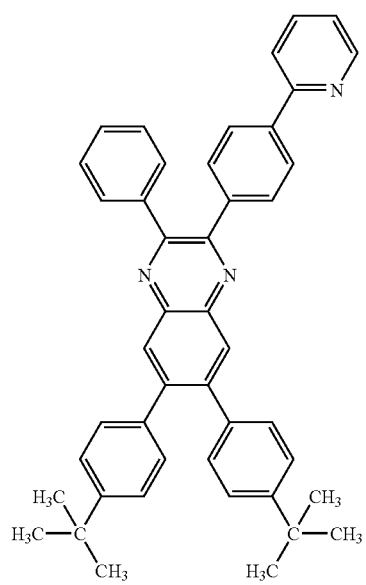
(258)
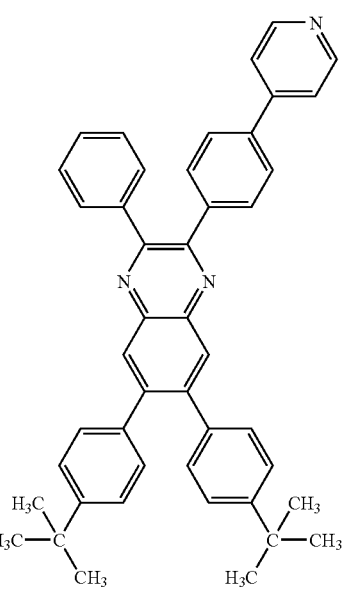

-continued
(259)
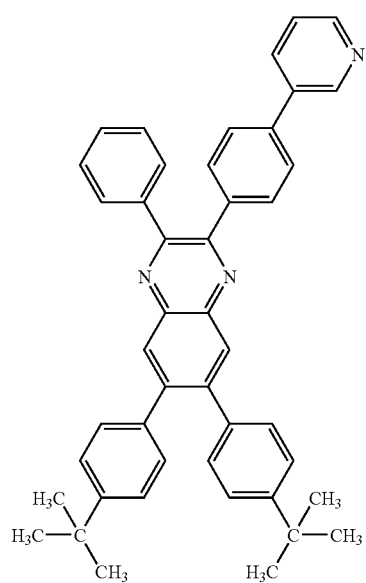
(260)
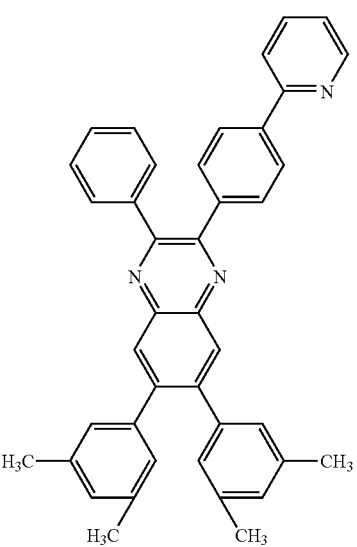
(261)
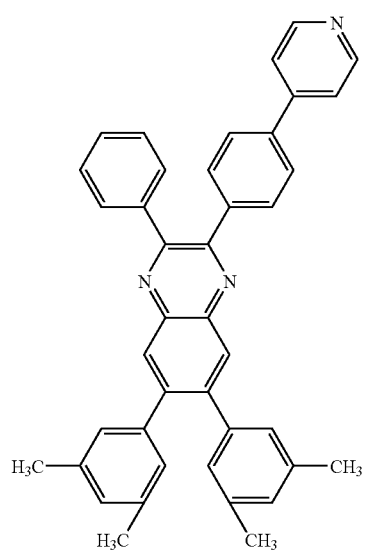
(262)
(263)
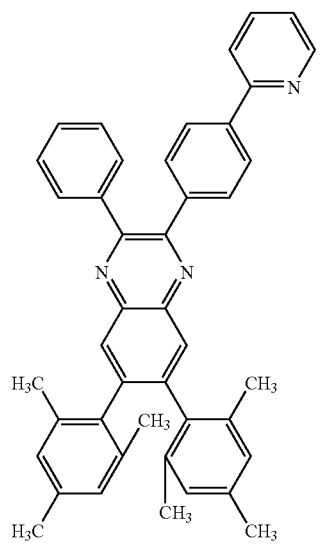
(264)
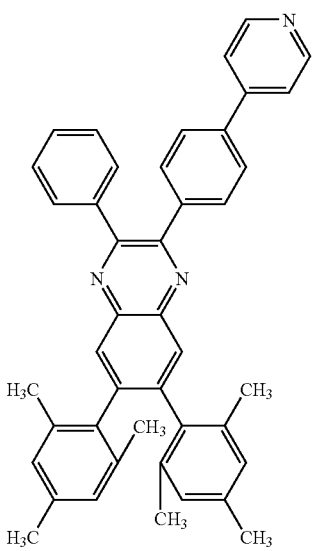

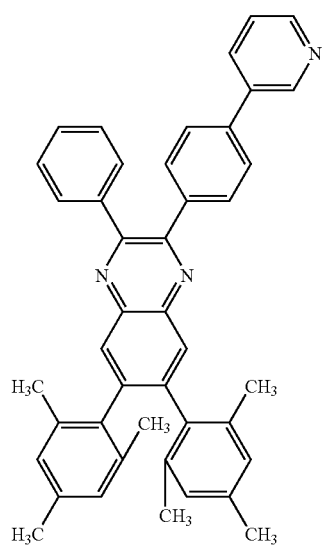
(265)
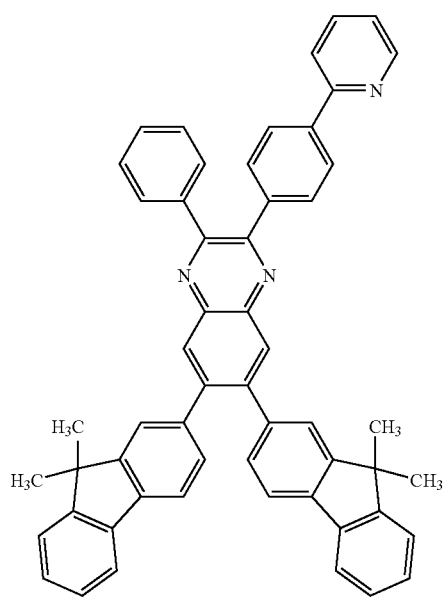
(266)
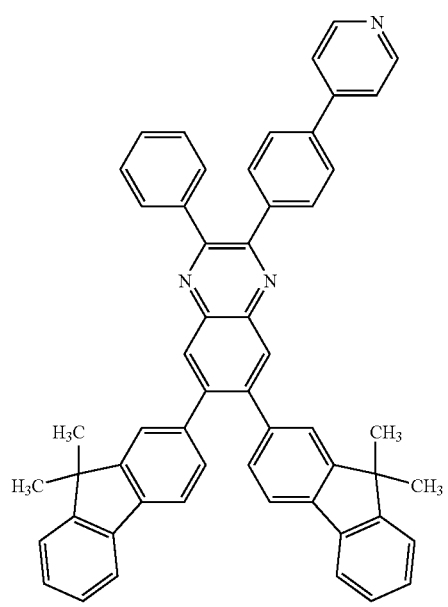
(267)
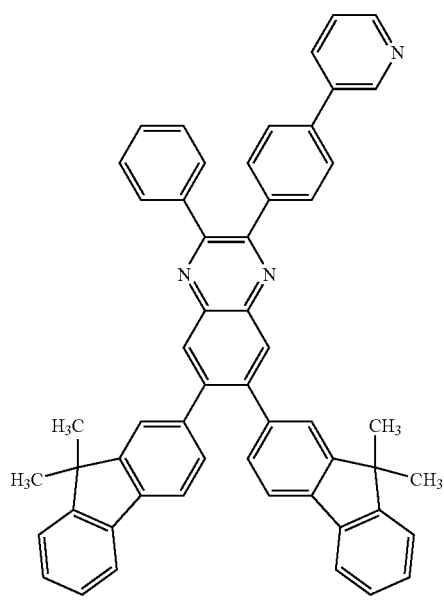
(268)

-continued
(269)
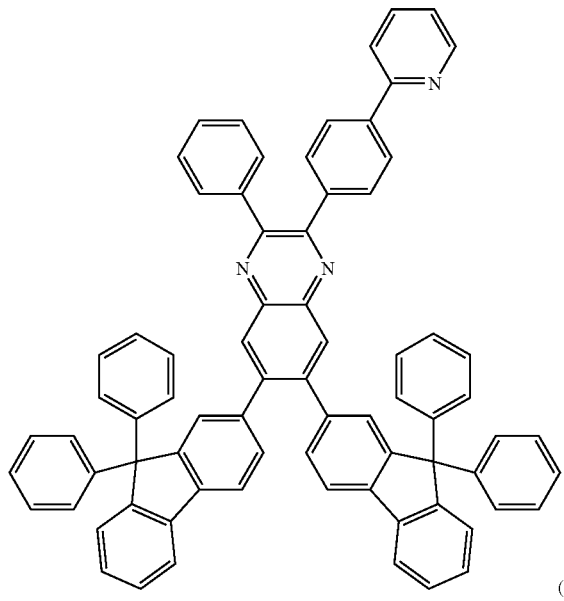
(270)
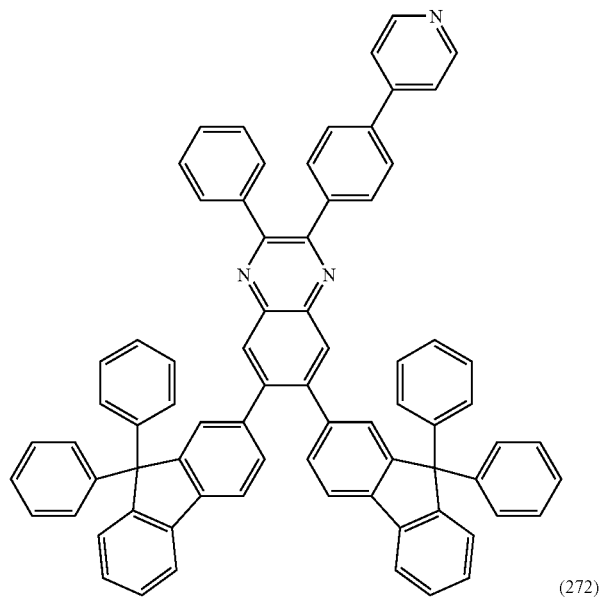
(271)
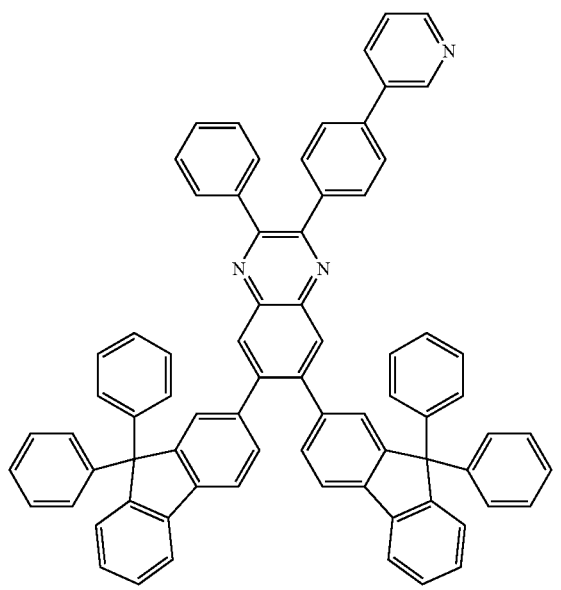
(272)
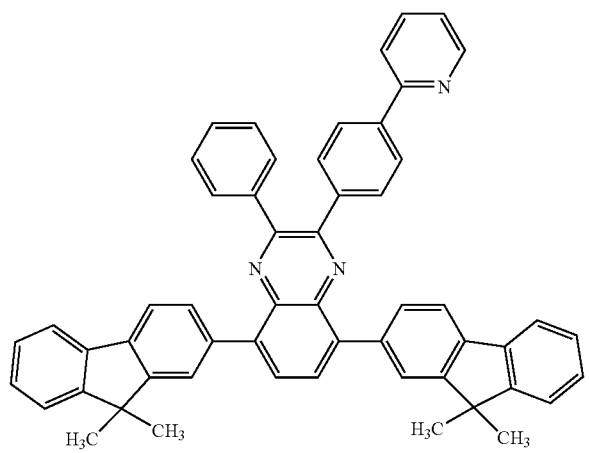
(273)
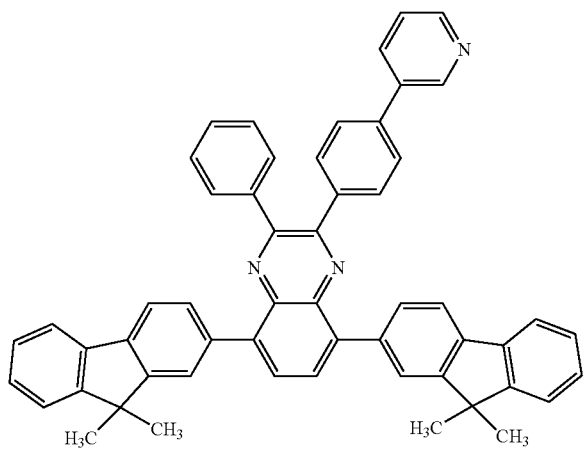
(274)
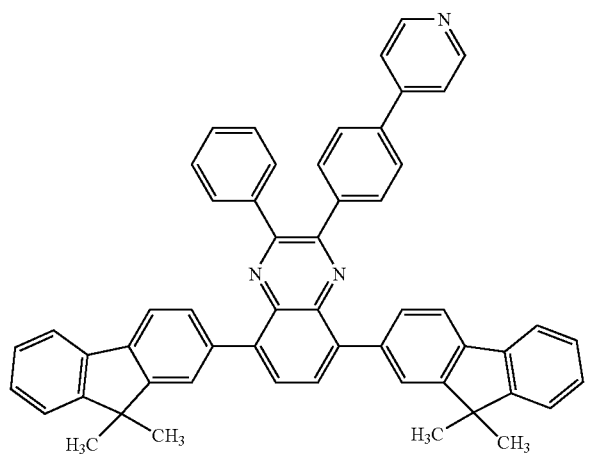

-continued
(275)
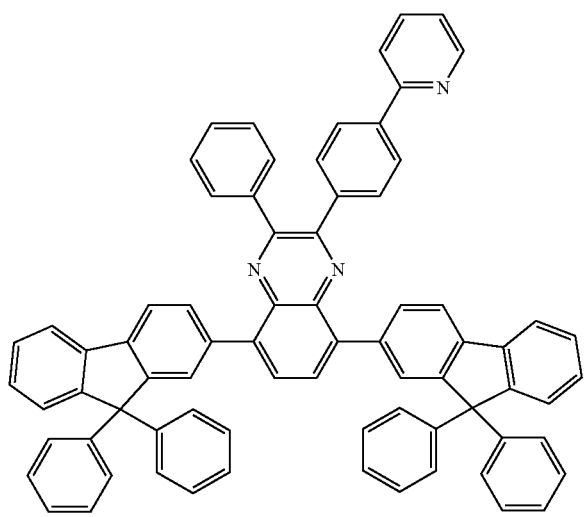
(276)
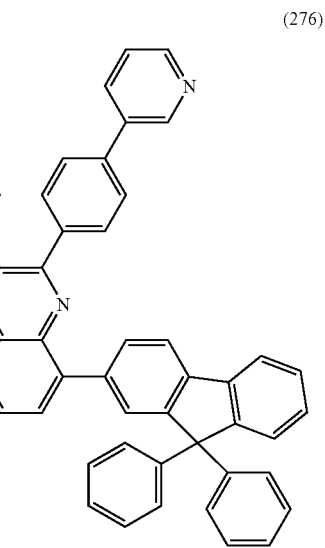
(277)
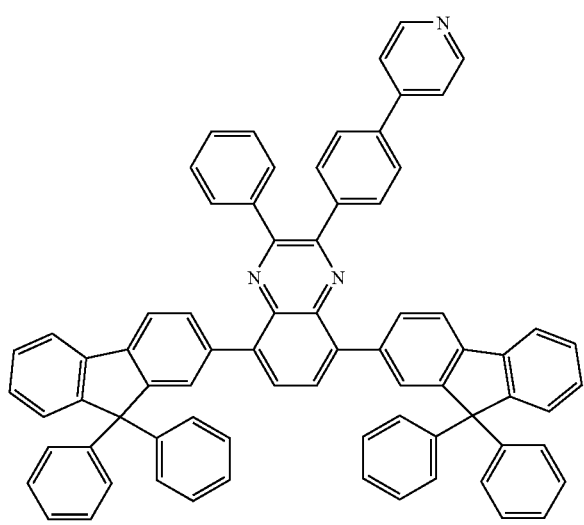
(278)
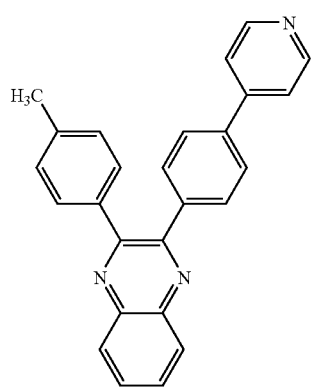
(279)
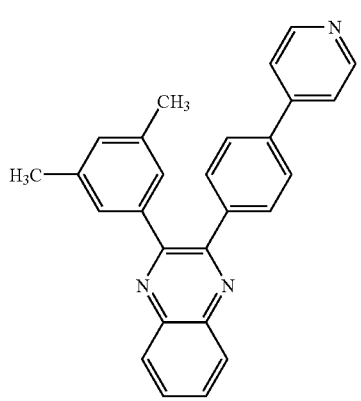
(280)
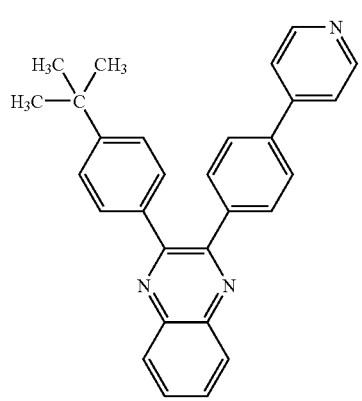

-continued
(281)
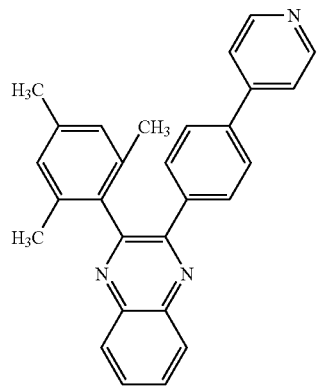
(282)
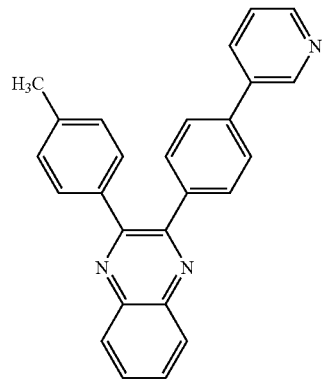
(283)
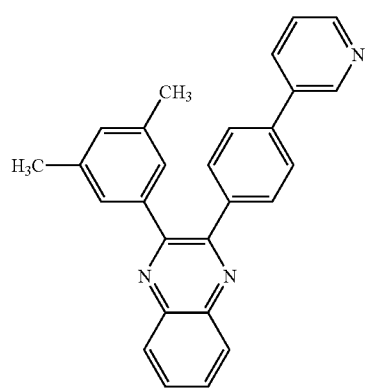
(284)
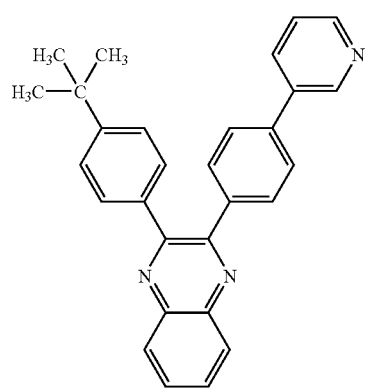
(285)
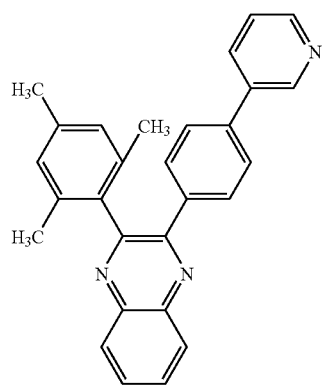
(286)
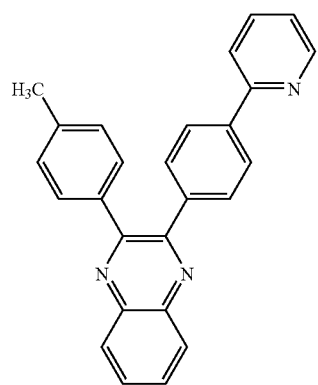
(287)
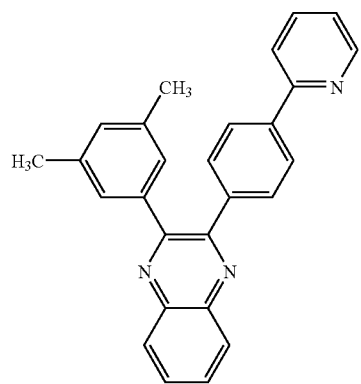
(288)
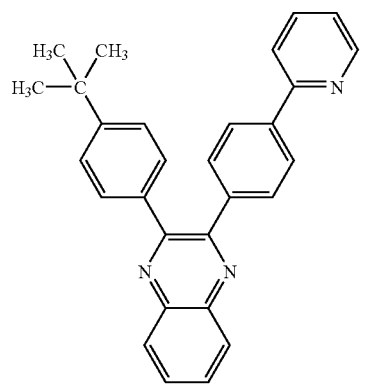

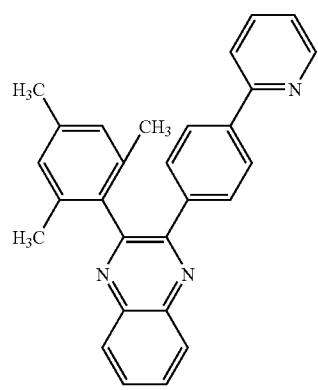 (289)
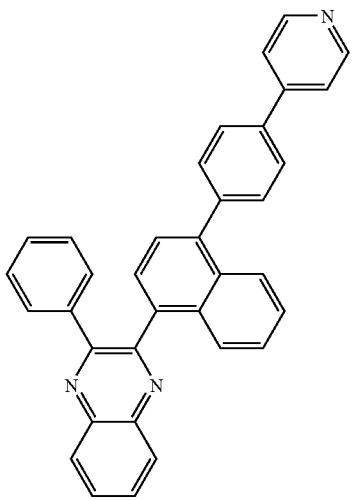 (290)
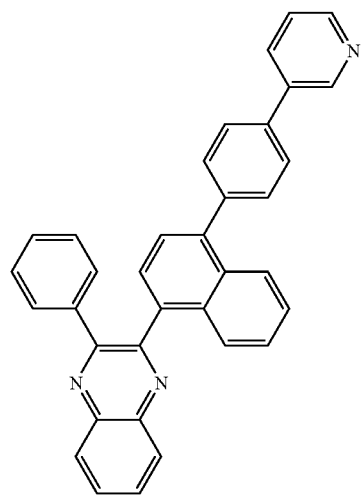 (291)
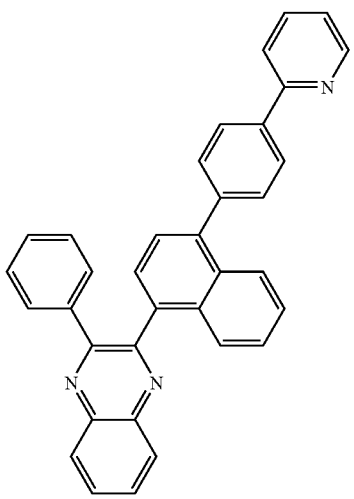 (292)
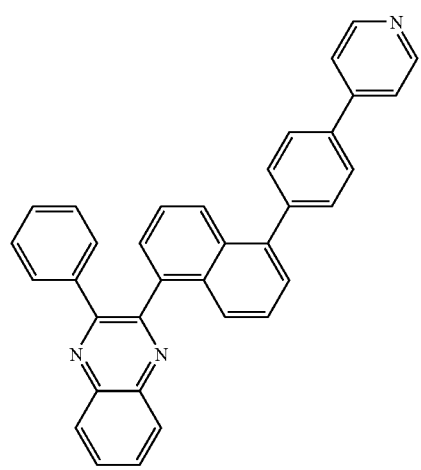 (293)
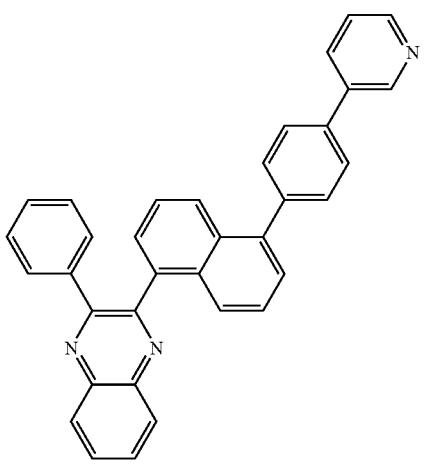 (294)

-continued
(295)
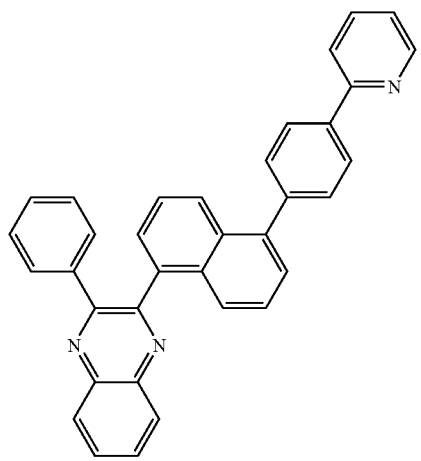
(296)
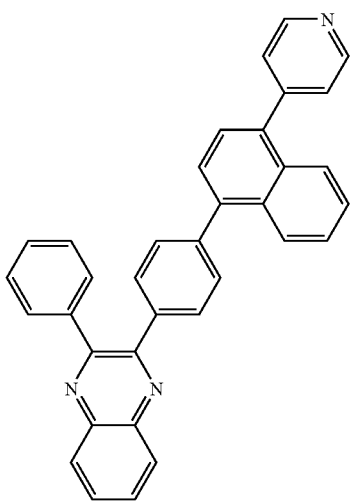
(297)
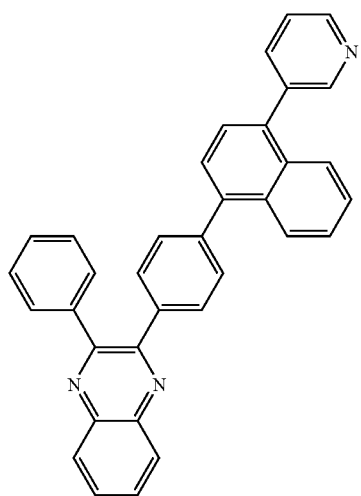
(298)
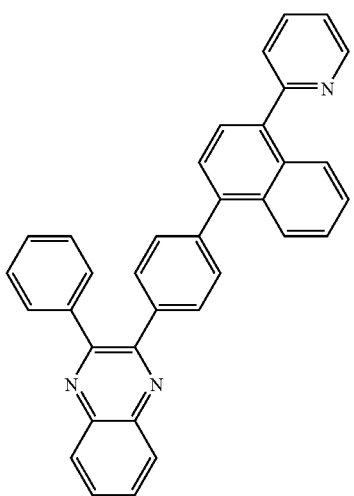
(299)
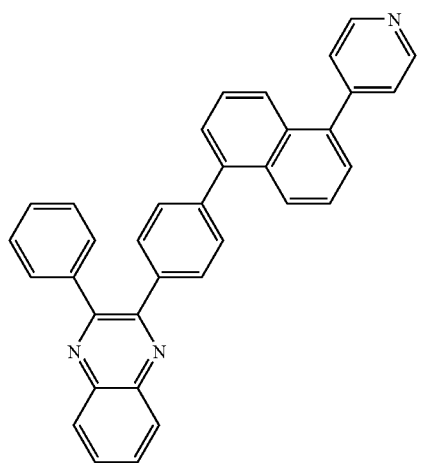
(300)
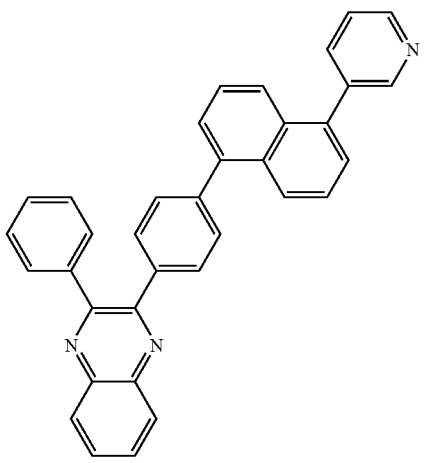

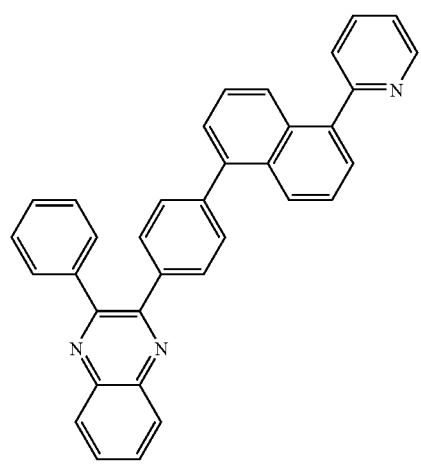 (301)
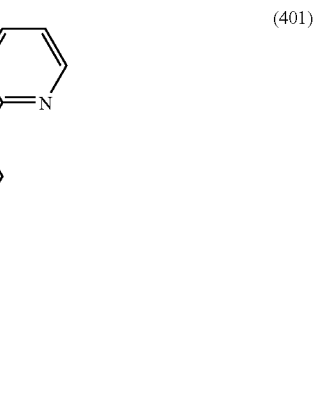 (401)
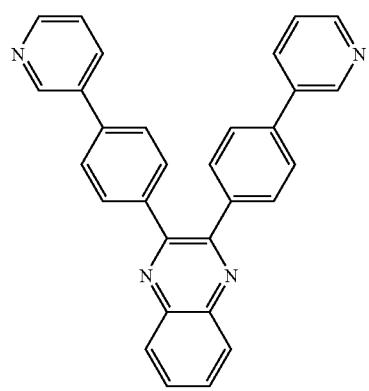 (402)
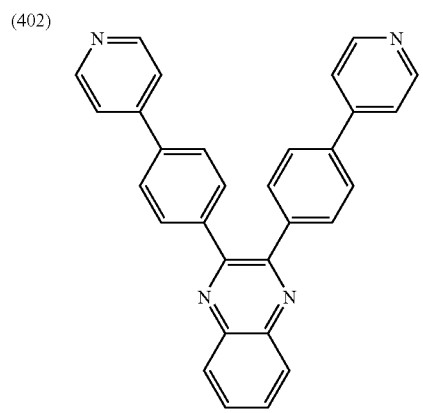 (403)
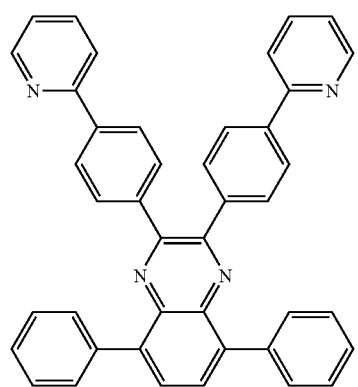 (404)
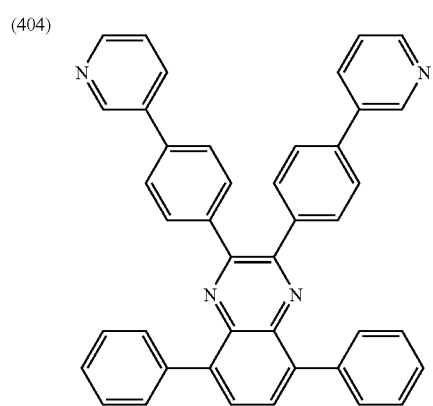 (405)

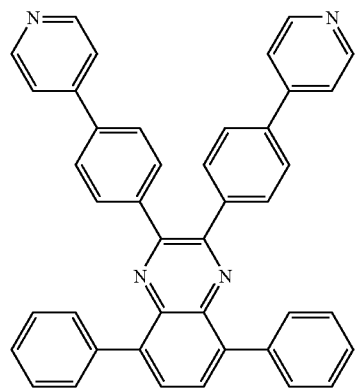
(406)
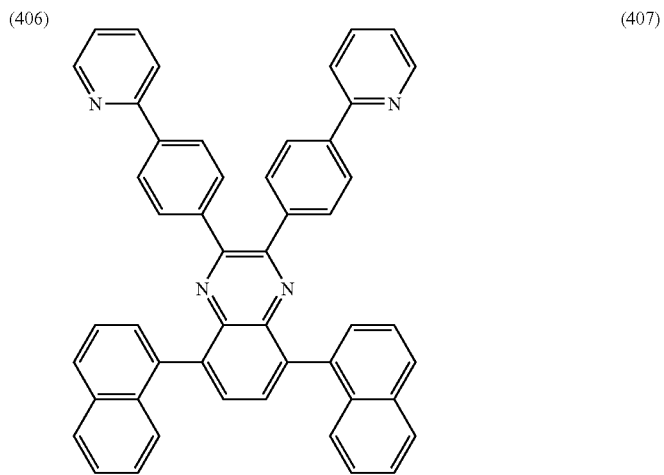
(407)
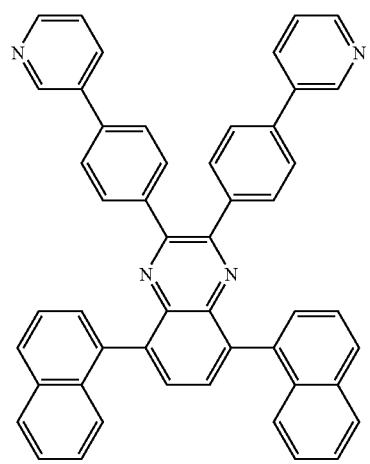
(408)
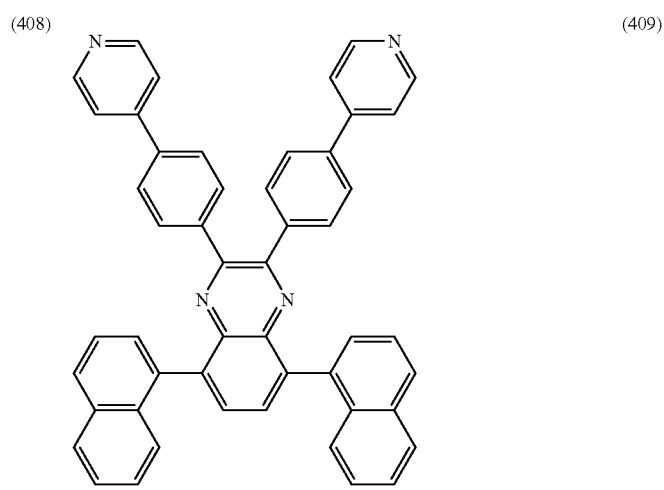
(409)
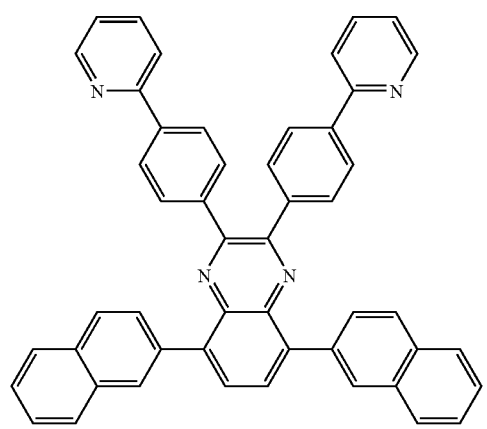
(410)
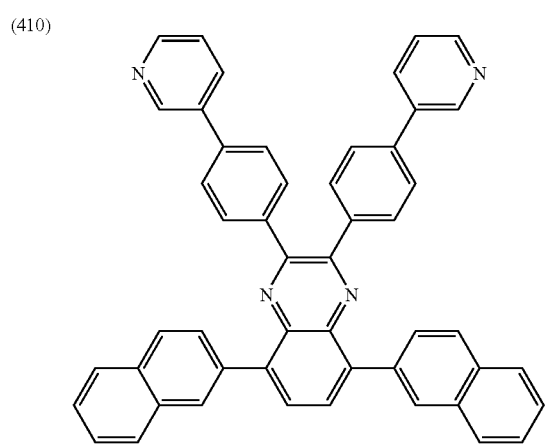
(411)

(412)
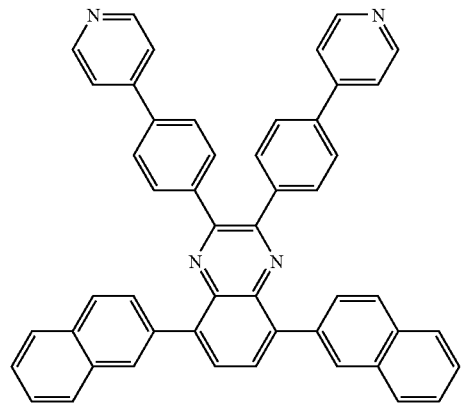
(413)
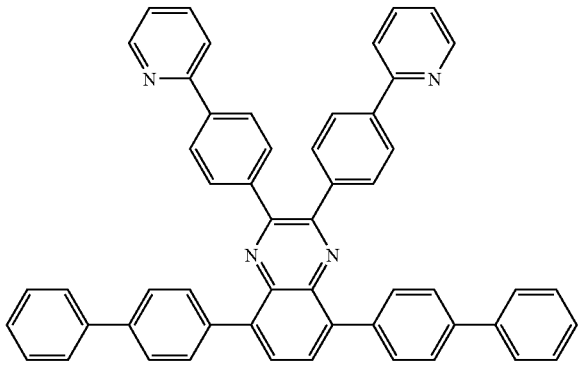
(414)
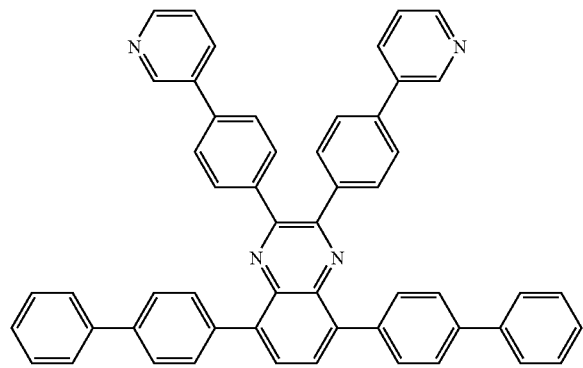
(415)
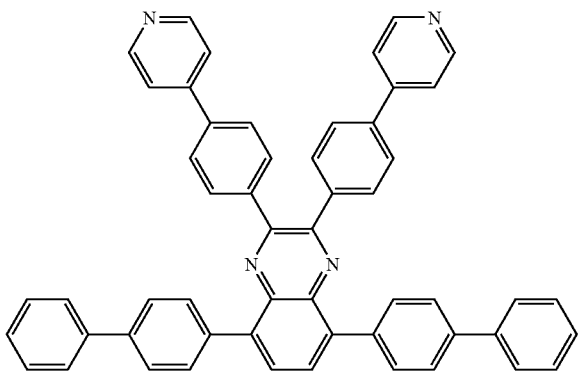
(416)
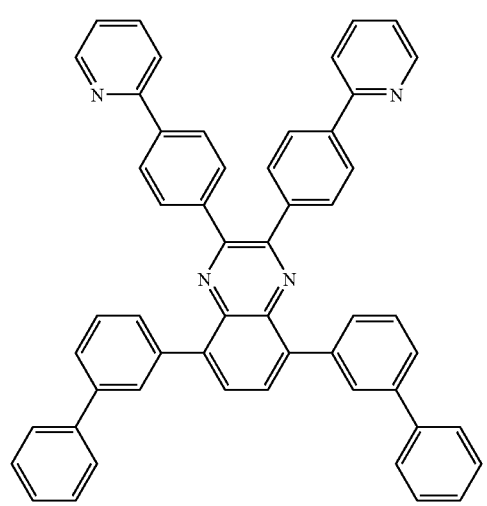
(417)
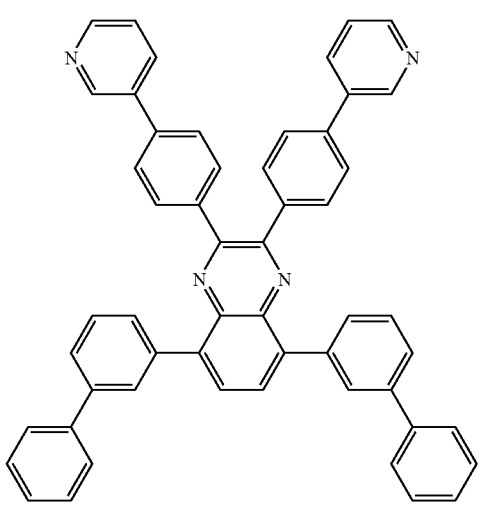

-continued
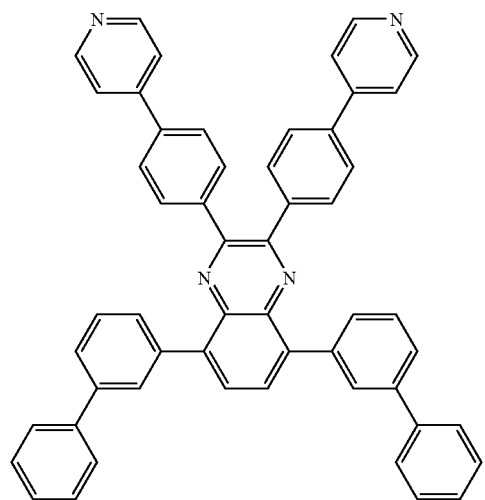
(418)
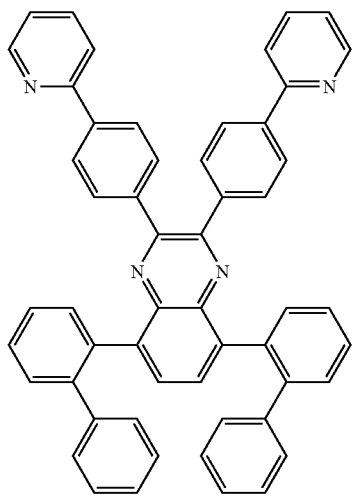
(419)
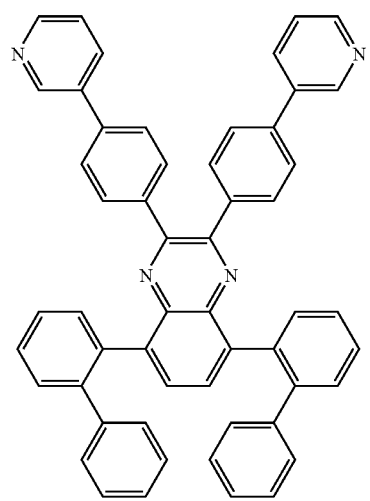
(420)
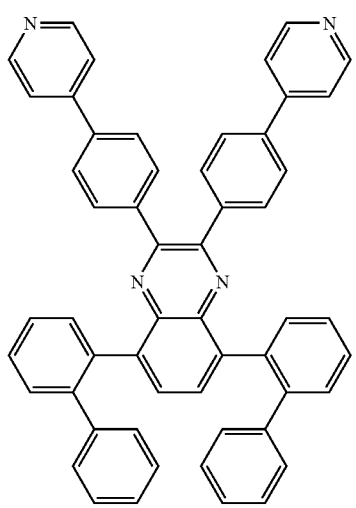
(421)
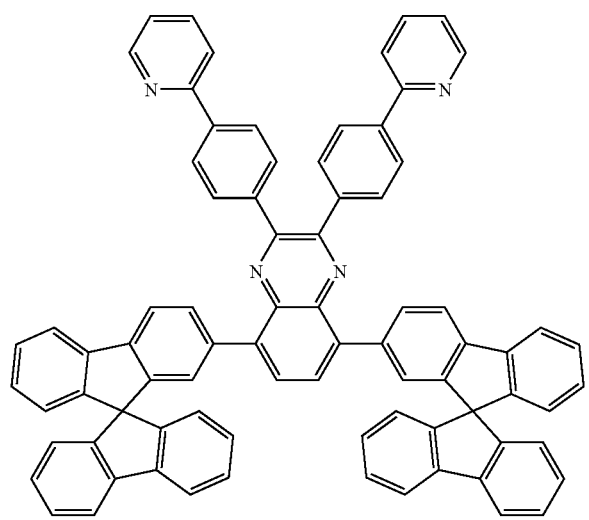
(422)
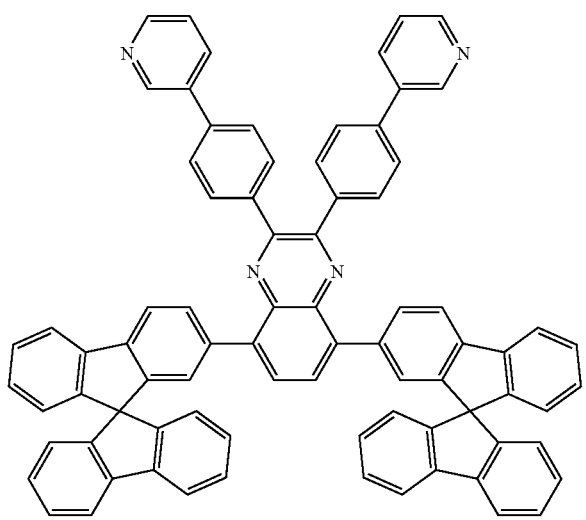
(423)

-continued
(424)
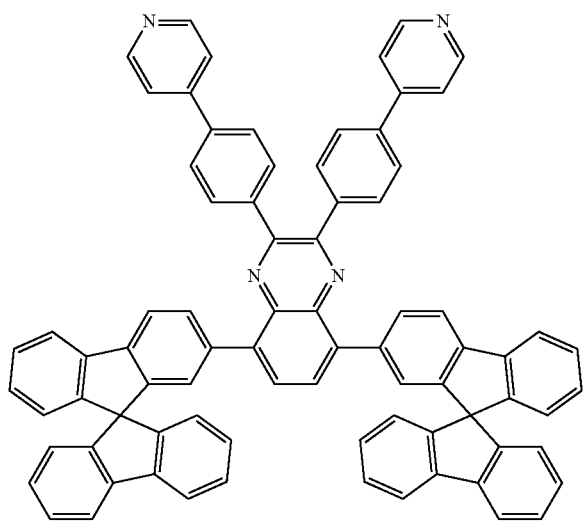
(425)
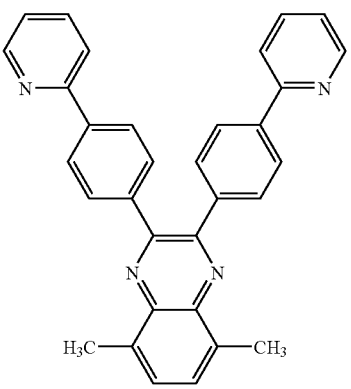
(426)
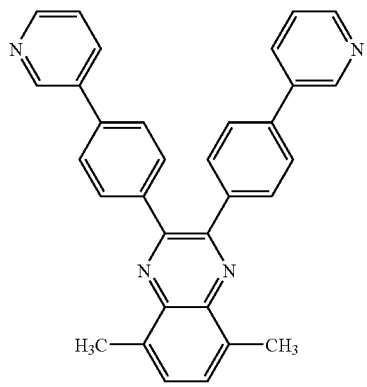
(427)
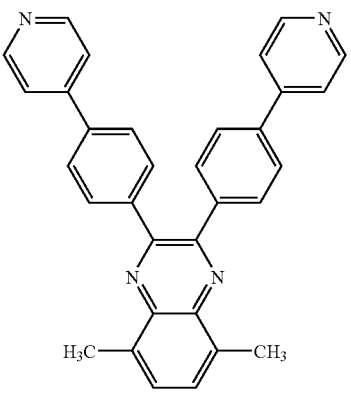
(428)
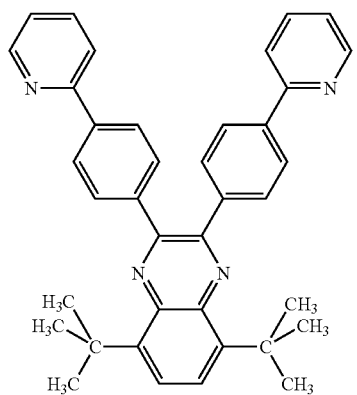
(429)
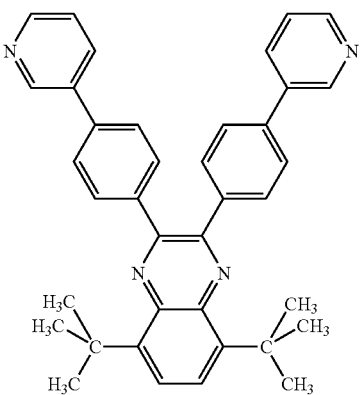

(430) 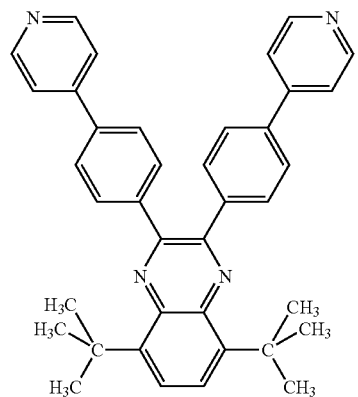
(431) 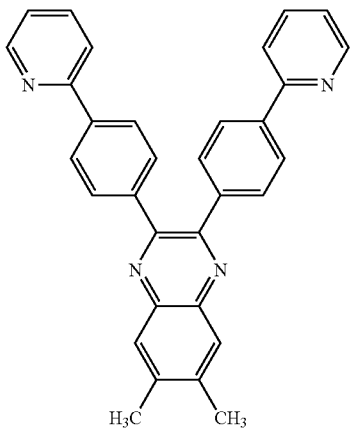
(432) 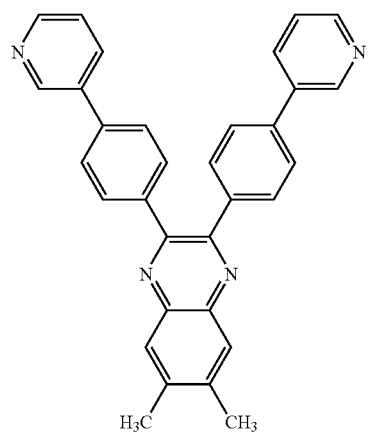
(433) 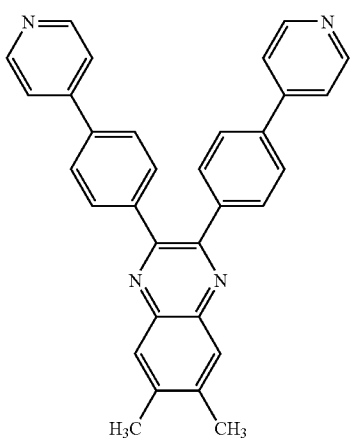
(434) 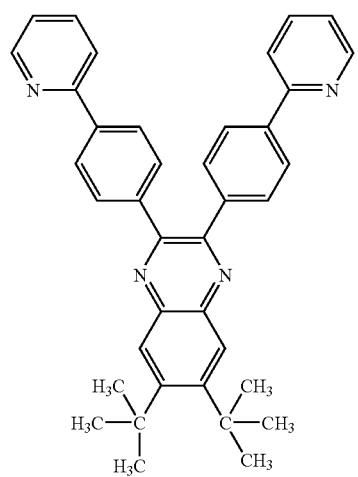
(435) 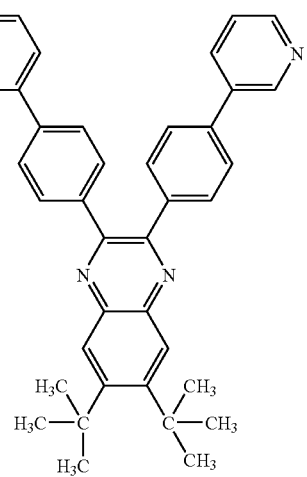

-continued
(436)
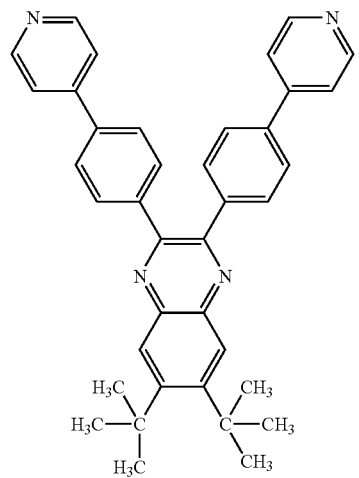
(437)
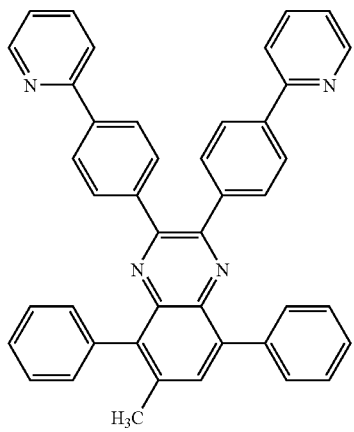
(438)
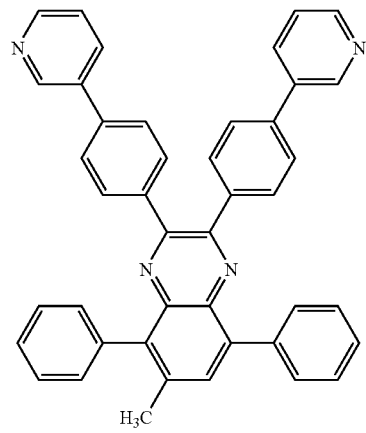
(439)
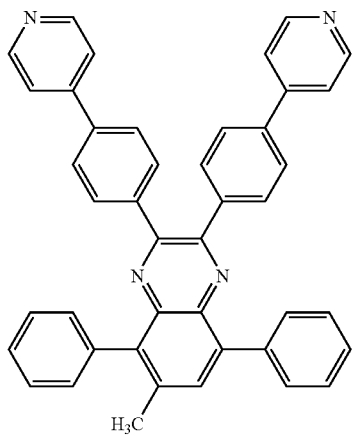
(440)
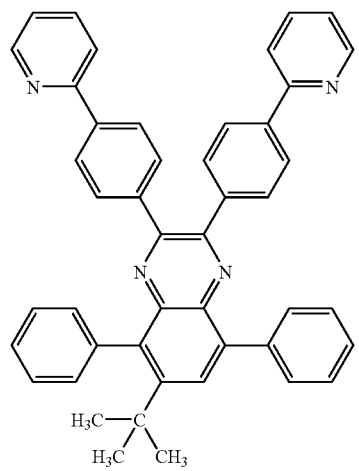
(441)
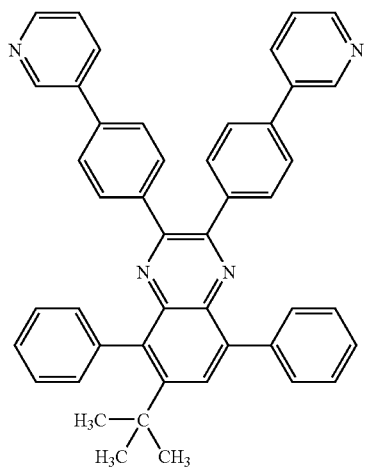

-continued
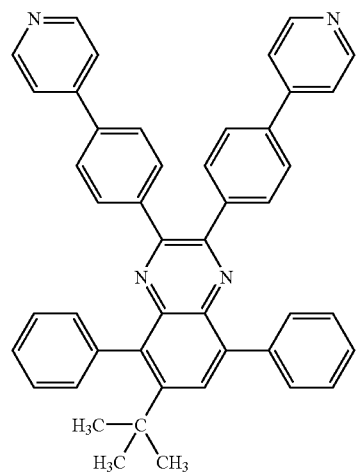
(442)
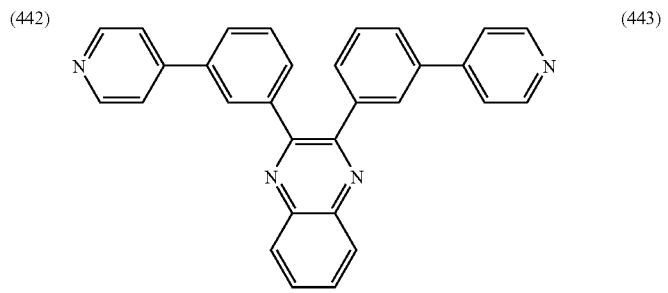
(443)
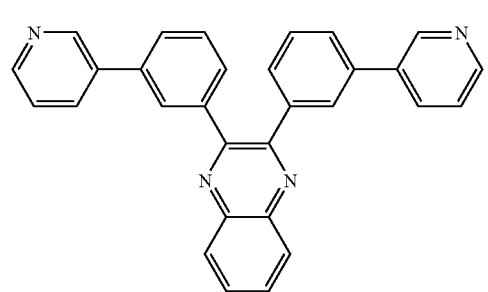
(444)
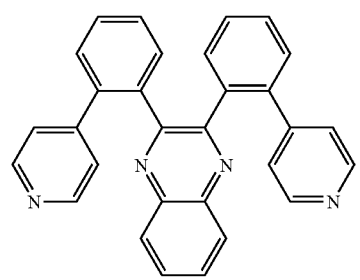
(446)
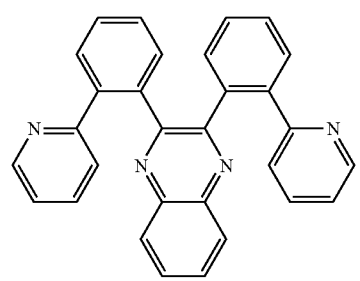
(448)
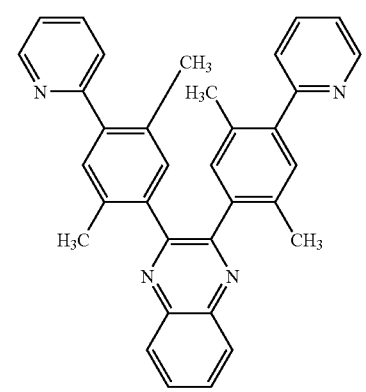
(449)

-continued
(450)
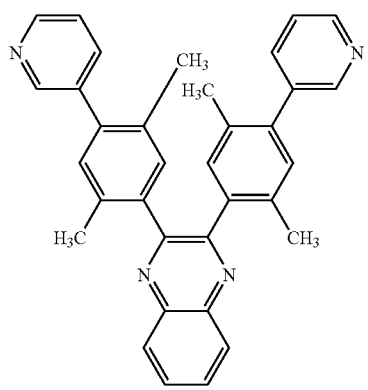
(451)
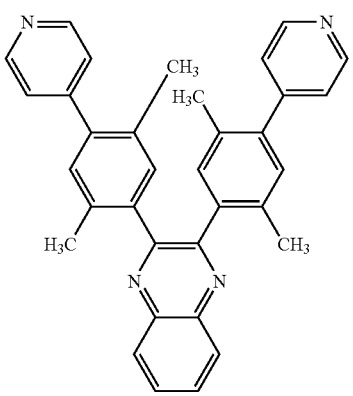
(452)
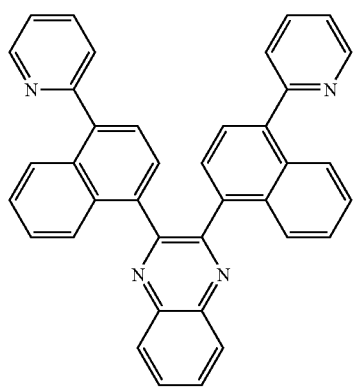
(453)
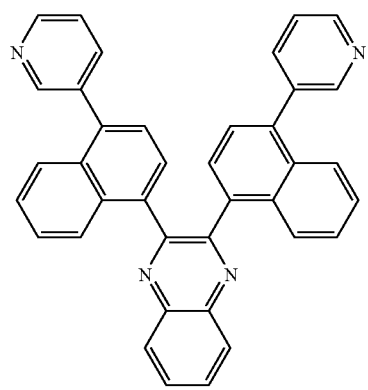
(454)
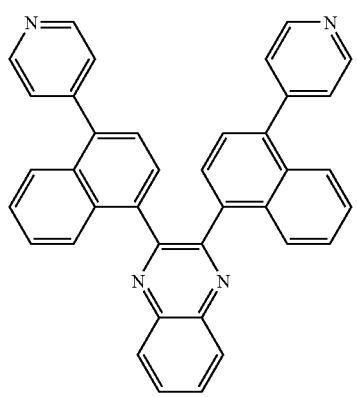
(455)
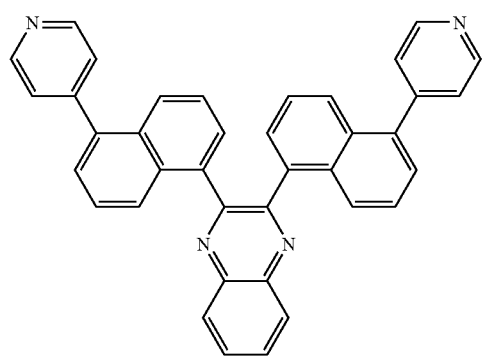
(456)
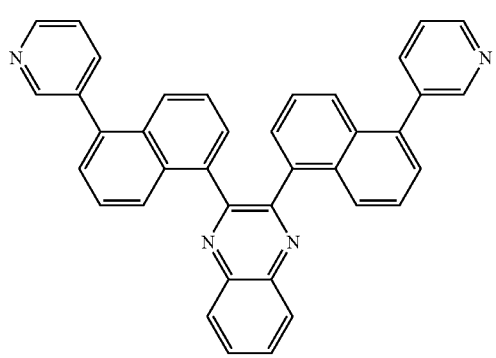
(457)
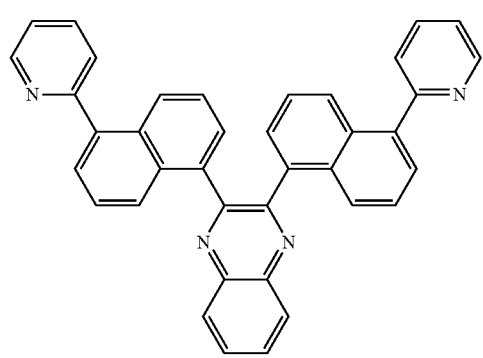

-continued
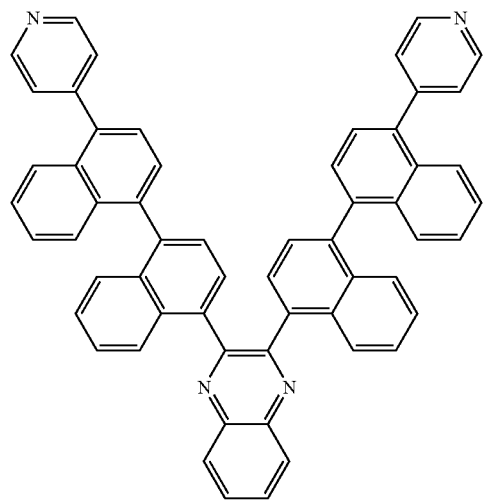
(458)
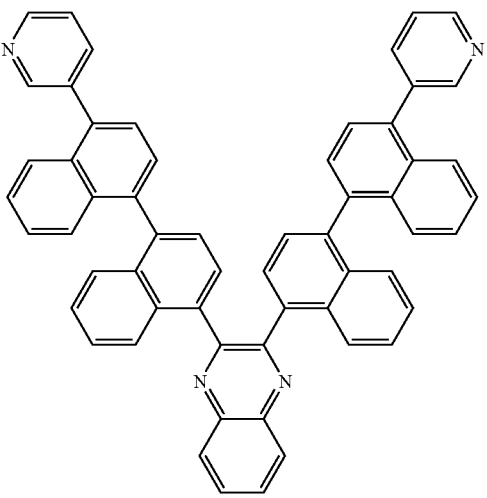
(459)
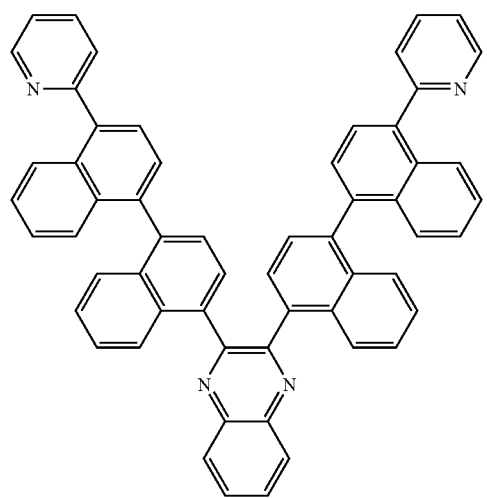
(460)
(461)
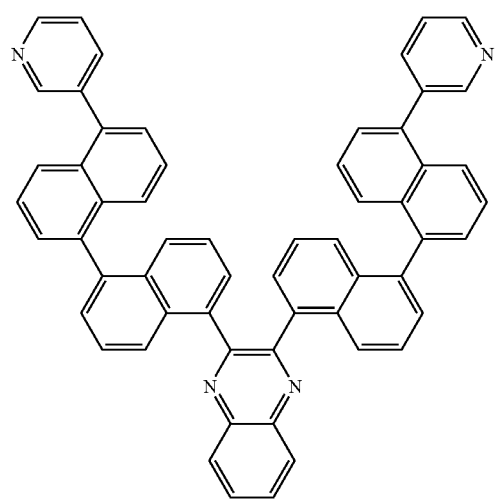
(462)
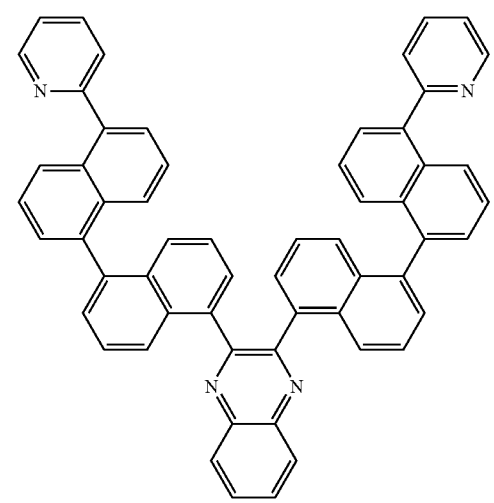
(463)

-continued
(464)
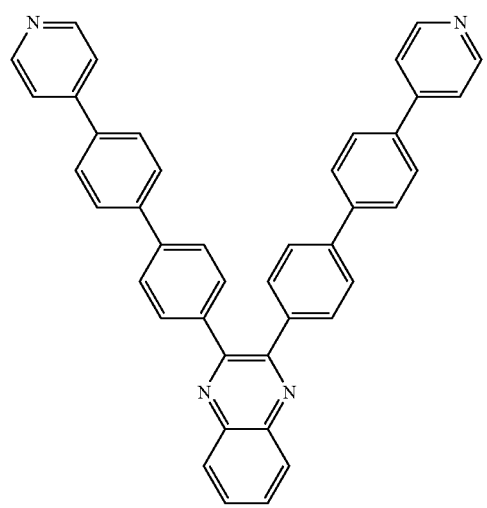
(465)
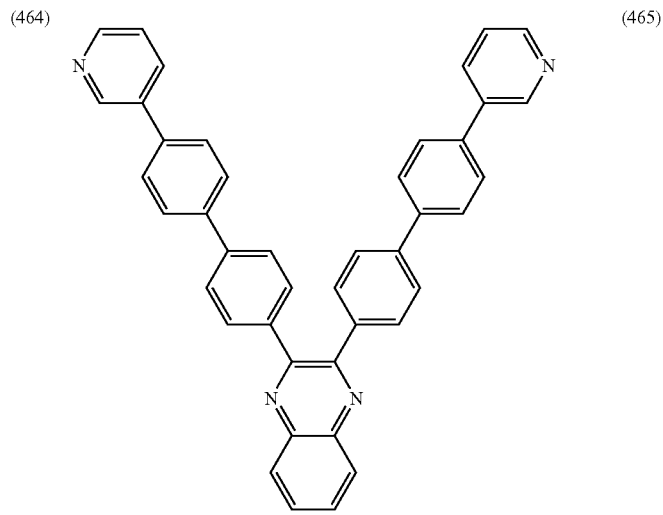
(466)
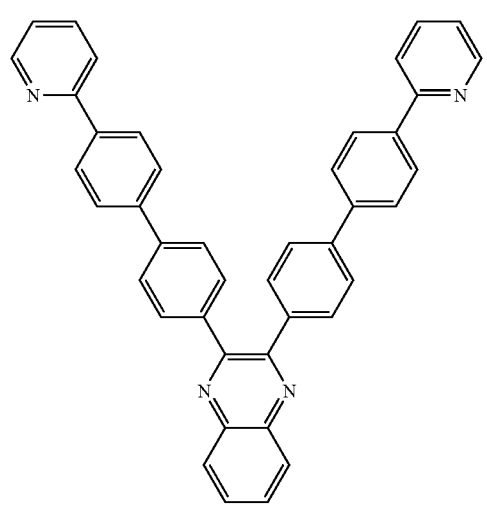
(467)
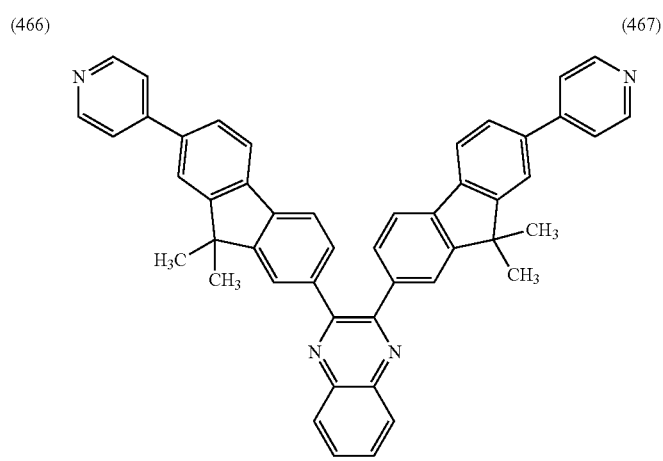
(468)
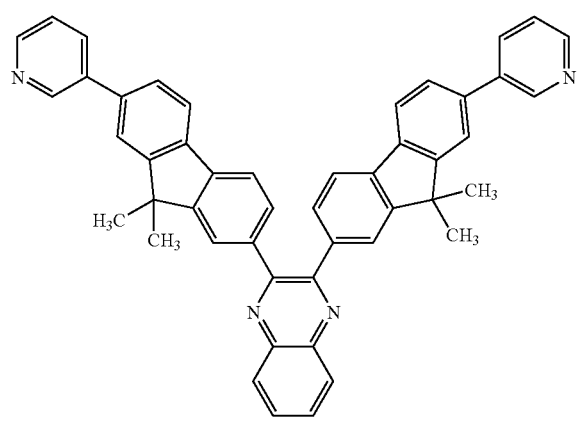
(469)
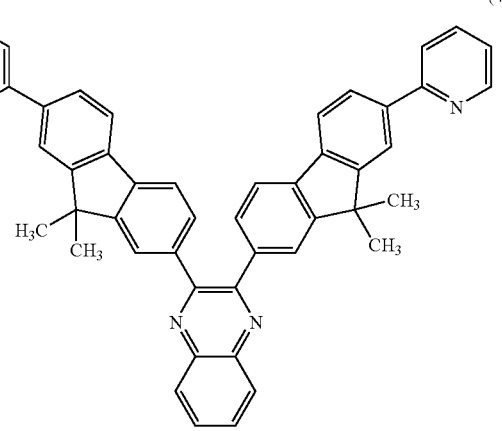

-continued
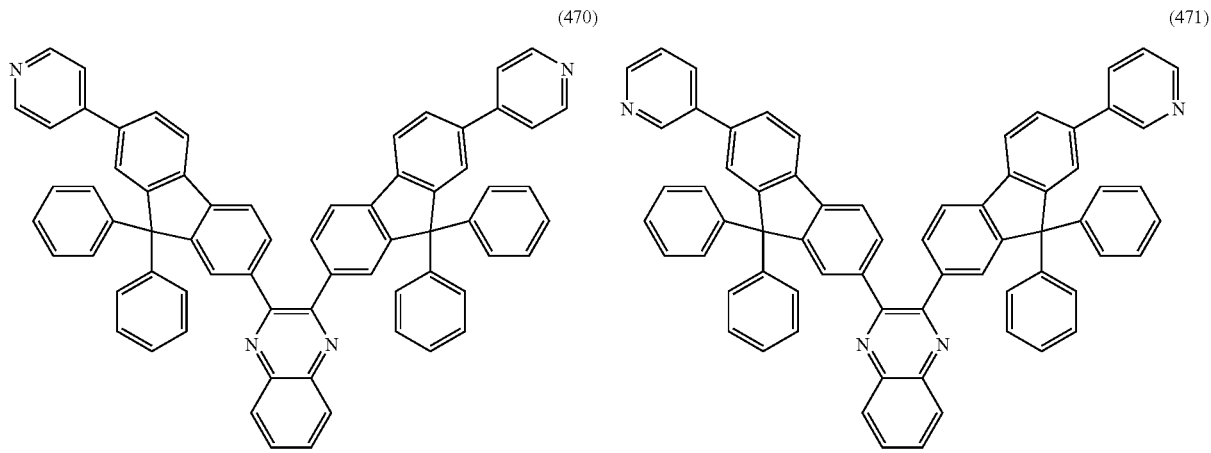
(470) (471)
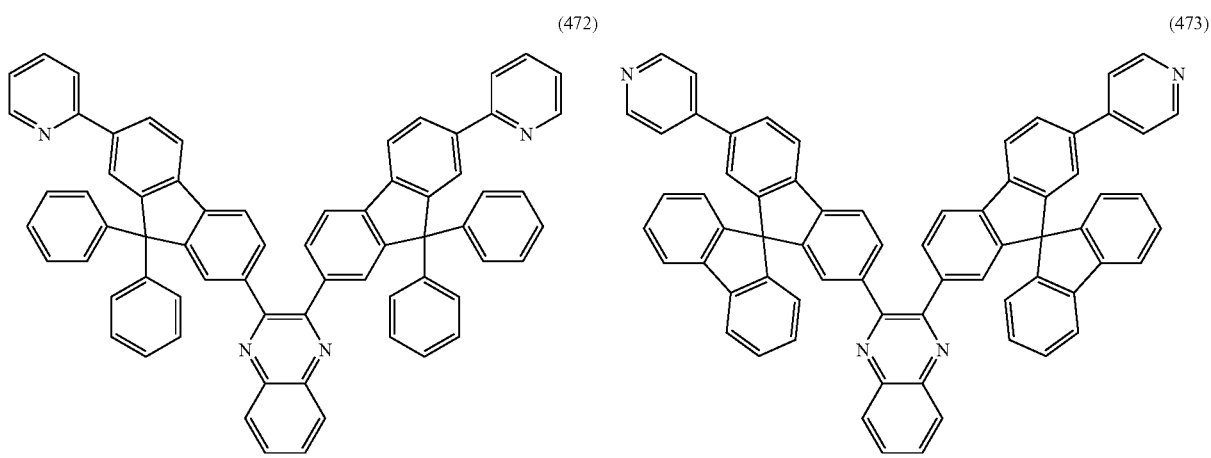
(472) (473)
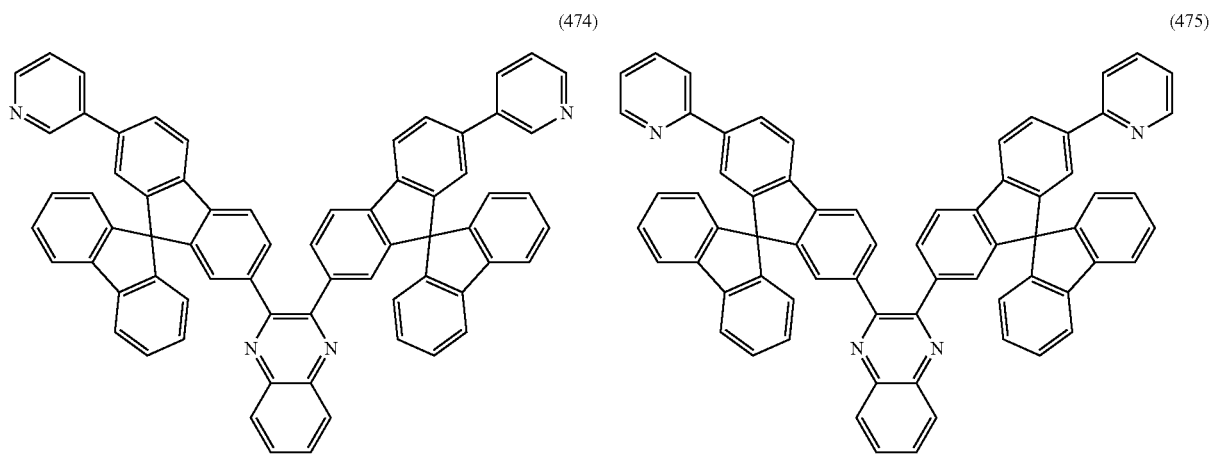
(474) (475)

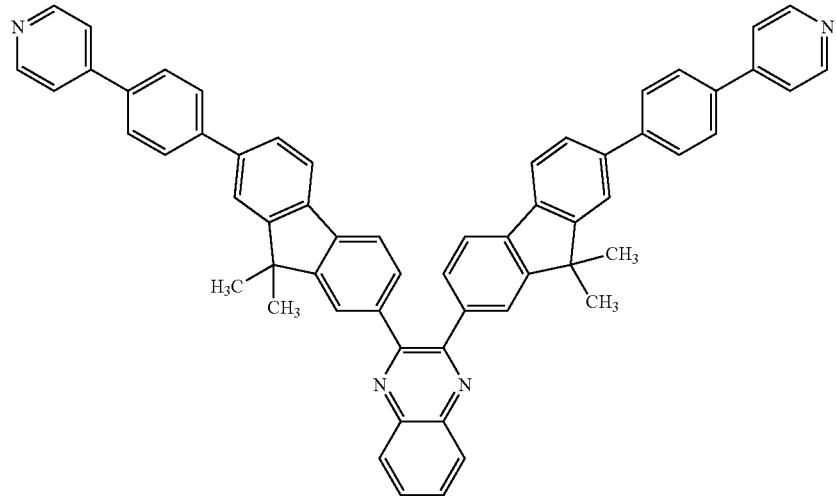
(476)
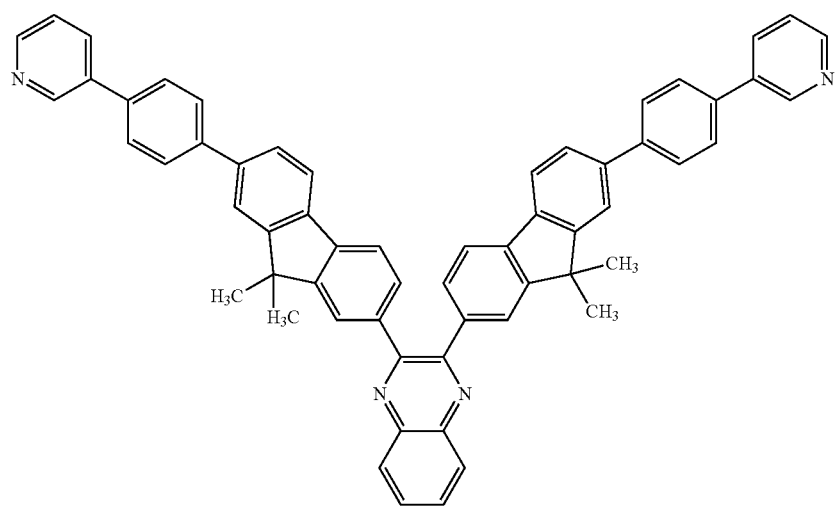
(477)
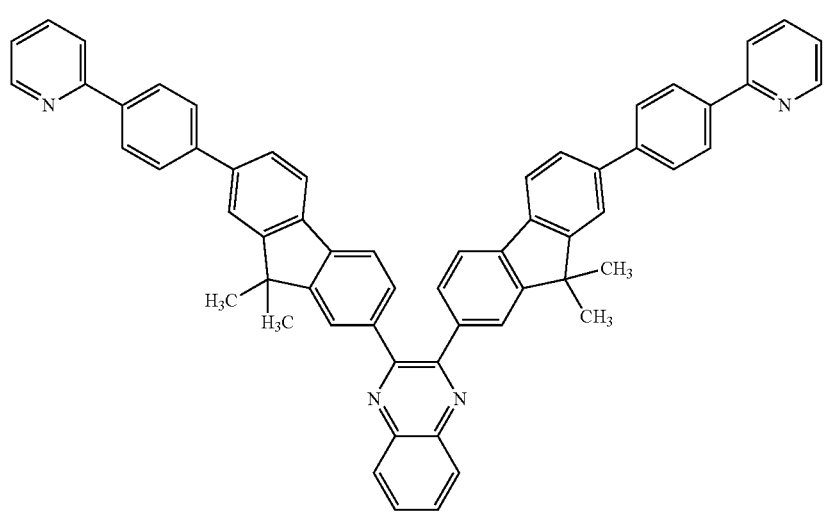
(478)

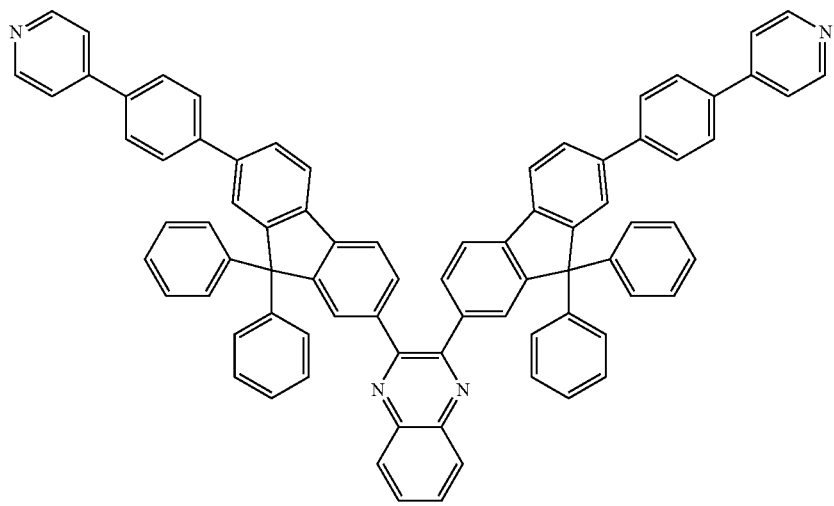
(479)
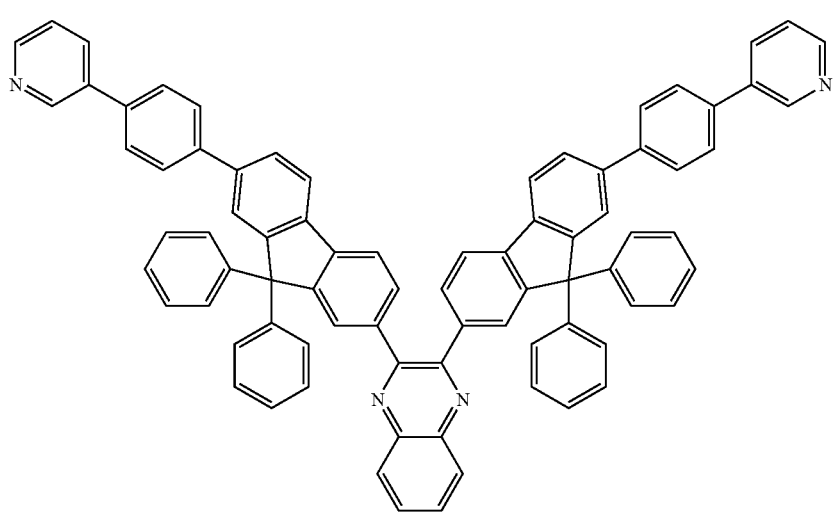
(480)
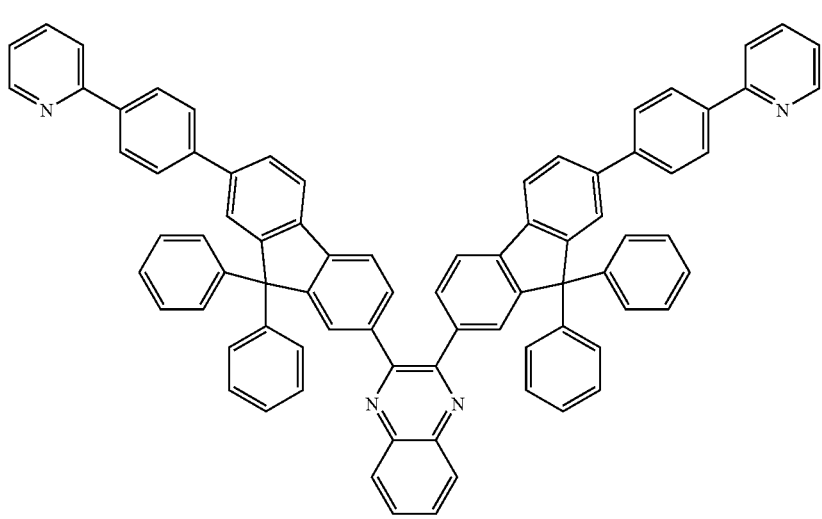
(481)

-continued
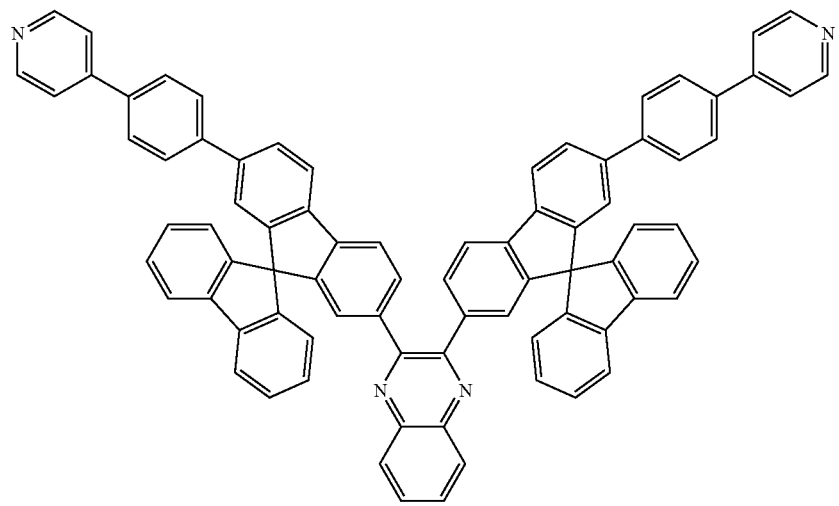
(482)
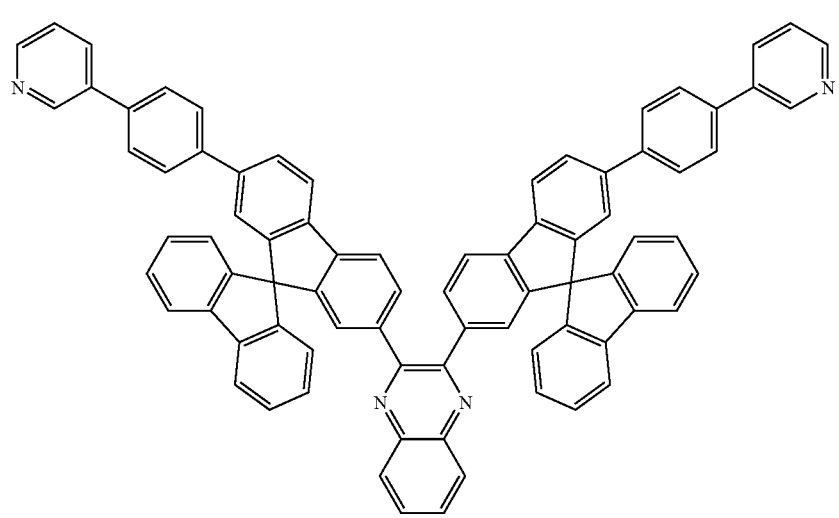
(483)
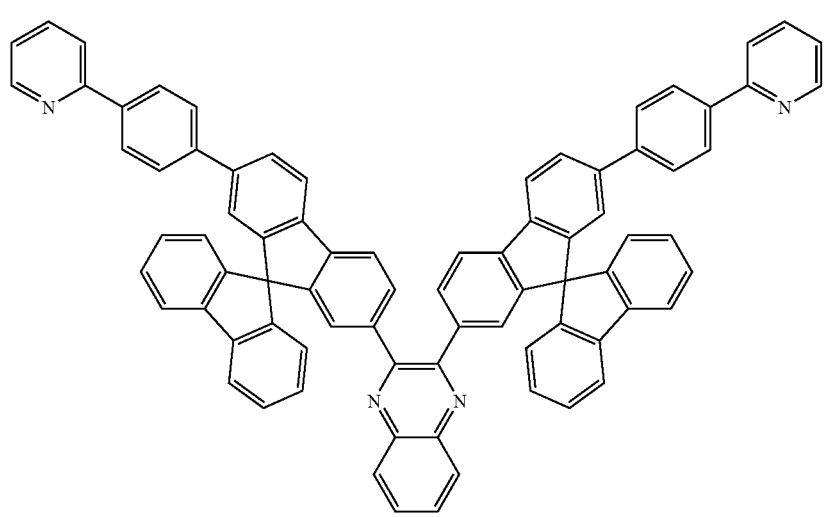
(484)

(485) 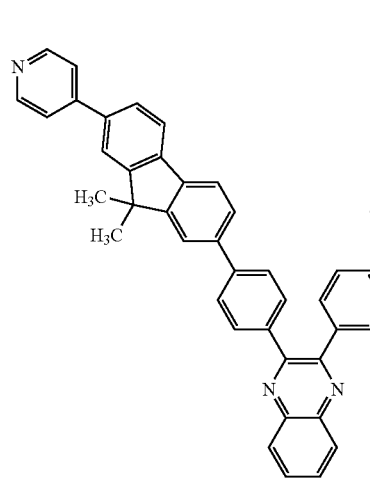
(486) 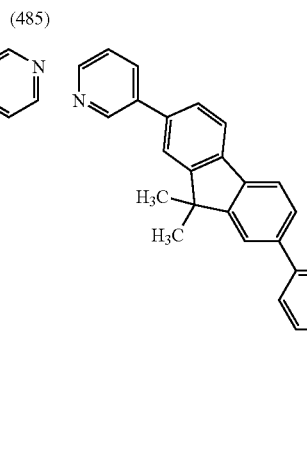
(487) 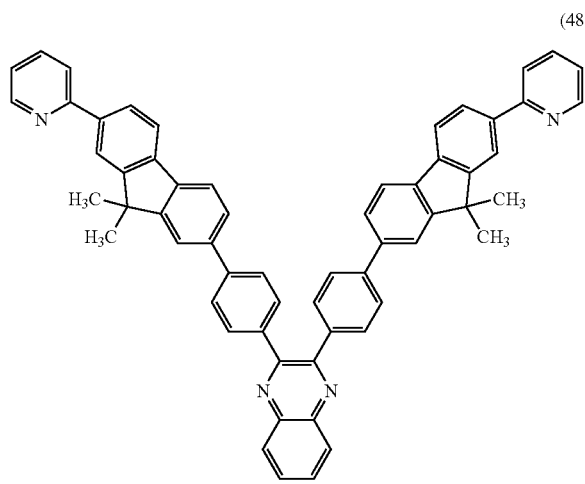
(488) 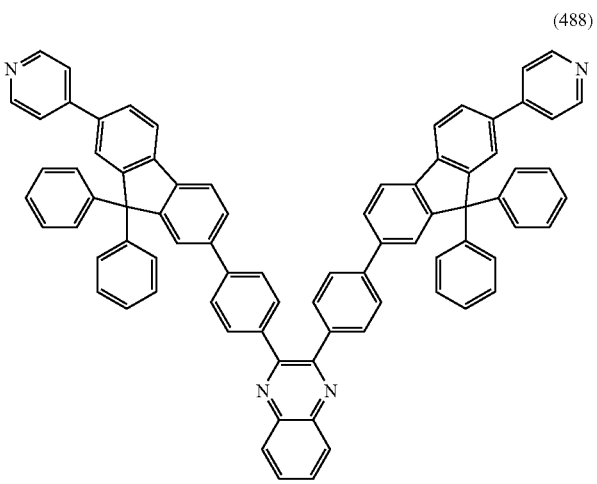
(489) 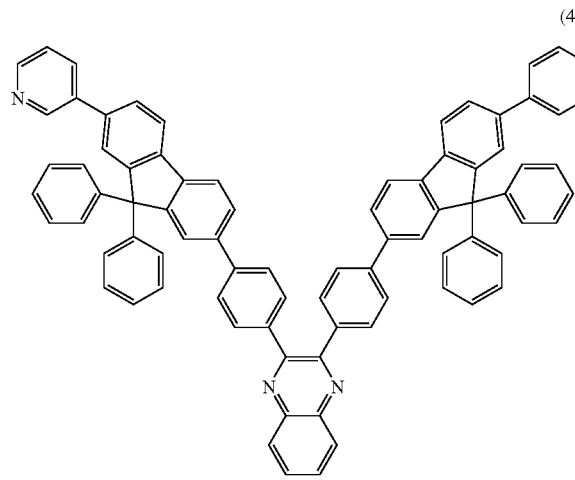
(490) 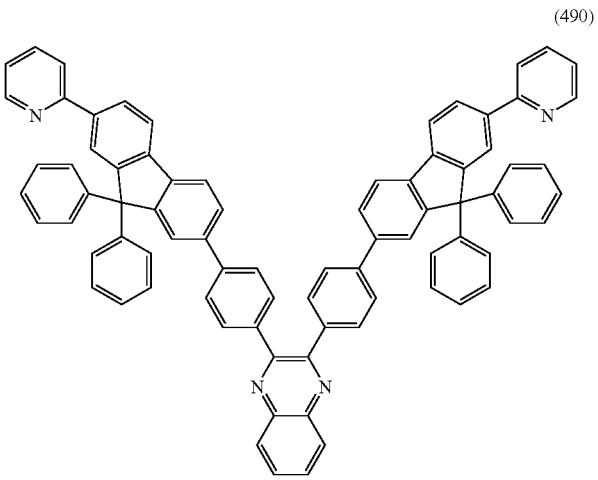

-continued
(491)
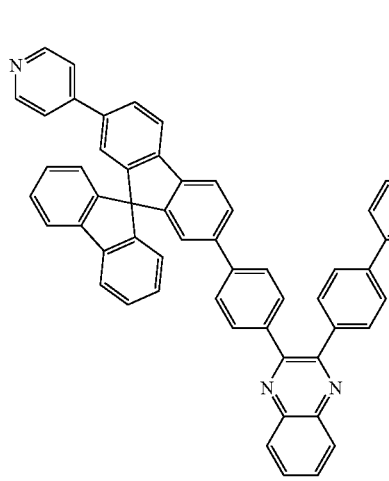
(492)
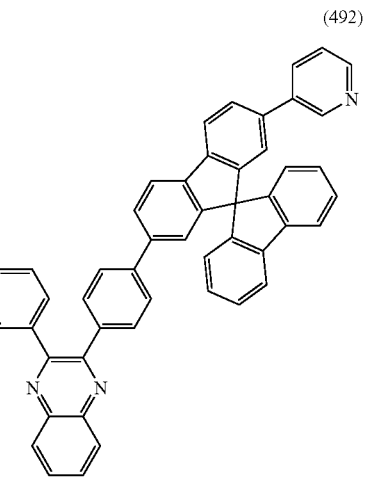
(493)
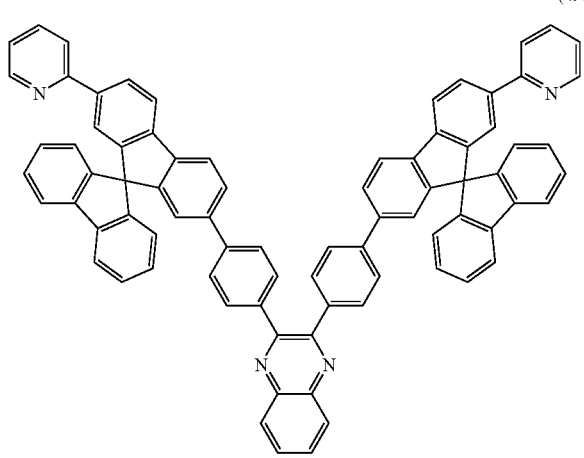
(494)
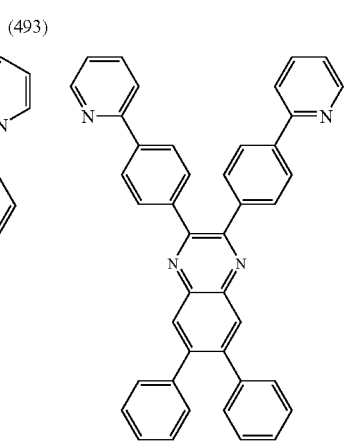
(495)
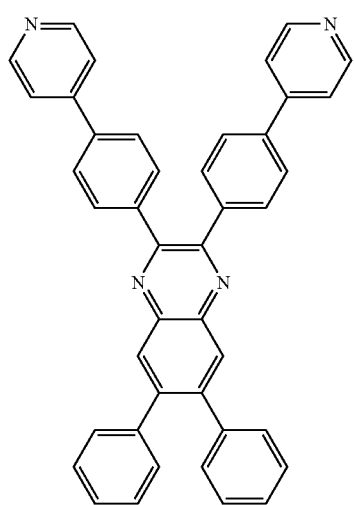
(496)
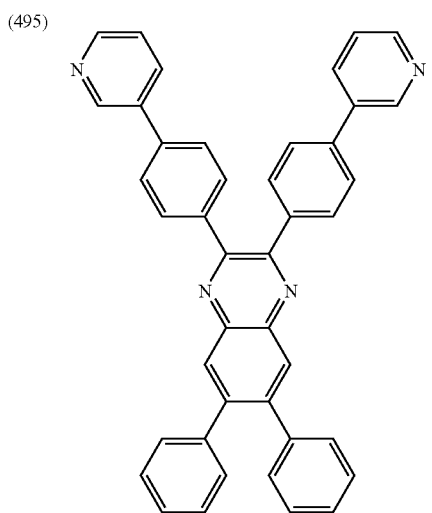

-continued
(497)
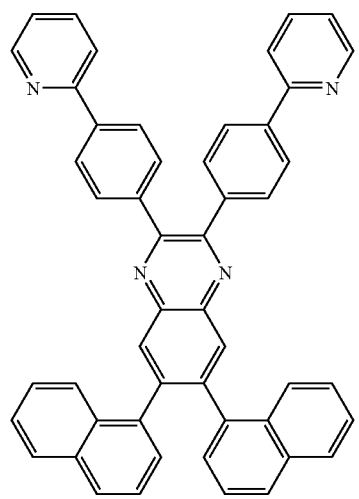
(498)
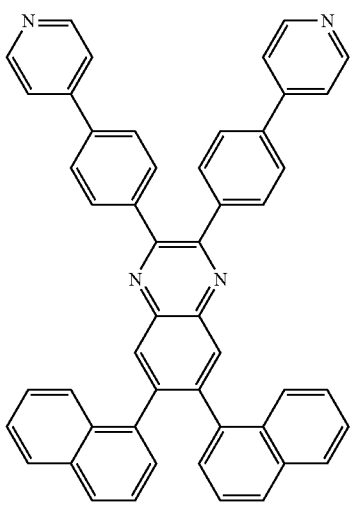
(499)
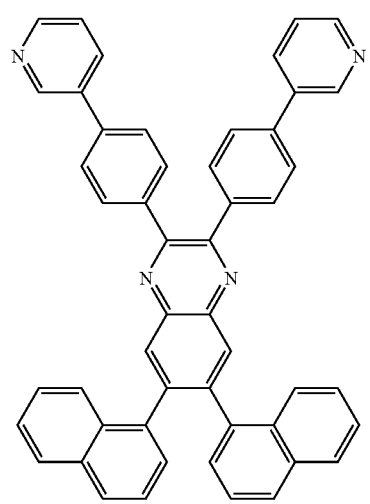
(500)
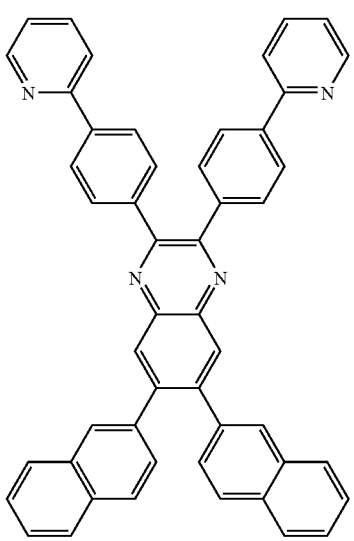
(501)
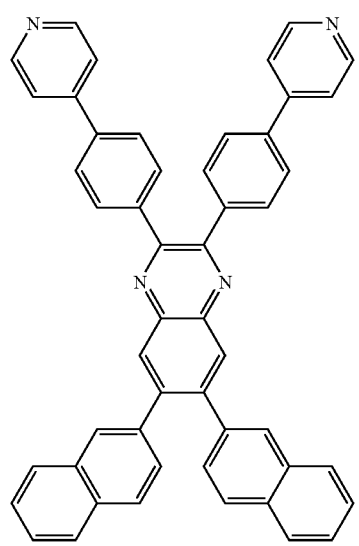
(502)
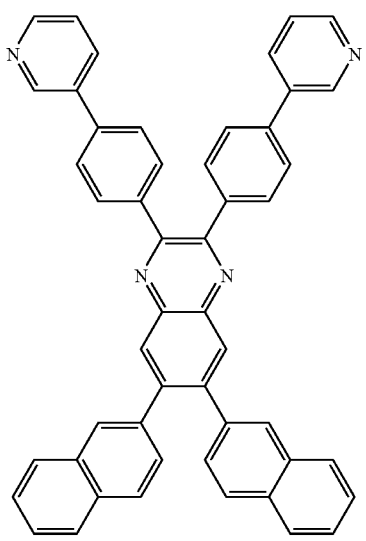

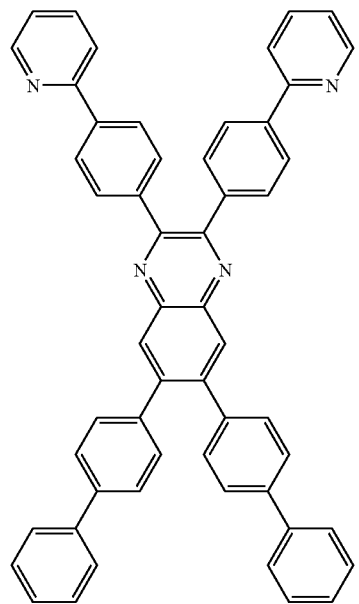
(503)
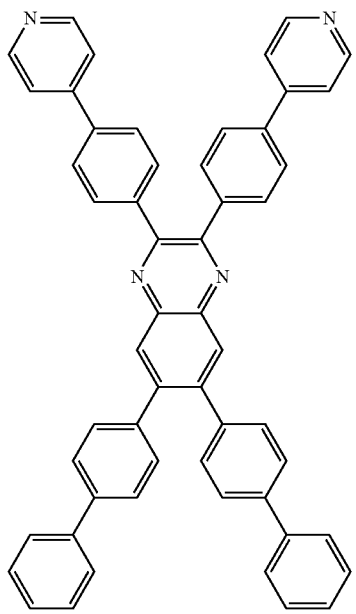
(504)
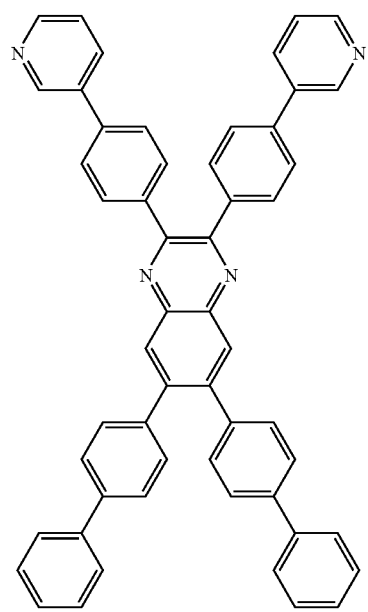
(505)
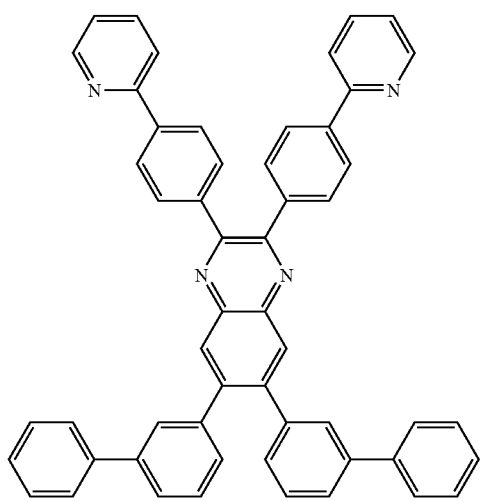
(506)

-continued
(507) 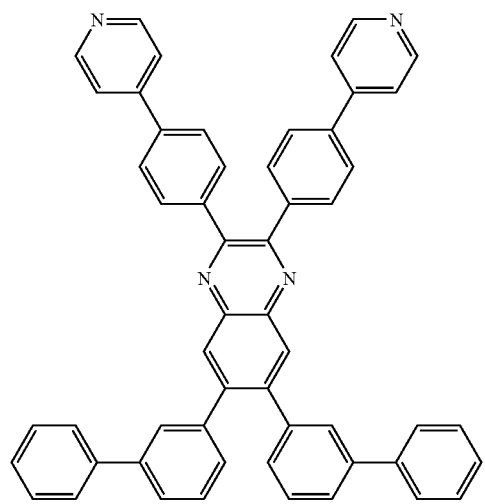
(508) 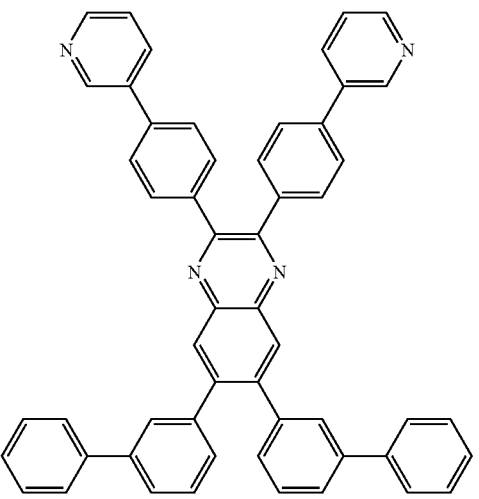
(509) 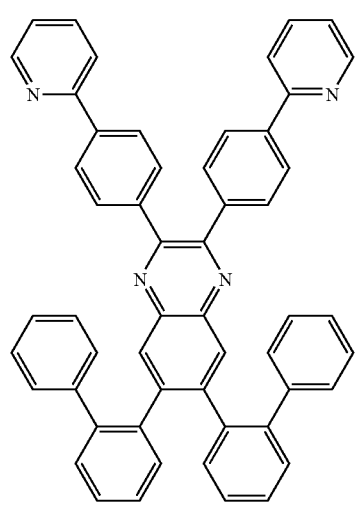
(510) 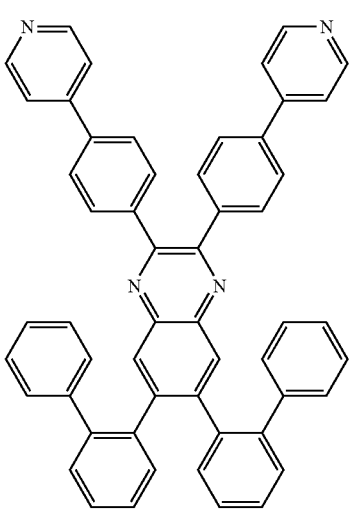
(511) 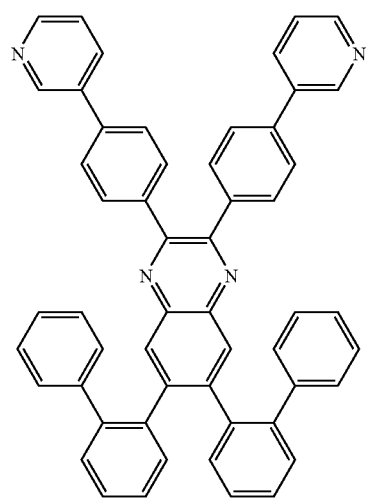
(512) 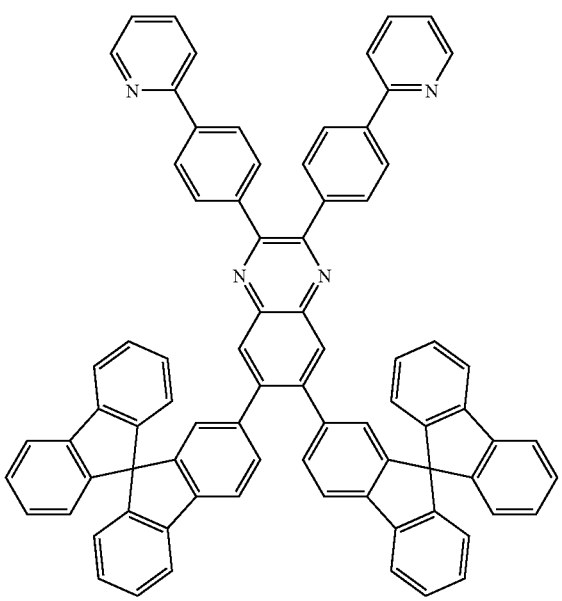

-continued
(513)
(515)
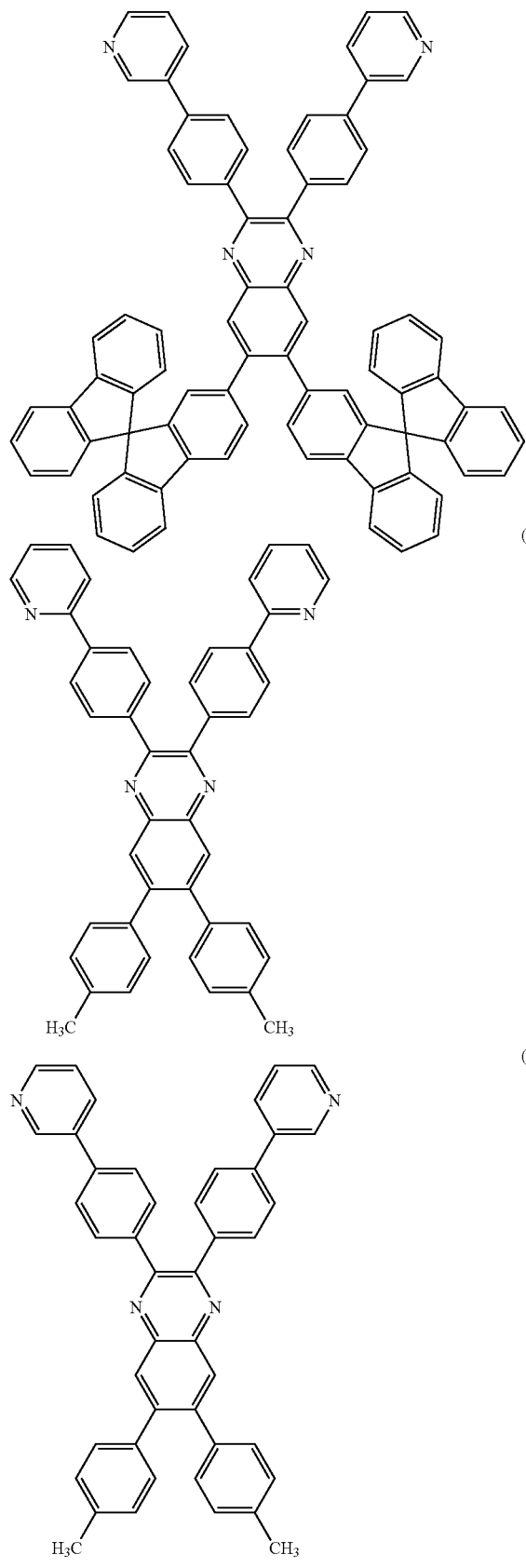
(516)
(517)
(518)
(519)
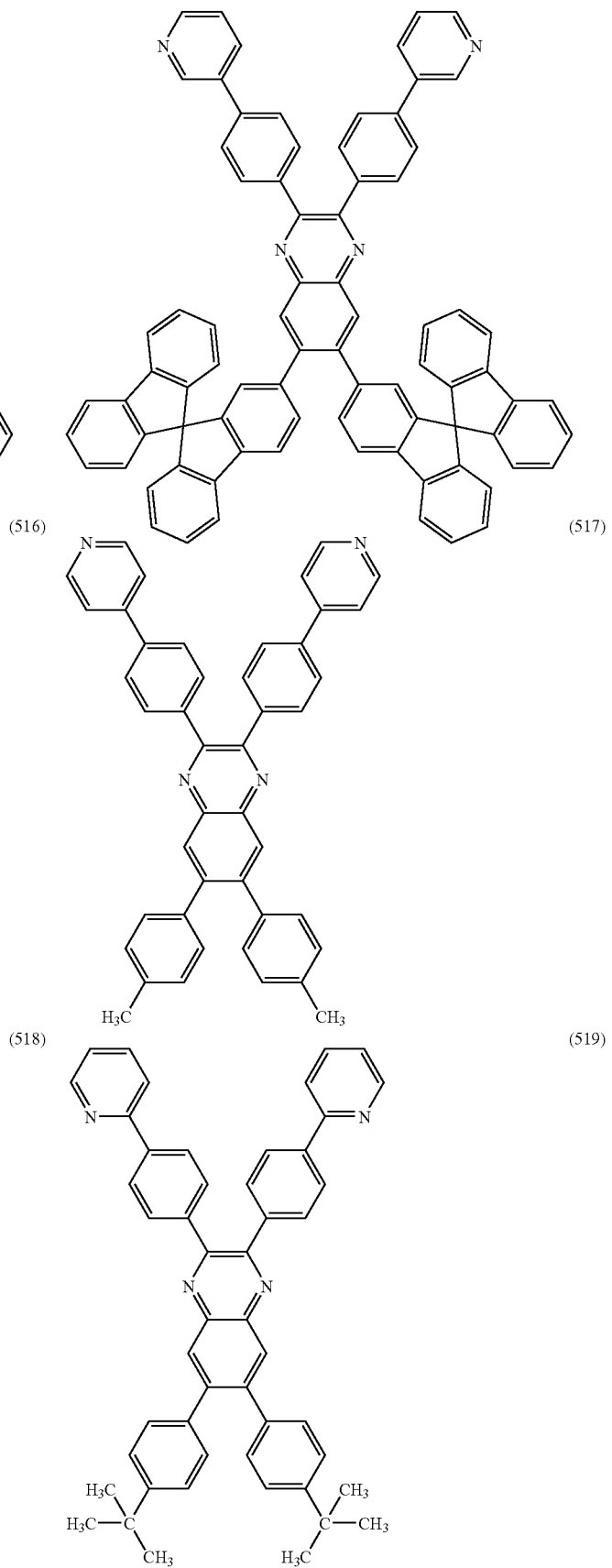

-continued
(520)
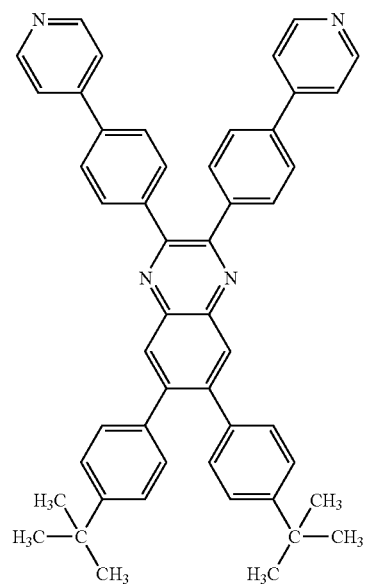
(521)
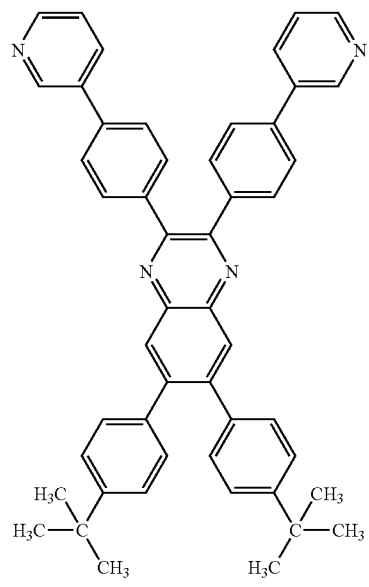
(522)
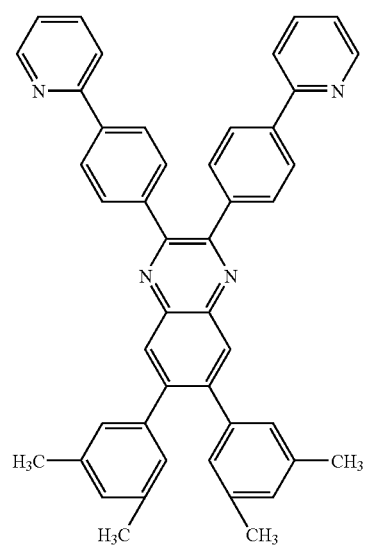
(523)
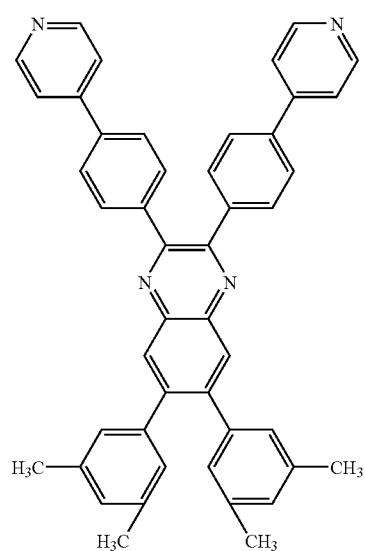
(524)
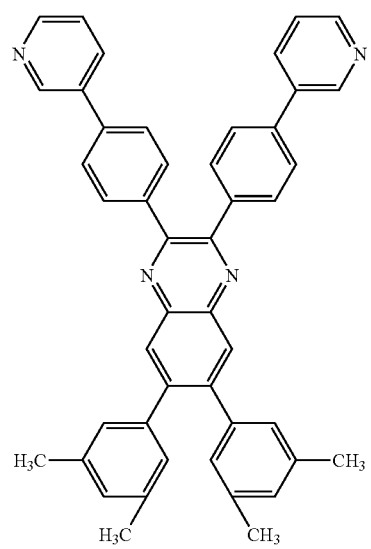
(525)
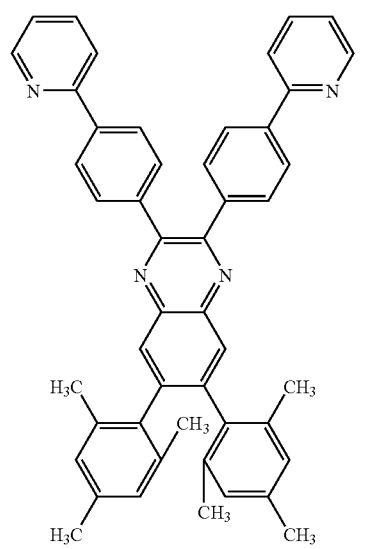

-continued
(526)
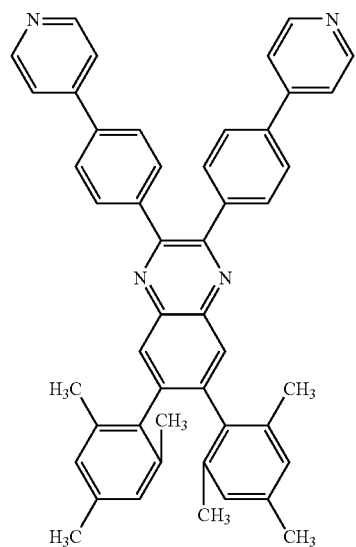
(527)
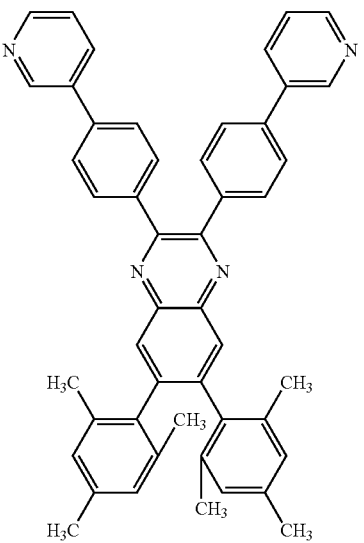
(528)
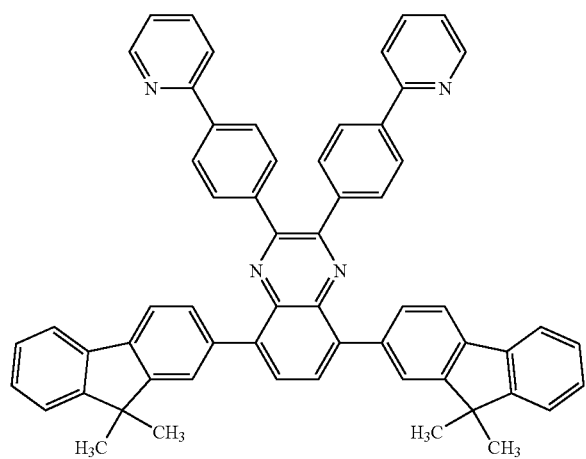
(529)
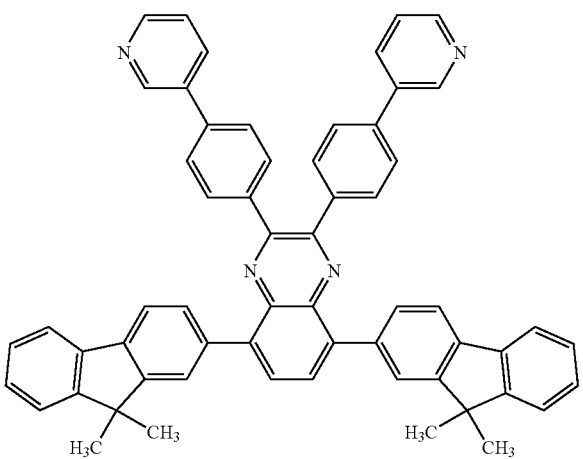
(530)
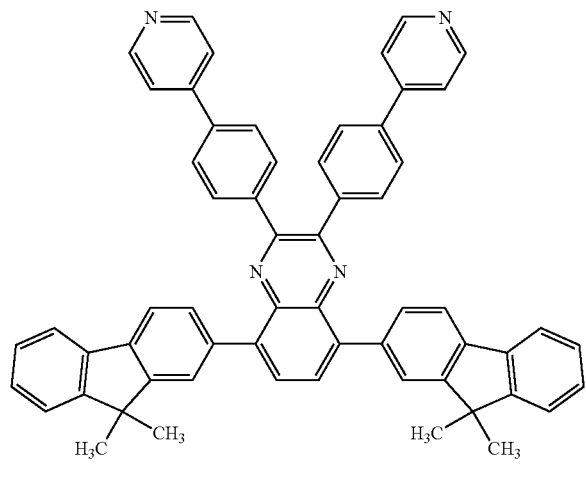
(531)
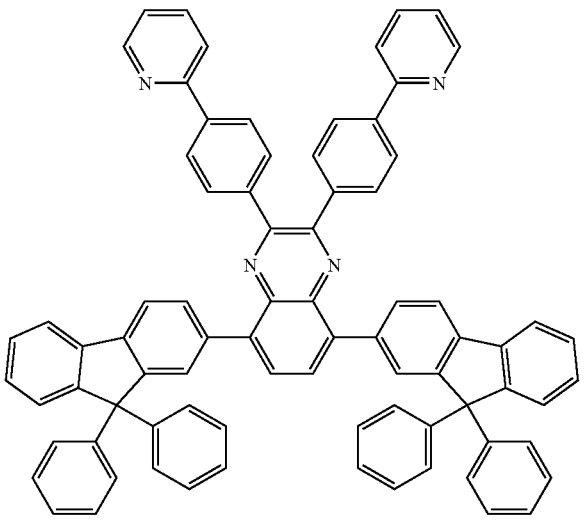

(532)
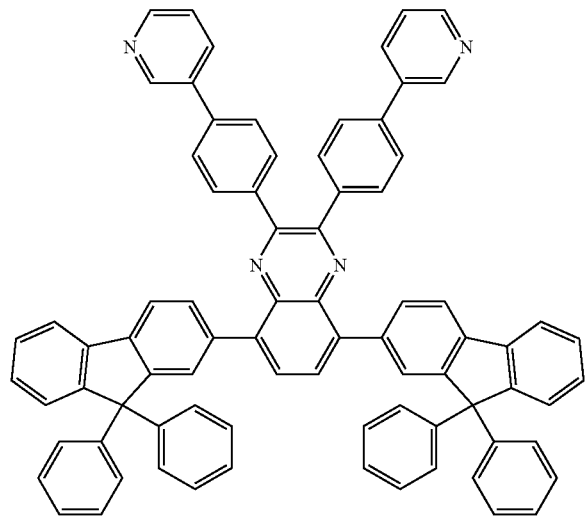
(533)
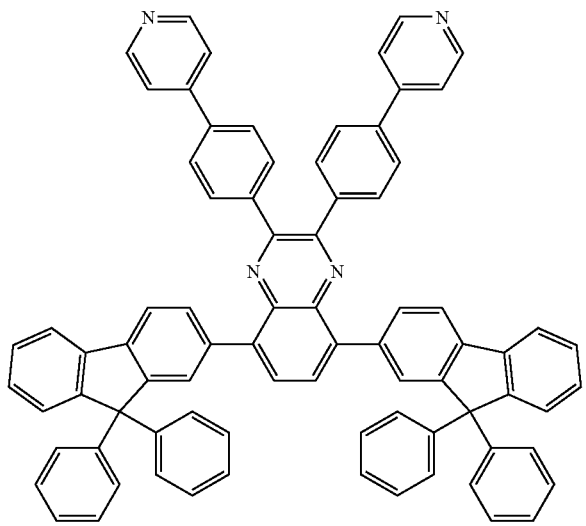
(534)
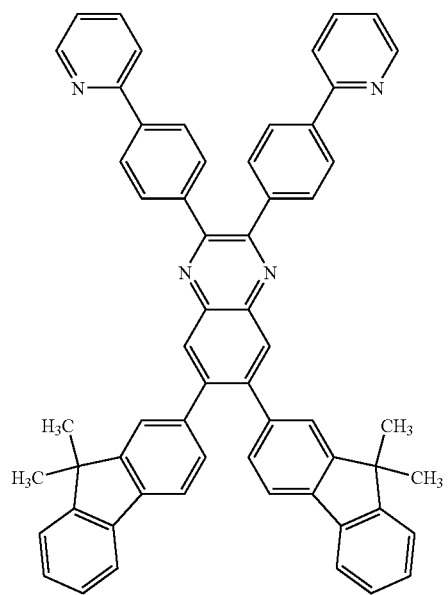
(535)
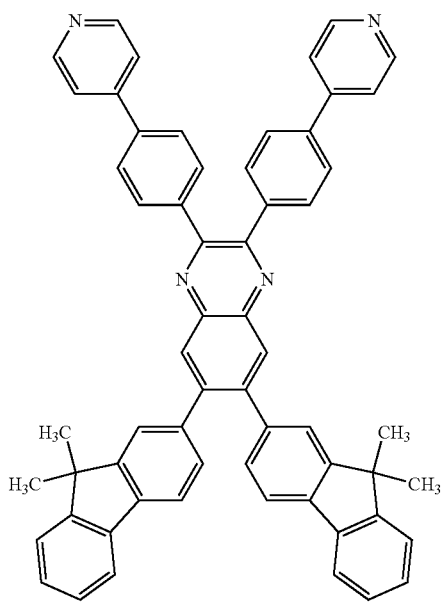

-continued
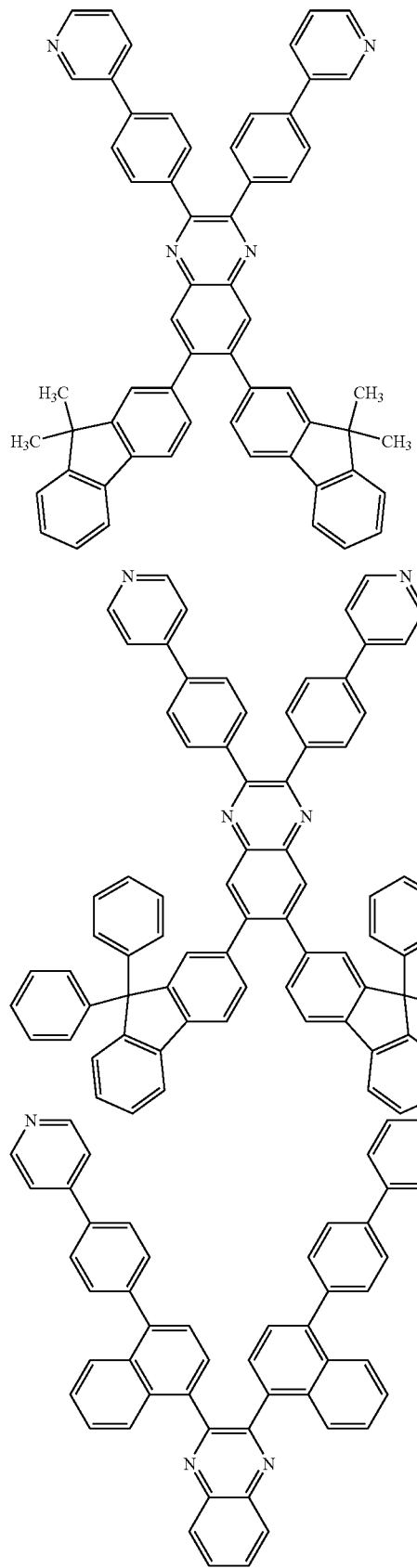
(536)
(538)
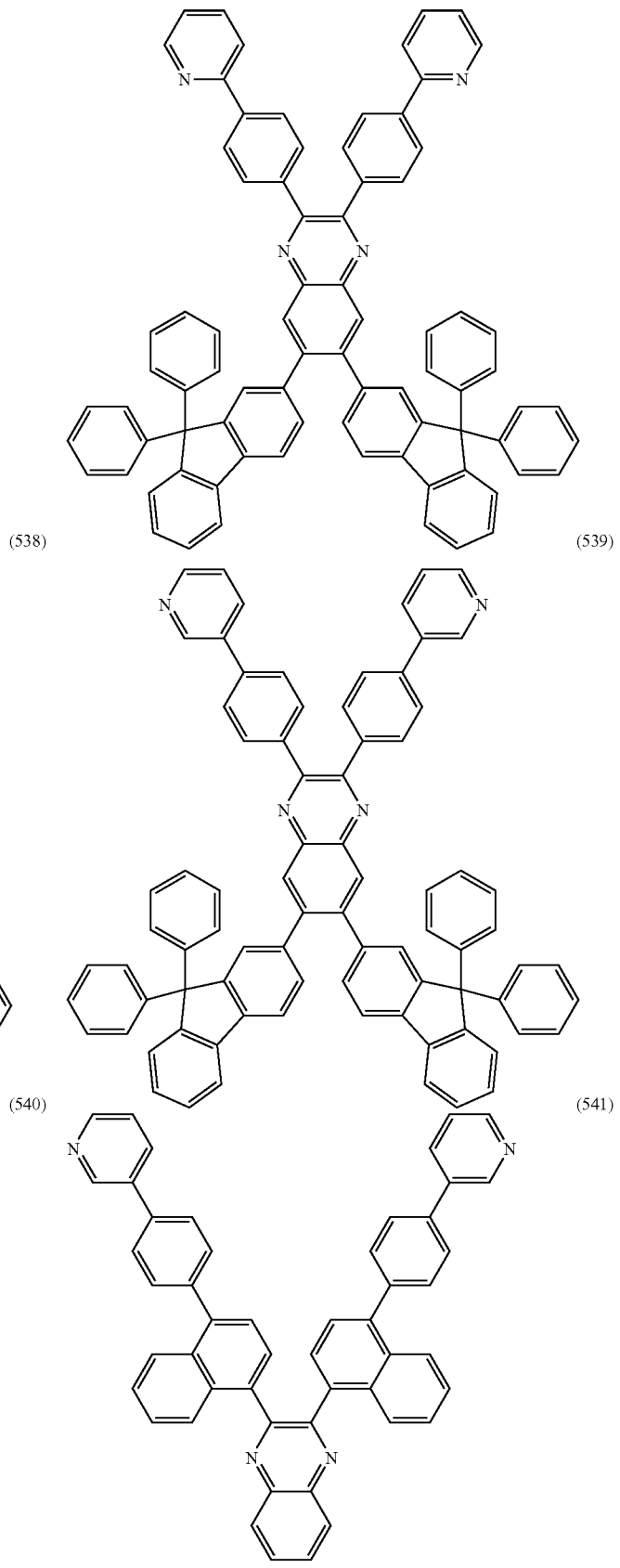
(537)
(539)
(540)
(541)

-continued
(542)
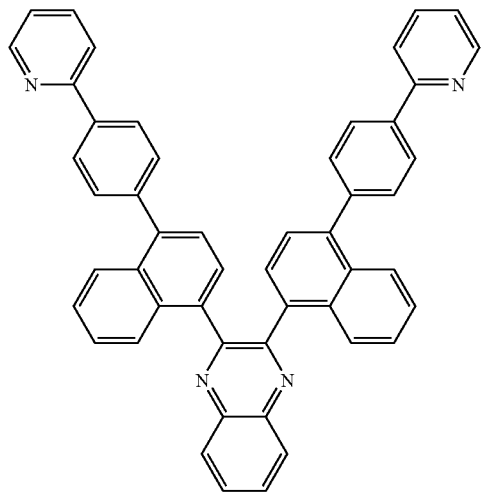
(543)
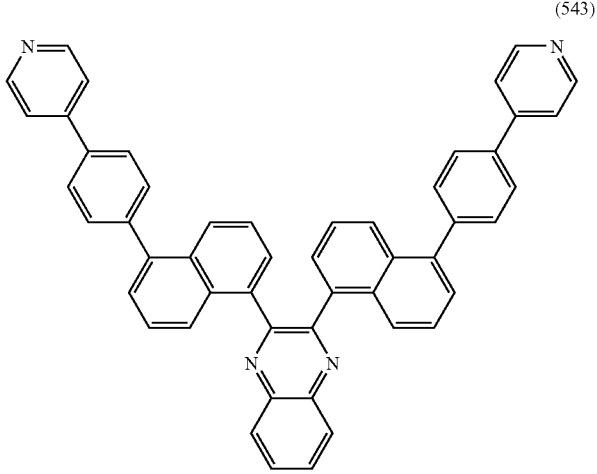
(544)
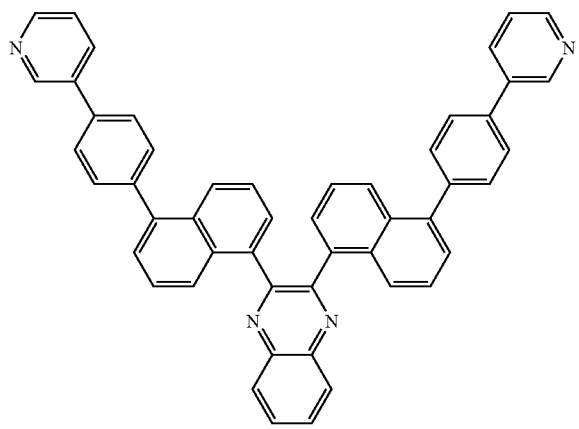
(545)
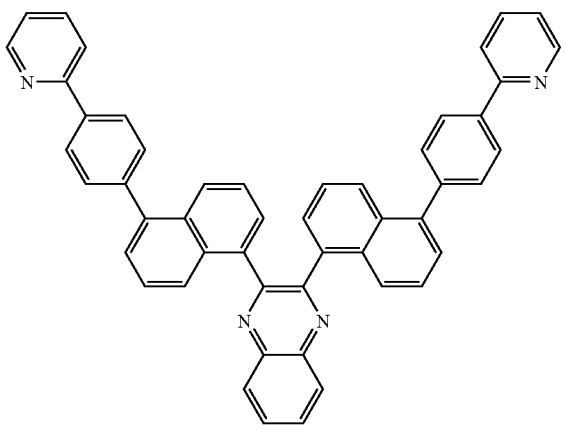
(546)
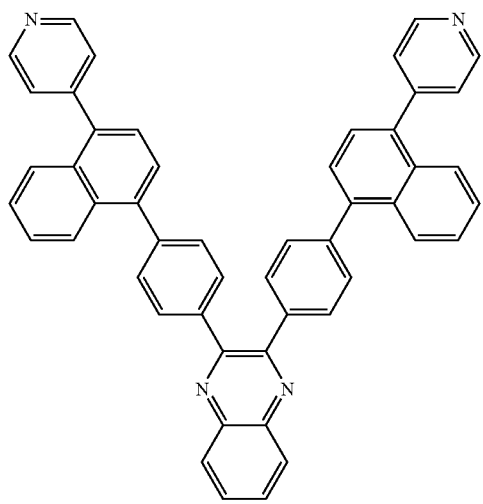
(547)
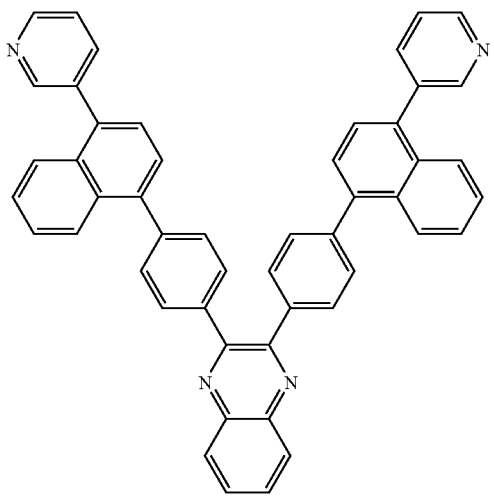

-continued
(548)
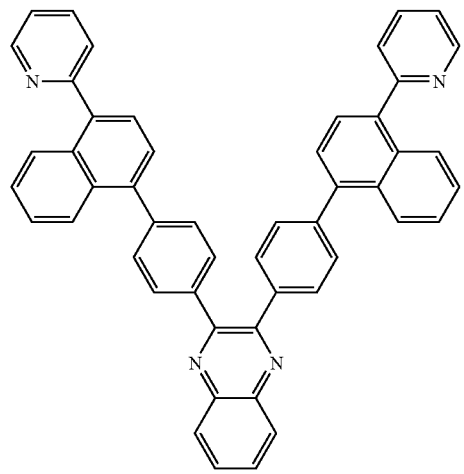
(549)
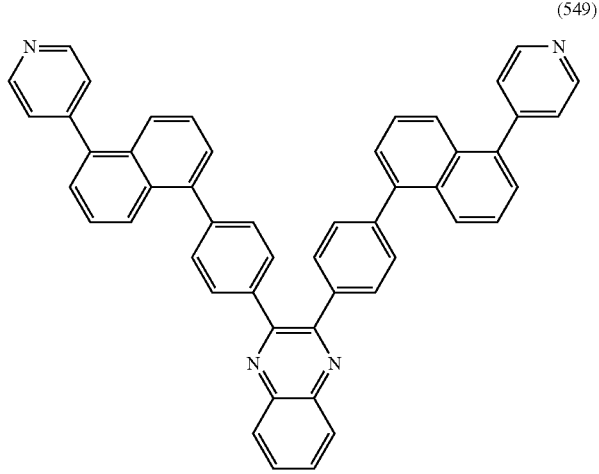
(550)
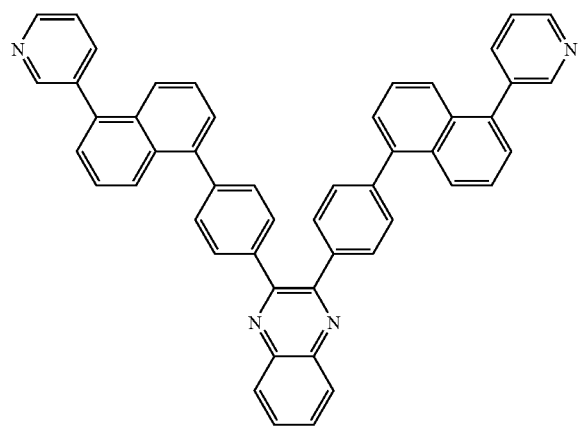
(551)
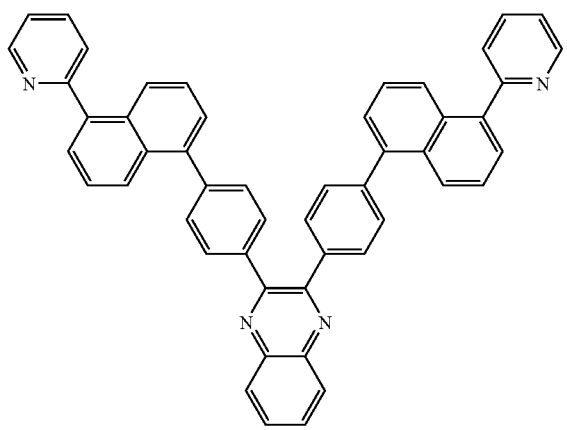
(552)
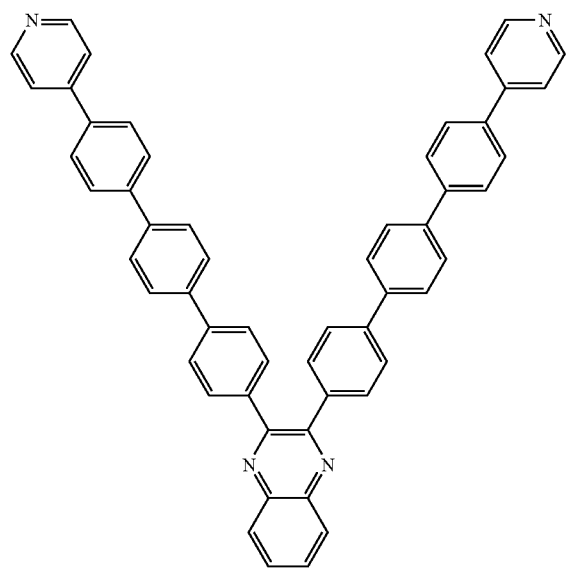
(553)
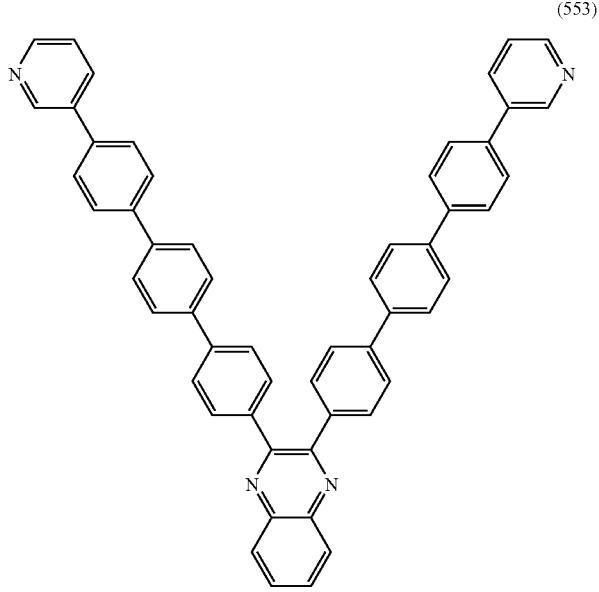

(554)

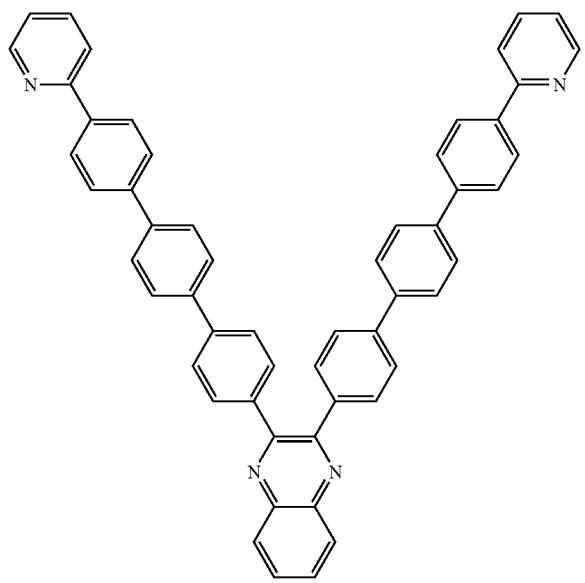

As a method for synthesizing a quinoxaline derivative of the present invention, various kinds of reactions can be applied. For example, a quinoxaline derivative of the present invention can be synthesized by synthetic reactions described below.

<Method for Synthesizing Compound Represented by General Formula (G11)>

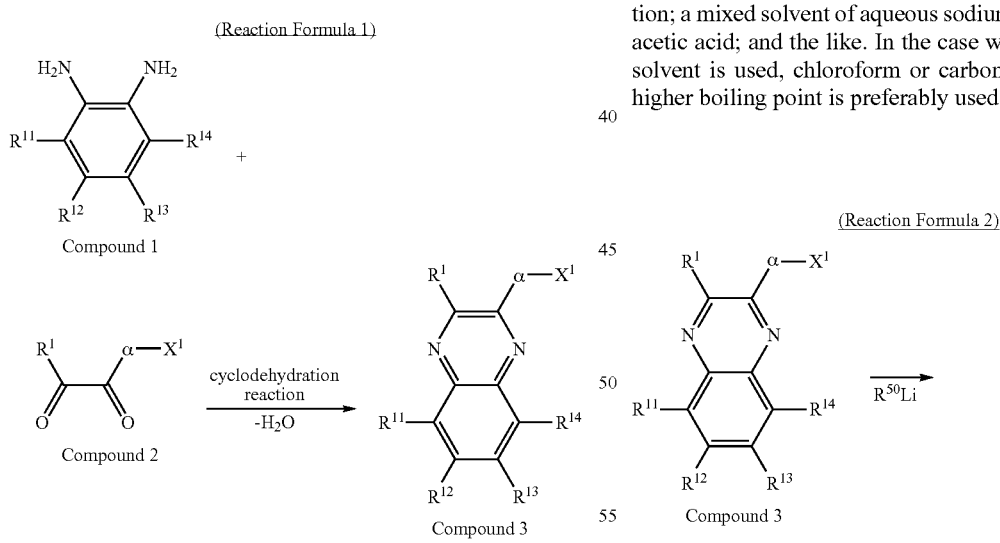

First, a 1,2-phenylenediamine derivative (Compound 1) and a diketone derivative (Compound 2), each of which may include a substitutent, are subjected to a cyclodehydration reaction, whereby a quinoxaline derivative (Compound 3) can be obtained (Reaction Formula 1). In Reaction Formula 1, α represents an arylene group having 6 to 13 carbon atoms; $R^{11}$ to $R^{14}$ each represent any of hydrogen, an alkyl group having 1 to 4 carbon atoms, and an aryl group having 6 to 13 carbon atoms; $R^1$ represents an alkyl group having 1 to 4 carbon atoms or an aryl group having 6 to 13 carbon atoms; and $X^1$ represents halogen or a triflate group. In the case where $X^1$ is halogen, chlorine, bromine, or iodine is preferable. Examples of solvents that can be used in Reaction Formula 1 are as follows: halogen-based solvents such as dichloromethane, chloroform, and carbon tetrachloride; alcohols such as ethanol, methanol, and isopropanol; acetic acid; an aqueous sodium carbonate solution; an aqueous sodium hydrogen sulfate solution; an aqueous sodium acetate solution; a mixed solvent of aqueous sodium acetate solution and acetic acid; and the like. In the case where a halogen-based solvent is used, chloroform or carbon tetrachloride having higher boiling point is preferably used.

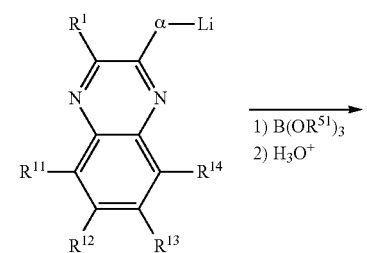

-continued

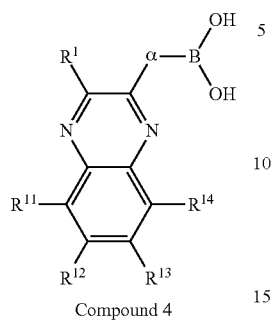

Compound 4

Next, as shown in Reaction Formula 2, the quinoxaline derivative (Compound 3) is lithiated with an alkyl lithium reagent and hydrolyzed with acid or water using a boron reagent, whereby a boronic acid of the quinoxaline derivative (Compound 4) can be obtained. In Reaction Formula 2, α represents an arylene group having 6 to 13 carbon atoms; $R^{11}$ to $R^{14}$ each represent any of hydrogen, an alkyl group having 1 to 4 carbon atoms, and an aryl group having 6 to 13 carbon atoms; $R^1$ represents an alkyl group having 1 to 4 carbon atoms or an aryl group having 6 to 13 carbon atoms; $X^1$ represents halogen; $R^{50}$ represents an alkyl group having 1 to 6 carbon atoms; and $R^{51}$ represents an alkyl group having 1 to 6 carbon atoms. Examples of solvents that can be used in Reaction Formula 2 are ether-based solvents such as diethyl ether, tetrahydrofuran (THF), and cyclopentyl methyl ether. Examples of alkyl lithium reagents are n-butyllithium in which $R^{50}$ is an n-butyl group, t-butyllithium in which $R^{50}$ is a t-butyl group, methyllithium in which $R^{50}$ is a methyl group, and the like. Examples of boron reagents are trimethyl borate in which $R^{51}$ is a methyl group, triisopropyl borate in which $R^{51}$ is an isopropyl group, and the like. Further, the boronic acid obtained in Reaction Formula 2 may be protected with ethyl alcohol, propyl alcohol, or the like or may be protected with dial such as ethylene glycol or pinacol to form a ring structure, whereby an organoboron compound may be obtained.

(Reaction Formula 3)

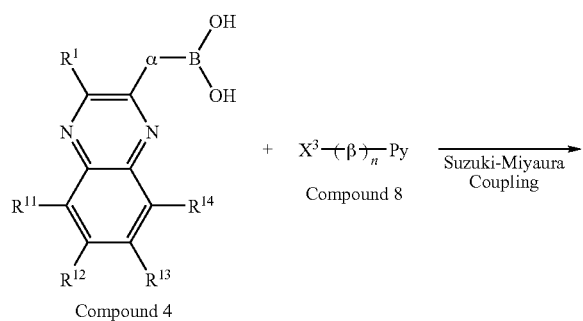

Compound 4

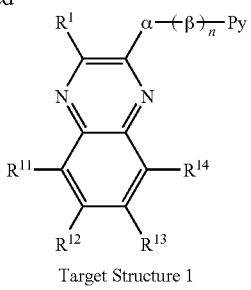

Target Structure 1

Next, the boronic acid of the quinoxaline derivative (Compound 4) and a pyridine derivative (Compound 8) are coupled by Suzuki-Miyaura Coupling, whereby a pyridyl quinoxaline derivative (Target Substance 1) represented by the general formula (G11) can be obtained. In Reaction Formula 3, $X^3$ represents halogen or a triflate group; $R^{11}$ to $R^{14}$ each represent any of hydrogen, an alkyl group having 1 to 4 carbon atoms, and an aryl group having 6 to 13 carbon atoms; $R^1$ represents an alkyl group having 1 to 4 carbon atoms or an aryl group having 6 to 13 carbon atoms; Py represents a pyridyl group; α represents an arylene group having 6 to 13 carbon atoms; β represents an arylene group having 6 to 13 carbon atoms; and n represents an integer of 0 or 1. In the case where $X^3$ is halogen, chlorine, bromine, or iodine is preferable and bromine or iodine is more preferable. Examples of palladium catalysts that can be used in Reaction Formula 3 are palladium(II) acetate, tetrakis(triphenylphosphine)palladium(0), and the like. Examples of ligands of palladium catalysts that can be used in Reaction Formula 3 are tri(ortho-tolyl)phosphine, triphenylphosphine, tricyclohexylphosphine, and the like. Examples of bases that can be used in Reaction Formula 3 are organic bases such as sodium t-butoxide, inorganic bases such as potassium carbonate, and the like. Examples of solvents that can be used in Reaction Formula 3 are as follows: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of ether such as ethylene glycol dimethyl ether, and water; and the like. Further, a mixed solvent of toluene and water or a mixed solvent of toluene, ethanol, and water is more preferable. In Reaction Formula 3, instead of Compound 4, an organoboron compound may be used, which is obtained by protecting the boronic acid of Compound 4 with ethyl alcohol, propyl alcohol, or the like. Alternatively, an organoboron compound having a ring structure may be used, which is obtained by protecting the boronic acid of Compound 4 with diol such as ethylene glycol or pinacol. Further, instead of Suzuki-Miyaura Coupling, cross coupling using an organoaluminum compound, an organozirconium compound, an organozinc compound, an organotin compound, or the like may be used.

(Reaction Formula 4)

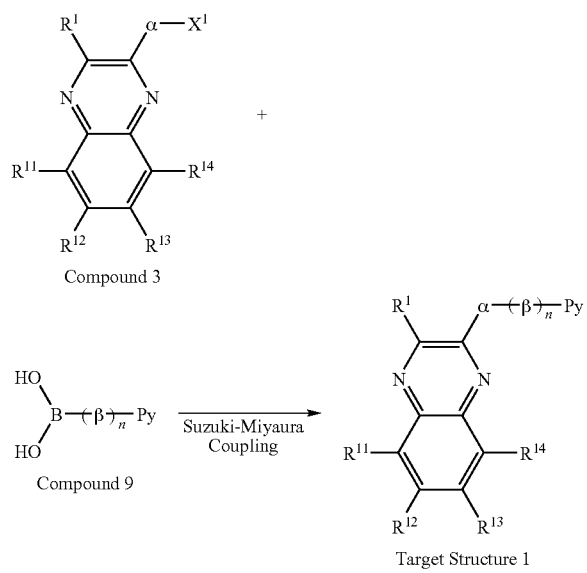

Compound 3

Compound 9

Target Structure 1

The compound (Target Substance 1) represented by the general formula (G11) can also be obtained by coupling of the quinoxaline derivative (Compound 3) and the boronic acid of the pyridine derivative (Compound 9) by Suzuki-Miyaura Coupling. In Reaction Formula 4, $X^1$ represents halogen or a triflate group, and in the case where $X^1$ is halogen, chlorine, bromine, or iodine is preferable, and bromine or iodine is more preferable. $R^{11}$ to $R^{14}$ each represent any of hydrogen, an alkyl group having 1 to 4 carbon atoms, and an aryl group having 6 to 13 carbon atoms; $R^1$ represents an alkyl group having 1 to 4 carbon atoms or an aryl group having 6 to 13 carbon atoms; Py represents a pyridyl group; α represents an arylene group having 6 to 13 carbon atoms; β represents an arylene group having 6 to 13 carbon atoms; and n represents an integer of 0 or 1. Examples of palladium catalysts that can be used in Reaction Formula 4 are palladium(II) acetate, tetrakis(triphenylphosphine)palladium(0), and the like. Examples of ligands of palladium catalysts that can be used in Reaction Formula 4 are tri(ortho-tolyl)phosphine, triphenylphosphine, tricyclohexylphosphine, and the like. Examples of bases that can be used in Reaction Formula 4 are organic bases such as sodium t-butoxide, inorganic bases such as potassium carbonate, and the like. Examples of solvents that can be used in Reaction Formula 4 are as follows: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of ether such as ethylene glycol dimethyl ether, and water; and the like. Further, a mixed solvent of toluene and water or a mixed solvent of toluene, ethanol, and water is more preferable. In Reaction Formula 4, instead of Compound 9, an organoboron compound may be used, which is obtained by protecting the boronic acid of Compound 9 with ethyl alcohol, propyl alcohol, or the like. Alternatively, an organoboron compound having a ring structure may be used, which is obtained by protecting the boronic acid of Compound 9 with diol such as ethylene glycol or pinacol. Further, instead of Suzuki-Miyaura Coupling, cross coupling using an organoaluminum compound, an organozirconium compound, an organozinc compound, an organotin compound, or the like may be used.

<Method for Synthesizing Compound Represented by General Formula (G21)>

(Reaction Formula 5)

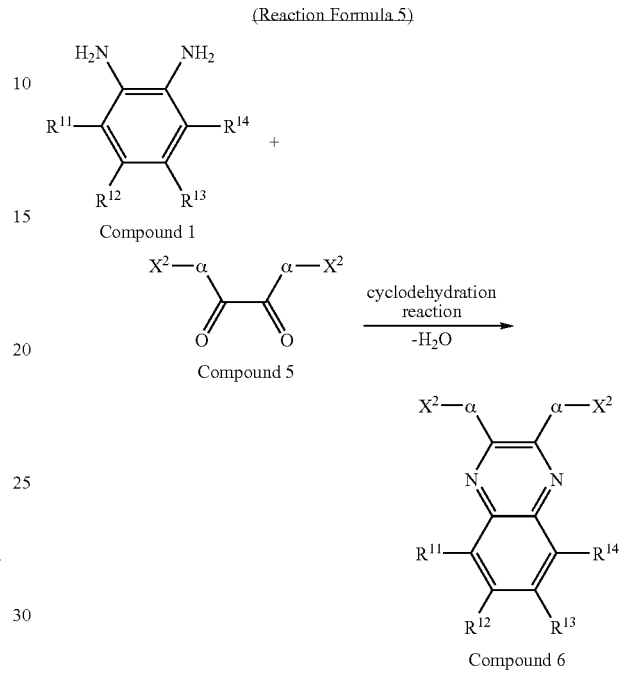

Compound 1

Compound 5

Compound 6

First, a 1,2-phenylenediamine derivative (Compound 1) and a diketone derivative (Compound 5), each of which may include a substitutent, are subjected to a dehydration condensation reaction, whereby a quinoxaline derivative (Compound 6) can be obtained (Reaction Formula 5). In Reaction Formula 5, α represents an arylene group having 6 to 13 carbon atoms; $R^{11}$ to $R^{14}$ each represent any of hydrogen, an alkyl group having 1 to 4 carbon atoms, and an aryl group having 6 to 13 carbon atoms; and $X^2$ represents halogen or a triflate group. In the case where $X^2$ is halogen, chlorine, bromine, or iodine is preferable. Examples of solvents that can be used in Reaction Formula 5 are halogenated methane-based solvents such as dichloromethane, chloroform, and carbon tetrachloride. Because high temperature is preferable for the dehydration condensation reaction, chloroform or carbon tetrachloride having high boiling point is preferably used.

(Reaction Formula 6)

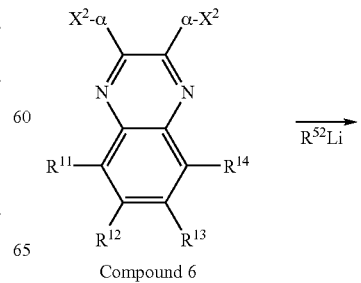

Compound 6

149
-continued

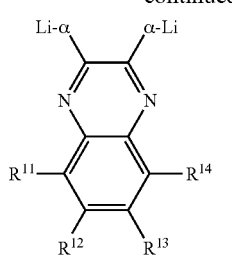

1) B(OR$^{53}$)$_3$
2) H$_3$O$^+$

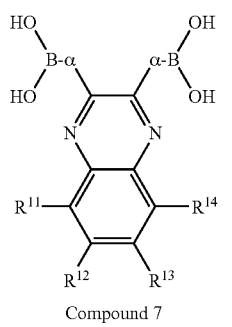

Compound 7

Next, as shown in Reaction Formula 6, the quinoxaline derivative (Compound 6) is lithiated with an alkyl lithium reagent and hydrolyzed with acid or water using a boron reagent, whereby a boronic acid of the quinoxaline derivative (Compound 7) can be obtained. In Reaction Formula 6, $R^{11}$ to $R^{14}$ each represent any of hydrogen, an alkyl group having 1 to 4 carbon atoms, and an aryl group having 6 to 13 carbon atoms; α represents an arylene group having 6 to 13 carbon atoms; $X^2$ represents halogen; $R^{52}$ represents an alkyl group having 1 to 6 carbon atoms; and $R^{53}$ represents an alkyl group having 1 to 6 carbon atoms. Examples of solvents that can be used in Reaction Formula 6 are ether-based solvents such as diethyl ether, tetrahydrofuran (THF), and cyclopentyl methyl ether. Examples of alkyl lithium reagents are n-butyllithium in which $R^{52}$ is an n-butyl group, tert-butyllithium in which $R^{52}$ is a tert-butyl group, methyllithium in which $R^{53}$ is a methyl group, and the like. Examples of boron reagents are trimethyl borate in which $R^{53}$ is a methyl group, triisopropyl borate in which $R^{53}$ is an isopropyl group, and the like. Further, the boronic acid obtained in Reaction Formula 6 may be protected with ethyl alcohol, propyl alcohol, or the like or may be protected with diol such as ethylene glycol or pinacol to form a ring structure, whereby an organoboron compound may be obtained.

(Reaction Formula 7)

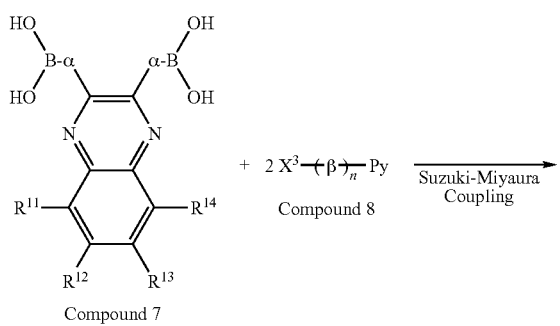

+ 2 X$^3$—(β)$_n$—Py  →  Suzuki-Miyaura Coupling

Compound 8

Compound 7

150
-continued

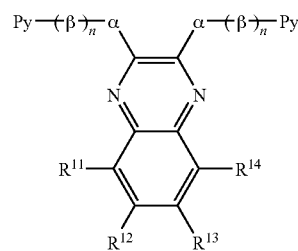

Target Structure 2

Next, the boronic acid of the quinoxaline derivative (Compound 7) and a pyridine derivative (Compound 8) are coupled by Suzuki-Miyaura Coupling, whereby a pyridyl quinoxaline derivative (Target Substance 2) represented by the general formula (G21) can be obtained (Reaction Formula 7). In Reaction Formula 7, $X^3$ represents halogen or a triflate group; Py represents a pyridyl group; $R^{11}$ to $R^{14}$ each represent any of hydrogen, an alkyl group having 1 to 4 carbon atoms, and an aryl group having 6 to 13 carbon atoms; α represents an arylene group having 6 to 13 carbon atoms; 13 represents an arylene group having 6 to 13 carbon atoms; and n represents an integer of 0 or 1. In the case where $X^3$ is halogen, chlorine, bromine, or iodine is preferable, and bromine or iodine is more preferable. Examples of palladium catalysts that can be used in Reaction Formula 7 are palladium(II) acetate, tetrakis(triphenylphosphine)palladium(0), and the like. Examples of ligands of palladium catalysts that can be used in Reaction Formula 7 are tri(ortho-tolyl)phosphine, triphenylphosphine, tricyclohexylphosphine, and the like. Examples of bases that can be used in Reaction Formula 7 are organic bases such as sodium t-butoxide, inorganic bases such as potassium carbonate, and the like. Examples of solvents that can be used in Reaction Formula 7 are as follows: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of ether such as ethylene glycol dimethyl ether, and water; and the like. Further, a mixed solvent of toluene and water or a mixed solvent of toluene, ethanol, and water is more preferable. In Reaction Formula 7, instead of Compound 7, an organoboron compound may be used, which is obtained by protecting the boronic acid of Compound 7 with ethyl alcohol, propyl alcohol, or the like. Alternatively, an organoboron compound having a ring structure may be used, which is obtained by protecting the boronic acid of Compound 7 with diol such as ethylene glycol or pinacol. Further, instead of Suzuki-Miyaura Coupling, cross coupling using an organoaluminum compound, an organozirconium compound, an organozinc compound, an organotin compound, or the like may be used.

(Reaction Formula 8)

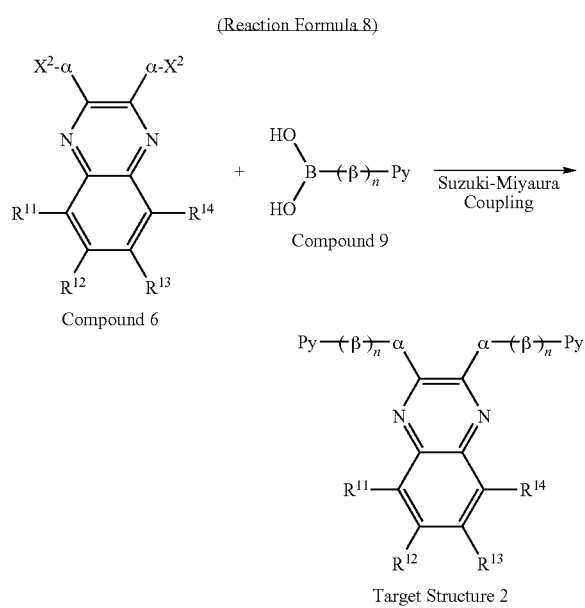

Compound 6

Target Structure 2

The compound (Target Substance 2) represented by the general formula (G21) can also be obtained by coupling of the quinoxaline derivative (Compound 6) and the boronic acid of the pyridine derivative (Compound 9) by Suzuki-Miyaura Coupling. $X^2$ represents halogen or a triflate group, and in the case where $X^2$ is halogen, chlorine, bromine, or iodine is preferable, and bromine or iodine is more preferable. Py represents a pyridyl group; $R^{11}$ to $R^{14}$ each represent any of hydrogen, an alkyl group having 1 to 4 carbon atoms, and an aryl group having 6 to 13 carbon atoms; cc represents an arylene group having 6 to 13 carbon atoms; β represents an arylene group having 6 to 13 carbon atoms; and n represents an integer of 0 or 1. Examples of palladium catalysts that can be used in Reaction Formula 8 are palladium(II) acetate, tetrakis(triphenylphosphine)palladium(0), and the like. Examples of ligands of palladium catalysts that can be used in Reaction Formula 8 are tri(ortho-tolyl)phosphine, triphenylphosphine, tricyclohexylphosphine, and the like. Examples of bases that can be used in Reaction Formula 8 are organic bases such as sodium t-butoxide, inorganic bases such as potassium carbonate, and the like. Examples of solvents that can be used in Reaction Formula 8 are as follows: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of ether such as ethylene glycol dimethyl ether, and water; and the like. Further, a mixed solvent of toluene and water or a mixed solvent of toluene, ethanol, and water is more preferable. In Reaction Formula 8, instead of Compound 9, an organoboron compound may be used, which is obtained by protecting the boronic acid of Compound 9 with ethyl alcohol, propyl alcohol, or the like. Alternatively, an organoboron compound having a ring structure may be used, which is obtained by protecting the boronic acid of Compound 9 with diol such as ethylene glycol or pinacol. Further, instead of Suzuki-Miyaura Coupling, cross coupling using an organoaluminum compound, an organozirconium compound, an organozinc compound, an organotin compound, or the like may be used.

A quinoxaline derivative of the present invention has a structure in which at least one of carbon at a 2-position and carbon at a 3-position, and carbon of a pyridine ring are bound via an arylene group. Because a quinoxaline skeleton has an electron-transporting property and the pyridine ring also has an electron-transporting property, when at least one of carbon at a 2-position and carbon at a 3-position of quinoxaline, and carbon of a pyridine ring are bound via an arylene group, a quinoxaline derivative having a superior electron-transporting property can be obtained.

In addition, the molecular weight of a quinoxaline derivative in which both carbon at a 2-position and carbon at a 3-position of quinoxaline, and carbon of a pyridine ring are bound via an arylene group is larger than that of the quinoxaline derivative in which at least one of carbon at a 2-position and carbon at a 3-position of quinoxaline, and carbon of a pyridine ring are bound via an arylene group, and the thermophysical property thereof is higher. In addition, because the thermophysical property is higher, improvement in stability of a film quality (suppression of crystallization) can be expected.

Furthermore, a quinoxaline derivative of the present invention is superior in an electron-transporting property. Thus, by use of the quinoxaline derivative of the present invention for an electronic device such as a light-emitting element or an organic transistor, favorable electric characteristics can be obtained.

Embodiment Mode 2

In this embodiment mode, modes of light-emitting elements using any of the quinoxaline derivatives shown in Embodiment Mode 1 will be described with reference to FIG. 1 and FIG. 2.

A light-emitting element of the present invention has a plurality of layers between a pair of electrodes. The plurality of layers is a combination of layers formed of a substance with a high carrier-injecting property and a substance with a high carrier-transporting property which are stacked so that a light-emitting region can be formed in a region away from the electrodes, that is, so that carriers can be recombined in an area away from the electrodes.

In this embodiment mode, the light-emitting element includes a first electrode 102, a second electrode 104, and an EL layer 103 which is formed between the first electrode 102 and the second electrode 104. Note that in this embodiment mode, description will be made below in such conditions that the first electrode 102 functions as an anode and the second electrode 104 functions as a cathode. In other words, when voltage is applied to the first electrode 102 and the second electrode 104 such that potential of the first electrode 102 becomes higher than that of the second electrode 104, light emission can be obtained. Such a case will be described below.

A substrate 101 is used as a support of the light-emitting element. The substrate 101 can be formed of, for example, glass, plastic, metal, or the like. Note that materials other than glass, plastic, or metal can be used as long as they can function as a support of a light-emitting element. Note that in the case where light from the light-emitting element is extracted outside through the substrate, the substrate 101 preferably has a light-transmitting property.

As for the first electrode 102, a metal, an alloy, a conductive compound, a mixture thereof, or the like having a high work function (specifically, preferably 4.0 eV or higher) is preferably used. As examples, indium tin oxide (ITO), indium tin oxide containing silicon or silicon oxide, indium zinc oxide (IZO), indium oxide containing tungsten oxide and zinc oxide (IWZO), and the like can be given. A film of such a conductive metal oxide is generally formed by sputtering, but may also be formed by an inkjet method, a spin coating method, or the like by application of a sol-gel method or the like. For example, a film of indium zinc oxide (IZO) can be formed by a sputtering method using a target in which zinc oxide is added to indium oxide at 1 wt % to 20 wt %. In addition, a film of indium oxide containing tungsten oxide and zinc oxide (IWZO) can be formed by a sputtering method using a target in which tungsten oxide and zinc oxide are included in indium oxide at 0.5 wt % to 5 wt % and at 0.1 wt % to 1 wt %, respectively. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), nitride of a metal material (e.g., titanium nitride), and the like can be given as examples.

In the case where a layer including a composite material described below is used as a layer in contact with the first electrode 102, various metals, alloys, electrically conductive compounds, or a mixture thereof can be used for the first electrode 102 regardless of the work function. For example, aluminum (Al), silver (Ag), an alloy containing aluminum (AlSi), or the like can be used. Besides, any of the following materials with a low work function can be used for the first electrode: elements belonging to Group 1 and Group 2 of the periodic table, that is, alkali metals such as lithium (Li) and cesium (Cs) and alkaline earth metals such as magnesium (Mg), calcium (Ca), and strontium (Sr); alloys thereof (MgAg, AlLi); rare earth metals such as europium (Eu) and ytterbium (Yb); alloys thereof; and the like. A film of an alkali metal, an alkaline earth metal, or an alloy thereof can be formed by a vacuum evaporation method. In addition, a film of an alloy including an alkali metal or an alkaline earth metal can be formed by a sputtering method. Further, a film can be formed using a silver paste or the like by an inkjet method or the like.

The EL layer 103 shown in this embodiment mode includes a hole-injecting layer 111, a hole-transporting layer 112, a light-emitting layer 113, an electron-transporting layer 114, and an electron-injecting layer 115. Note that it is acceptable as long as the EL layer 103 include a quinoxaline derivative shown in Embodiment Mode 1. Thus, the structure of other stacked layers is not specifically limited. That is, there is no particular limitation on the stacked structure of the EL layer 103, and a quinoxaline derivative shown in Embodiment Mode 1 may be appropriately combined with a layer formed of a substance having a high electron-transporting property, a substance having a high hole-transporting property, a substance having a high electron-injecting property, a substance having a high hole-injecting property, a bipolar substance (a substance having high electron-transporting and hole-transporting properties), a substance having a high light-emitting property, or the like to form the EL layer 103. For example, the EL layer 103 can be formed by an appropriate combination of a hole-injecting layer, a hole-transporting layer, a light-emitting layer, an electron-transporting layer, an electron-injecting layer, and the like. Specific materials for each of the layers are given below.

The hole-injecting layer 111 is a layer including a substance having a high hole-injecting property. As a substance having a high hole-injecting property, molybdenum oxide, vanadium oxide, ruthenium oxide, tungsten oxide, manganese oxide, or the like can be used. Besides, as examples of a low molecular organic compound, a phthalocyanine-based compound such as phthalocyanine (abbr.: H₂Pc), copper(II) phthalocyanine (abbr.: CuPc), or vanadyl phthalocyanine (VOPc); an aromatic amine compound such as 4,4',4''-tris(N,N-diphenylamino)triphenylamine (abbr.: TDATA), 4,4',4''-tris[N-(3-methylphenyl)-N-phenylamino]triphenylamine (abbr.: MTDATA), 4,4'-bis[N-(4-diphenylaminophenyl)-N-phenylamino]biphenyl (abbr.: DPAB), 4,4'-bis(N-{4-[N'-(3-methylphenyl)-N'-phenylamino]phenyl}-N-phenylamino) biphenyl (abbr.: DNTPD), 1,3,5-tris[N-(4-diphenylaminophenyl)-N-phenylamino]benzene (abbr.: DPA3B), 3-[N-(9-phenylcarbazol-3-yl)-N-phenylamino]-9-phenylcarbazole (abbr.: PCzPCA1), 3,6-bis[N-(9-phenylcarbazol-3-yl)-N-phenylamino]-9-phenylcarbazole (abbr.: PCzPCA2), or 3-[N-(1-naphthyl)-N-(9-phenylcarbazol-3-yl) amino]-9-phenylcarbazole (abbr.: PCzPCN1); and the like can be given.

Alternatively, for the hole-injecting layer 111, a composite material in which an acceptor substance is mixed into a substance having a high hole-transporting property can be used. Note that by using a material in which an acceptor substance is mixed into a substance having a high hole-transporting property, a material for forming the electrode can be selected regardless of its work function. In other words, besides a material with a high work function, a material with a low work function may also be used for the first electrode 102. A composite material of those substances can be formed by co-evaporation of a substance having a high hole-transporting property and an acceptor substance.

Note that in this specification, the term "composite" refers to not only a state where two materials are simply mixed but also a state where a plurality of materials is mixed so that charge can be given and received between the materials.

As an organic compound used for the composite material, various compounds such as an aromatic amine compound, a carbazole derivative, an aromatic hydrocarbon, and a high molecular compound (an oligomer, a dendrimer, a polymer, or the like) can be used. Note that the organic compound used for the composite material is preferably an organic compound having a high hole-transporting property. Specifically, a substance having a hole mobility of $10^{-6}$ cm²/Vs or higher is preferably used. However, other substances may also be used as long as the hole-transporting properties thereof are higher than the electron-transporting properties thereof. Examples of organic compounds that can be used for the composite material are specifically listed below.

Examples of organic compounds which can be used for the composite material are as follows: aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbr.: NPB or α-NPD), and N,N'-bis(3-methylphenyl)-N,N'-diphenyl-[1,1'-biphenyl]-4,4'-diamine (abbr.: TPD); carbazole derivatives such as 4,4'-di(N-carbazolyl)biphenyl (abbr.: CBP), 1,3,5-tris[4-(N-carbazolyl)phenyl]benzene (abbr.: TCPB), 9-[4-(10-phenyl-9-anthryl)phenyl]-9H-carbazole (abbr.: CzPA), and 1,4-bis[4-(N-carbazolyl)phenyl]-2,3,5,6-tetraphenylbenzene; and aromatic hydrocarbon compounds such as 2-tert-butyl-9,10-di(2-naphthyl)anthracene (abbr.: t-BuDNA), 2-tert-butyl-9,10-di(1-naphthyl)anthracene, 9,10-bis(3,5-diphenylphenyl) anthracene (abbr.: DPPA), 2-tert-butyl-9,10-bis(4-phenylphenyl)anthracene (abbr.: t-BuDBA), 9,10-di(2-naphthyl)anthracene (abbr.: DNA); 9,10-diphenylanthracene (abbr.: DPAnth), 2-tert-butylanthracene (abbr.: t-BuAnth), 9,10-bis(4-methyl-1-naphthyl)anthracene (abbr.: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'- bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbr.: DPVBi), and 9,10-bis[4-(2,2-diphenylvinyl)phenyl]anthracene (abbr.: DPVPA).

Examples of the acceptor substance are as follows: organic compounds such as 7,7,8,8-tetracyano-2,3,5,6-tetrafluoro-quinodimethane (abbr.: $F_4$-TCNQ) and chloranil; and transition metal oxides. Other examples are oxides of metals belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air and its hygroscopic property is low so that it can be easily handled.

Furthermore, for the hole-injecting layer 111, a high molecular compound (an oligomer, a dendrimer, a polymer, or the like) can be used. Examples of high molecular compounds include poly(N-vinylcarbazole) (abbr.: PVK), poly (4-vinyltriphenylamine) (abbr.: PVTPA), poly[N-(4-{N'-[4-(4-diphenylamino)phenyl]phenyl-N'-phenylamino}phenyl) methacrylamide] (abbr.: PTPDMA), and poly[N,N'-bis(4-butylphenyl)-N,N'-bis(phenyl)benzidine (abbr.: Poly-TPD). In addition, a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS), can be used.

Moreover, a composite material formed by using the above-mentioned high molecular compound such as PVK, PVTPA, PTPDMA, or Poly-TPD and the above-mentioned acceptor substance can be used for the hole-injecting layer 111.

The hole-transporting layer 112 is a layer including a substance having a high hole-transporting property. As a substance having a high hole-transporting property, a low molecular compound can be used, and examples thereof include aromatic amine compounds such as NPB (or α-NPD), TPD, 4,4'-bis[N-(9,9-dimethylfluoren-2-yl)-N-phenylamino]biphenyl (abbr.: DFLDPBi), and 4,4'-bis[N-(spiro-9,9'-bifluoren-2-yl)-N-phenylamino]biphenyl (abbr.: BSPB). The substances mentioned here mainly have a hole mobility of $10^{-6}$ $cm^2$/Vs or higher. However, other substances may also be used as long as the hole-transporting properties thereof are higher than the electron-transporting properties thereof. Note that the layer including a substance having a high hole-transporting property is not limited to a single layer, but two or more layers including any of the above-mentioned substances may be stacked.

Furthermore, for the hole-transporting layer 112, a composite material in which an acceptor substance is contained in the above-mentioned substance having a high hole-transporting property can be used.

Moreover, for the hole-transporting layer 112, a high molecular compound such as PVK, PVTPA, PTPDMA, or Poly-TPD can be used.

The light-emitting layer 113 is a layer including a substance having a high light-emitting property, and various materials can be used for the light-emitting layer 113. For example, as a substance having a high light-emitting property, a fluorescent compound which emits fluorescence or a phosphorescent compound which emits phosphorescence can be used.

Examples of phosphorescent compounds which can be used for the light-emitting layer include the following organometallic complexes. Examples of materials for blue light emission are as follows: bis[2-(4',6'-difluorophenyl)pyridinato-N,$C^{2'}$]iridium(III) tetrakis(1-pyrazolyl)borate (abbr.: FIr6), bis[2-(4',6'-difluorophenyl)pyridinato-N,$C^{2'}$]iridium (III) picolinate (abbr.: FIrpic), bis[2-(3',5'bistrifluoromethylphenyl)pyridinato-N,$C^{2'}$]iridium(III)picolinate (abbr.: Ir($CF_3$ppy)$_2$(pic)), bis[2-(4',6'-difluorophenyl)pyridinato-N, $C^{2'}$]iridium acetylacetonate (abbr.: FIr(acac)), and the like. Examples of materials for green light emission are as follows: tris(2-phenylpyridinato-N,$C^{2'}$)iridium(III) (abbr.: Ir(ppy)$_3$), bis(2-phenylpyridinato-N,$C^{2'}$)iridium(III) acetylacetonate (abbr.: Ir(ppy)$_2$(acac)), bis(1,2-diphenyl-1H-benzimidazolato)iridium(III)acetylacetonate (abbr.: Ir(pbi)$_2$(acac)), bis (benzo[h]quinolinato)iridium(III) acetylacetonate (abbr.: Ir(bzq)$_2$(acac)), and the like. Examples of materials for yellow light emission are as follows: bis(2,4-diphenyl-1,3-oxazolato-N,$C^{2'}$)iridium(III)acetyl acetonate (abbr.: Ir(dpo)$_2$ (acac)), bis[2-(4'-perfluorophenylphenyl)pyridinato]iridium (III)acetylacetonate (abbr.: Ir(p-PF-ph)$_2$(acac)), bis(2-phenylbenzothiazolato-N,$C^{2'}$)iridium(III)acetylacetonate (abbr.: Ir(bt)$_2$(acac)), and the like. Examples of materials for orange light emission are as follows: tris(2-phenylquinolinato-N,$C^{2'}$)iridium(III) (abbr.: Ir(pq)$_3$), bis(2-phenylquinolinato-N,$C^{2'}$)iridium(III) acetylacetonate (abbr.: Ir(pq)$_2$ (acac)), and the like. Examples of materials for red light emission are organometallic complexes such as bis[2-(T-benzo[4,5-α]thienyl)pyridinato-N,$C^{3'}$]iridium(III)acetylacetonate (abbr.: Ir(btp)$_2$(acac)), bis(1-phenylisoquinolinato-N,$C^{2'}$)iridium(III) acetylacetonate (abbr.: Ir(piq)$_2$(acac)), (acetylacetonato)bis[2,3-bis(4-fluorophenyl)quinoxalinato] iridium(III) (abbr.: Ir(Fdpq)$_2$(acac)), and 2,3,7,8,12,13,17, 18-octaethyl-21H,23H-porphyrin platinum(II) (abbr.: PtOEP). In addition, a rare earth metal complex such as tris(acetylacetonato)(monophenanthroline)terbium(III) (abbr.: Tb(acac)$_3$(Phen)), tris(1,3-diphenyl-1,3-propanedionato)(monophenanthroline)europium(III) (abbr.: Eu(DBM)$_3$ (Phen)), or tris[1-(2-thenoyl)-3,3,3-trifluoroacetonato] (monophenanthroline)europium(III) (abbr.: Eu(TTA)$_3$ (Phen)) performs light emission (electron transition between different multiplicities) from a rare earth metal ion; therefore, such a rare earth metal complex can be used as a phosphorescent compound.

Examples of fluorescent compounds which can be used for the light-emitting layer are as follows. Examples of materials for blue light emission are as follows: N,N'-bis[4-(9H-carbazol-9-yl)phenyl]-N,N'-diphenylstilbene-4,4'-diamine (abbr.: YGA2S), 4-(9H-carbazol-9-yl)-4'-(10-phenyl-9-anthryl) triphenylamine (abbr.: YGAPA), and the like. Examples of materials for green light emission are as follows: N-(9,10-diphenyl-2-anthryl)-N,9-diphenyl-9H-carbazol-3-amine (abbr.: 2PCAPA), N-[9,10-bis(1,1'-biphenyl-2-yl)-2-anthryl]-N,9-diphenyl-9H-carbazol-3-amine (abbr.: 2PCAB-PhA), N-(9,10-diphenyl-2-anthryl)-N,N',N'-triphenyl-1,4-phenylenediamine (abbr.: 2DPAPA), N-[9,10-bis(1,1'-biphenyl-2-yl)-2-anthryl]-N,N',N'-triphenyl-1,4-phenylenediamine (abbr.: 2DPABPhA), N-[9,10-bis(1,1'-biphenyl-2-yl)]-N-[4-(9H-carbazol-9-yl)phenyl]-N-phenylanthracen-2-amine (abbr.: 2YGABPhA), N,N,9-triphenylanthracen-9-amine (abbr.: DPhAPhA), and the like. Examples of materials for yellow light emission are as follows: rubrene, 5,12-bis(1,1'-biphenyl-4-yl)-6,11-diphenyltetracene (abbr.: BPT), and the like. Examples of materials for red light emission are as follows N,N,N',N'-tetrakis(4-methylphenyl)tetracene-5,11-diamine (abbr.: p-mPhTD), 7,13-diphenyl-N,N,N',N'-tetrakis(4-methylphenyl)acenaph-tho[1,2-α]fluoranthene-3,10-d iamine (abbr.: p-mPhAFD), and the like.

Note that the light-emitting layer may have a structure in which any of the above substances having a high light-emitting property (guest material) is dispersed into another substance (host material). As a substance into which the substance having a light-emitting property is dispersed, various kinds of materials can be used, and it is preferable to use a substance whose lowest unoccupied molecular orbital (LUMO) level is higher than that of the substance having a light-emitting property and whose highest occupied molecular orbital (HOMO) level is lower than that of the substance having a light-emitting property.

Specific examples of the substance into which the substance having a light-emitting property is dispersed are as follows: metal complexes such as tris(8-quinolinolato)aluminum(III) (abbr.: Alq), tris(4-methyl-8-quinolinolato)aluminum(III) (abbr.: Almq$_3$), bis(10-hydroxybenzo[h]quinolinato)beryllium(II) (abbr.: BeBq$_2$), bis(2-methyl-8-quinolinolato)(4-phenylphenolato)aluminum(III) (abbr.: BAlq), bis(8-quinolinolato)zinc(II) (abbr.: Znq), bis[2-(2-benzoxazolyl)phenolato]zinc(II) (abbr.: ZnPBO), and bis[2-(2-benzothiazolyl)phenolato]zinc(II) (abbr.: ZnBTZ); heterocyclic compounds such as 2-(4-biphenylyl)-5-(4-tert-butylphenyl)-1,3,4-oxadiazole (abbr.: PBD), 1,3-bis[5-(p-tert-butylphenyl)-1,3,4-oxadiazol-2-yl]benzene (abbr.: OXD-7), 3-(4-biphenylyl)-4-phenyl-5-(4-tert-butylphenyl)-1,2,4-triazole (abbr.: TAZ01), 2,2',2''-(1,3,5-benzenetriyl)tris(1-phenyl-1H-benzimidazole) (abbr.: TPBI), bathophenanthroline (abbr.: BPhen), and bathocuproine (abbr.: BCP); condensed aromatic compounds such as 9-[4-(10-phenyl-9-anthryl)phenyl]-9H-carbazole (abbr.: CzPA), 3,6-diphenyl-9-[4-(10-phenyl-9-anthryl)phenyl]-9H-carbazole (abbr.: DPCzPA), 9,10-bis(3,5-diphenylphenyl)anthracene (abbr.: DPPA), 9,10-di(2-naphthyl)anthracene (abbr.: DNA), 2-tert-butyl-9,10-di(2-naphthyl)anthracene (abbr.: t-BuDNA), 9,9'-bianthryl (abbr.: BANT), 9,9'-(stilbene-3,3'-diyl)diphenanthrene (abbr.: DPNS), 9,9'-(stilbene-4,4'-diyl)diphenanthrene (abbr.: DPNS2), 3,3',3''-(benzene-1,3,5-triyl)tripyrene (abbr.: TPB3), 9,10-diphenylanthracene (abbr.: DPAnth), and 6,12-dimethoxy-5,11-diphenylchrysene; aromatic amine compounds such as N,N-dipheyl-9-[4-(10-phenyl-9-anthryl)phenyl]-9H-carbazol-3-amine (abbr.: CzAlPA), 4-(10-phenyl-9-anthryl)triphenylamine (abbr.: DPhPA), N,9-diphenyl-N-[4-(10-phenyl-9-anthryl)phenyl]-9H-carbazol-3-amine (abbr.: PCAPA), N,9-diphenyl-N-{4-[4-(10-phenyl-9-anthryl)phenyl]phenyl}-9H-carbazol-3-amine (abbr.: PCAPBA), N-(9,10-diphenyl-2-anthryl)-N,9-diphenyl-9H-carbazol-3-amine (abbr.: 2PCAPA), NPB (or α-NPD), TPD, DFLDPBi, and BSPB; and the like.

As the substance into which the substance having a light-emitting property is dispersed, a plurality of kinds of substances can be used. For example, in order to suppress crystallization, a substance for suppressing crystallization such as rubrene or the like may be further added. Furthermore, in order to efficiently transfer energy to the substance having a light-emitting property, NPB, Alq, or the like may be further added.

When the light-emitting layer 103 has a structure in which the substance having a high light-emitting property is dispersed into another substance, crystallization of the light-emitting layer 113 can be suppressed. Further, concentration quenching due to high concentration of the substance having a high light-emitting property can be suppressed.

Note that for the light-emitting layer 113, a high molecular compound can be used. Specifically, examples of materials for blue light emission are as follows: poly(9,9-dioctylfluorene-2,7-diyl) (abbr.: POF), poly[(9,9-dioctylfluorene-2,7-diyl)-co-(2,5-dimethoxybenzene-1,4-diyl)] (abbr.: PF-DMOP), poly{(9,9-dioctylfluorene-2,7-diyl)-co-[N,N'-di-(p-butylphenyl)-1,4-diaminobenzene]}, (abbr.: TAB-PFH), and the like. Examples of materials for green light emission are as follows: poly(p-phenylenevinylene) (abbr.: PPV), poly[(9,9-dihexylfluorene-2,7-diyl)-all-co-(benzo[2,1,3]thiadiazole-4,7-diyl)] (abbr.: PFBT), poly[(9,9-dioctyl-2,7-divinylenefluorenylene)-alt-co-(2-methoxy-5-(2-ethylhexyloxy)-1,4-phenylene)], and the like. Examples of materials for orange to red light emission are as follows: poly[2-methoxy-5-(2'-ethylhexoxy)-1,4-phenylenevinylene] (abbr.: MEH-PPV), poly(3-butylthiophene-2,5-diyl) (abbr.: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbr.: CN-PPV-DPD), and the like.

The electron-transporting layer 114 is a layer including a substance having a high electron-transporting property. The quinoxaline derivative shown in Embodiment Mode 1 is superior in an electron-transporting property, so the quinoxaline derivative can be suitably used for the electron-transporting layer 114. Note that the electron-transporting layer is not limited to a single layer, and may be a stack of two or more layers.

In the case where the electron-transporting layer has a stacked structure of two or more layers, an example of another substance having a high electron-transporting property is a low molecular organic compound, and examples thereof are metal complexes such as tris(4-methyl-8-quinolinolato)aluminum(III) (abbr.: Almq$_3$), bis(10-hydroxybenzo[h]quinolinato)beryllium(II) (abbr.: BeBq$_2$), bis(2-methyl-8-quinolinolato)(4-phenylphenolato)aluminum (III) (abbr.: BAlq), bis(8-quinolinolato)zinc(II) (abbr.: Znq), bis[2-(2-benzoxazolyl)phenolato]zinc(II) (abbr.: ZnPBO), and bis[2-(2-benzothiazolyl)phenolato]zinc(II) (abbr.: ZnBTZ). Further, examples other than metal complexes are heterocyclic compounds such as 2-(4-biphenylyl)-5-(4-tert-butylphenyl)-1,3,4-oxadiazole (abbr.: PBD), 1,3-bis[5-(p-tert-butylphenyl)-1,3,4-oxadiazol-2-yl]benzene (abbr.: OXD-7), 3-(4-biphenylyl)-4-phenyl-5-(4-tert-butylphenyl)-1,2,4-triazole (abbr.: TAZ01), 2,2',2''-(1,3,5-benzenetriyl)tris(1-phenyl-1H-benzimidazole) (abbr.: TPBI), bathophenanthroline (abbr.: BPhen), and bathocuproine (abbr.: BCP). The substances mentioned here mainly have an electron mobility of $10^{-6}$ cm$^2$/Vs or higher. Note that substances other than the substances mentioned above may also be used for the electron-transporting layer as long as the electron-transporting properties thereof are higher than the hole-transporting properties thereof. Note that the electron-transporting layer is not limited to a single layer, but two or more layers including the above-mentioned substances may be stacked.

In the case where the electron-transporting layer has a stacked structure of two or more layers, an example of another substance having a high electron-transporting property is a high molecular compound. Examples thereof are poly[(9,9-dihexylfluorene-2,7-diyl)-co-(pyridine-3,5-diyl)] (abbr.: PF-Py), poly[(9,9-dioctylfluorene-2,7-diyl)-co-(2,2'-bipyridine-6,6'-diyl)] (abbr.: PF-BPy), and the like.

The electron-injecting layer 115 is a layer including a substance having a high electron-injecting property. As a substance having a high electron-injecting property, an alkali metal, an alkaline earth metal, or a compound thereof such as lithium fluoride (LiF), cesium fluoride (CsF), or calcium fluoride (CaF$_2$) can be used. For example, a layer of a substance having an electron-transporting property which further includes an alkali metal, an alkaline earth metal, or a compound thereof, for example, a layer of Alq which further includes magnesium (Mg), can be used. Note that as the electron-injecting layer, it is preferable to use the layer formed of a substance having an electron-transporting property which further includes an alkali metal or an alkaline earth metal because electrons can be efficiently injected from the second electrode 104.

As a substance for forming the second electrode 104, a metal, an alloy, an electrically conductive compound, a mixture thereat or the like with a low work function (specifically, a work function of 3.8 eV or lower is preferable) can be used. Specific examples of such cathode materials are given as follows: elements belonging to Group 1 and Group 2 of the periodic table, that is, alkali metals such as lithium (Li) and cesium (Cs) and alkaline earth metals such as magnesium (Mg), calcium (Ca), and strontium (Sr); alloys thereof (MgAg, AlLi); rare earth metals such as europium (Eu) and ytterbium (Yb); alloys thereof; and the like. A film of an alkali metal, an alkaline earth metal, or an alloy thereof can be formed by a vacuum evaporation method. In addition, a film of an alloy including an alkali metal or an alkaline earth metal can be formed by a sputtering method. Further, a film can be formed using a silver paste or the like by an inkjet method or the like.

In the case where the electron-injecting layer 115 which is a layer functioning to promote electron injection is provided between the second electrode 104 and the electron-transporting layer 114, the second electrode 104 can be formed using various conductive materials such as Al, Ag, ITO, and indium tin oxide containing silicon or silicon oxide, regardless of their work functions. A film of such a conductive material can be formed by a sputtering method, an inkjet method, a spin coating method, or the like.

Various methods can be used for forming the EL layer, regardless of whether they are dry methods or wet methods. For example, a vacuum evaporation method, an inkjet method, a spin coating method, or the like may be used. As described above, the EL layer generally includes a hole-injecting layer, a hole-transporting layer, a light-emitting layer, an electron-transporting layer, an electron-injecting layer, and the like. In forming these layers, film formation methods which are suitable for materials for forming the layers are preferably used, but one common film formation method can also be used. Note that in forming each electrode, a similar method can also be employed as described above.

For example, the EL layer may be formed by a wet method using a high molecular compound selected from the above-mentioned materials. Alternatively, the EL layer can be formed by a wet method using a low molecular organic compound. Furthermore, the EL layer may be formed by a dry method such as a vacuum evaporation method using a low molecular organic compound.

The electrodes may be formed by a wet method using a sol-gel method, or by a wet method using a paste of a metal material. Further, the electrodes may be formed by a dry method such as a sputtering method or a vacuum evaporation method.

For example, in the case where a light-emitting element of the present invention is applied to a display device and the display device is manufactured using a large-sized substrate, it is preferable to form the light-emitting layer by a wet method. When the light-emitting layer is formed by an inkjet method, it becomes easy to form the light-emitting layers separately for different colors even when a large-sized substrate is used.

In a light-emitting element of the present invention having the above-described structure, current flows due to a potential difference generated between the first electrode 102 and the second electrode 104, whereby holes and electrons are recombined in the EL layer 103 and light emission is obtained.

Light emission is extracted to the outside through one of or both the first electrode 102 and the second electrode 104. Accordingly, one of or both the first electrode 102 and the second electrode 104 are electrodes having a light-transmitting property. For example, when only the first electrode 102 has a light-transmitting property, light emission is extracted from the substrate side through the first electrode 102. Alternatively, when only the second electrode 104 has a light-transmitting property, light emission is extracted from the side opposite to the substrate through the second electrode 104. When both the first electrode 102 and the second electrode 104 have a light-transmitting property, light emission is extracted from both the substrate side and the side opposite to the substrate through the first electrode 102 and the second electrode 104.

Note that the structure of the layers provided between the first electrode 102 and the second electrode 104 is not limited to the above structure. Any structure other than the above structure can be employed as long as a light-emitting region where holes and electrons are recombined with each other is positioned away from the first electrode 102 and the second electrode 104 so as to prevent light-quenching that can be caused by proximity of the light-emitting region to metal and as long as the quinoxaline derivative shown in Embodiment Mode 1 is included.

That is, there is no particular limitation on the stacked structure of layers, and the quinoxaline derivative shown in Embodiment Mode 1 may be appropriately combined with a layer formed of a substance having a high electron-transporting property, a substance having a high hole-transporting property, a substance having a high electron-injecting property, a substance having a high hole-injecting property, a bipolar substance (a substance having high electron-transporting and hole-transporting properties), or the like.

Figure 2:
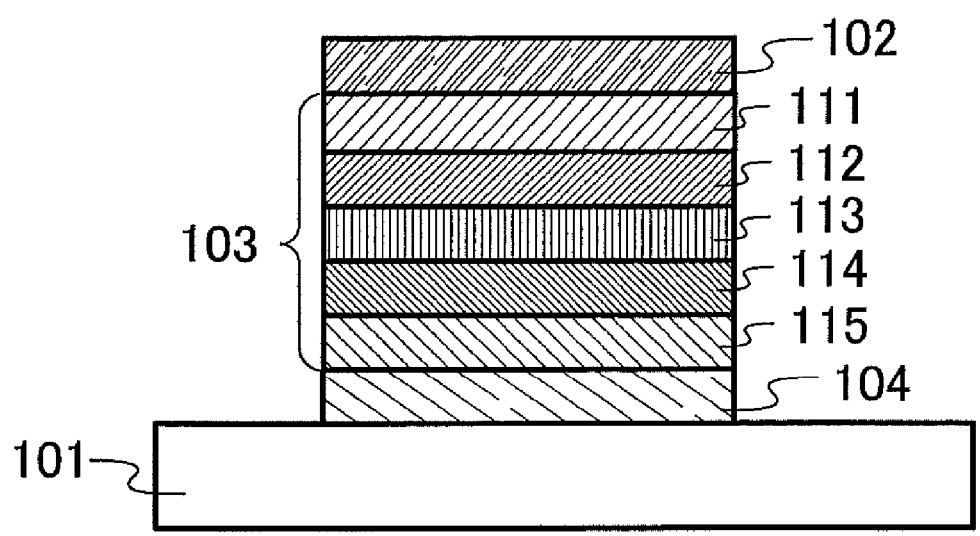
FIG. 2 is a diagram illustrating a light-emitting element of the present invention.

In addition, as illustrated in FIG. 2, a structure may be employed in which the second electrode 104 serving as a cathode, the EL layer 103, and the first electrode 102 serving as an anode are stacked sequentially over the substrate 101. In FIG. 2, a structure is employed in which the electron-injecting layer 115, the electron-transporting layer 114, the light-emitting layer 113, the hole-transporting layer 112, and the hole-injecting layer 111 are stacked sequentially over the second electrode 104.

Note that in this embodiment mode, the light-emitting element is formed over a substrate made of glass, plastic, or the like. By forming a plurality of such light-emitting elements over a substrate, a passive matrix light-emitting device can be manufactured. Moreover, for example, thin film transistors (TFTs) may be formed over a substrate made of glass, plastic, or the like and light-emitting elements may be manufactured over electrodes which are electrically connected to the TFTs. Thus, an active matrix light-emitting device which controls the driving of light-emitting elements with PFTs can be manufactured. Note that a structure of the TFT is not particularly limited, and either a staggered TFT or an inverted staggered TFT may be used. In addition, a driving circuit formed over a TFT substrate may be formed using an n-channel TFT and a p-channel TFT, or may be formed using either an n-channel TFT or a p-channel TFT. In addition, the crystallinity of a semiconductor film used for the TFT is not particularly limited. Either an amorphous semiconductor film or a crystalline semiconductor film may be used for the TFT. Further, a single crystal semiconductor film may be used. A single crystal semiconductor film can be formed by a Smart Cut (registered trademark) method or the like.

Because the quinoxaline derivatives shown in Embodiment Mode 1 have an excellent electron-transporting property, the quinoxaline derivatives can be suitably used for an electron-transporting layer of the light-emitting element. By using any of the quinoxaline derivatives shown in Embodiment Mode 1, a light-emitting element with low driving voltage can be obtained. In addition, a light-emitting element with low power consumption can be obtained.

Note that this embodiment mode can be appropriately combined with another embodiment mode.

Embodiment Mode 3

In this embodiment mode, a structure in which any of the quinoxaline derivatives shown in Embodiment Mode 1 is used for a light-emitting layer is described as one mode of a light-emitting element of the present invention.

Because the quinoxaline derivatives shown in Embodiment Mode 1 have an excellent electron-transporting property, the quinoxaline derivatives can each be used as a host material in a light-emitting layer having a structure in which a substance with a high light-emitting property (guest material) is dispersed in another substance (host material).

In the case where any of the quinoxaline derivatives shown in Embodiment Mode 1 is used as a host material and where a guest material emits fluorescence, it is preferable to use, as a guest material, a substance whose lowest unoccupied molecular orbital (LUMO) level is lower than that of each quinoxaline derivative show in Embodiment Mode 1 and whose highest occupied molecular orbital (HOMO) level is higher than that of each quinoxaline derivative shown in Embodiment Mode 1. Examples of materials for blue light emission are as follows N,N'-bis[4-(9H-carbazol-9-yl)phenyl]-N,N'-diphenylstilbene-4,4'-diamine (abbr.: YGA2S), 4-(9H-carbazol-9-yl)-4'-(10-phenyl-9-anthryl)triphenylamine (abbr.: YGAPA), and the like. Examples of materials for green light emission are as follows: N-(9,10-diphenyl-2-anthryl)-N,9-diphenyl-9H-carbazol-3-amine (abbr.: 2PCAPA), N-[9,10-bis(1,1'-biphenyl-2-yl)-2-anthryl]-N,9-diphenyl-9H-carbazol-3-amine (abbr.: 2PCABPhA), N-(9,10-diphenyl-2-anthryl)-N,N',N'-triphenyl-1,4-phenylenediamine (abbr.: 2DPAPA), N-[9,10-bis(1,1'-biphenyl-2-yl)-2-anthryl]-N,N',N'-triphenyl-1,4-phenylenediamine (abbr.: 2DPABPhA), N-[9,10-bis(1,1'-biphenyl-2-yl)]-N-[4-(9H-carbazol-9-yl)phenyl]-N-phenylanthracen-2-amine (abbr.: 2YGABPhA), N,N,9-triphenylanthracen-9-amine (abbr.: DPhAPhA), and the like. Examples of materials for yellow light emission are as follows: rubrene, 5,12-bis(1,1'-biphenyl-4-yl)-6,11-diphenyltetracene (abbr.: BPT), and the like. Examples of materials for red light emission are as follows N,N,N',N'-tetrakis(4-methylphenyl)tetracene-5,11-diamine (abbr.: p-mPhTD), 7,13-diphenyl-N,N,N',N'-tetrakis(4-methylphenyl)acenaphtho[1,2-a]fluoranthene-3,10-diamine (abbr.: p-mPhAFD), and the like.

Alternatively, in the case where the quinoxaline derivative shown in Embodiment Mode 1 is used as a host material and where a guest material emits phosphorescence, it is preferable to use, as a guest material, a substance having lower triplet excitation energy than the quinoxaline derivative shown in Embodiment Mode 1. Examples include organometallic complexes such as bis[2-(2'-benzo[4,5-α]thienyl)pyridinato-N,$C^{3'}$]iridium(III) acetylacetonate (abbr.: Ir(btp)$_2$(acac)), bis (1-phenylisoquinolinato-N,$C^{2'}$)iridium(III) acetylacetonate (abbr.: Ir(piq)$_2$(acac)), (acetylacetonato)bis[2,3-bis(4-fluorophenyl)quinoxalinato]iridium(III) (abbr.: Ir(Fdpq)$_2$(acac)), and 2,3,7,8,12,13,17,18-octaethyl-21H,23H-porphyrin platinum(II) (abbr.: PtOEP).

Because the quinoxaline derivatives shown in Embodiment Mode 1 have an excellent electron-transporting property, by using any of the quinoxaline derivatives for a light-emitting layer, the light-emitting layer having a high electron-transporting property can be obtained. Such a light-emitting layer can provide light emission with high efficiency when a guest material with high electron-trapping property is used.

As the substance (host material) into which the substance having a light-emitting property (guest material) is dispersed, a plurality of kinds of substances can be used. Thus, the light-emitting layer may include a second host material in addition to any of the quinoxaline derivatives shown in Embodiment Mode 1. Since the quinoxaline derivatives shown in Embodiment Mode 1 have an excellent electron-transporting property, it is preferable to use a material having an excellent hole-transporting property as the second host material. With such a structure, the light-emitting layer has a hole-transporting property and an electron-transporting property, and the recombination probability of holes and electrons in the light-emitting layer is increased, so that light emission with high efficiency can be obtained. Further, a light-emitting element with low driving voltage can be obtained.

Note that this embodiment mode can be appropriately combined with another embodiment mode.

Embodiment Mode 4

In this embodiment mode, a structure in which any of the quinoxaline derivatives shown in Embodiment Mode 1 is used for an electron-injecting layer is described as one mode of a light-emitting element of the present invention.

Because the quinoxaline derivatives shown in Embodiment Mode 1 also have an excellent electron-injecting property, the quinoxaline derivatives can each be used for an electron-injecting layer of a light-emitting element. In the case where any of the quinoxaline derivatives shown in Embodiment Mode 1 is used for an electron-injecting layer, it is preferable for the electron-injecting layer to include an alkali metal, an alkaline earth metal, or a compound thereof in addition to any of the quinoxaline derivatives shown in Embodiment Mode 1. With such a structure, an electron-injecting property from an electrode serving as a cathode is increased, and a light-emitting element with low driving voltage can be obtained.

Note that this embodiment mode can be appropriately combined with another embodiment mode.

Embodiment Mode 5

In this embodiment mode, a mode of a light-emitting element according to the present invention in which a plurality of light-emitting units is stacked (hereinafter this light-emitting element is referred to as a stacked-type element) will be described with reference to FIG. 3. This light-emitting element is a stacked-type light-emitting element including a plurality of light-emitting units between a first electrode and a second electrode. The structure of each light-emitting unit can be similar to the structure described in Embodiment Modes 2 to 4. In other words, the light-emitting element described in Embodiment Mode 2 is a light-emitting element having one light-emitting unit. In this embodiment mode, a light-emitting element having a plurality of light-emitting units will be described.

Figure 3:
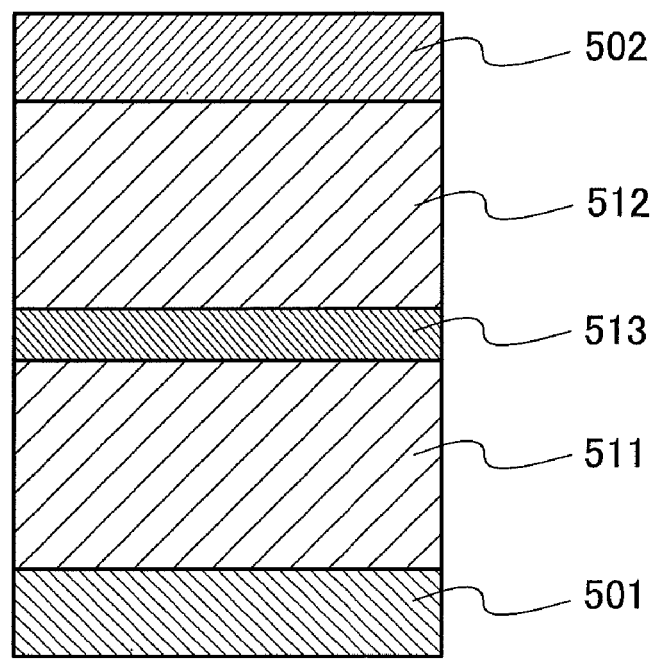
FIG. 3 is a diagram illustrating a light-emitting element of the present invention.

In FIG. 3, a first light-emitting unit 511, a charge-generating layer 513, and a second light-emitting unit 512 are stacked between a first electrode 501 and a second electrode 502. As the first electrode 501 and the second electrode 502, electrodes similar to the electrodes shown in Embodiment Mode 2 can be employed. Note that the first light-emitting unit 511 and the second light-emitting unit 512 may have the same structure or different structures, and may have a structure similar to the structure shown in Embodiment Mode 2.

The charge-generating layer 513 is a layer which injects electrons into a light-emitting unit on one side and injects holes into a light-emitting unit on the other side when voltage is applied to the first electrode 501 and the second electrode 502, and may be either a single layer or a stacked structure of two or more layers. As a stacked structure of two or more layers, a structure in which a hole-injecting layer and an electron-injecting layer are stacked is preferable.

As the hole-injecting layer, a semiconductor or an insulator, such as molybdenum oxide, vanadium oxide, rhenium oxide, or ruthenium oxide, can be used. Alternatively, the hole-injecting layer may have a structure in which an acceptor substance is added to a substance having a high hole-transporting property. The layer including a substance having a high hole-transporting property and an acceptor substance is formed of the composite material shown in Embodiment Mode 2 and includes, as an acceptor substance, 7,7,8,8-tetracyano-2,3,5,6-tetrafluoroquinodimethane (abbr.: $F_4$-TCNQ) or metal oxide such as vanadium oxide, molybdenum oxide, or tungsten oxide. As the substance having a high hole-transporting property, various compounds such as an aromatic amine compound, a carbazole derivative, an aromatic hydrocarbon, a high molecular compound (an oligomer, a dendrimer, and a polymer, or the like) can be used. Note that a substance having a hole mobility of $10^{-6}$ $cm^2/Vs$ or higher is preferably employed as the substance having a high hole-transporting property. However, other substances may also be used as long as the hole-transporting properties thereof are higher than the electron-transporting properties thereof. Since the composite material of the substance having a high hole-transporting property and the acceptor substance has excellent carrier-injecting and carrier-transporting properties, low-voltage driving and low-current driving can be realized.

As the electron-injecting layer, an insulator or a semiconductor, such as lithium oxide, lithium fluoride, or cesium carbonate, can be used. Alternatively, the electron-injecting layer may have a structure in which a donor substance is added to a substance having a high electron-transporting property. As the donor substance, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transporting property, the materials shown in Embodiment Mode 2 can be used. Note that a substance having an electron mobility of $10^{-6}$ $cm^2/Vs$ or higher is preferably employed as the substance having a high electron-transporting property. However, other substances may also be used as long as the electron-transporting properties thereof are higher than the hole-transporting properties thereof. Since the composite material of the substance having a high electron-transporting property and the donor substance has excellent carrier-injecting and carrier-transporting properties, low-voltage driving and low-current driving can be realized.

Further, the electrode materials shown in Embodiment Mode 2 can be used for the charge-generating layer 513. For example, the charge-generating layer 513 may be formed with a combination of a layer including a substance having a hole-transporting property and metal oxide with a transparent conductive film. Note that a layer having a high light-transmitting property is preferably used as the charge-generating layer in terms of light extraction efficiency.

In any case, it is acceptable as long as the charge-generating layer 513 interposed between the first light-emitting unit 511 and the second light-emitting unit 512 injects electrons into a light-emitting unit on one side and injects holes into a light-emitting unit on the other side when voltage is applied to the first electrode 501 and the second electrode 502. For example, any structure is acceptable for the charge-generating layer 513 as long as the charge-generating layer 513 injects electrons into the first light-emitting unit 511 and holes into the second light-emitting unit 512 when voltage is applied so that potential of the first electrode becomes higher than potential of the second electrode.

In this embodiment mode, the light-emitting element having two light-emitting units is described. However, the present invention can similarly be applied to a light-emitting element in which three or more light-emitting units are stacked. When a charge-generating layer is provided between a pair of electrode layers so as to partition a plurality of light-emitting units, like the light-emitting element of this embodiment mode, a long-life element in a high luminance range can be realized while current density is kept low. When the light-emitting element is applied to lighting, voltage drop due to resistance of an electrode material can be suppressed, thereby achieving homogeneous light emission in a large area. Moreover, a light-emitting device with low driving voltage and low power consumption can be realized.

When light-emitting units are formed to emit light of different colors from each other, a light-emitting element as a whole can provide light emission of a desired color. For example, when a light-emitting element having two light-emitting units is formed such that the emission color of the first light-emitting unit and the emission color of the second light-emitting unit are complementary to each other, the light-emitting element can provide white light emission as a whole. Note that "complementary colors" refer to colors which can produce an achromatic color when mixed. That is, when light emitted from substances which emit light of complementary colors is mixed, white light emission can be obtained. The same can be applied to a light-emitting element which has three light-emitting units. For example, the light-emitting element as a whole can provide white light emission when the emission color of the first light-emitting unit is red, the emission color of the second light-emitting unit is green, and the emission color of the third light-emitting unit is blue.

Note that this embodiment mode can be appropriately combined with another embodiment mode.

Embodiment Mode 6

In this embodiment mode, a light-emitting device having a light-emitting element of the present invention will be described.

Figure 4A:
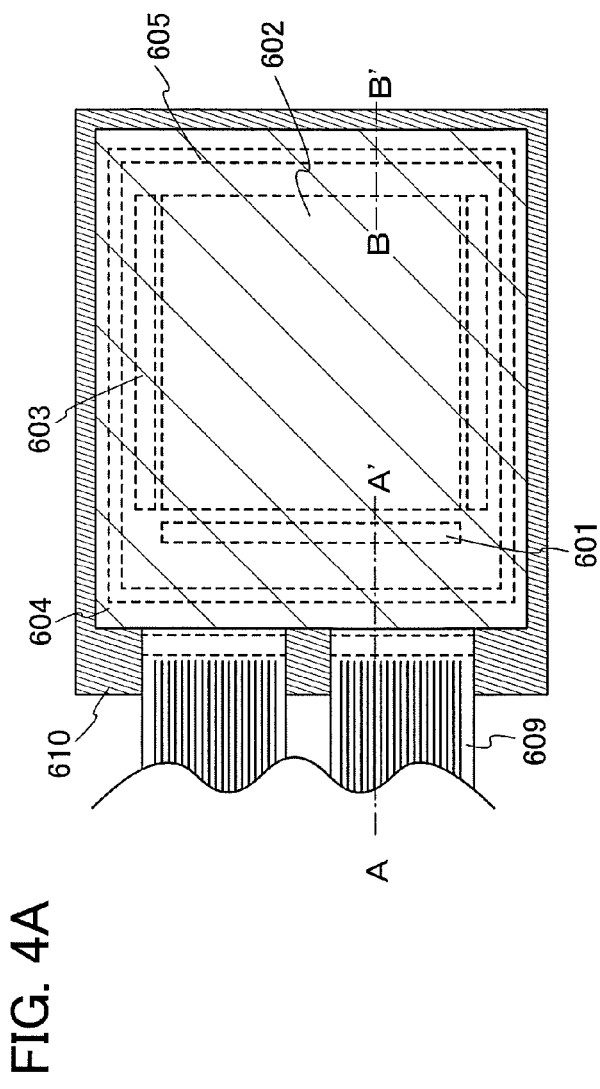
FIGS. 4A and 4B are diagrams illustrating a light-emitting device of the present invention.
Figure 4B:
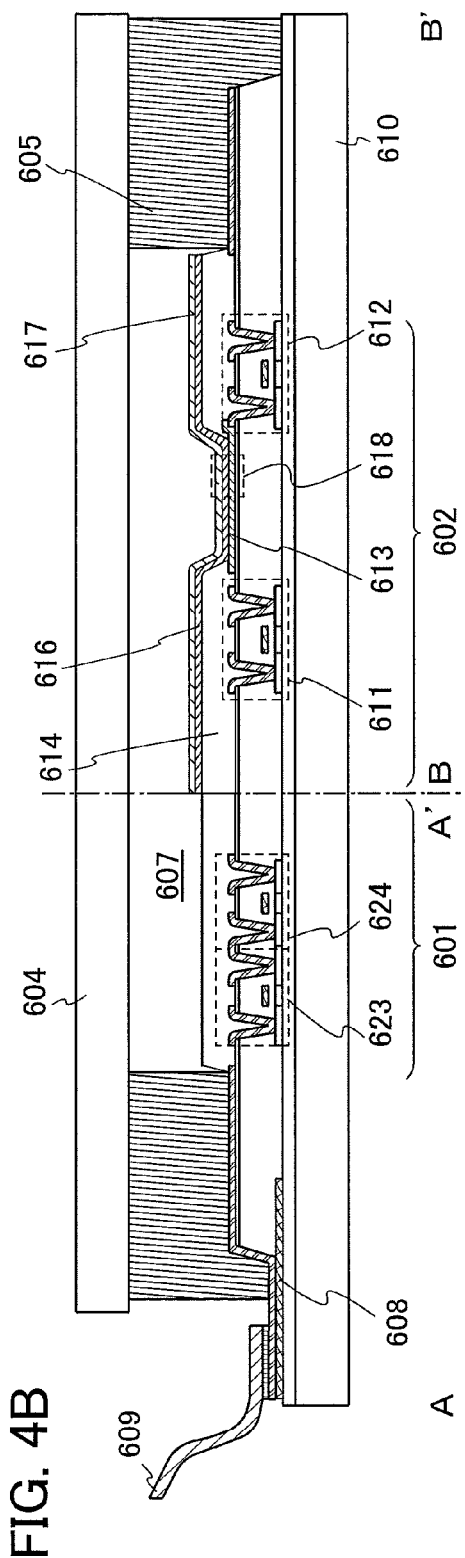

A light-emitting device having a light-emitting element of the present invention in a pixel portion is described in this embodiment mode with reference to FIGS. 4A and 4B. Note that FIG. 4A is a top view illustrating the light-emitting device and FIG. 4B is a cross-sectional view of FIG. 4A taken along lines A-A' and B-B'. This light-emitting device includes a driver circuit portion (source side driver circuit) 601, a pixel portion 602, and a driver circuit portion (gate side driver circuit) 603, which are indicated by dotted lines, in order to control the light emission of the light-emitting element. Further, reference numeral 604 denotes a sealing substrate and reference numeral 605 denotes a sealing material. Reference numeral 607 denotes a space surrounded by the sealing material 605.

Note that a leading wiring 608 is a wiring for transmitting signals that are input to the source side driver circuit 601 and the gate side driver circuit 603. The leading wiring 608 receives video signals, clock signals, start signals, reset signals, and the like from an FPC (flexible printed circuit) 609 that serves as an external input terminal. Although only an FPC is illustrated here, this FPC may be provided with a printed wiring board (PWB). The light-emitting device in this specification includes not only a light-emitting device itself but also a light-emitting device with an FPC or a PWB attached thereto.

Then, a cross-sectional structure is described with reference to FIG. 4B. The driver circuit portions and the pixel portion are provided over an element substrate 610, but only the source side driver circuit 601, which is the driver circuit portion, and one pixel of the pixel portion 602 are illustrated in FIG. 4B.

Note that a CMOS circuit which is a combination of an n-channel TFT 623 and a p-channel TFT 624 is formed in the source side driver circuit 601. The driver circuit may be formed with various CMOS circuits, PMOS circuits, or NMOS circuits. In this embodiment mode, a driver-integrated type in which a driver circuit is formed over the substrate provided with the pixel portion is described; however, the present invention is not limited to this type, and the driver circuit can be formed outside the substrate.

The pixel portion 602 includes a plurality of pixels each having a switching TFT 611, a current controlling TFT 612, and a first electrode 613 that is electrically connected to a drain of the current controlling TFT 612. Note that an insulator 614 is formed to cover the edge portion of the first electrode 613. Here, a positive photosensitive acrylic resin film is used to form the insulator 614.

Further, in order to improve the coverage, the insulator 614 is provided such that either an upper edge portion or a lower edge portion of the insulator 614 has a curved surface with a curvature. For example, when positive photosensitive acrylic is used as a material for the insulator 614, it is preferable that only an upper edge portion of the insulator 614 have a curved surface with a radius of curvature (0.2 μm to 3 μm). The insulator 614 can be formed using either a negative type that becomes insoluble in an etchant by light irradiation or a positive type that becomes soluble in an etchant by light irradiation.

An EL layer 616 and a second electrode 617 are formed over the first electrode 613. Here, various metals, alloys, electrically conductive compounds, or mixtures thereof can be used for a material of the first electrode 613. If the first electrode is used as an anode, it is preferable that the first electrode be formed using a metal, an alloy, an electrically conductive compound, or a mixture thereof with a high work function (preferably, a work function of 4.0 eV or higher) among such materials. For example, the first electrode 613 can be formed using a single-layer film such as an indium tin oxide film containing silicon, an indium zinc oxide film, a titanium nitride film, a chromium film, a tungsten film, a Zn film, a Pt film, or the like; a stacked film of a titanium nitride film and a film containing aluminum as its main component; or a three-layer structure of a titanium nitride film, a film containing aluminum as its main component, and a titanium nitride film. Note that when a stacked structure is employed, the first electrode 613 has low resistance as a wiring, forms a favorable ohmic contact, and can serve as an anode.

The EL layer 616 is formed by various methods such as an evaporation method using an evaporation mask, an inkjet method, a spin coating method, and the like. The EL layer 616 includes the layer for controlling carrier transfer shown in Embodiment Modes 2 to 5. Any of a low molecular compound, a high molecular compound (an oligomer, a dendrimer, and a polymer, or the like) may be employed as a material for the EL layer 616. As the material for the EL layer, not only an organic compound but also an inorganic compound may be used.

As the material for the second electrode 617, various types of metals, alloys, electrically conductive compounds, mixtures thereof, and the like can be used. If the second electrode is used as a cathode, it is preferable that the second electrode be formed using a metal, an alloy, an electrically conductive compound, a mixture thereof, or the like with a low work function (preferably, a work function of 3.8 eV or lower) among such materials. Examples include: elements belonging to Group 1 and Group 2 of the periodic table, that is, alkali metals such as lithium (Li) and cesium (Cs) and alkaline earth metals such as magnesium (Mg), calcium (Ca), and strontium (Sr); alloys thereof (MgAg, AlLi); and the like. In the case where light generated in the EL layer 616 is transmitted through the second electrode 617, the second electrode 617 may also be formed using a stacked layer of a thin metal film with a small film thickness and a transparent conductive film (indium tin oxide (ITO), indium tin oxide containing silicon or silicon oxide, indium zinc oxide (IZO), indium oxide containing tungsten oxide and zinc oxide (IWZO), or the like).

By attaching the sealing substrate 604 and the element substrate 610 to each other with the sealing material 605, a light-emitting element 618 is provided in the space 607 which is surrounded by the element substrate 610, the sealing substrate 604, and the sealing material 605. Note that the space 607 is filled with a filler. There are also cases where the space 607 may be filled with an inert gas (such as nitrogen or argon) as such a filler, or where the space 607 may be filled with the sealing material 605.

As the sealing material 605, an epoxy-based resin is preferably used. In addition, it is desirable that a material thereof allows as little moisture or oxygen as possible to permeate. As the sealing substrate 604, a plastic substrate formed of fiberglass-reinforced plastics (FRP), polyvinyl fluoride (PVF), polyester, acrylic, or the like can be used besides a glass substrate or a quartz substrate.

As described above, the light-emitting device including a light-emitting element of the present invention can be obtained.

A light-emitting device of the present invention includes any of the light-emitting elements shown in Embodiment Modes 2 to 5. Driving voltage of each light-emitting element shown in Embodiment Modes 2 to 5 is low; therefore, a light-emitting device with low power consumption can be obtained.

Figure 5A:
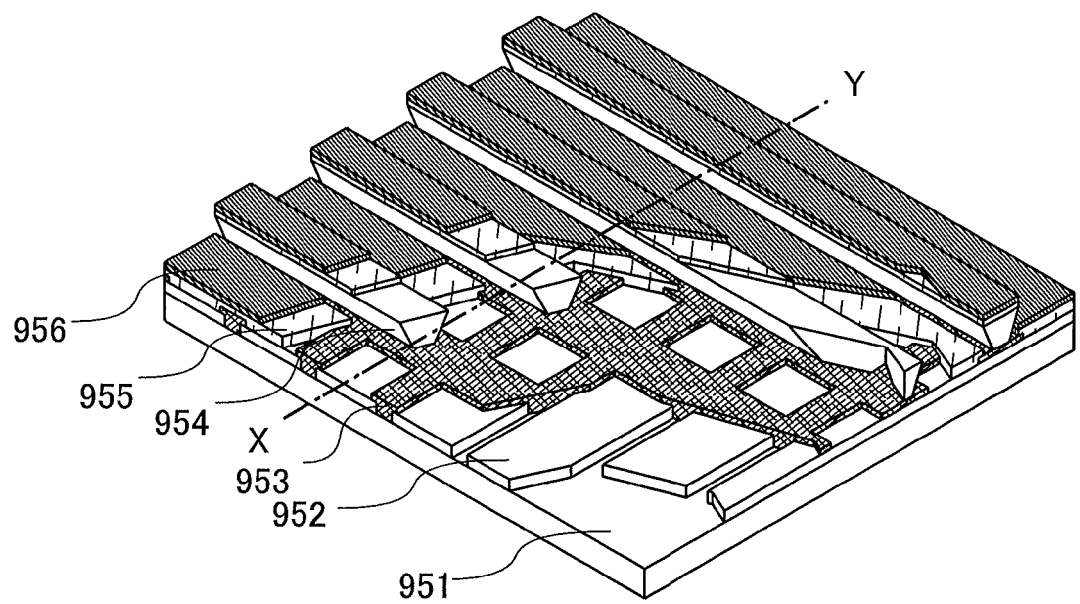
FIGS. 5A and 5B are diagrams illustrating a light-emitting device of the present invention.
Figure 5B:
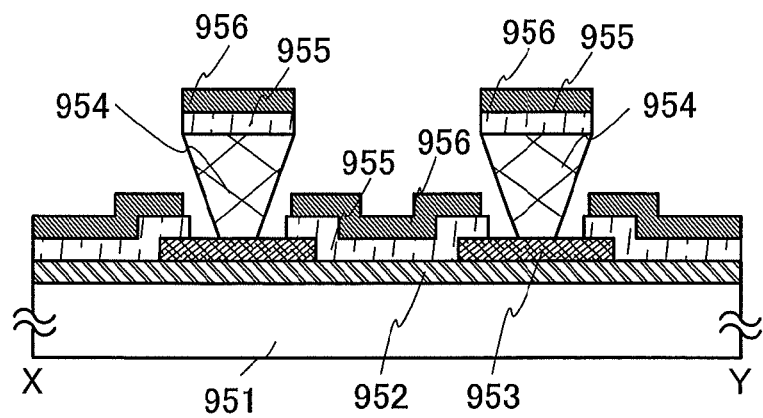

As described above, an active matrix light-emitting device that controls driving of a light-emitting element with a transistor is described in this embodiment mode; however, a passive matrix light-emitting device may be used. FIGS. 5A and 5B illustrate a passive matrix light-emitting device manufactured according to the present invention. Note that FIG. 5A is a perspective view of the light-emitting device and FIG. 5B is a cross-sectional view of FIG. 5A taken along a line X-Y. In FIGS. 5A and 5B, an EL layer 955 is provided between an electrode 952 and an electrode 956 over a substrate 951. The edge portion of the electrode 952 is covered with an insulating layer 953. A partition layer 954 is provided over the insulating layer 953. The sidewalls of the partition layer 954 slope so that the distance between one sidewall and the other sidewall is gradually reduced toward the surface of the substrate. In other words, a cross section taken along the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other one of the pair of parallel sides). The EL layer 955 and the electrode 956 can be patterned by providing the partition layer 954 in this manner. In addition, in a passive matrix light-emitting device, a light-emitting device with low power consumption can be obtained by including a light-emitting element with low driving voltage according to the present invention.

Note that this embodiment mode can be appropriately combined with another embodiment mode.

Embodiment Mode 7

In this embodiment mode, an electronic device of the present invention which includes the light-emitting device shown in Embodiment Mode 6 will be described. An electronic device of the present invention includes any of the light-emitting elements described in Embodiment Modes 2 to 5 and a display portion with low power consumption.

Examples of electronic devices each manufactured using a light-emitting device of the present invention can be given as follows: cameras such as video cameras and digital cameras, goggle type displays, navigation systems, audio reproducing devices (car audio sets, audio component sets, and the like), computers, game machines, portable information terminals (mobile computers, cellular phones, portable game machines, electronic book readers, and the like), image reproducing devices each provided with a storage medium (specifically, devices each provided with a display device that can reproduce a storage medium such as a digital versatile disc (DVD) and display the image), and the like. Specific examples of these electronic devices are illustrated in FIGS. 6A to 6D.

Figure 6A:
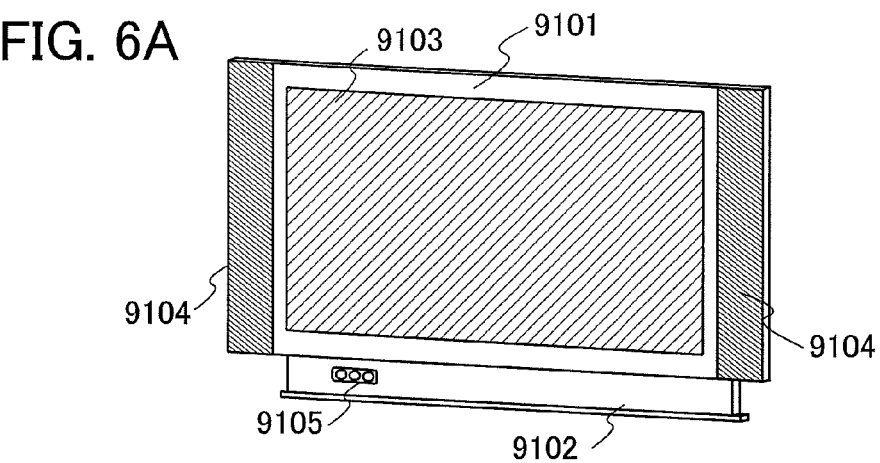
FIGS. 6A to 6D are diagrams each illustrating an electronic device of the present invention.

FIG. 6A illustrates a television device of this embodiment mode, which includes a housing 9101, a support 9102, a display portion 9103, speaker portions 9104, a video input terminal 9105, and the like. In the display portion 9103 of this television device, light-emitting elements similar to those described in Embodiment Modes 2 to 5 are arranged in matrix. Features of the light-emitting elements are that driving voltage is low and power consumption is low. The display portion 9103 which includes the light-emitting elements has similar features. Therefore, in this television device, low power consumption is achieved. With such features, a power supply circuit can be significantly reduced or downsized in the television device; therefore, reduction in size and weight of the housing 9101 and the support 9102 can be achieved. In the television device of this embodiment mode, reduction in power consumption and reduction in size and weight are achieved; therefore, a product which is suitable for living environment can be provided.

Figure 6B:
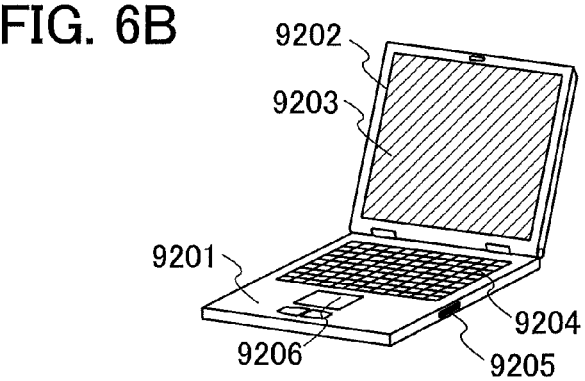

FIG. 6B illustrates a computer of this embodiment mode, which includes a main body 9201, a housing 9202, a display portion 9203, a keyboard 9204, an external connection port 9205, a pointing device 9206, and the like. In the display portion 9203 of this computer, light-emitting elements similar to those described in Embodiment Modes 2 to 5 are arranged in matrix. Features of the light-emitting element are that driving voltage is low and power consumption is low. The display portion 9203 which includes the light-emitting elements has similar features. Therefore, in this computer, lower power consumption is achieved. With such features, a power supply circuit can be significantly reduced or downsized in the computer; therefore, reduction in size and weight of the main body 9201 and the housing 9202 can be achieved. In the computer of this embodiment mode, reduction in power consumption and reduction in size and weight are achieved; therefore, a product which is suitable for environment can be provided.

Figure 6C:
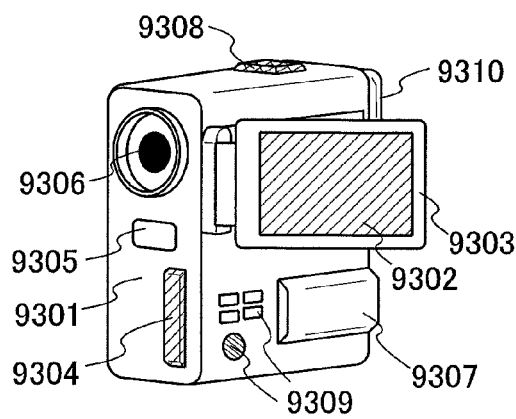

FIG. 6C illustrates a camera that includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiment Modes 2 to 5 are arranged in matrix. Features of the light-emitting elements are that driving voltage is low and power consumption is low. The display portion 9302 which includes the light-emitting elements has similar features. Therefore, in this camera, lower power consumption is achieved. With such features, a power supply circuit can be significantly reduced or downsized in the camera; therefore, reduction in size and weight of the main body 9301 can be achieved. In the camera of this embodiment mode, reduction in power consumption and reduction in size and weight are achieved; therefore, a product which is suitable for being carried around can be provided.

Figure 6D:
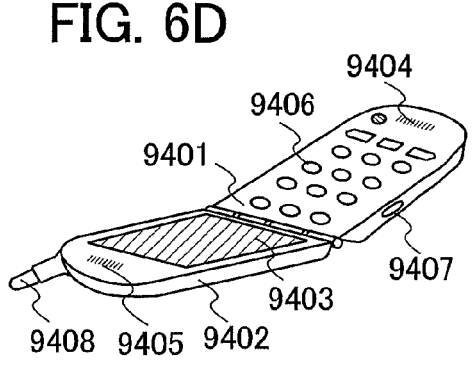

FIG. 6D illustrates a cellular phone of this embodiment mode, which includes a main body 9401, a housing 9402, a display portion 9403, an audio input portion 9404, an audio output portion 9405, operation keys 9406, an external connection port 9407, an antenna 9408, and the like. In the display portion 9403 of this cellular phone, light-emitting elements similar to those described in Embodiment Modes 2 to 5 are arranged in matrix. Features of the light-emitting elements are that driving voltage is low and power consumption is low. The display portion 9403 which includes the light-emitting elements has similar features. Therefore, in this cellular phone, lower power consumption is achieved. With such features, a power supply circuit can be significantly reduced or downsized in the cellular phone; therefore, reduction in size and weight of the main body 9401 and the housing 9402 can be achieved. In the cellular phone of this embodiment mode, reduction in power consumption and reduction in size and weight are achieved; therefore, a product which is suitable for being carried around can be provided.

Figure 12A:
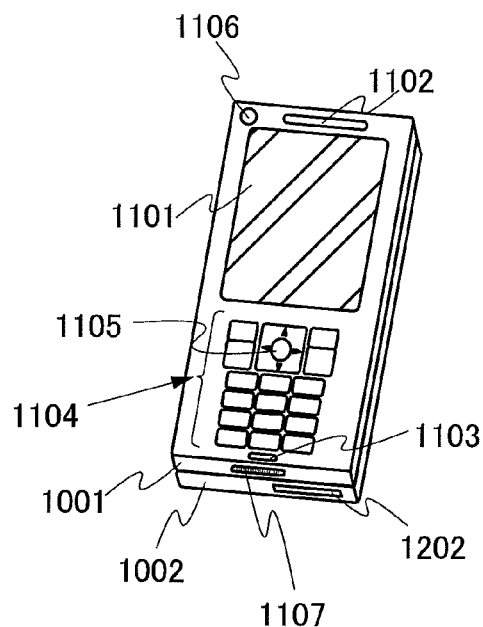
FIGS. 12A to 12C are diagrams illustrating an electronic device of the present invention.
Figure 12B:
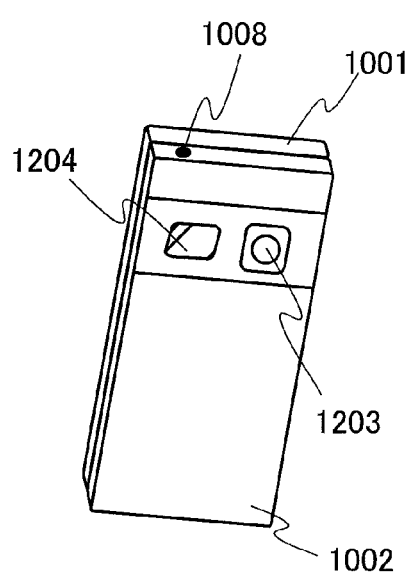
Figure 12C:
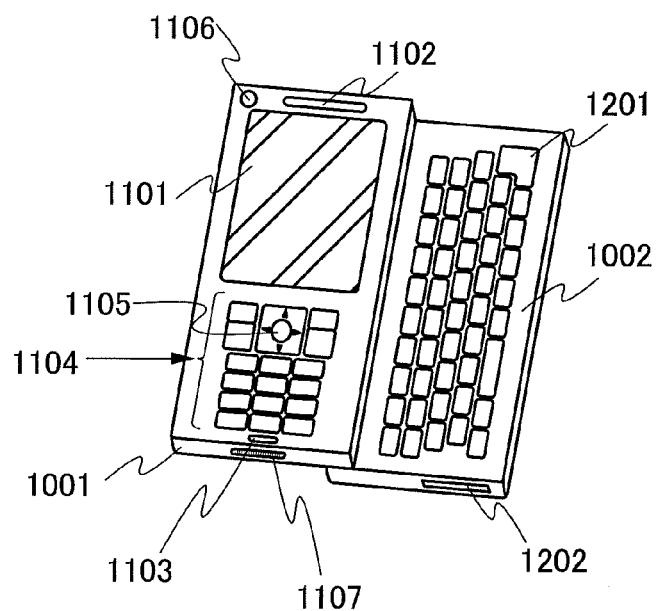

FIGS. 12A to 12C illustrate an example of a structure of a cellular phone, which is different from a structure of the cellular phone of FIG. 6D. FIG. 12A is a front view, FIG. 12B is a rear view, and FIG. 12C is a development view. The cellular phone in FIGS. 12A to 12C is a so-called smartphone which has both a function as a phone and a function as a portable information terminal, and incorporates a computer to conduct a variety of data processing in addition to voice calls.

The cellular phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, an earphone terminal 1008, and the like, while the housing 1002 includes a keyboard 1201, an external memory slot 1202, a camera lens 1203, a light 1204, and the like. In addition, an antenna is incorporated in the housing 1001.

In addition to the above structure, the cellular phone may incorporate a non-contact IC chip, a small-sized memory device, or the like.

In the display portion 1101, the light-emitting device shown in Embodiment Mode 6 can be incorporated, and a display direction can be appropriately changed depending on the usage mode. The cellular phone is provided with the camera lens 1106 on the same surface as the display portion 1101; therefore, the cellular phone can be used as a videophone. Further, a still image and a moving image can be taken with the camera lens 1203 and the light 1204 using the display portion 1101 as a viewfinder. The speaker 1102 and the microphone 1103 can be used for video calls, recording, reproducing, and the like without being limited to voice calls. With the use of the operation keys 1104, making and receiving calls, inputting simple information such as e-mail or the like, scrolling the screen, moving the cursor, and the like are possible. Furthermore, the housing 1001 and the housing 1002 (FIG. 12A), which are overlapped with each other, are developed by sliding as show in FIG. 12C and can be used as a portable information terminal. In this case, smooth operation can be conducted using the keyboard 1201 and the pointing device 1105. The external connection terminal 1107 can be connected to an AC adaptor and various types of cables such as a USB cable, and charging, data communication with a computer, and the like are possible. Furthermore, a large amount of data can be stored and moved by inserting a storage medium into the external memory slot 1202.

In addition to the above functions, the cellular phone may include an infrared communication function, a television receiving function, or the like.

Figure 7:
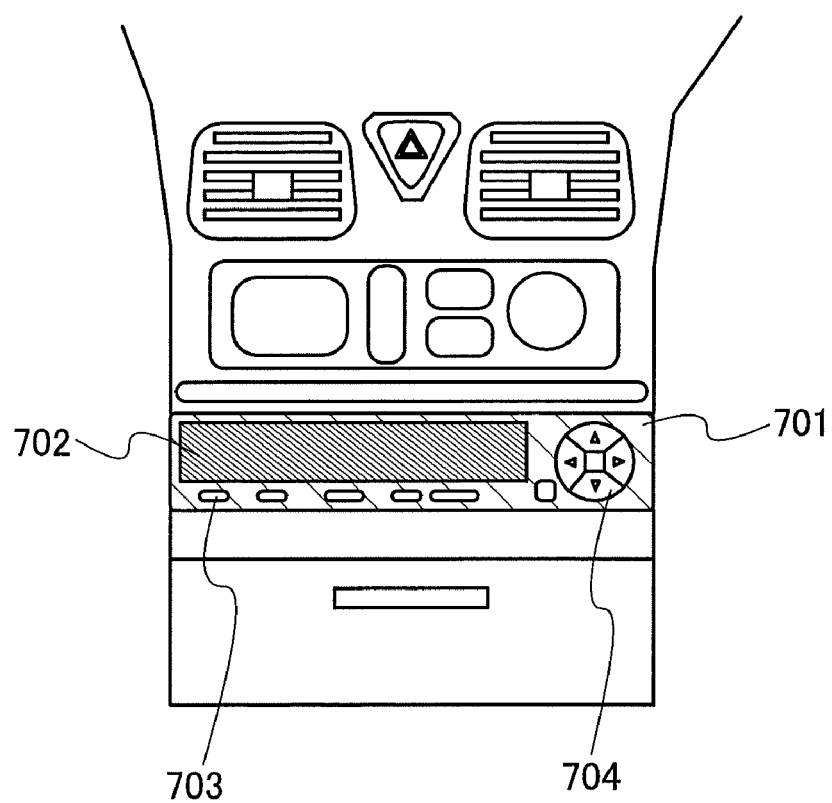
FIG. 7 is a diagram illustrating an electronic device of the present invention.

FIG. 7 illustrates an audio reproducing device, specifically, a car audio system, which includes a main body 701, a display portion 702, and operation switches 703 and 704. The display portion 702 can be realized with the light-emitting device (passive matrix type or active matrix type) described in Embodiment Mode 6. Further, the display portion 702 may be formed using a segment type light-emitting device. In any case, the use of a light-emitting element of the present invention makes it possible to form a bright display portion while achieving low power consumption, with the use of a vehicle power source (12 V to 42 V). Furthermore, although this embodiment mode describes an in-car audio system, a light-emitting device of the present invention may also be used in portable audio systems or audio systems for home use.

Figure 8:
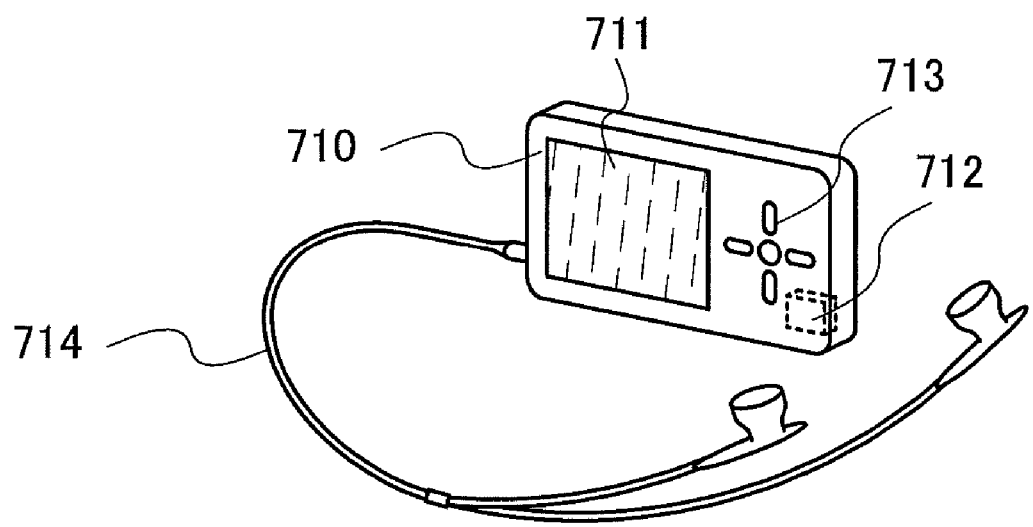
FIG. 8 is a diagram illustrating an electronic device of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that headphones or wireless earphones can be used instead of the earphones 714. The display portion 711 can be realized with the light-emitting device (passive matrix type or active matrix type) described in Embodiment Mode 6. Further, the display portion 711 may be formed using a segment type light-emitting device. In any case, the use of a light-emitting element of the present invention makes it possible to form a bright display portion which can display images even when using a secondary battery (a nickel-hydrogen battery or the like) while achieving low power consumption. As the memory portion 712, a hard disk or a nonvolatile memory is used. For example, by using a NAND-type nonvolatile memory with a recording capacity of 20 to 200 gigabytes (GB) and by operating the operating portion 713, an image or a sound (music) can be recorded and reproduced. Note that in the display portion 702 and the display portion 711, white characters are displayed against a black background, and thus, power consumption can be reduced. This is particularly effective for portable audio systems.

As described above, the applicable range of the light-emitting device manufactured by applying the present invention is so wide that the light-emitting device is applicable to electronic devices in various fields. By applying the present invention, an electronic device which has a display portion consuming low power can be manufactured.

A light-emitting device to which the present invention is applied has a light-emitting element with high light emission efficiency and can also be used as a lighting device. One mode of using a light-emitting element to which the present invention is applied as a lighting device is described with reference to FIG. 9.

Figure 9:
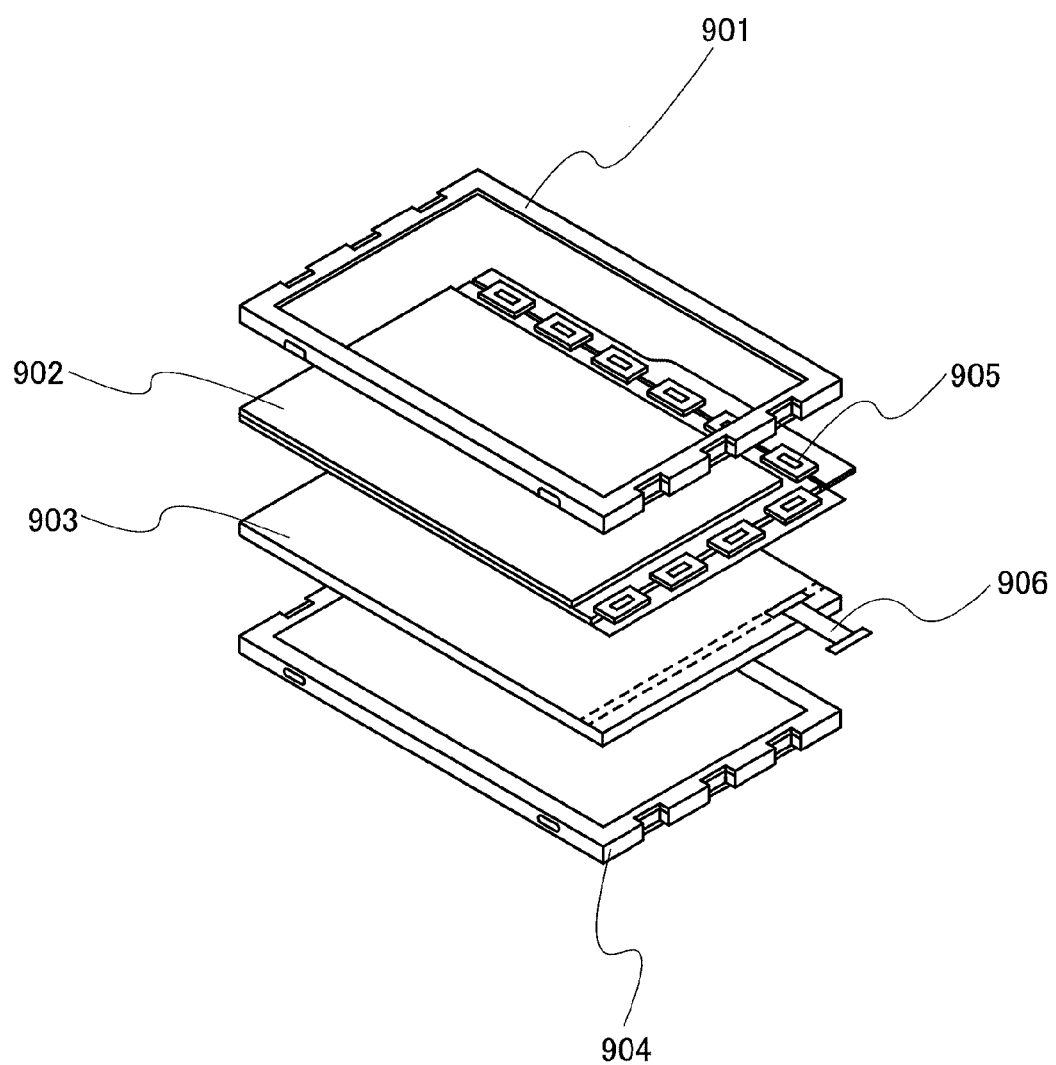
FIG. 9 is a diagram illustrating an electronic device of the present invention.

FIG. 9 illustrates a liquid crystal display device using the light-emitting device to which the present invention is applied as a backlight, as an example of the electronic device using a light-emitting device according to the present invention as a lighting device. The liquid crystal display device illustrated in FIG. 9 includes a housing 901, a liquid crystal layer 902, a backlight 903, and a housing 904, and the liquid crystal layer 902 is connected to a driver IC 905. The light-emitting device to which the present invention is applied is used as the backlight 903, and current is supplied through a terminal 906.

Because the light-emitting device according to the present invention is thin and consumes less power, reduction in thickness and power consumption of a liquid crystal display device is possible by using a light-emitting device according to the present invention as a backlight of the liquid crystal display device. Moreover, a light-emitting device according to the present invention is a plane emission type lighting device and can have a large area. Thus, the backlight can have a large area, and a liquid crystal display device having a large area can also be obtained.

Figure 10:
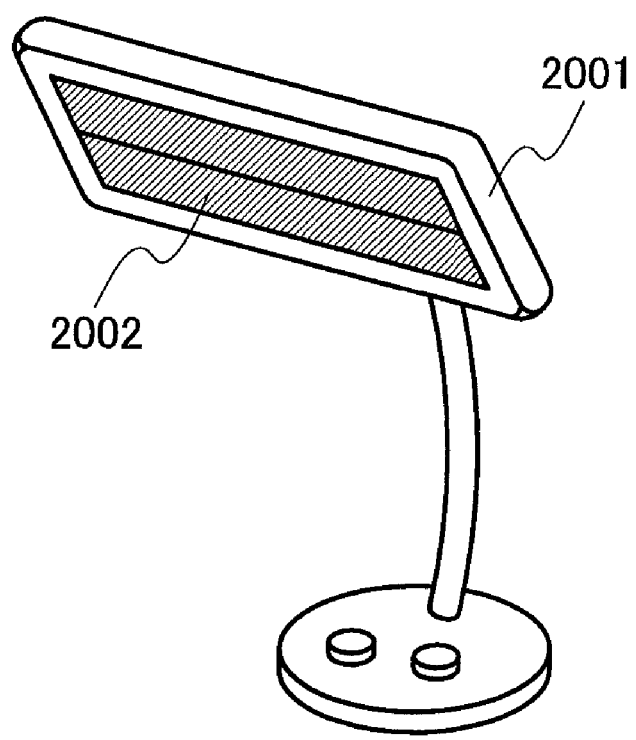
FIG. 10 is a diagram illustrating a lighting device of the present invention.

FIG. 10 illustrates an example in which a light-emitting device according to the present invention is used as a desk lamp, which is one of lighting devices. The desk lamp illustrated in FIG. 10 includes a housing 2001 and a light source 2002, and a light-emitting device according to the present invention is used as the light source 2002. Because a light-emitting device of the present invention consumes less power, the desk lamp also consumes less power.

Figure 11:
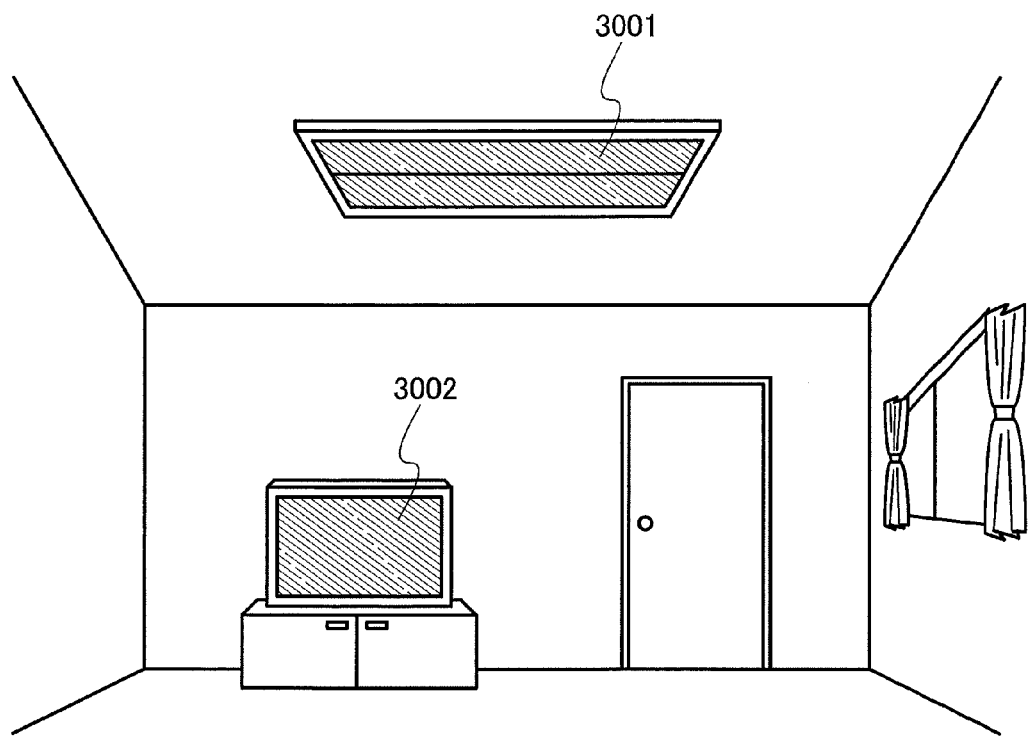
FIG. 11 is a diagram illustrating a lighting device of the present invention.

FIG. 11 illustrates an example in which a light-emitting device to which the present invention is applied is used as an interior lighting device 3001. Because a light-emitting device according to the present invention can have a large area, a light-emitting device according to the present invention can be used as a lighting device having a large area. Moreover, because a light-emitting device according to the present invention consumes less power, a light-emitting device according to the present invention can be used as a lighting device which consumes less power. Thus, a television device 3002 according to the present invention as illustrated in FIG. 6A may be placed in a room where a light-emitting device to which the present invention is applied is used as the interior lighting device 3001, and public broadcasting or movies can be watched there. In such a case, since both devices consume less power, environmental load can be reduced.

Note that this embodiment mode can be appropriately combined with another embodiment mode.

Embodiment 1

In this embodiment, a method for synthesizing 2-phenyl-3-[4-(2-pyridyl)phenyl]quinoxaline (abbr.: 2Py1PQ) represented by the structural formula (101) is described.

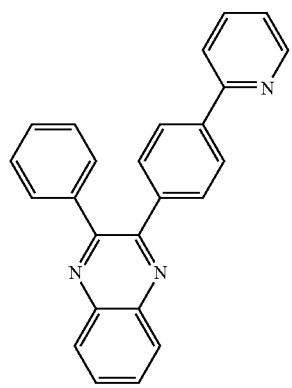

(101)

Step 1: Synthesis of (4-bromophenyl)phenylacetylene

A synthetic scheme of (4-bromophenyl)phenylacetylene is shown in (A-1).

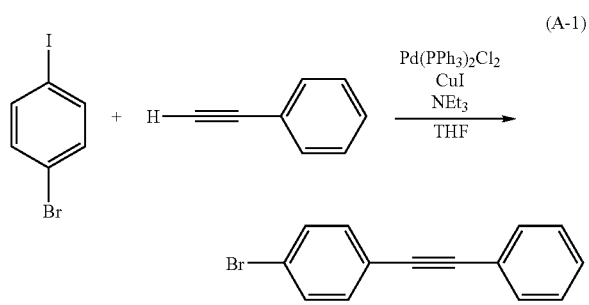

(A-1)

In a 500 mL three-necked flask were placed 14 g (51 mmol) of p-bromoiodobenzene, 5.2 g (52 mmol) of phenylacetylene, and 98 mg (0.50 mmol) of copper(I) iodide. After the atmosphere in the flask was replaced with nitrogen, 200 mL of tetrahydrofuran and 9.0 mL of triethylamine were added to the flask, and the mixture was degassed by being stirred under reduced pressure. To this mixture was added 0.34 mg (0.50 mmol) of bis(triphenylphosphine)palladium(II)dichloride, and the mixture was stirred under nitrogen stream at room temperature for 20 hours. After a predetermined time, a 3% aqueous hydrochloric acid solution was added to the mixture, and an organic substance was extracted with ethyl acetate from the aqueous layer. The obtained extract was washed with a saturated aqueous sodium chloride solution together with the organic layer and then dried over magnesium sulfate. The mixture was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was condensed to obtain a solid. The obtained solid was recrystallized with hexane; thus, 7.4 g of target light-brown powder was obtained with a yield of 55%.

Step 2: Synthesis of 1-(4-bromophenyl)-2-phenylethanedione

A synthetic scheme of 1-(4-bromophenyl)-2-phenylethanedione is shown in (A-2).

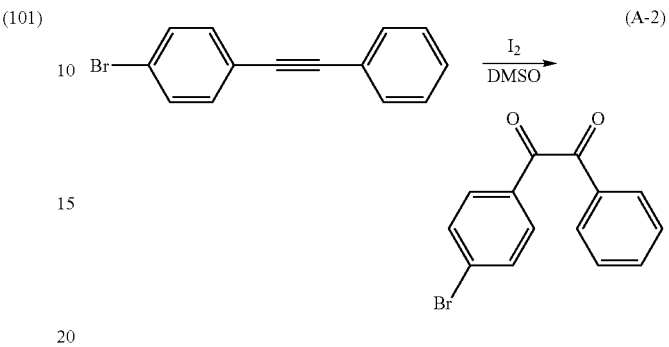

(A-2)

In a 300 mL three-necked flask were placed 7.4 g (28 mmol) of (4-bromophenyl)phenylacetylene, 3.7 g (14 mmol) of iodine, and 70 mL of dimethyl sulfoxide. The solution was stirred under nitrogen stream at 155° C. for 4 hours. After a predetermined time, the solution was cooled to room temperature and added to a 1 wt % aqueous sodium thiosulfate solution; then, a solid was precipitated. The solid was collected by suction filtration. The obtained solid was dissolved in ethyl acetate, and the solution was subjected to suction filtration through Celite (produced by Wako Pure Chemical Industries, Ltd., Catalog No. 531-16855). The filtrate was condensed to obtain a solid. The obtained solid was recrystallized with ethyl acetate/hexane; thus, 4.5 g of target pale-yellow powder was obtained with a yield of 71%.

Step 3: Synthesis of 2-(4-bromophenyl)-3-phenylquinoxaline

A synthetic scheme of 2-(4-bromophenyl)-3-phenylquinoxaline is shown in (A-3).

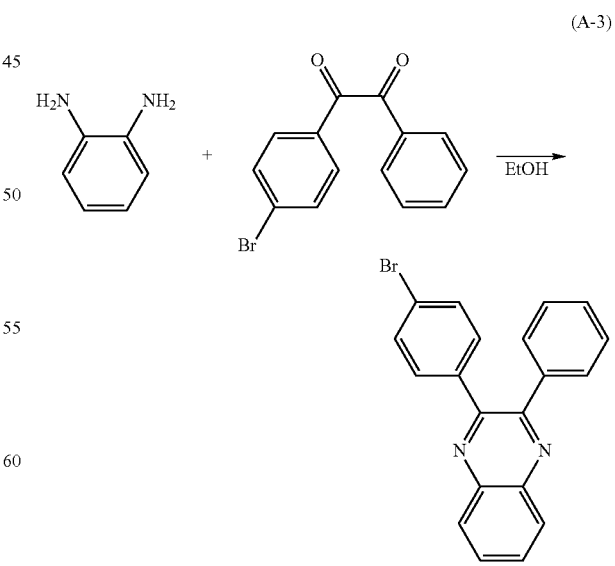

(A-3)

In a 200 mL recovery flask were placed 4.5 g (15 mmol) of 1-(4-bromophenyl)-2-phenylethanedione, 1.8 g (17 mmol) of ortho-phenylenediamine, and 50 mL of ethanol. This solution was refluxed under nitrogen stream for 2.5 hours. After a predetermined time, the solution was cooled to room temperature, and the precipitated solid was collected by suction filtration. The collected solid was washed with ethanol; thus, 5.2 g of target white powder was obtained with a yield of 92%.

Step 4: Synthesis of
4-(3-phenylquinoxalin-2-yl)phenylboronic acid

A synthetic scheme of 4-(3-phenylquinoxalin-2-yl)phenylboronic acid is shown in (A-4).

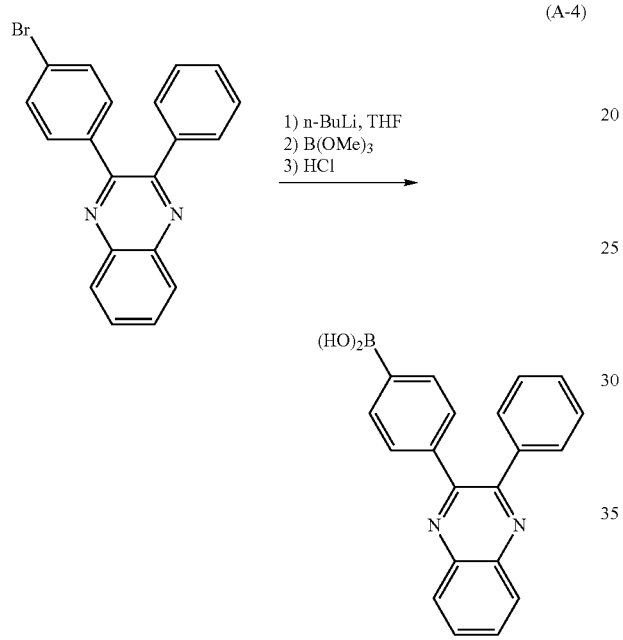

(A-4)

1) n-BuLi, THF
2) B(OMe)$_3$
3) HCl

In a 300 mL three-necked flask was placed 5.0 g (13 mmol) of 2-(4-bromophenyl)-3-phenylquinoxaline, and the atmosphere in the flask was replaced with nitrogen. There was added 40 mL of tetrahydrofuran, and the mixture was cooled to −78° C. under nitrogen stream. After cooling, 10 mL (16 mmol) of 1.6 M n-butyllithium was dripped thereinto, and the mixture was stirred at the same temperature for 1 hour. After a predetermined time, there was added 3.1 mL (27 mmol) of trimethyl borate, and the temperature of the solution was raised to room temperature, and then, the solution was stirred for 10 hours. After a predetermined time, the solution was cooled to 0° C., to which 100 mL of 0.1M hydrochloric acid was added, and the solution was stirred for 1 hour. After a predetermined time, an organic substance was extracted with ethyl acetate from the aqueous layer. The extract was washed with a saturated aqueous sodium chloride solution together with the organic layer and then dried over magnesium sulfate. The mixture was subjected to suction filtration through Celite (produced by Wako Pure Chemical Industries, Ltd., Catalog No. 531-16855). The obtained filtrate was condensed to obtain a solid. The solid was recrystallized with ethyl acetate/hexane; thus, 3.0 g of target pale-yellow powder was obtained with a yield of 66%.

Step 5: Synthesis of
2-phenyl-3-[4-(2-pyridyl)phenyl]quinoxaline (abbr.: 2Py1PQ)

A synthetic scheme of 2Py1PQ is shown in (A-5).

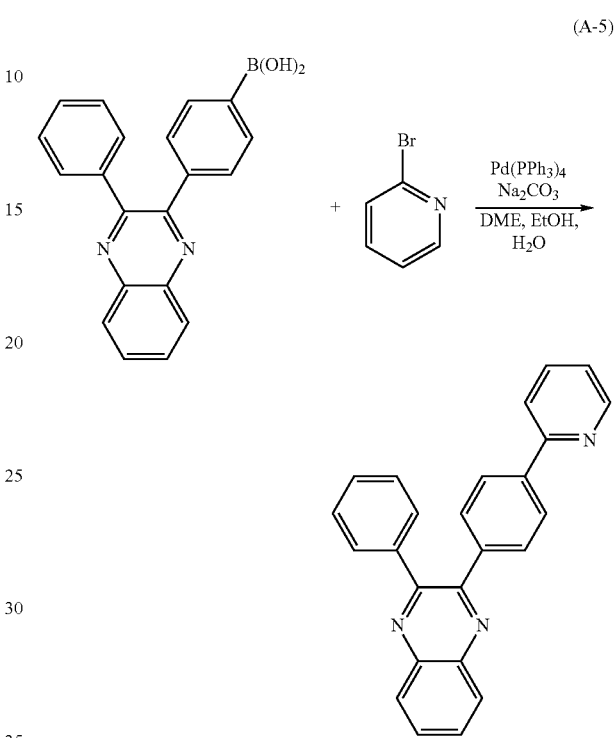

(A-5)

In a 100 mL three-necked flask were placed 1.3 g (4.0 mmol) of 4-(3-phenylquinoxalin-2-yl)phenylboronic acid, 0.65 g (4.1 mmol) of 2-bromopyridine, 1.1 g (10 mmol) of sodium carbonate, 5.0 mL of water, 10 mL of ethylene glycol dimethyl ether (DME), and 4.0 mL of ethanol. The mixture was degassed by being stirred under reduced pressure, and the atmosphere in the flask was replaced with nitrogen. To the mixture was added 49 mg (0.043 mmol) of tetrakis(triphenylphosphine)palladium(0), which was refluxed under nitrogen stream for 7 hours. After a predetermined time, water was added to the mixture, and an organic substance was extracted with ethyl acetate from the aqueous layer. The extract was washed with a saturated aqueous sodium hydrogen carbonate solution and a saturated aqueous sodium chloride solution together with the organic layer, and the organic layer was then dried over magnesium sulfate. The obtained mixture was subjected to suction filtration through Celite (produced by Wako Pure Chemical Industries, Ltd., Catalog No. 531-16855), and the filtrate was condensed to obtain a solid. The obtained solid was purified by silica gel column chromatography (developing solvent: chloroform) and further recrystallized with chloroform/hexane; thus, 1.1 g of target white powder was obtained with a yield of 77%.

Then, 1.1 g of the obtained target substance was subjected to sublimation purification at 165° C. under an argon stream (flow rate: 3.0 mL/min) and a pressure of 10 Pa for 18 hours; thus, 0.68 g of the target substance was obtained at a collection rate of 61%. The compound was measured by nuclear magnetic resonance (NMR) spectrometry and identified as 2-phenyl-3-[4-(2-pyridyl)phenyl]quinoxaline (abbr.: 2Py1PQ).

Figure 13A:
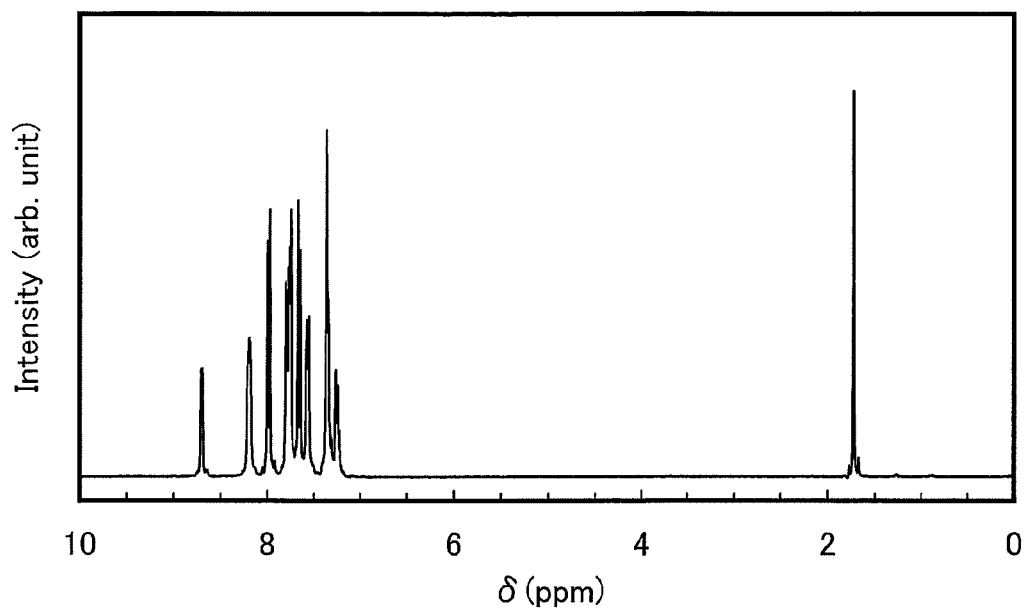
FIGS. 13A and 13B are diagrams each showing a $^1$H NMR chart of 2-phenyl-3-[4-(2-pyridyl)phenyl]quinoxaline (abbr.: 2Py1PQ).
Figure 13B:
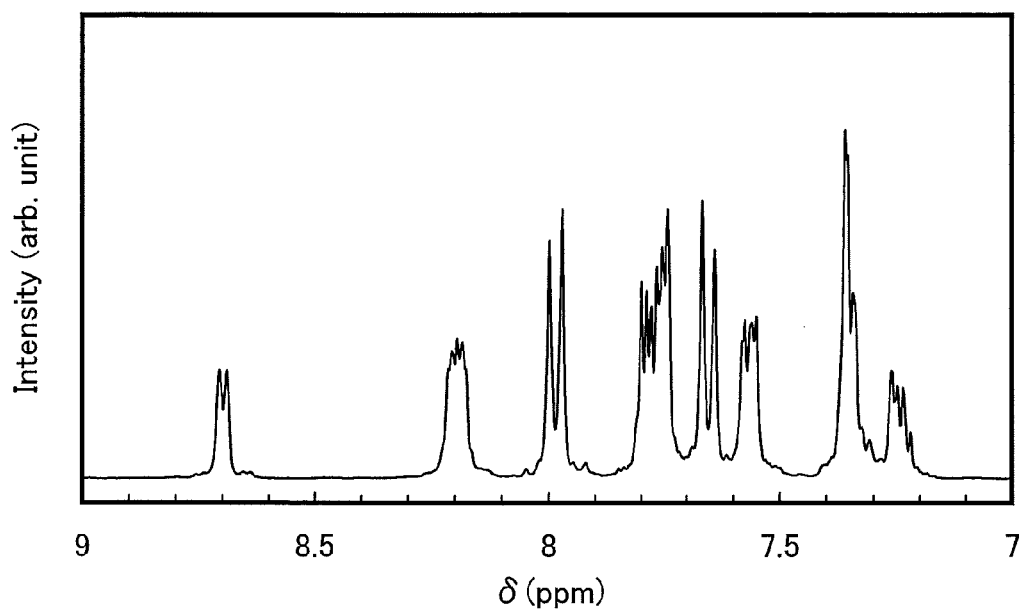

The $^1$H NMR data is given as follows. $^1$H NMR (300 MHz, CDCl$_3$): δ (ppm)=7.22-7.26 (m, 1H), 7.30-7.36 (m, 3H), 7.55-7.57 (m, 2H), 7.65 (d, J=8.1 Hz, 2H), 7.74-7.79 (m, 4H), 7.98 (d, J=8.4 Hz, 2H), 8.18-8.21 (m, 2H), 8.70 (d, J=4.8 Hz, 1H). FIGS. 13A and 13B show $^1$H NMR charts. Note that FIG. 13B shows an enlarged chart showing the range from 7.0 ppm to 9.0 ppm in FIG. 13A.

Thermogravimetry-differential thermal analysis (TG-DTA) of 2Py1PQ obtained was performed. The measurement was performed using a high vacuum differential type differential thermal balance (TG-DTA2410SA, manufactured by Bruker AXS K.K.). The measurement was performed under normal pressure at a rate of temperature rise of 10° C./min under a nitrogen stream (flow rate: 200 mL/min). It was found from the relationship between weight and temperature (thermogravimetry) that the 5% weight loss temperature was 303° C. and the melting point was 180° C.

Figure 14:
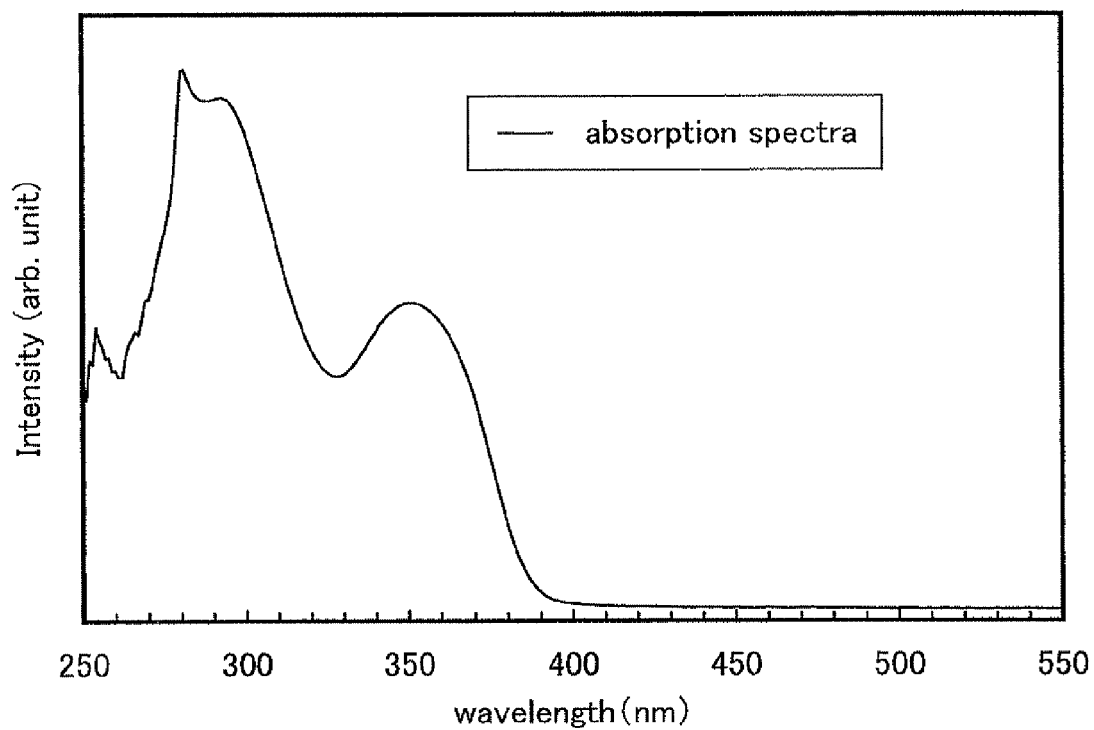
FIG. 14 is a diagram showing absorption spectrum of a toluene solution of 2-phenyl-3-[4-(2-pyridyl)phenyl]quinoxaline (abbr.: 2Py1PQ).

FIG. 14 shows absorption spectrum of a toluene solution of 2Py1PQ. The measurement was performed using an ultraviolet-visible spectrophotometer (V-550, manufactured by JASCO Corporation). The solution was placed in a quartz cell. The absorption spectrum from which the absorption spectrum of quartz is subtracted is shown in FIG. 14. In FIG. 14, the horizontal axis represents wavelength (nm) and the vertical axis represents intensity (arb. unit). In the case of the toluene solution, absorptions were observed at around 281 nm, 293 nm, and 351 nm.

Figure 15:
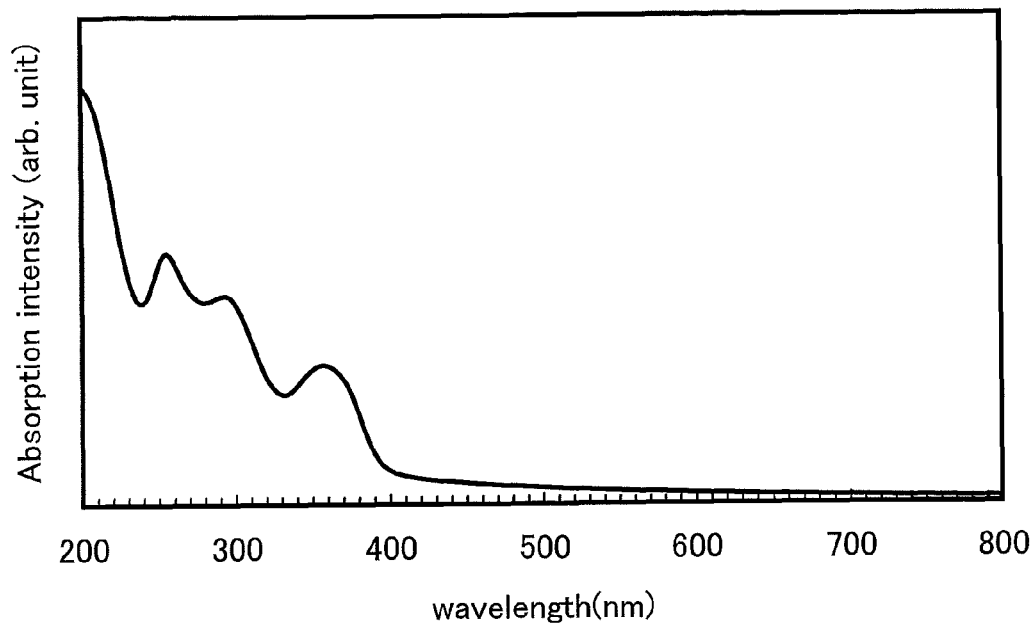
FIG. 15 is a diagram showing absorption spectrum of a thin film of 2-phenyl-3-[4-(2-pyridyl)phenyl]quinoxaline (abbr.: 2Py1PQ).
Figure 16:
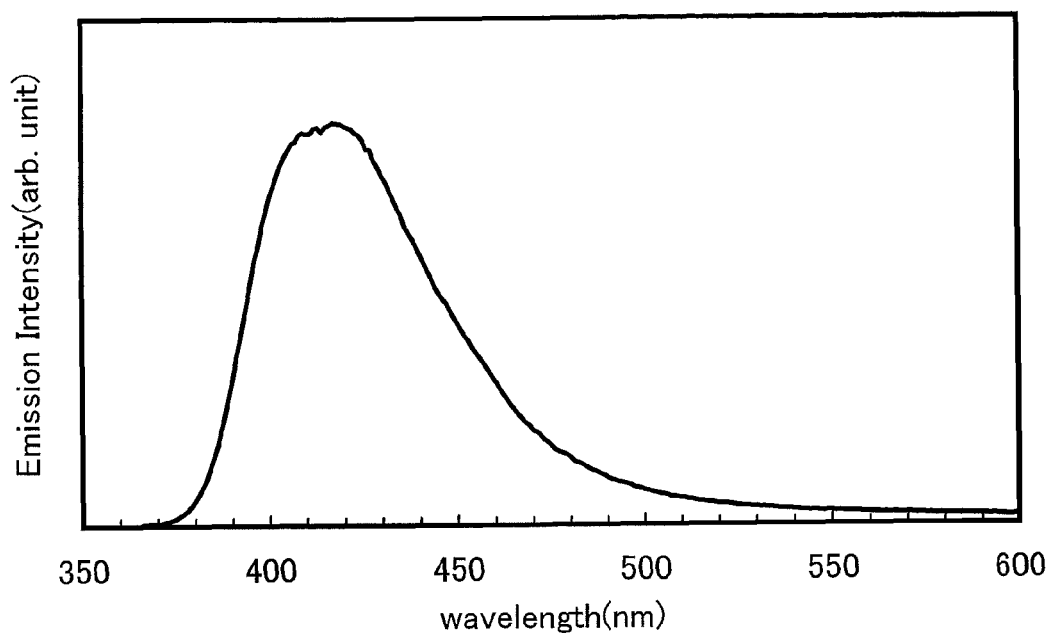
FIG. 16 is a diagram showing emission spectrum of a thin film of 2-phenyl-3-[4-(2-pyridyl)phenyl]quinoxaline (abbr.: 2Py1PQ).

FIG. 15 shows absorption spectrum of a thin film of 2Py1PQ and FIG. 16 shows emission spectrum of the thin film of 2Py1PQ. The measurement was performed using an ultraviolet-visible spectrophotometer (V-550, manufactured by JASCO Corporation). A sample was manufactured by evaporation of the thin film over a quartz substrate, and the absorption spectrum thereof, from which the absorption spectrum of quartz is subtracted, is shown in FIG. 15. In FIG. 15, the horizontal axis represents wavelength (nm) and the vertical axis represents absorption intensity (arb. Unit). In FIG. 16, the horizontal axis represents wavelength (nm) and the vertical axis represents emission intensity (arb. Unit). In the case of the thin film, an absorption was observed at around 358 nm. In addition, in the case of the thin film, the maximum emission wavelength was 417 nm (excitation wavelength: 357 nm).

In addition, the ionization potential of 2Py1PQ in a thin film form was 5.60 eV when measured in the air with a photoelectron spectrometer (AC-2, manufactured by RIKEN KEIKI CO., LTD.). As a result, it was found that the HOMO level was −5.60 eV. Furthermore, an absorption edge was obtained from a Tauc plot assuming direct transition based on the absorption spectrum data of the thin film of 2Py1PQ, and the absorption edge was estimated as an optical energy gap. As a result, the energy gap was 3.18 eV. The LUMO level was found to be −2.42 eV by calculation from the value of the energy gap and the HOMO level.

Embodiment 2

In this embodiment, a method for synthesizing 2-phenyl-3-[4-(3-pyridyl)phenyl]quinoxaline (abbr.: 3Py1PQ) represented by the structural formula (102) is described.

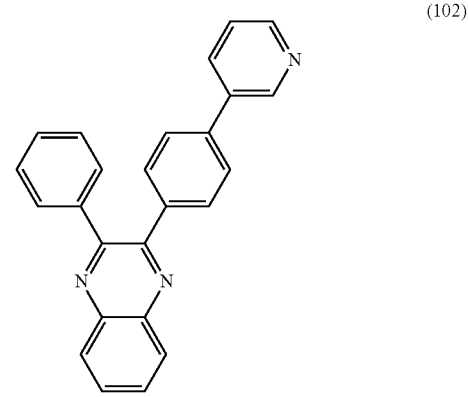

(102)

Step 1: Synthesis of 2-phenyl-3-[4-(3-pyridyl)phenyl]quinoxaline (abbr.: 3Py1PQ)

A synthetic scheme of 3Py1PQ is shown in (B-1).

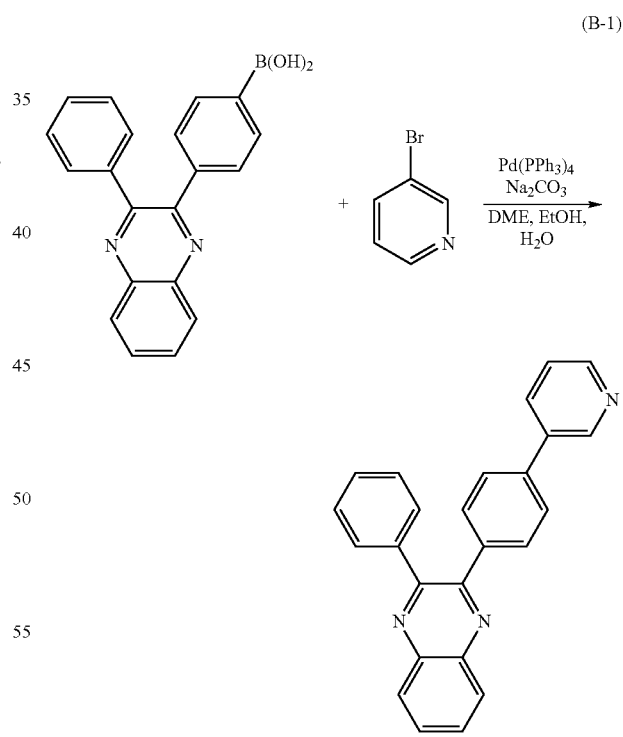

(B-1)

In a 100 mL three-necked flask were placed 1.2 g (3.9 mmol) of 4-(3-phenylquinoxalin-2-yl)phenylboronic acid, 0.73 g (4.6 mmol) of 3-bromopyridine, 0.99 g (9.3 mmol) of sodium carbonate, 5 mL of water, 10 mL of ethylene glycol dimethyl ether (DME), and 4 mL of ethanol. The mixture was degassed by being stirred under reduced pressure, and the atmosphere in the flask was replaced with nitrogen. There was added 50 mg (0.043 mmol) of tetrakis(triphenylphosphine)palladium(0), and the mixture was refluxed under nitrogen stream for 10 hours. After a predetermined time, water was added to the mixture, and an organic substance was extracted with chloroform from the aqueous layer. The extract was washed with a saturated aqueous sodium hydrogen carbonate solution and a saturated aqueous sodium chloride solution together with the organic layer, and the organic layer was then dried over magnesium sulfate. The obtained mixture was subjected to suction filtration through Celite (produced by Wako Pure Chemical Industries, Ltd., Catalog No. 531-16855), and the filtrate was condensed to obtain a solid. The obtained solid was purified by silica gel column chromatography (dichloromethane:ethyl acetate=10:1) and further recrystallized with ethyl acetate/hexane; thus, 1.0 g of target pale-yellow powder was obtained with a yield of 76%.

Then, 1.0 g of the obtained target substance was subjected to sublimation purification at 160° C. under an argon stream (flow rate: 3.0 mL/min) and a pressure of 10 Pa for 17 hours; thus, 0.83 g of the target substance was obtained at a collection rate of 83%. The compound was measured by nuclear magnetic resonance (NMR) spectrometry and identified as 2-phenyl-3-[4-(3-pyridyl)phenyl]quinoxaline (abbr.: 3Py1PQ).

Figure 17A:
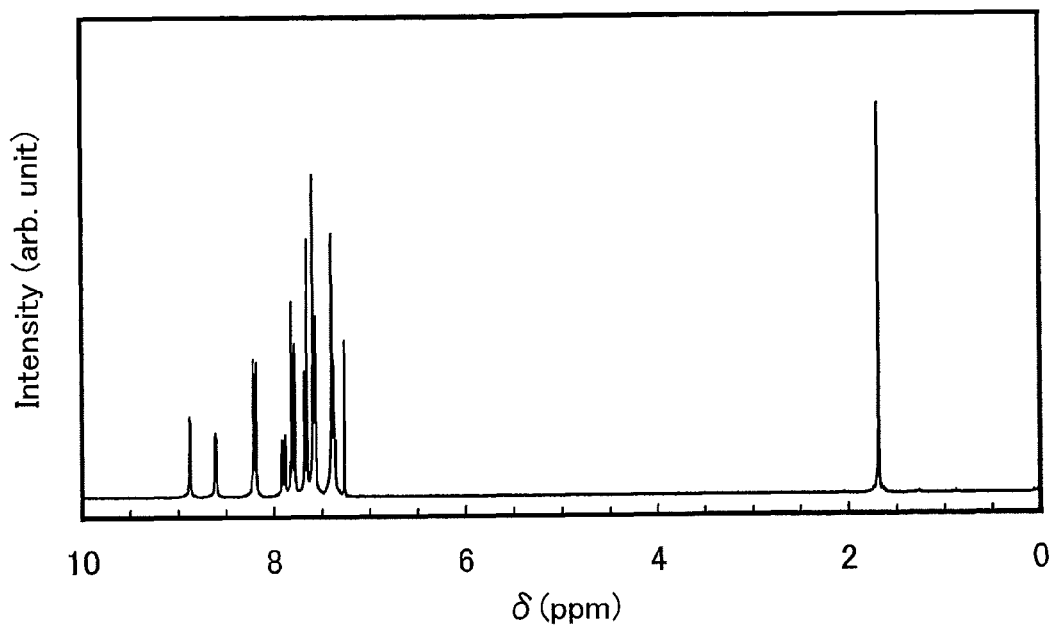
FIGS. 17A and 17B are diagrams each showing a $^1$H NMR chart of 2-phenyl-3-[4-(3-pyridyl)phenyl]quinoxaline (abbr.: 3Py1PQ).
Figure 17B:
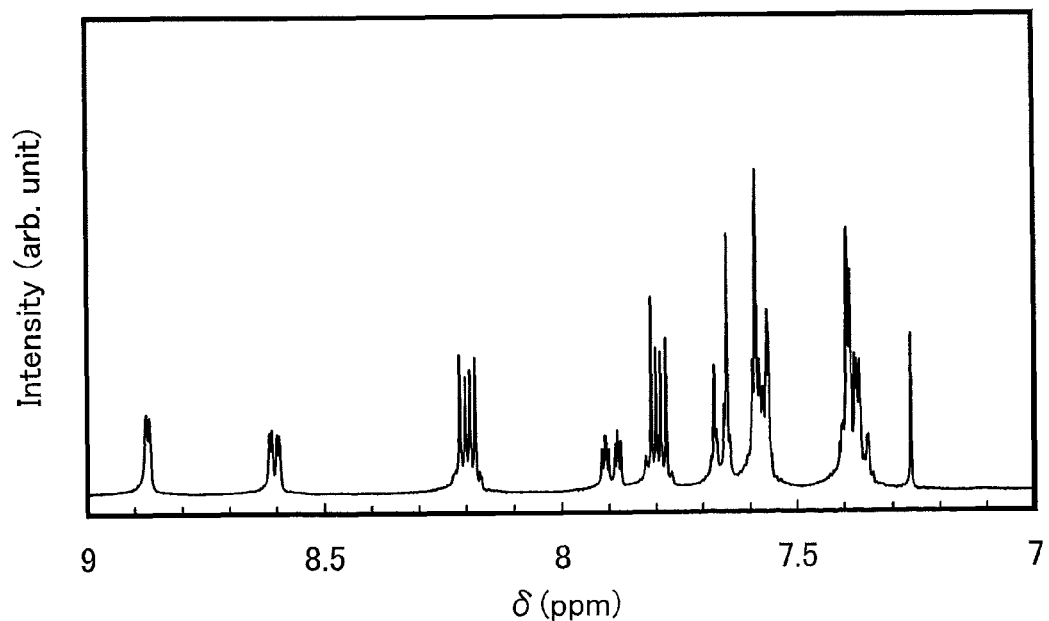

The $^1$H NMR data is given as follows. $^1$H NMR (300 MHz, CDCl$_3$): δ (ppm)=7.37-7.40 (m, 4H), 7.56-7.59 (m, 4H), 7.66 (dd, J$_1$=3.0 Hz, J$_2$=2.1 Hz, 2H), 7.76-7.82 (m, 2H), 7.88-7.91 (m, 1H), 8.18-8.21 (m, 2H), 8.60 (dd, J$_1$=4.8 Hz, J$_2$=1.5 Hz, 1H), 8.87 (d, J=2.1 Hz, 1H). FIGS. 17A and 17B show $^1$H NMR charts. Note that FIG. 17B shows an enlarged chart showing the range from 7.0 ppm to 9.0 ppm in FIG. 17A.

Thermogravimetry-differential thermal analysis (TG-DTA) of 3Py1PQ obtained was performed. The measurement was performed using a high vacuum differential type differential thermal balance (TG-DTA2410SA, manufactured by Bruker AXS K.K.). The measurement was performed under normal pressure at a rate of temperature rise of 10° C./min under a nitrogen stream (flow rate: 200 mL/min). It was found from the relationship between weight and temperature (thermogravimetry) that the 5% weight loss temperature was 309° C. and the melting point was 150° C.

Figure 18:
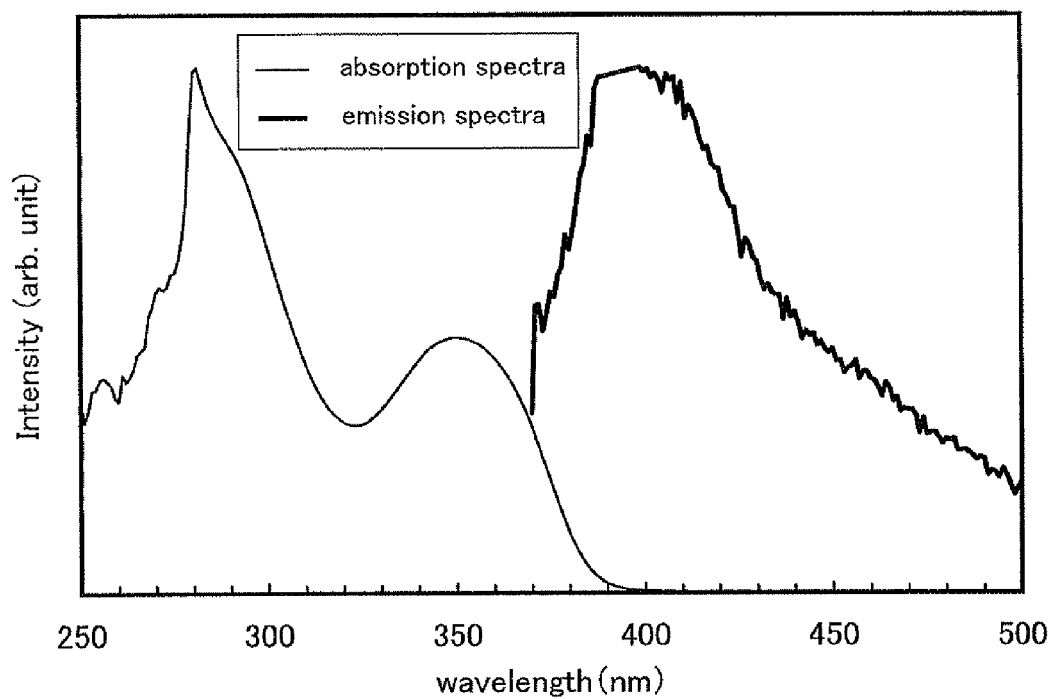
FIG. 18 is a diagram showing absorption spectrum and emission spectrum of a toluene solution of 2-phenyl-3-[4-(3-pyridyl)phenyl]quinoxaline (abbr.: 3Py1PQ).

FIG. 18 shows absorption spectrum and emission spectrum of a toluene solution of 3Py1PQ. The measurement was performed using an ultraviolet-visible spectrophotometer (V-550, manufactured by JASCO Corporation). The solution was placed in a quartz cell. The absorption spectrum from which the absorption spectrum of quartz is subtracted is shown in FIG. 18. In FIG. 18, the horizontal axis represents wavelength (nm) and the vertical axis represents intensity (arb. Unit). In the case of the toluene solution, absorptions were observed at around 281 nm and 350 nm. In addition, in the case of the toluene solution, the maximum emission wavelength was 399 nm (excitation wavelength: 350 nm).

Figure 19:
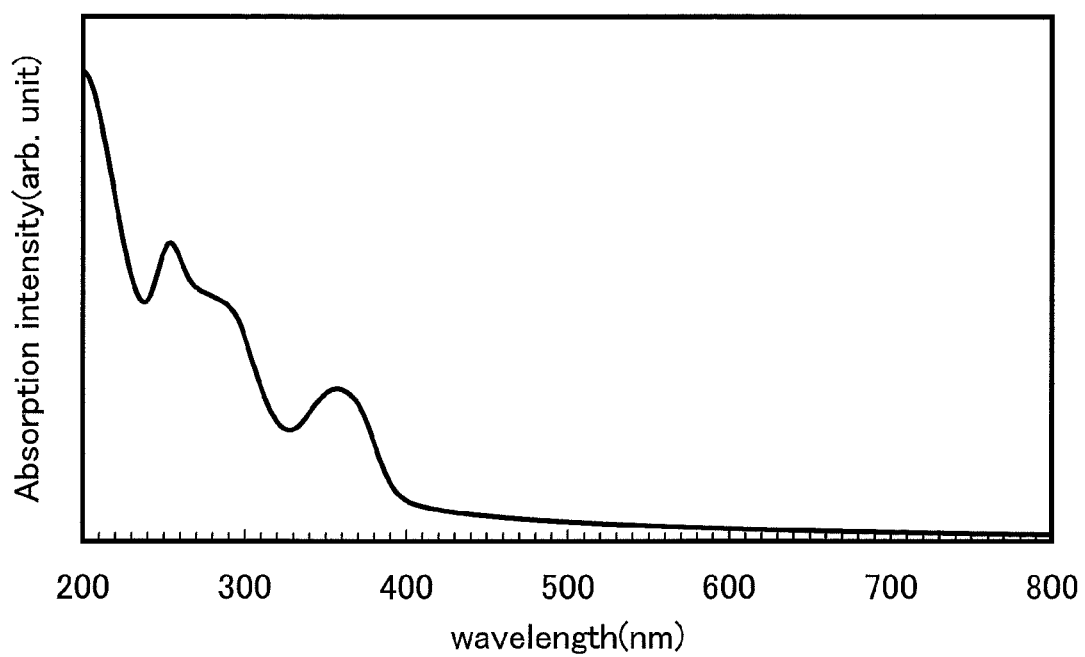
FIG. 19 is a diagram showing absorption spectrum of a thin film of 2-phenyl-3-[4-(3-pyridyl)phenyl]quinoxaline (abbr.: 3Py1PQ).
Figure 20:
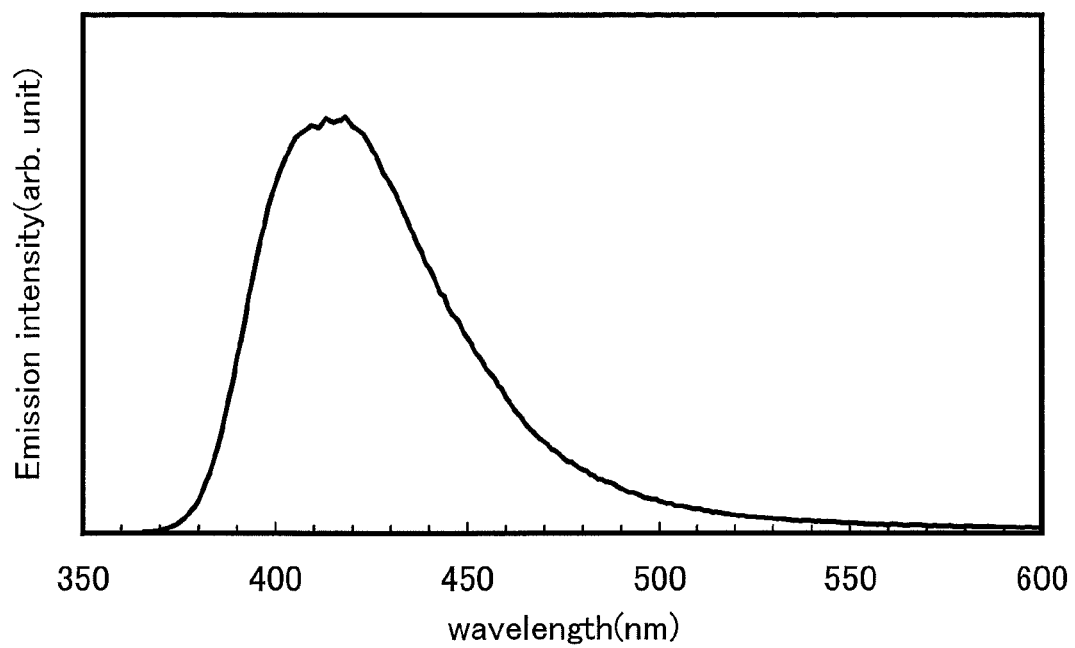
FIG. 20 is a diagram showing emission spectrum of a thin film of 2-phenyl-3-[4-(3-pyridyl)phenyl]quinoxaline (abbr.: 3Py1PQ).

FIG. 19 shows absorption spectrum of a thin film of 3Py1PQ and FIG. 20 shows emission spectrum of the thin film of 3Py1PQ. The measurement was performed using an ultraviolet-visible spectrophotometer (V-550, manufactured by JASCO Corporation). A sample was manufactured by evaporation of the thin film over a quartz substrate, and the absorption spectrum thereof, from which the absorption spectrum of quartz is subtracted, is shown in FIG. 19. In FIG. 19, the horizontal axis represents wavelength (nm) and the vertical axis represents absorption intensity (arb. Unit). In FIG. 20, the horizontal axis represents wavelength (nm) and the vertical axis represents emission intensity (arb. Unit). In the case of the thin film, an absorption was observed at around 357 nm.

In addition, in the case of the thin film, the maximum emission wavelength was 418 nm (excitation wavelength: 358 nm).

In addition, the ionization potential of 3Py1PQ in a thin film form was 5.64 eV when measured in the air with a photoelectron spectrometer (AC-2, manufactured by RIKEN KEIKI CO., LTD.). As a result, it was found that the HOMO level was −5.64 eV. Furthermore, an absorption edge was obtained from a Tauc plot assuming direct transition based on the absorption spectrum data of the thin film of 3Py1PQ, and the absorption edge was estimated as an optical energy gap. As a result, the energy gap was 3.18 eV. The LUMO level was found to be −2.46 eV by calculation from the value of the energy gap and the HOMO level.

Embodiment 3

In this embodiment, a method for synthesizing 2-phenyl-3-[4'-(3-pyridyl)biphenyl-4-yl]quinoxaline (abbr.: PPy1PQ) represented by the structural formula (195) is described.

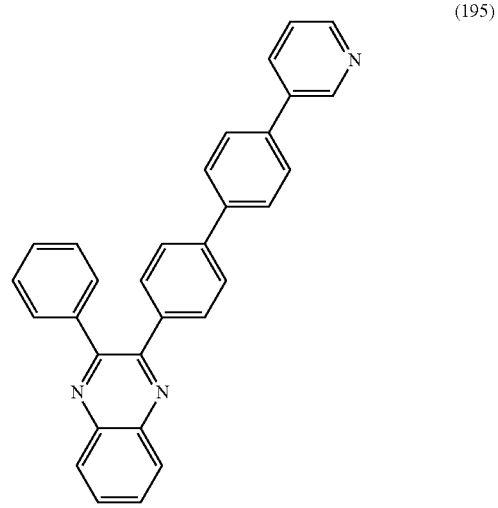

(195)

Step 1: Synthesis of 3-(4-bromophenyl)pyridine

A synthetic scheme of 3-(4-bromophenyl)pyridine is shown in (C-1).

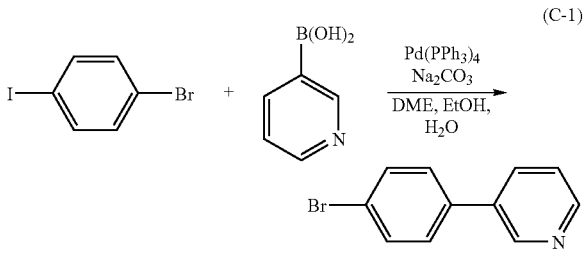

(C-1)

In a 100 mL three-necked flask were placed 2.4 g (20 mmol) of 3-pyridineboronic acid, 5.6 g (19 mmol) of para-bromoiodobenzene, and 4.5 g (42 mmol) of sodium carbonate. The atmosphere in the flask was replaced with nitrogen, and to the flask were added 15 mL of water, 25 mL of DME, and 10 mL of ethanol. The mixture was degassed by being stirred under reduced pressure, to which 0.22 g (0.19 mmol)

of tetrakis(triphenylphosphine)palladium(0) was added. The mixture was stirred under nitrogen stream at 80° C. for 12 hours. After a predetermined time, water was added to the mixture, and an organic substance was extracted with chloroform from the aqueous layer. The obtained extract was washed with a saturated aqueous sodium chloride solution together with the organic layer and then dried over magnesium sulfate. The mixture was subjected to suction filtration through Celite (produced by Wako Pure Chemical Industries, Ltd., Catalog No. 531-16855), and the filtrate was condensed to obtain an oily substance. The obtained substance was purified by silica gel column chromatography (hexane:ethyl acetate=3:1); thus, 1.8 g of the target yellow oily substance was obtained with a yield of 38%.

Step 2: Synthesis of 2-phenyl-3-[4'-(3-pyridyl)biphenyl-4-yl]quinoxaline (abbr.: PPy1PQ)

A synthetic scheme of PPy1PQ is shown in (C-2).

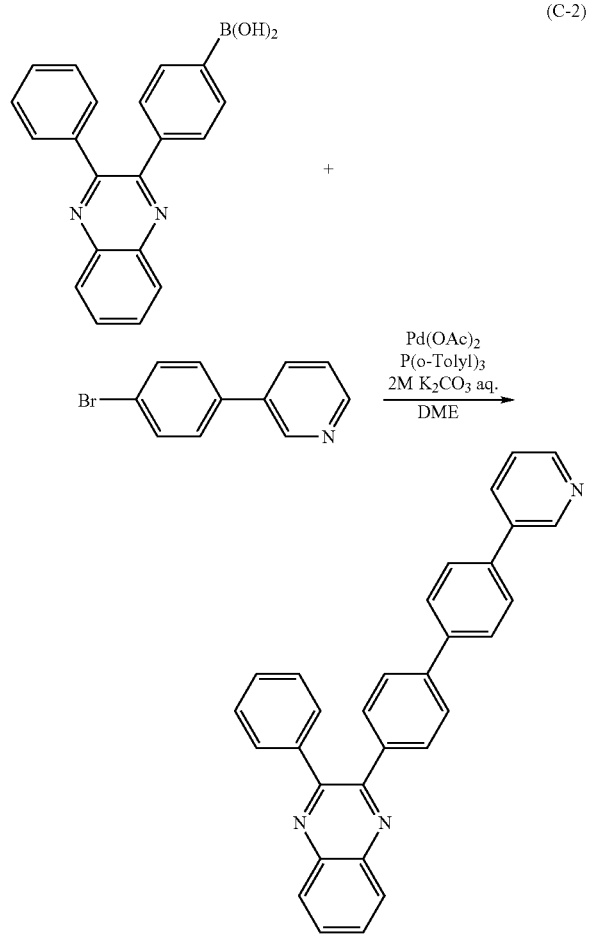

In a 100 mL three-necked flask were placed 0.93 g (4.0 mmol) of 3-(4-bromophenyl)pyridine, 1.3 g (4.0 mmol) of 4-(3-phenylquinoxalin-2-yl)phenylboronic acid, and 0.24 g (0.80 mmol) of tri(ortho-tolyl)phosphine. The atmosphere in the flask was replaced with nitrogen, and there were added 30 mL of ethylene glycol dimethyl ether (DME) and 4.0 mL of a 2.0 M aqueous potassium carbonate solution. The mixture was degassed by being stirred under reduced pressure, to which 14 mg (0.062 mmol) of palladium(II) acetate was added. The mixture was stirred under nitrogen stream at 80° C. for 10 hours. After a predetermined time, water was added to the mixture, and an organic substance was extracted with chloroform from the aqueous layer. The extract was washed with a saturated aqueous sodium chloride solution together with the organic layer, and the organic layer was then dried over magnesium sulfate. The mixture was subjected to suction filtration through Celite (produced by Wako Pure Chemical Industries, Ltd., Catalog No. 531-16855), and the filtrate was condensed to obtain a solid. The solid was purified by silica gel column chromatography (chloroform) and further recrystallized with chloroform/hexane; thus, 1.4 g of target white powder was obtained with a yield of 77%.

Then, 1.2 g of the obtained target substance was subjected to sublimation purification at 200° C. under an argon stream (flow rate: 3.0 mL/min) and a pressure of 10 Pa for 19 hours; thus, 0.53 g of the target substance was obtained at a collection rate of 43%. The compound was measured by nuclear magnetic resonance (NMR) spectrometry and identified as 2-phenyl-3-[4'-(3-pyridyl)biphenyl-4-yl]quinoxaline (abbr.: PPy1PQ).

Figure 21A:
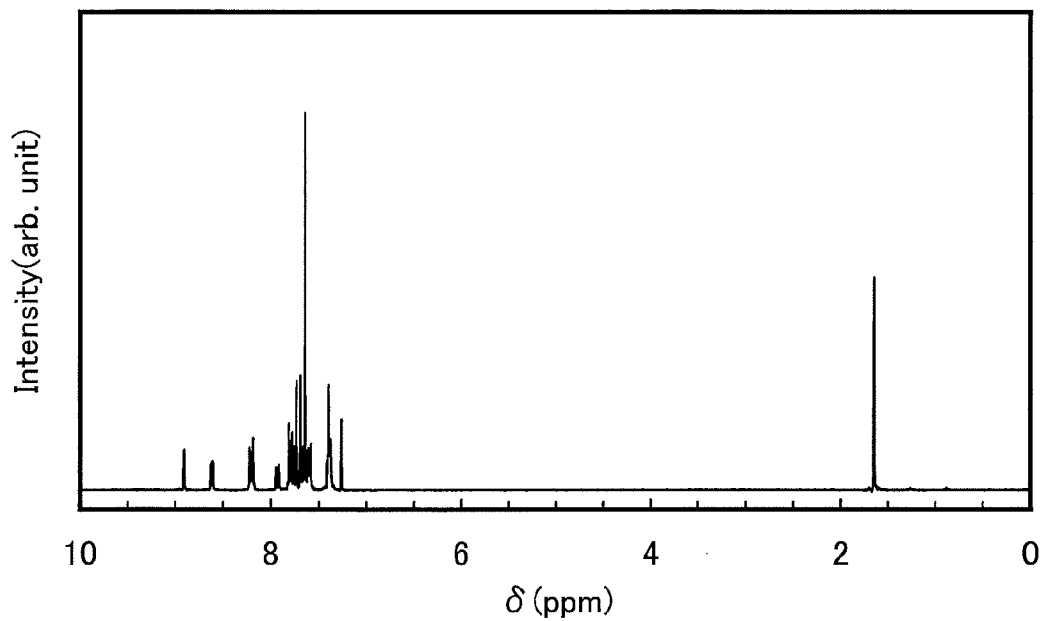
FIGS. 21A and 21B are diagrams each showing a $^1$H NMR chart of 2-phenyl-3-[4'-(3-pyridyl)biphenyl-4-yl]quinoxaline (abbr.: PPy1PQ).
Figure 21B:
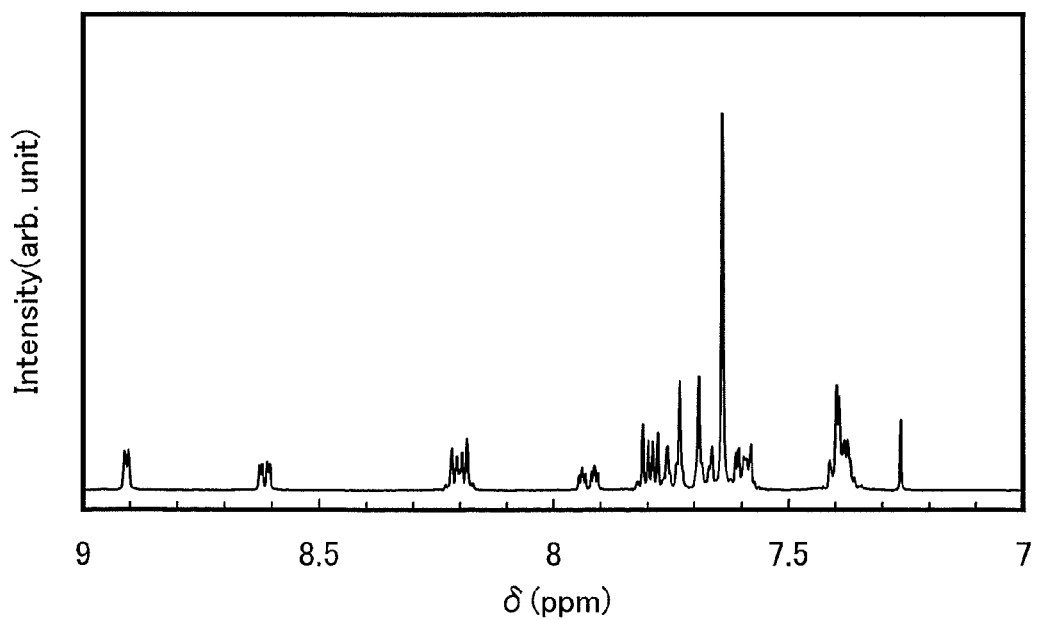

The $^1$H NMR data is given as follows. $^1$H NMR (300 MHz, CDCl$_3$): δ(ppm)=7.37-7.41 (m, 4H), 7.57-7.81 (m, 12H), 7.90-7.94 (m, 1H), 8.18-8.21 (m, 2H), 8.61 (dd, $J_1$=4.9 Hz, $J_2$=1.5 Hz, 1H), 8.90 (d, J=2.4 Hz, 1H). FIGS. 21A and 21B show $^1$H NMR charts. Note that FIG. 21B shows an enlarged chart showing the range from 7.0 ppm to 9.0 ppm in FIG. 21A.

Thermogravimetry-differential thermal analysis (TG-DTA) of PPy1PQ obtained was performed. The measurement was performed using a high vacuum differential type differential thermal balance (TG-DTA2410SA, manufactured by Bruker AXS K.K.). The measurement was performed under normal pressure at a rate of temperature rise of 10° C./min under a nitrogen stream (flow rate: 200 mL/min). It was found from the relationship between weight and temperature (thermogravimetry) that the 5% weight loss temperature was 346° C. and the melting point was 199° C.

Figure 22:
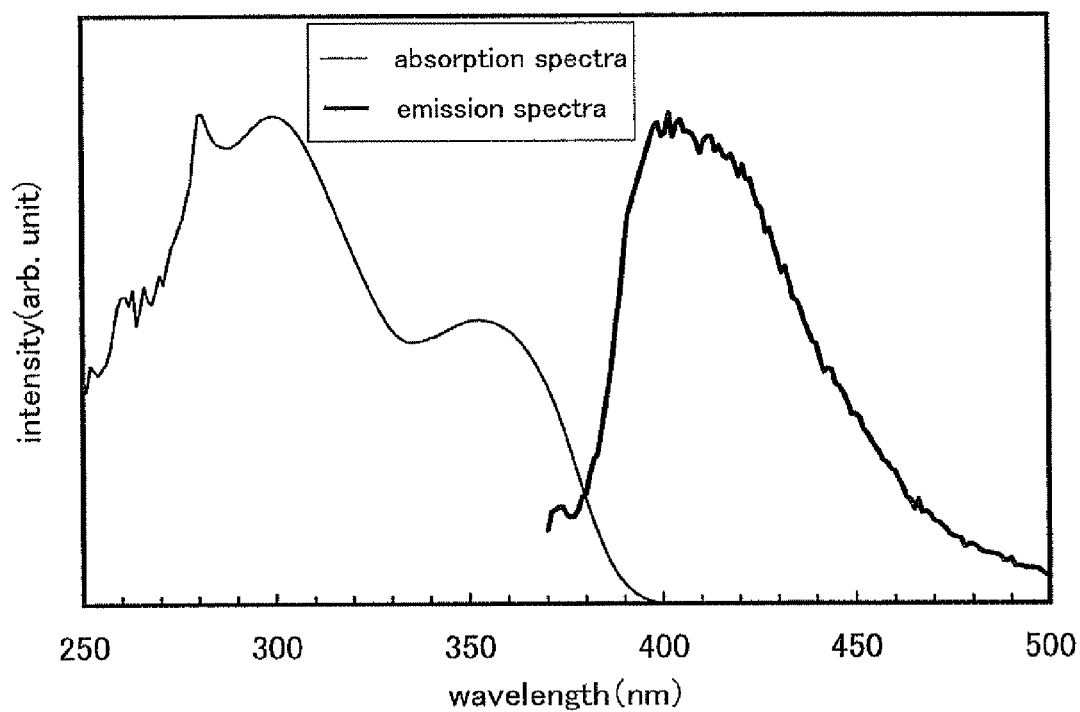
FIG. 22 is a diagram showing absorption spectrum and emission spectrum of a toluene solution of 2-phenyl-3-[4'-(3-pyridyl)biphenyl-4-yl]quinoxaline (abbr.: PPy1PQ).

FIG. 22 shows absorption spectrum and emission spectrum of a toluene solution of PPy1PQ. The measurement was performed using an ultraviolet-visible spectrophotometer (V-550, manufactured by JASCO Corporation). The solution was placed in a quartz cell. The absorption spectrum from which the absorption spectrum of quartz is subtracted is shown in FIG. 22. In FIG. 22, the horizontal axis represents wavelength (nm) and the vertical axis represents intensity (arb. Unit). In the case of the toluene solution, absorptions were observed at around 281 nm, 300 nm, and 352 nm. In addition, in the case of the toluene solution, the maximum emission wavelength was 402 nm (excitation wavelength: 352 nm).

Figure 23:
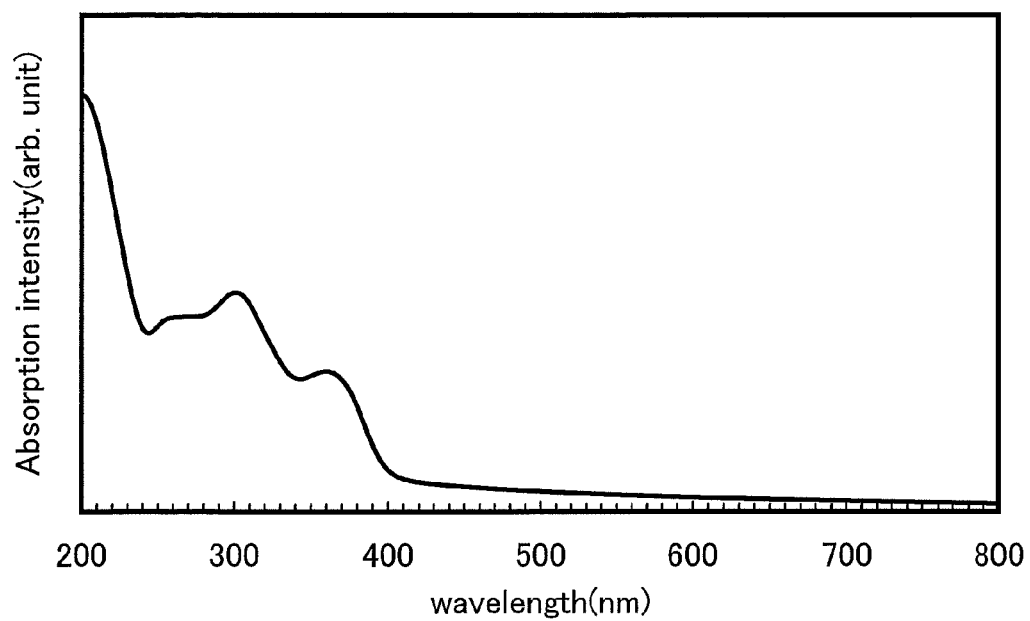
FIG. 23 is a diagram showing absorption spectrum of a thin film of 2-phenyl-3-[4'-(3-pyridyl)biphenyl-4-yl]quinoxaline (abbr.: PPy1PQ).
Figure 24:
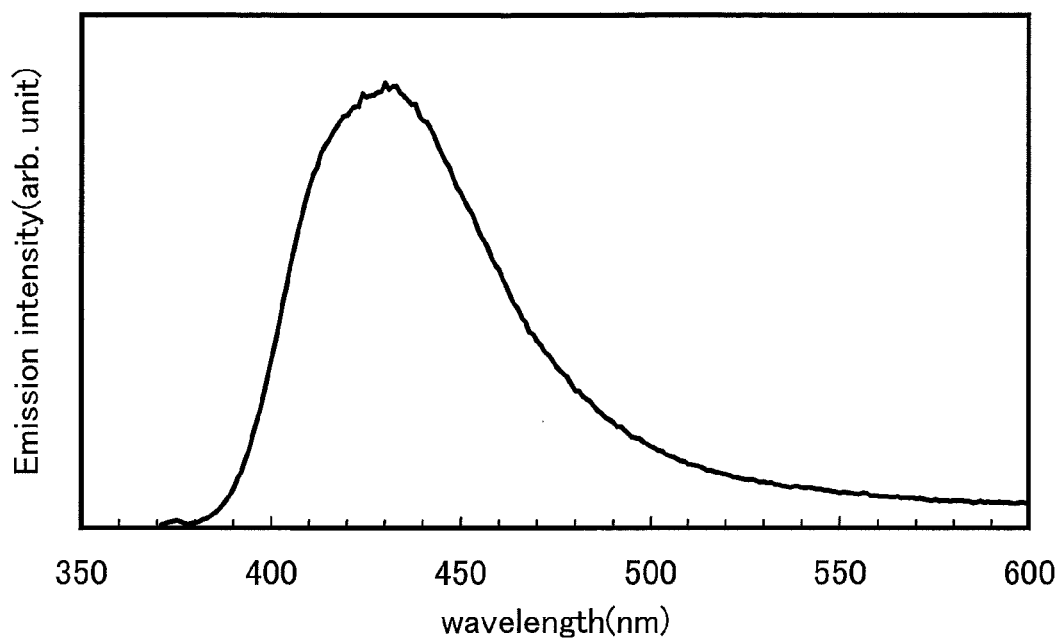
FIG. 24 is a diagram showing emission spectrum of a thin film of 2-phenyl-3-[4'-(3-pyridyl)biphenyl-4-yl]quinoxaline (abbr.: PPy1PQ).

FIG. 23 shows absorption spectrum of a thin film of PPy1PQ and FIG. 24 shows emission spectrum of the thin film of PPy1PQ. The measurement was performed using an ultraviolet-visible spectrophotometer (V-550, manufactured by JASCO Corporation). A sample was manufactured by evaporation of the thin film over a quartz substrate, and the absorption spectrum thereof, from which the absorption spectrum of quartz is subtracted, is shown in FIG. 23. In FIG. 23, the horizontal axis represents wavelength (nm) and the vertical axis represents absorption intensity (arb. Unit). In FIG. 24, the horizontal axis represents wavelength (nm) and the vertical axis represents emission intensity (arb. Unit). In the case of the thin film, an absorption was observed at around 355 nm. In addition, in the case of the thin film, the maximum emission wavelength was 433 nm (excitation wavelength: 360 nm).

In addition, the ionization potential of PPy1PQ in a thin film form was 5.69 eV when measured in the air with a photoelectron spectrometer (AC-2, manufactured by RIKEN KEIKI CO., LTD.). As a result, it was found that the HOMO level was −5.69 eV. Furthermore, an absorption edge was obtained from a Tauc plot assuming direct transition based on the absorption spectrum data of the thin film of PPy1PQ, and the absorption edge was estimated as an optical energy gap. As a result, the energy gap was 3.14 eV. The LUMO level was found to be −2.55 eV by calculation from the value of the energy gap and the HOMO level.

Embodiment 4

In this embodiment, a method for synthesizing 2,3-bis[4-(3-pyridyl)phenyl]quinoxaline (abbr.: 3Py2PQ) represented by the structural formula (402) is described.

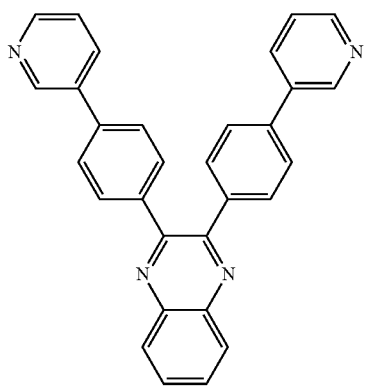

(402)

Step 1: Synthesis of
2,3-bis(4-bromophenyl)quinoxaline

A synthetic scheme of 2,3-bis(4-bromophenyl)quinoxaline is shown in (D-1).

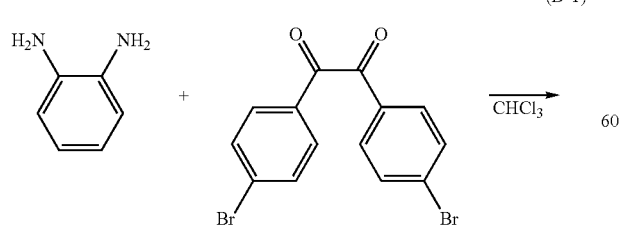

(D-1)

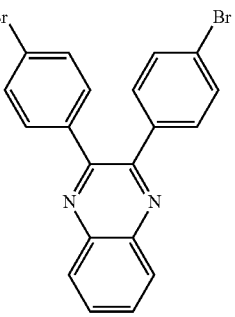

In a 500 mL three-necked flask were placed 30 g (82 mmol) of 4,4′-dibromobenzil, 9.3 g (86 mmol) of 1,2-phenylenediamine, and 300 mL of chloroform, which were refluxed under nitrogen stream at 80° C. for 5 hours. After a predetermined time, the solution was cooled to room temperature, and there was added water. The aqueous layer was extracted with chloroform, and the extract and the organic layer were dried together over magnesium sulfate. After drying, the mixture was subjected to suction filtration, and the filtrate was condensed. The obtained solid was dissolved in toluene, and the solution was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina. The filtrate was condensed; thus, 30 g of target white powder of 2,3-bis(4-bromophenyl)quinoxaline was obtained with a yield of 99%.

Step 2: Synthesis of
4,4′-(quinoxaline-2,3-diyl)diphenylboronic acid

A synthetic scheme of 4,4′-(quinoxaline-2,3-diyl)diphenylboronic acid is shown in (D-2).

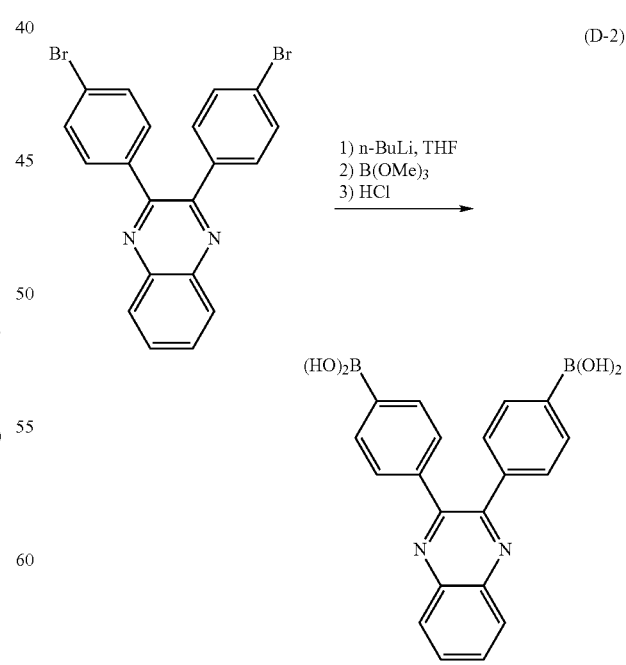

(D-2)

In a 500 mL three-necked flask was placed 10 g (22 mmol) of 2,3-bis(4-bromophenyl)quinoxaline, and the atmosphere in the flask was replaced with nitrogen. There was added 100 mL of tetrahydrofuran, and the mixture was cooled to −78° C. under nitrogen stream. After cooling, 31 mL (49 mmol) of 1.6 M n-butyllithium was dripped thereinto, and the mixture was stirred at the same temperature for 1 hour. After a predetermined time, there was added 10 mL (90 mmol) of trimethyl borate, and the temperature of the solution was raised to room temperature, and then, the solution was stirred for 10 hours. After a predetermined time, the solution was cooled to 0° C., and to the solution was added 100 mL of 0.1 M hydrochloric acid and the solution was then stirred for 1 hour. From the aqueous layer of the obtained mixture, an organic substance was extracted with ethyl acetate. The extract was washed with a saturated aqueous sodium chloride solution together with the organic layer and then dried over magnesium sulfate. The mixture was subjected to suction filtration through Celite (produced by Wako Pure Chemical Industries, Ltd., Catalog No. 531-16855), and the filtrate was condensed. The obtained solid was recrystallized with ethyl acetate; thus, 7.2 g of target yellow powder was obtained with a yield of 85%.

Step 3: Synthesis of
2,3-bis[4-(3-pyridyl)phenyl]quinoxaline (abbr.:
3Py2PQ)

A synthetic scheme of 3Py2PQ is shown in (D-3).

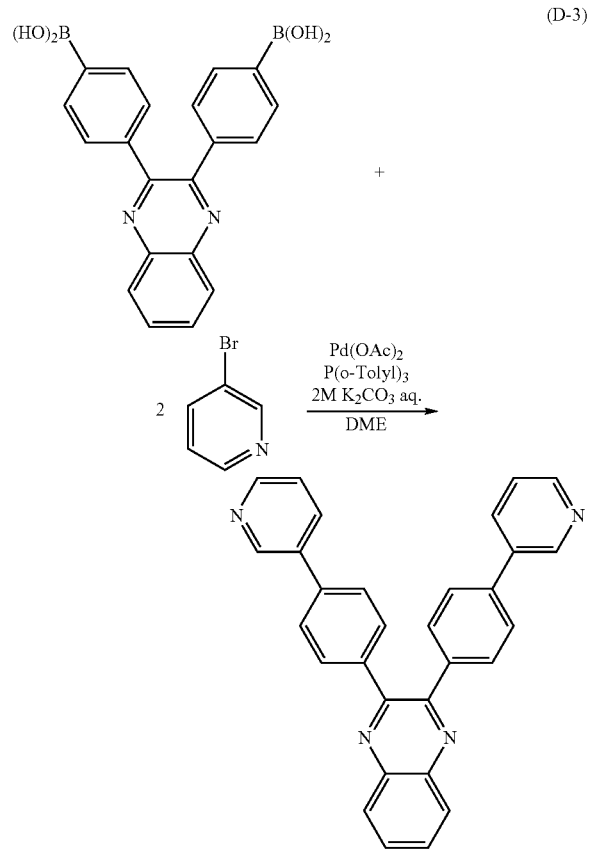

In a 100 mL three-necked flask were placed 2.0 g (5.4 mmol) of 4,4'-(quinoxaline-2,3-diyl)diphenylboronic acid, 1.9 g (11 mmol) of 3-bromopyridine, and 0.63 g (2.0 mmol) of tri(ortho-tolyl)phosphine. The atmosphere in the flask was replaced with nitrogen, and there was added 20 mL of ethyl-ene glycol dimethyl ether (DME) and 5.6 mL of a 2.0 M aqueous potassium carbonate solution. The mixture was degassed by being stirred under reduced pressure, and there was added 48 mg (0.21 mmol) of palladium(II) acetate, and then, the mixture was refluxed under nitrogen stream for 6 hours. After a predetermined time, water was added to the mixture, and an organic substance was extracted with chloroform from the aqueous layer. The extract was washed with a saturated aqueous sodium chloride solution together with the organic layer, and the organic layer was then dried over magnesium sulfate. The mixture was subjected to suction filtration through Celite (produced by Wako Pure Chemical Industries, Ltd., Catalog No. 531-16855), and the filtrate was condensed to obtain a solid. The solid was purified by silica gel column chromatography (chloroform:ethyl acetate=10:1) and further recrystallized with chloroform/hexane; thus, 1.5 g of target pale-yellow powder was obtained with a yield of 66%.

Then, 1.0 g of the obtained target substance was subjected to sublimation purification at 230° C. under an argon stream (flow rate: 3.0 mL/min) and a pressure of 10 Pa for 17 hours; thus, 0.74 g of the target substance was obtained at a collection rate of 69%. The compound was measured by nuclear magnetic resonance (NMR) spectrometry and identified as 2,3-bis[4-(3-pyridyl)phenyl]quinoxaline (abbr.: 3Py2PQ).

Figure 25A:
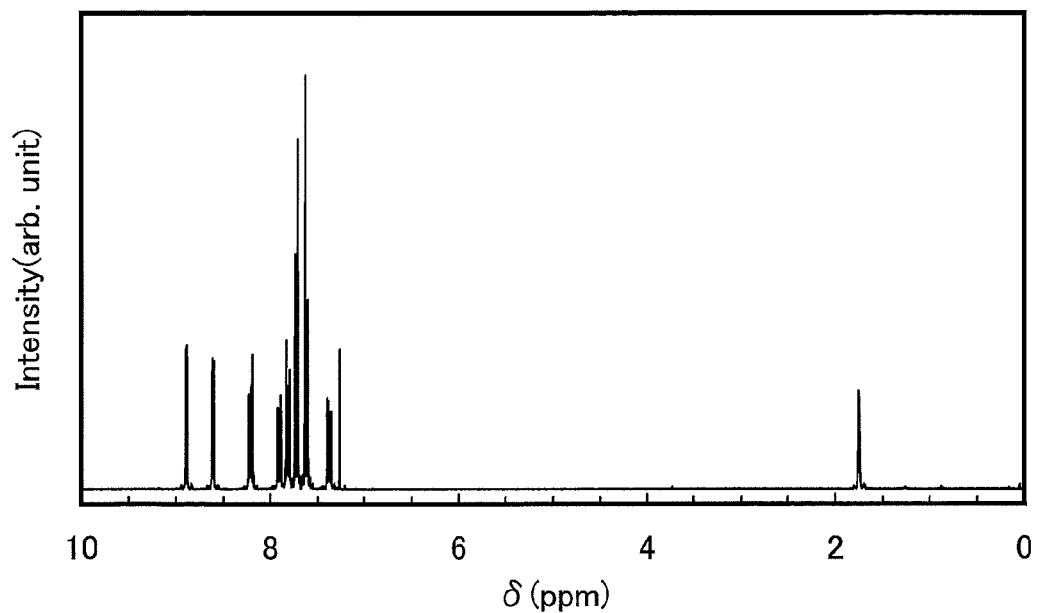
FIGS. 25A and 25B are diagrams each showing a $^1$H NMR chart of 2,3-bis[4-(3-pyridyl)phenyl]quinoxaline (abbr.: 3Py2PQ).
Figure 25B:
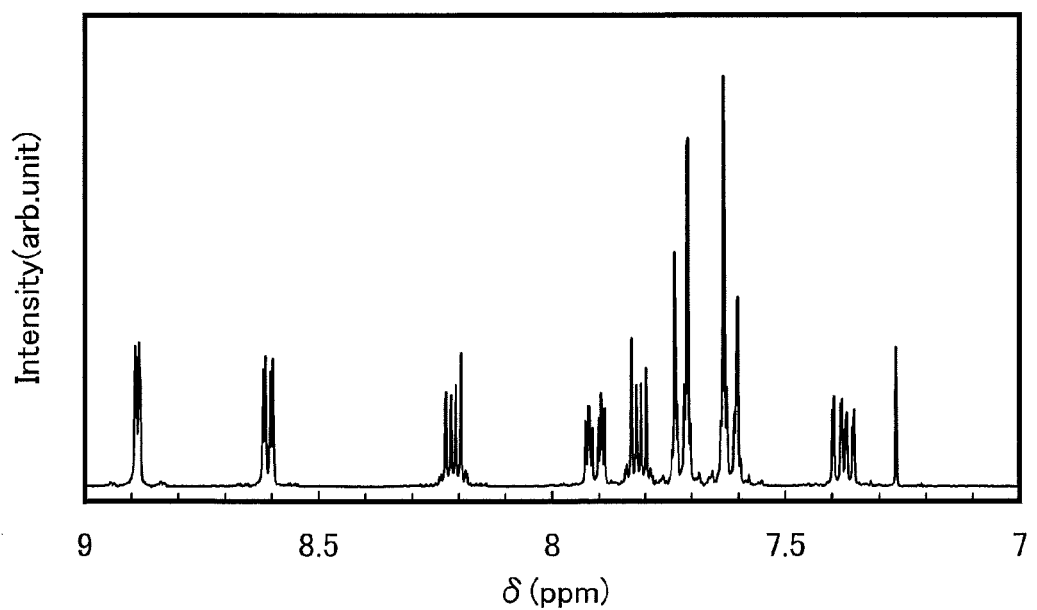

The $^1$H NMR data is given as follows. $^1$H NMR (300 MHz, CDCl$_3$): δ (ppm) 7.35-7.39 (m, 2H), 7.61 (dd, J$_1$=8.7 Hz, J$_2$=2.1 Hz, 4H), 7.72 (dd, J$_1$=6.4 Hz, J$_2$=2.4 Hz, 4H), 7.79-7.83 (m, 2H), 7.88-7.92 (m, 2H), 8.19-8.22 (m, 2H), 8.61 (dd, J$_1$=4.8 Hz, J$_2$=1.5 Hz, 2H), 8.90 (d, J=2.4 Hz, 2H). FIGS. 25A and 25B show $^1$H NMR charts. Note that FIG. 25B shows an enlarged chart showing the range from 7.0 ppm to 9.0 ppm in FIG. 25A.

Figure 26A:
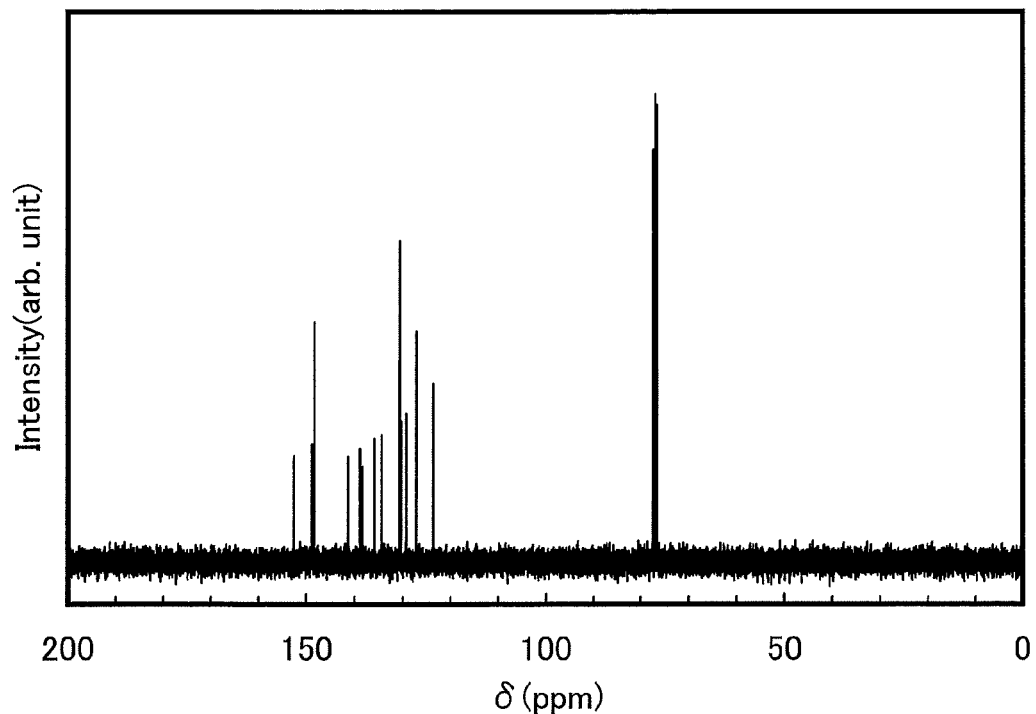
FIGS. 26A and 26B are diagrams each showing a $^{13}$C NMR chart of 2,3-bis[4-(3-pyridyl)phenyl]quinoxaline (abbr.: 3Py2PQ).
Figure 26B:
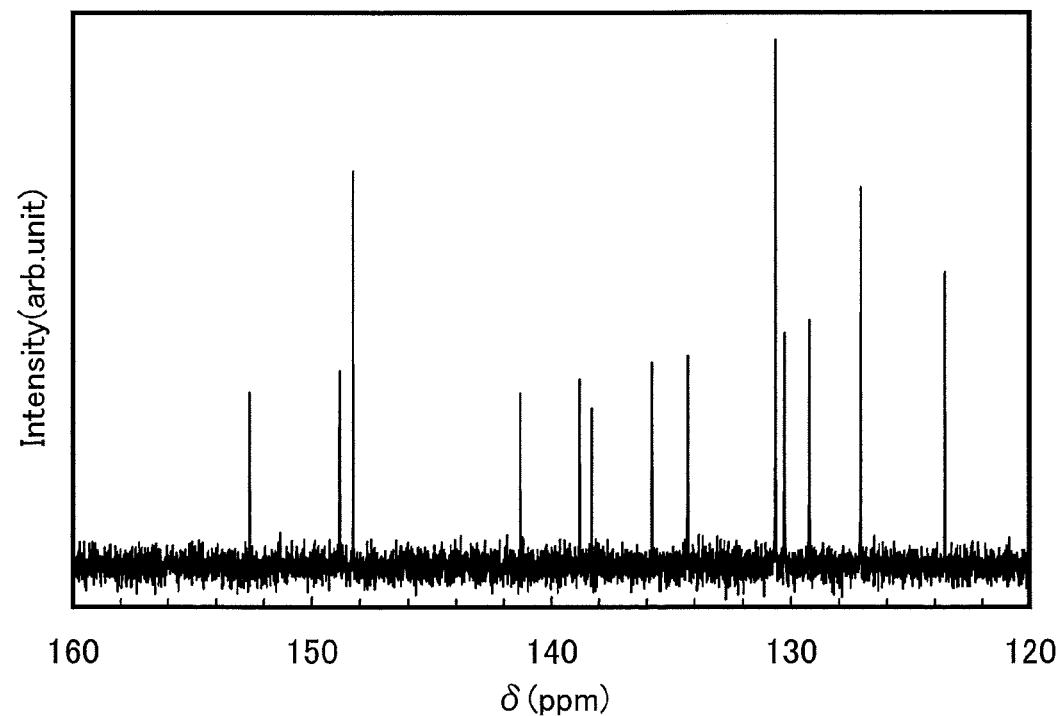

In addition, the $^{13}$C NMR data is given as follows. $^{13}$C NMR (75 MHz, CDCl$_3$): δ (ppm)=123.58, 127.10, 129.24, 130.25, 130.63, 134.29, 135.79, 138.31, 138.81, 141.30, 148.27, 148.83, 152.59. FIGS. 26A and 26B show $^{13}$C NMR charts. Note that FIG. 26B shows an enlarged chart showing the range from 120.0 ppm to 160.0 ppm in FIG. 26A.

Thermogravimetry-differential thermal analysis (TG-DTA) of 3Py2PQ obtained was performed. The measurement was performed using a high vacuum differential type differential thermal balance (TG-DTA2410SA, manufactured by Bruker AXS K.K.). The measurement was performed under normal pressure at a rate of temperature rise of 10° C./min under a nitrogen stream (flow rate: 200 mL/min). It was found from the relationship between weight and temperature (thermogravimetry) that the 5% weight loss temperature was 380° C. and the melting point was 208° C., which is indicative of high thermal stability.

Figure 27:
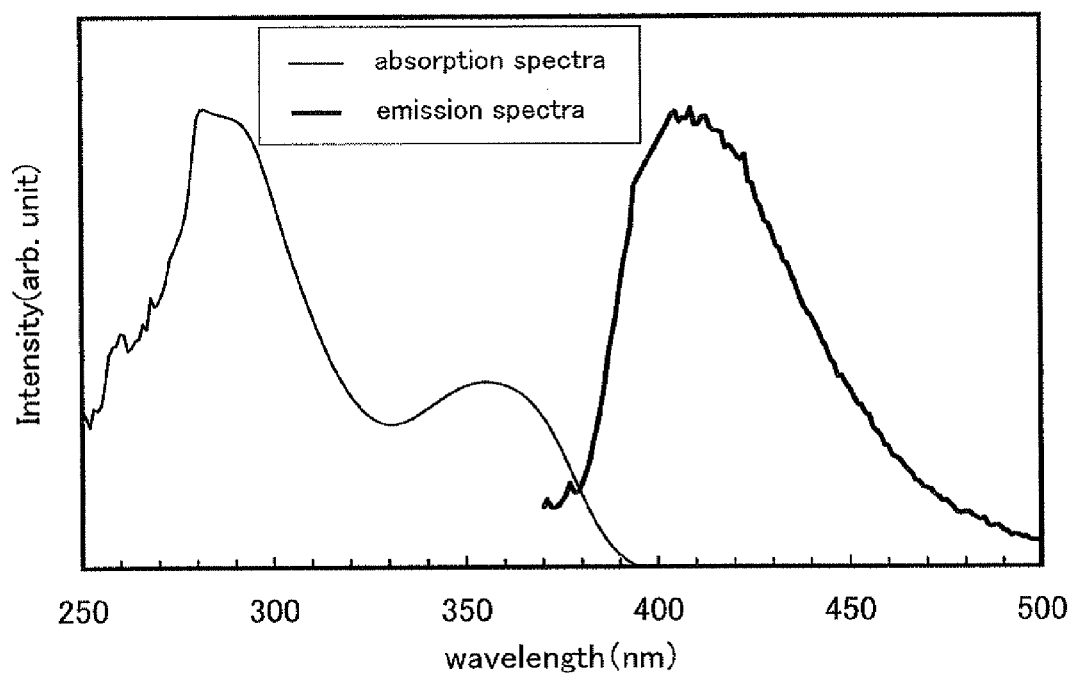
FIG. 27 is a diagram showing absorption spectrum and emission spectrum of a toluene solution of 2,3-bis[4-(3-pyridyl)phenyl]quinoxaline (abbr.: 3Py2PQ).

FIG. 27 shows absorption spectrum and emission spectrum of a toluene solution of 3Py2PQ. The measurement was performed using an ultraviolet-visible spectrophotometer (V-550, manufactured by JASCO Corporation). The solution was placed in a quartz cell. The absorption spectrum from which the absorption spectrum of quartz is subtracted is shown in FIG. 27. In FIG. 27, the horizontal axis represents wavelength (nm) and the vertical axis represents intensity (arb. Unit). In the case of the toluene solution, absorptions were observed at around 282 nm and 355 nm. In addition, in the case of the toluene solution, the maximum emission wavelength was 407 nm (excitation wavelength: 356 nm).

Figure 28:
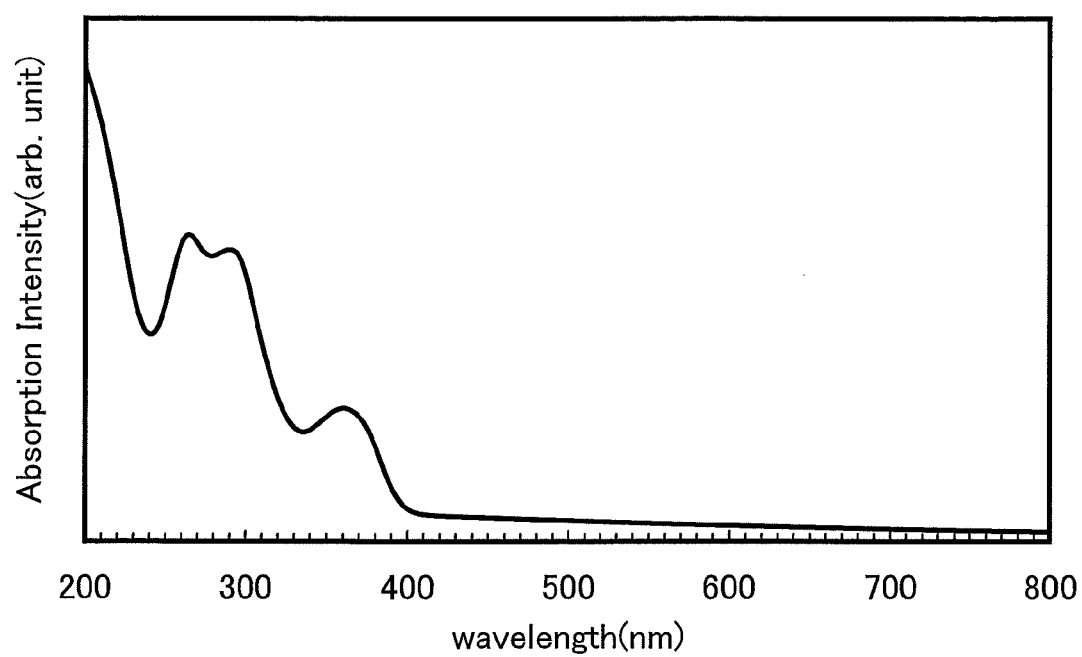
FIG. 28 is a diagram showing absorption spectrum of a thin film of 2,3-bis[4-(3-pyridyl)phenyl]quinoxaline (abbr.: 3Py2PQ).
Figure 29:
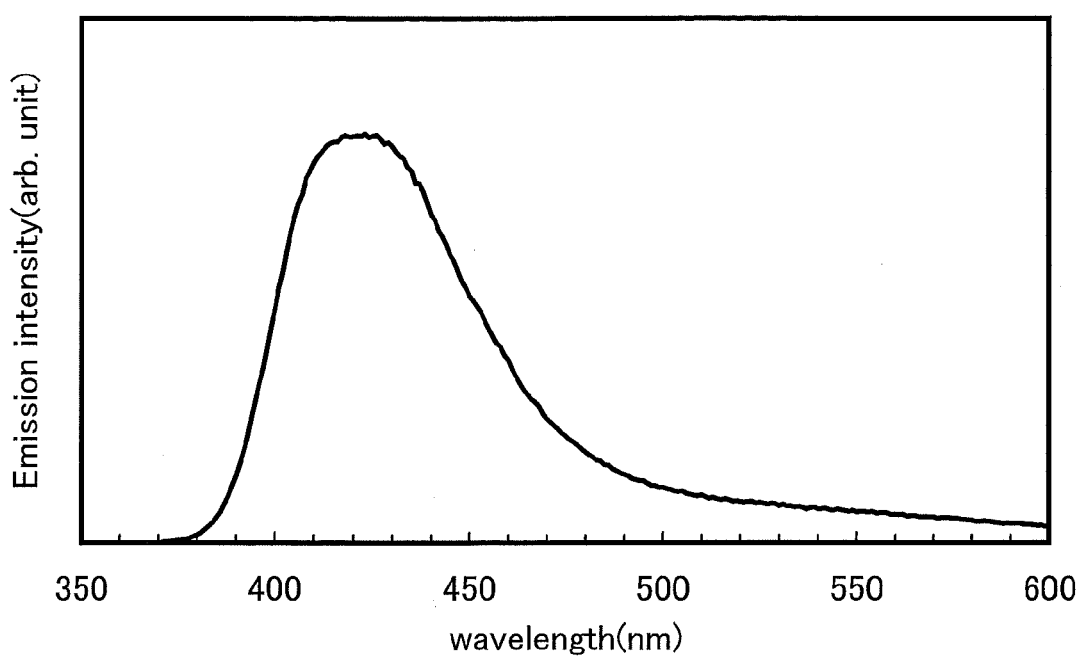
FIG. 29 is a diagram showing emission spectrum of a thin film of 2,3-bis[4-(3-pyridyl)phenyl]quinoxaline (abbr.: 3Py2PQ).

FIG. 28 shows absorption spectrum of a thin film of 3Py2PQ and FIG. 29 shows emission spectrum of the thin film of 3Py2PQ. The measurement was performed using an ultraviolet-visible spectrophotometer (V-550, manufactured by JASCO Corporation). A sample was manufactured by evaporation of the thin film over a quartz substrate, and the absorption spectrum thereof, from which the absorption spectrum of quartz is subtracted, is shown in FIG. 28. In FIG. 28, the horizontal axis represents wavelength (nm) and the vertical axis represents absorption intensity (arb. Unit). In FIG. 29, the horizontal axis represents wavelength (nm) and the vertical axis represents emission intensity (arb. Unit). In the case of the thin film, an absorption was observed at around 360 nm. In addition, in the case of the thin film, the maximum emission wavelength was 422 nm (excitation wavelength: 304 nm).

In addition, the ionization potential of 3Py2PQ in a thin film form was 5.61 eV when measured in the air with a photoelectron spectrometer (AC-2, manufactured by RIKEN KEIKI CO., LTD.). As a result, it was found that the HOMO level was −5.61 eV. Furthermore, an absorption edge was obtained from a Tauc plot assuming direct transition based on the absorption spectrum data of the thin film of 3Py2PQ, and the absorption edge was estimated as an optical energy gap. As a result, the energy gap was 3.16 eV. The LUMO level was found to be −2.45 eV by calculation from the value of the energy gap and the HOMO level.

Embodiment 5

Figure 30:
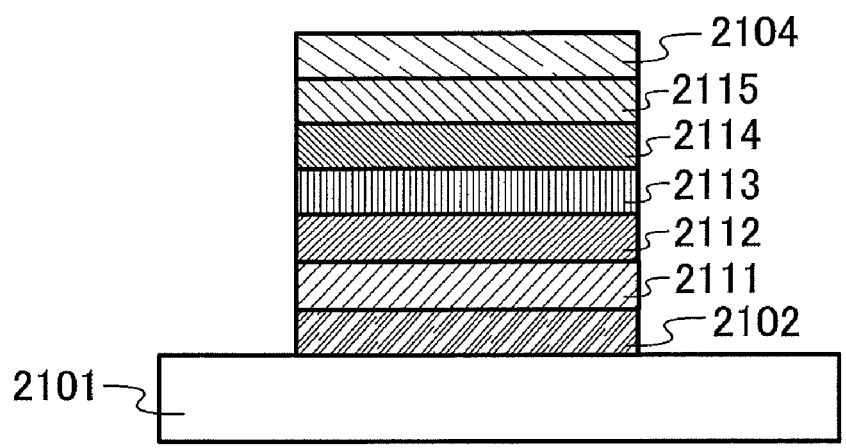
FIG. 30 is a diagram illustrating light-emitting elements of Embodiments.

In this embodiment, light-emitting elements of the present invention are described with reference to FIG. 30. Structural formulas of materials used in this embodiment are given below. Note that the materials, the structural formulas of which have already been shown, are omitted.

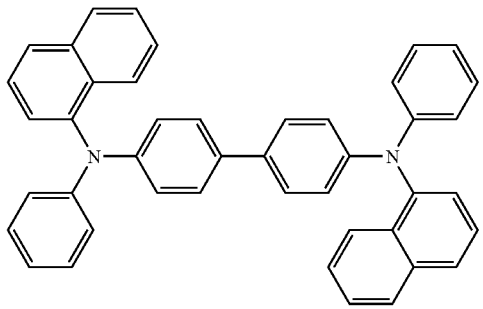
NPB

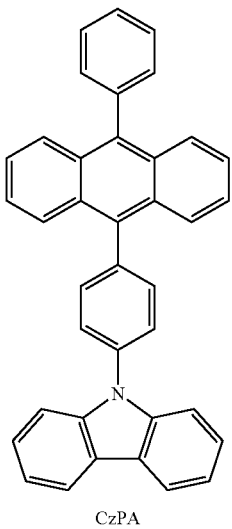
CzPA

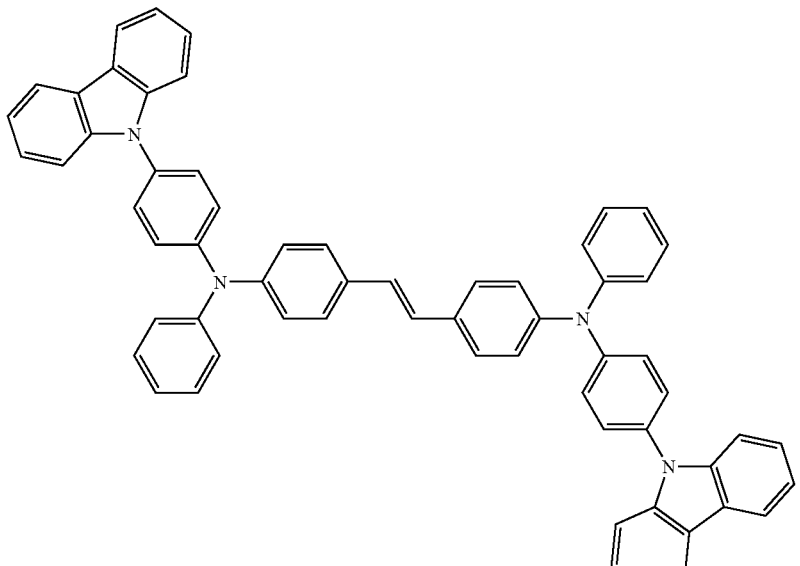
YGA2S

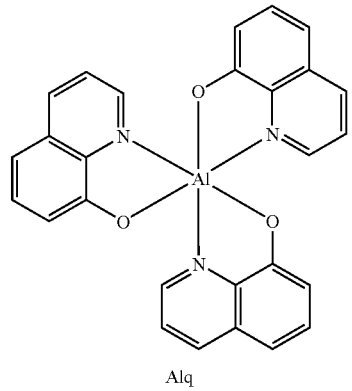
Alq

Methods for manufacturing light-emitting elements of this embodiment are hereinafter described.

(Light-Emitting Element 1)

First, a film of indium tin oxide containing silicon oxide (ITSO) was formed over a glass substrate 2101 by a sputtering method to form a first electrode 2102. Note that the thickness was 110 nm and the electrode area was 2 mm×2 mm.

Next, the substrate provided with the first electrode 2102 was fixed to a substrate holder provided in a vacuum evaporation apparatus such that the side on which the first electrode was formed faced downward. After the pressure in a film formation chamber was lowered to approximately $10^{-4}$ Pa, a layer 2111 containing a composite material of an organic compound and an inorganic compound was formed on the first electrode 2102 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino] biphenyl (abbr.: NPB) was formed to a thickness of 10 nm on the layer 2111 containing a composite material by an evaporation method employing resistance heating to form a hole-transporting layer Then, a light-emitting layer 2113 was formed to a thickness of 30 nm on the hole-transporting layer 2112 by co-evaporation of 9-[4-(10-phenyl-9-anthryl)phenyl]-9H-carbazole (abbr.: CzPA) and N,N'-bis[4-(9H-carbazol-9-yl)phenyl]-N, N'-diphenylstilbene-4,4'-diamine (abbr.: YGA2S). Here, the weight ratio of CzPA to YGA2S was adjusted to be 1:0.04 (=CzPA:YGA2S).

After that, a film of 2-phenyl-3-[4-(2-pyridyl)phenyl]quinoxaline (abbr.: 2Py1PQ) represented by the structural formula (101) was formed to a thickness of 30 nm on the light-emitting layer 2113 by an evaporation method employing resistance heating to form an electron-transporting layer 2114.

Furthermore, a film of lithium fluoride was formed to a thickness of 1 nm on the electron-transporting layer 2114 to form an electron-injecting layer 2115.

Lastly, a film of aluminum was formed to a thickness of 200 nm on the electron-injecting layer 2115 by an evaporation method employing resistance heating to form a second electrode 2104. Accordingly, a light-emitting element 1 was manufactured.

(Light-Emitting Element 2)

A light-emitting element 2 was formed like the light-emitting element 1 by using the same substrate and using 2-phenyl-3-[4-(3-pyridyl)phenyl]quinoxaline (abbr.: 3Py1PQ) represented by the structural formula (102) instead of 2Py1PQ. That is, a film of 2-phenyl-3-[4-(3-pyridyl)phenyl] quinoxaline (abbr.: 3Py1PQ) represented by the structural formula (102) was formed to a thickness of 30 nm to form the electron-transporting layer 2114. Except for the electron-transporting layer 2114, the light-emitting element 2 was formed like the light-emitting element 1.

(Comparative Light-Emitting Element 3)

A comparative light-emitting element 3 was formed like the light-emitting element 1 by using the same substrate and using tris(8-quinolinolato)aluminum(III) (abbr.: Alq) instead of 2Py1PQ. That is, a film of tris(8-quinolinolato)aluminum (III) (abbr.: Alq) was formed to a thickness of 30 nm to form the electron-transporting layer 2114. Except for the electron-transporting layer 2114, the comparative light-emitting element 3 was formed like the light-emitting element 1.

The light-emitting element 1, the light-emitting element 2, and the comparative light-emitting element 3 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 31:
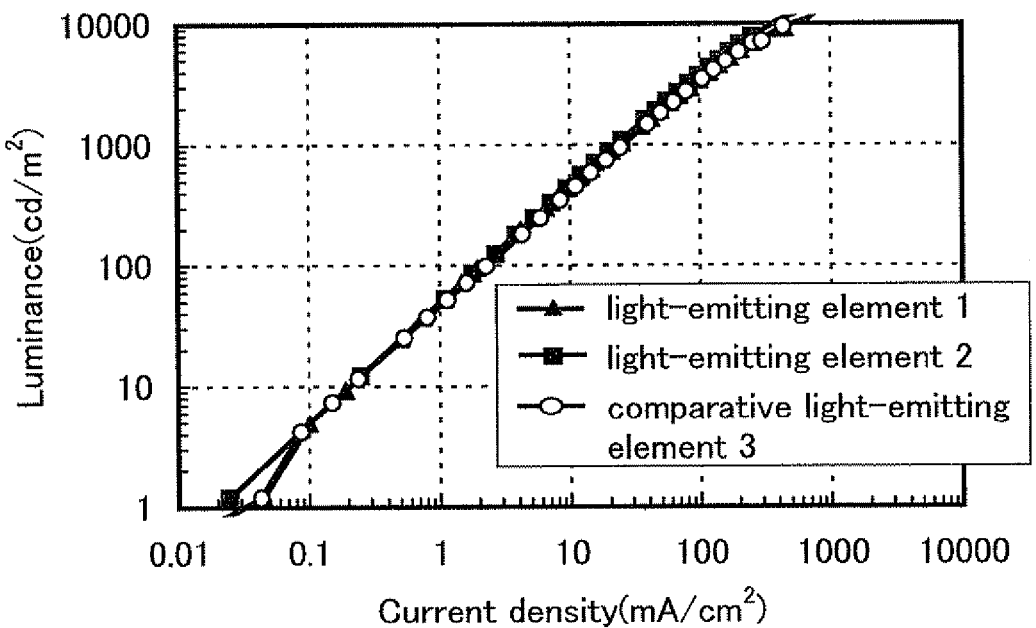
FIG. 31 is a diagram showing current density-luminance characteristics of light-emitting elements manufactured in Embodiment 5.
Figure 32:
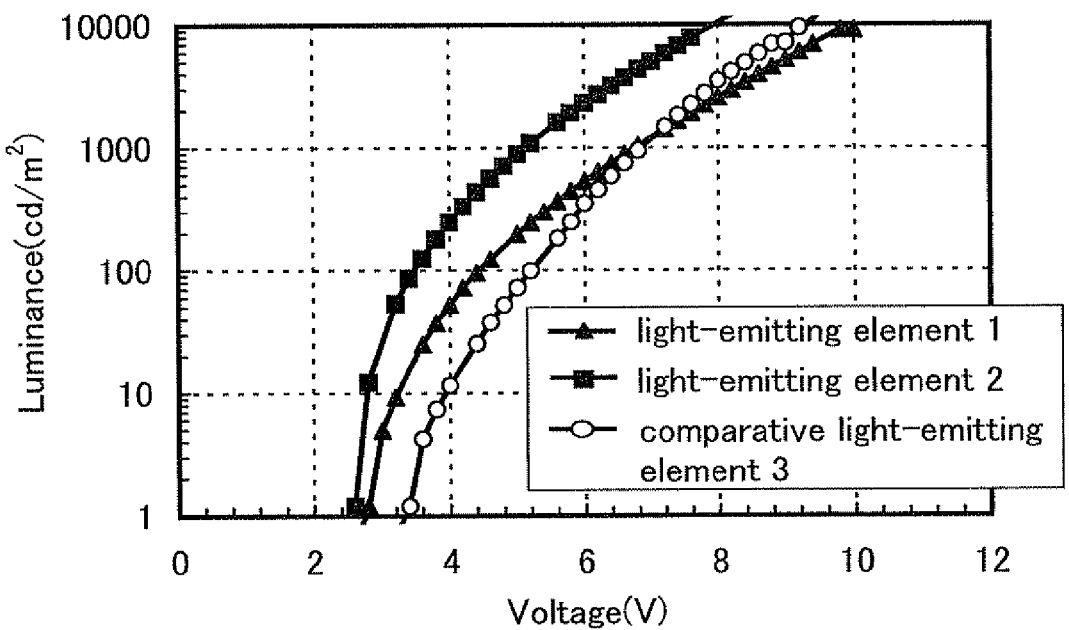
FIG. 32 is a diagram showing voltage-luminance characteristics of the light-emitting elements manufactured in Embodiment 5.
Figure 33:
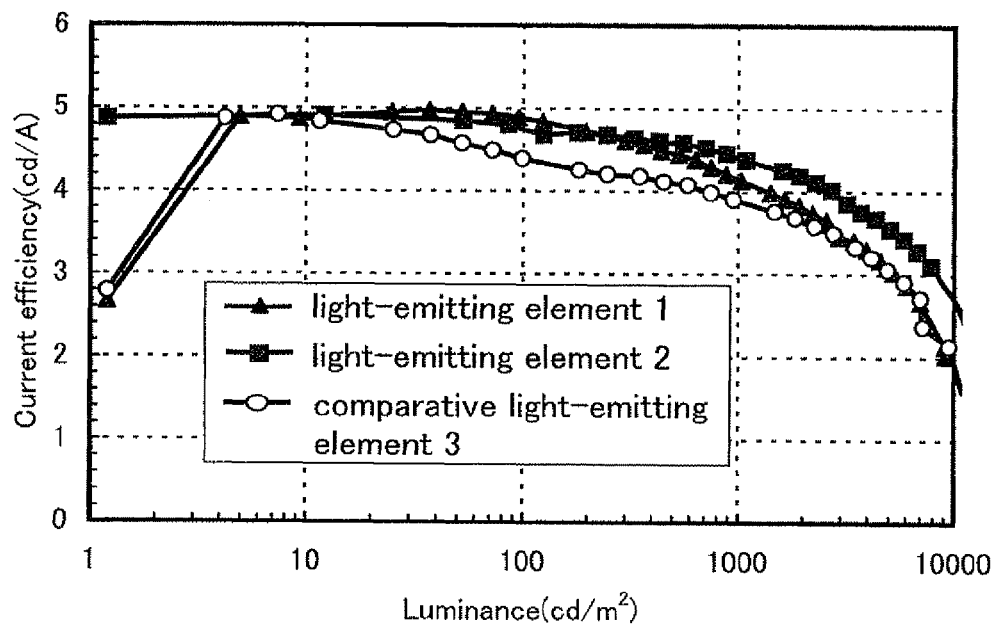
FIG. 33 is a diagram showing luminance-current efficiency characteristics of the light-emitting elements manufactured in Embodiment 5.
Figure 34:
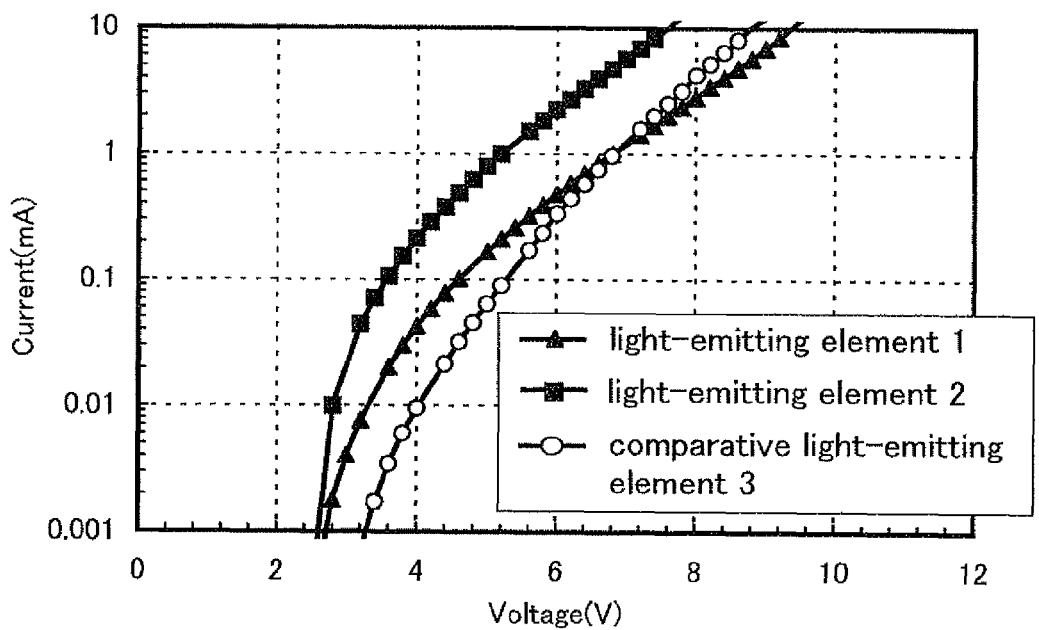
FIG. 34 is a diagram showing voltage-current characteristics of the light-emitting elements manufactured in Embodiment 5.

FIG. 31 shows current density-luminance characteristics of the light-emitting element 1, the light-emitting element 2, and the comparative light-emitting element 3. FIG. 32 shows the voltage-luminance characteristics. FIG. 33 shows the luminance-current efficiency characteristics. FIG. 34 shows the voltage-current characteristics. Note that FIGS. 31 and 32 show raw measurement data and FIGS. 33 and 34 show the results of calculations based on the measurement data.

Figure 35:
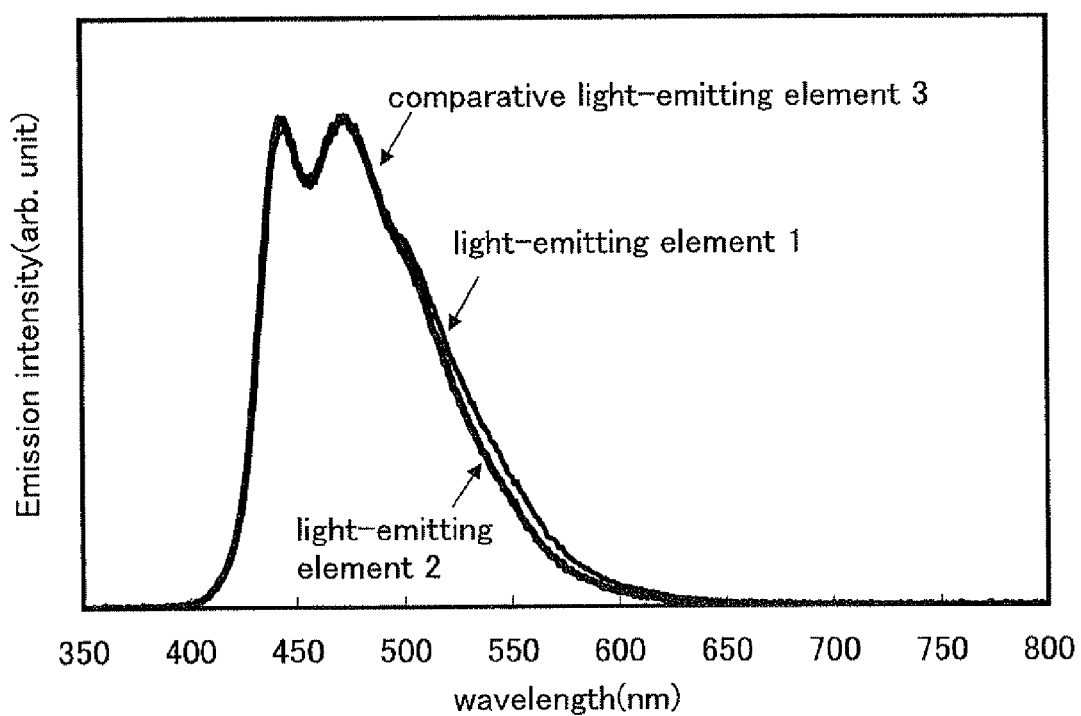
FIG. 35 is a diagram showing emission spectra of the light-emitting elements manufactured in Embodiment 5.

FIG. 35 shows emission spectra when a current of 1 mA flows. It can be seen from FIG. 35 that light emission of each of the light-emitting element 1, the light-emitting element 2, and the comparative light-emitting element 3 results from YGA2S.

The comparative light-emitting element 3 provides blue light emission where the CIE chromaticity coordinates are (x=0.16, y=0.17) when the luminance is 950 cd/m². The current efficiency is 3.9 cd/A when the luminance is 950 cd/m². When the luminance is 950 cd/m², the voltage is 6.8 V; the current density, 24.3 mA/cm²; and the power efficiency, 1.8 lm/W.

On the other hand, the light-emitting element 1 provides blue light emission where the CIE chromaticity coordinates are (x=0.17, y=0.19) when the luminance is 1040 cd/m². The current efficiency is 4.1 cd/A when the luminance is 1040 cd/m². When the luminance is 1040 cd/m², the voltage is 6.8 V; the current density, 25.1 mA/cm²; and the power efficiency, 1.9 lm/W.

It can be seen from FIG. 34 that the light-emitting element 1 and the comparative light-emitting element 3 require the same or substantially the same amount of voltage to allow the same amount of electric current to flow. However, as shown in FIG. 33, the light-emitting element 1 has higher current efficiency than the comparative light-emitting element 3. Thus, the light-emitting element 1 consumes less electric power than the comparative light-emitting element 3.

The light-emitting element 2 provides blue light emission where the CIE chromaticity coordinates are (x=0.17, y=0.19) when the luminance is 1090 cd/m². The current efficiency is 4.4 cd/A when the luminance is 1090 cd/m². When the luminance is 1090 cd/m², the voltage was 5.2 V; the current density, 24.8 mA/cm²; and the power efficiency, 2.6 lm/W.

It can be seen from FIG. 34 that the light-emitting element 2 requires lower voltage than the comparative light-emitting element 3 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 33 that the light-emitting element 2 has higher current efficiency than the comparative light-emitting element 3. Thus, as shown in FIG. 32, the light-emitting element 2 requires lower voltage than the comparative light-emitting element 3 to provide the same luminance.

That is, it can be seen that the light-emitting element 2 requires lower voltage and consumes less power than the comparative light-emitting element 3 to provide the same luminance.

By application of the present invention, a light-emitting element with low driving voltage can be obtained. In addition, a light-emitting element which consumes less power can be obtained.

Embodiment 6

In this embodiment, light-emitting elements of the present invention are described with reference to FIG. 30. Methods for manufacturing light-emitting elements of this embodiment are hereinafter described.

(Light-Emitting Element 4)

First, a film of indium tin oxide containing silicon oxide (ITO) was formed over a glass substrate 2101 by a sputtering method to form a first electrode 2102. Note that the thickness was 110 nm and the electrode area was 2 mm×2 mm.

Next, the substrate provided with the first electrode 2102 was fixed to a substrate holder provided in a vacuum evaporation apparatus such that the side on which the first electrode was formed faced downward. After the pressure in a film formation chamber was lowered to approximately $10^{-4}$ Pa, a layer 2111 containing a composite material of an organic compound and an inorganic compound was formed on the first electrode 2102 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino] biphenyl (abbr.: NPB) was formed to a thickness of 10 nm on the layer 2111 containing a composite material by an evaporation method employing resistance heating to form a hole-transporting layer 2112.

Then, a light-emitting layer 2113 was formed to a thickness of 30 nm on the hole-transporting layer 2112 by co-evaporation of 9-[4-(10-phenyl-9-anthryl)phenyl]-9H-carbazole (abbr.: CzPA) and N,N'-bis[4-(9H-carbazol-9-yl)phenyl]-N, N'-diphenylstilbene-4,4'-diamine (abbr.: YGA2S). Here, the weight ratio of CzPA to YGA2S was adjusted to be 1:0.04 (=CzPA:YGA2S).

After that, a film of 2-phenyl-3-[4'-(3-pyridyl)biphenyl-4-yl]quinoxaline (abbr.: PPy1PQ) represented by the structural formula (195) was formed to a thickness of 30 nm on the light-emitting layer 2113 by an evaporation method employing resistance heating to form an electron-transporting layer 2114.

Furthermore, a film of lithium fluoride was formed to a thickness of 1 nm on the electron-transporting layer 2114 to form an electron-injecting layer 2115.

Lastly, a film of aluminum was formed to a thickness of 200 nm on the electron-injecting layer 2115 by an evaporation method employing resistance heating to form a second electrode 2104. Accordingly, a light-emitting element 4 was manufactured.

(Comparative Light-Emitting Element 5)

A comparative light-emitting element 5 was formed like the light-emitting element 4 by using the same substrate and using tris(8-quinolinolato)aluminum(III) (abbr.: Alq) instead of PPy1PQ. That is, a film of tris(8-quinolinolato)aluminum (III) (abbr.: Alq) was formed to a thickness of 30 nm to form the electron-transporting layer 2114. Except for the electron-transporting layer 2114, the comparative light-emitting element 5 was formed like the light-emitting element 4.

The light-emitting element 4 and the comparative light-emitting element 5 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 36:
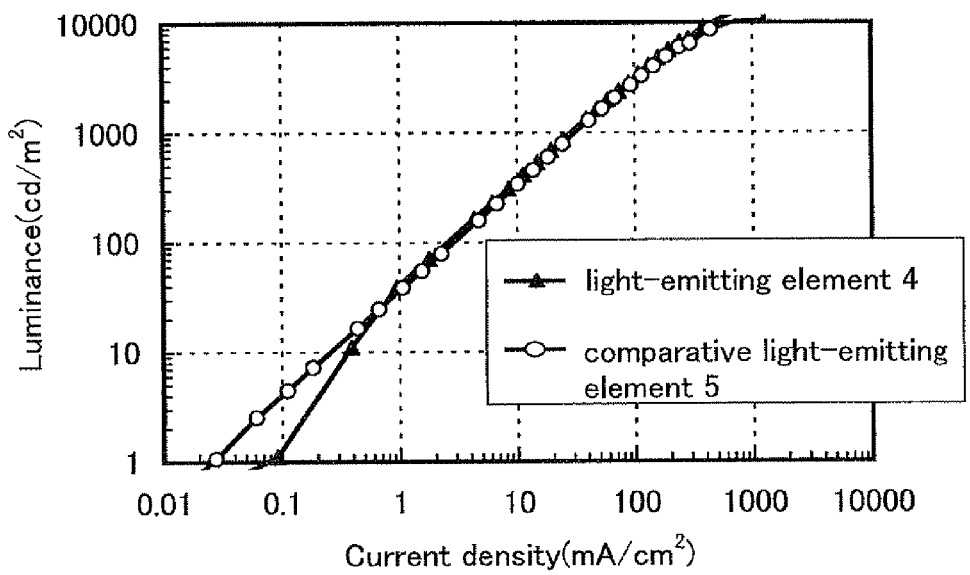
FIG. 36 is a diagram showing current density-luminance characteristics of light-emitting elements manufactured in Embodiment 6.
Figure 37:
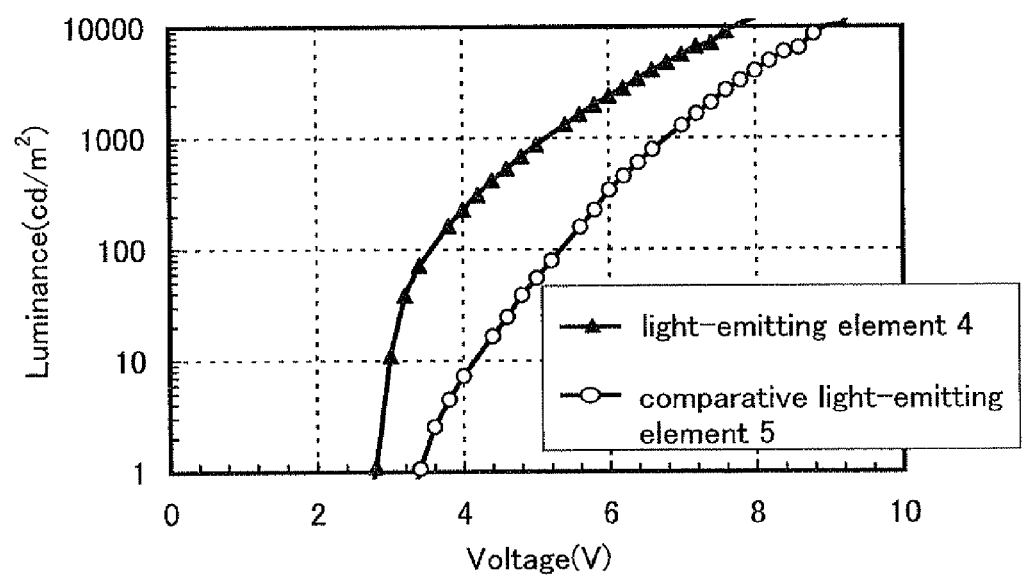
FIG. 37 is a diagram showing voltage-luminance characteristics of the light-emitting elements manufactured in Embodiment 6.
Figure 38:
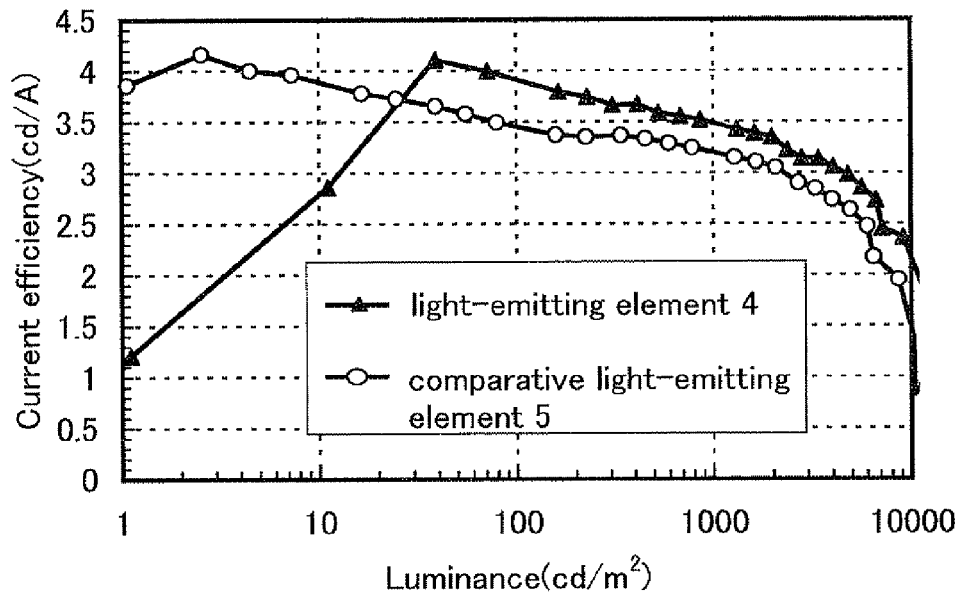
FIG. 38 is a diagram showing luminance-current efficiency characteristics of the light-emitting elements manufactured in Embodiment 6.
Figure 39:
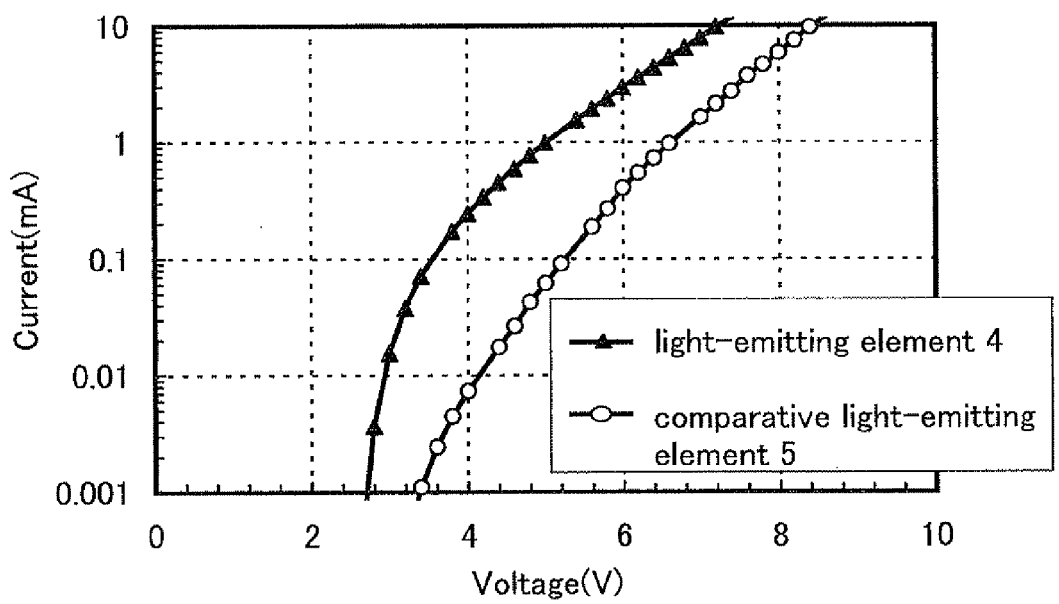
FIG. 39 is a diagram showing voltage-current characteristics of the light-emitting elements manufactured in Embodiment 6.

FIG. 36 shows current density-luminance characteristics of the light-emitting element 4 and the comparative light-emitting element 5. FIG. 37 shows the voltage-luminance characteristics. FIG. 38 shows the luminance-current efficiency characteristics. FIG. 39 shows the voltage-current characteristics. Note that FIGS. 36 and 37 show raw measurement data and FIGS. 38 and 39 show the results of calculations based on the measurement data.

Figure 40:
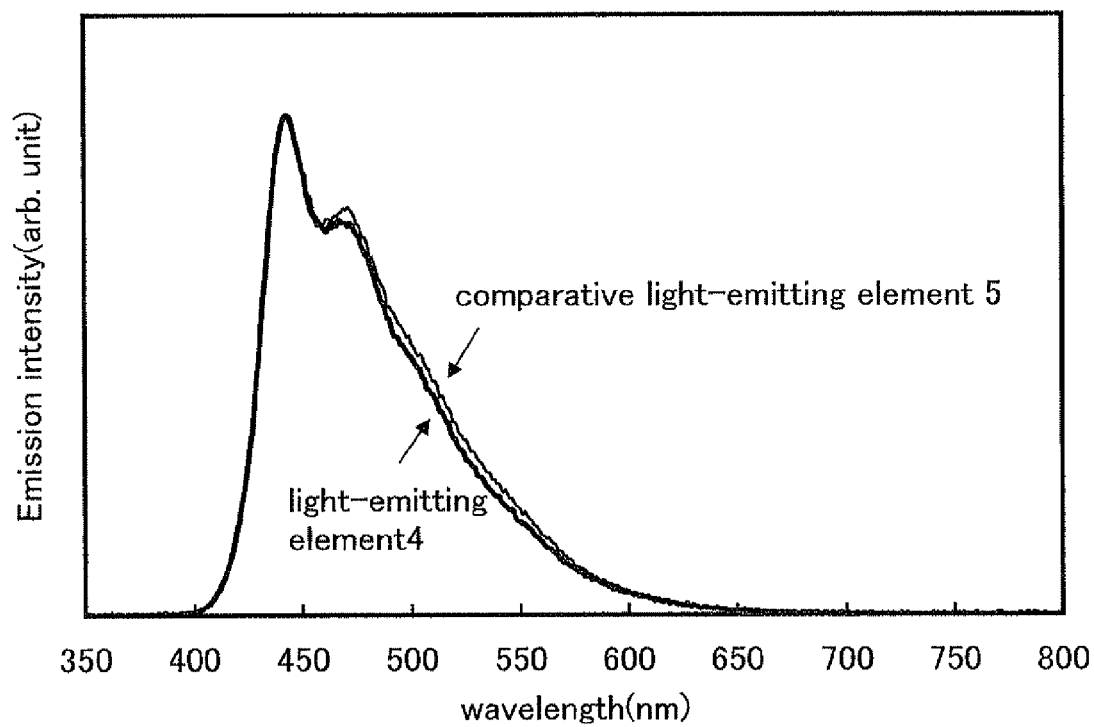
FIG. 40 is a diagram showing emission spectra of the light-emitting elements manufactured in Embodiment 6.

FIG. 40 shows emission spectra when a current of 1 mA flows. It can be seen from FIG. 40 that light emission of each of the light-emitting element 4 and the comparative light-emitting element 5 results from YGA2S.

The comparative light-emitting element 5 provides blue light emission where the CIE chromaticity coordinates are (x=0.16, y=0.18) when the luminance is 790 cd/m$^2$. The current efficiency is 3.2 cd/A when the luminance is 790 cd/m$^2$. When the luminance is 790 cd/m$^2$, the voltage is 6.6 V; the current density, 24.2 mA/cm$^2$; and the power efficiency, 1.5 lm/W.

The light-emitting element 4 provides blue light emission where the CIE chromaticity coordinates are (x=0.16, y=0.17) when the luminance is 860 cd/m$^2$. The current efficiency is 3.5 cd/A when the luminance is 860 cd/m$^2$. When the luminance is 860 cd/m$^2$, the voltage is 5.0 V; the current density, 24.6 mA/cm$^2$; and the power efficiency, 2.2 lm/W.

It can be seen from FIG. 39 that the light-emitting element 4 requires lower voltage than the comparative light-emitting element 5 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 38 that the light-emitting element 4 has higher current efficiency than the comparative light-emitting element 5. Thus, as shown in FIG. 37, the light-emitting element 4 requires lower voltage than the comparative light-emitting element 5 to provide the same luminance.

That is, it can be seen that the light-emitting element 4 requires lower voltage and consumes less power than the comparative light-emitting element 5 to provide the same luminance.

By application of the present invention, a light-emitting element with low driving voltage can be obtained. In addition, a light-emitting element which consumes less power can be obtained.

Embodiment 7

Figure 41:
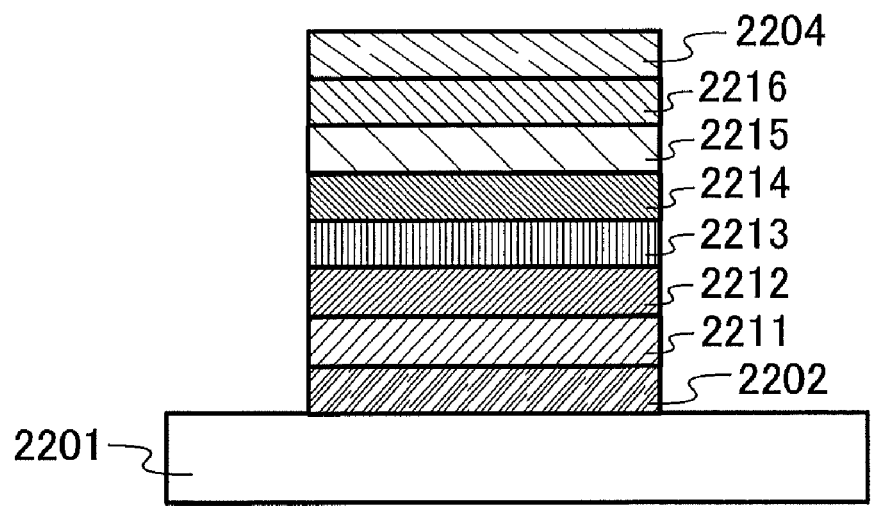
FIG. 41 is a diagram illustrating light-emitting elements of Embodiments.

In this embodiment, light-emitting elements of the present invention are described with reference to FIG. 41. Structural formulas of materials used in this embodiment are given below. Note that the materials, the structural formulas of which have already been shown, are omitted.

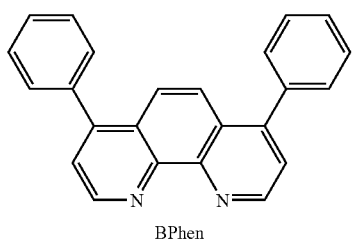

BPhen

Methods for manufacturing light-emitting elements of this embodiment are hereinafter described.

(Light-Emitting Element 6)

First, a film of indium tin oxide containing silicon oxide (ITSO) was formed over a glass substrate 2201 by a sputtering method to form a first electrode 2202. Note that the thickness was 110 nm and the electrode area was 2 mm×2 mm.

Next, the substrate provided with the first electrode 2202 was fixed to a substrate holder provided in a vacuum evaporation apparatus such that the side on which the first electrode was formed faced downward. After the pressure in a film formation chamber was lowered to approximately $10^{-4}$ Pa, a layer 2211 containing a composite material of an organic compound and an inorganic compound was formed on the first electrode 2202 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino]biphenyl (abbr.: NPB) was formed to a thickness of 10 nm on the layer 2211 containing a composite material by an evaporation method employing resistance heating to form a hole-transporting layer 2212.

Then, a light-emitting layer 2213 was formed to a thickness of 30 nm on the hole-transporting layer 2212 by co-evaporation of 9-[4-(10-phenyl-9-anthryl)phenyl]-9H-carbazole (abbr.: CzPA) and N,N'-bis[4-(9H-carbazol-9-yl)phenyl]-N,N'-diphenylstilbene-4,4'-diamine (abbr.: YGA2S). Here, the weight ratio of CzPA to YGA2S was adjusted to be 1:0.04 (=CzPA:YGA2S).

After that, a film of 2-phenyl-3-[4-(2-pyridyl)phenyl]quinoxaline (abbr.: 2Py1PQ) represented by the structural formula (101) was formed to a thickness of 10 nm on the light-emitting layer 2213 by an evaporation method employing resistance heating to form an electron-transporting layer (A) 2214. Moreover, a film of bathophenanthroline (abbr.: BPhen) was formed to a thickness of 20 nm on the electron-transporting layer (A) 2214 to form an electron-transporting layer (B) 2215. Thus, the light-emitting elements of this embodiment have a structure in which two electron-transporting layers are stacked.

Furthermore, a film of lithium fluoride was formed to a thickness of 1 nm on the electron-transporting layer (B) 2215 to form an electron-injecting layer 2216.

Lastly, a film of aluminum was formed to a thickness of 200 nm on the electron-injecting layer 2216 by an evaporation method employing resistance heating to a second electrode 2204. Accordingly, a light-emitting element 6 was manufactured.

(Light-Emitting Element 7)

A light-emitting element 7 was formed like the light-emitting element 6 by using the same substrate and using 2-phenyl-3-[4-(3-pyridyl)phenyl]quinoxaline (abbr.: 3Py1PQ) represented by the structural formula (102) instead of 2Py1PQ. That is, a film of 2-phenyl-3-[4-(3-pyridyl)phenyl]quinoxaline (abbr.: 3Py1PQ) represented by the structural formula (102) was formed to a thickness of 10 nm to form the electron-transporting layer (A) 2214. Except for the electron-transporting layer (A) 2214, the light-emitting element 7 was formed like the light-emitting element 6.

(Comparative Light-Emitting Element 8)

A comparative light-emitting element 8 was formed like the light-emitting element 6 by using the same substrate and using tris(8-quinolinolato)aluminum(III) (abbr.: Alq) instead of 2Py1PQ. That is, a film of tris(8-quinolinolato)aluminum (III) (abbr.: Alq) was formed to a thickness of 10 nm to form the electron-transporting layer (A) 2214. Except for the electron-transporting layer (A) 2214, the comparative light-emitting element 8 was formed like the light-emitting element 6.

The light-emitting element 6, the light-emitting element 7, and the comparative light-emitting element 8 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 42:
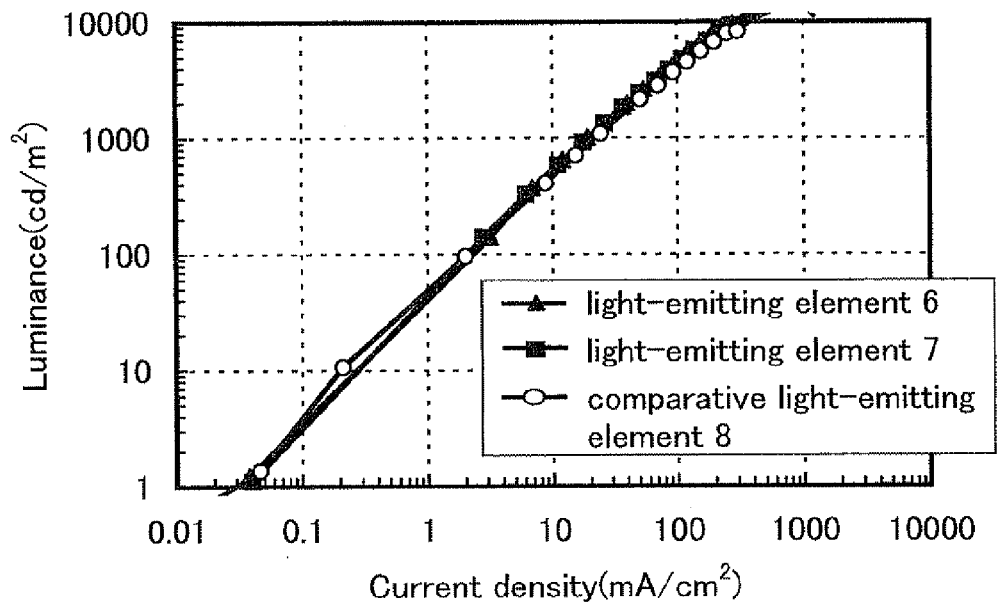
FIG. 42 is a diagram showing current density-luminance characteristics of light-emitting elements manufactured in Embodiment 7.
Figure 43:
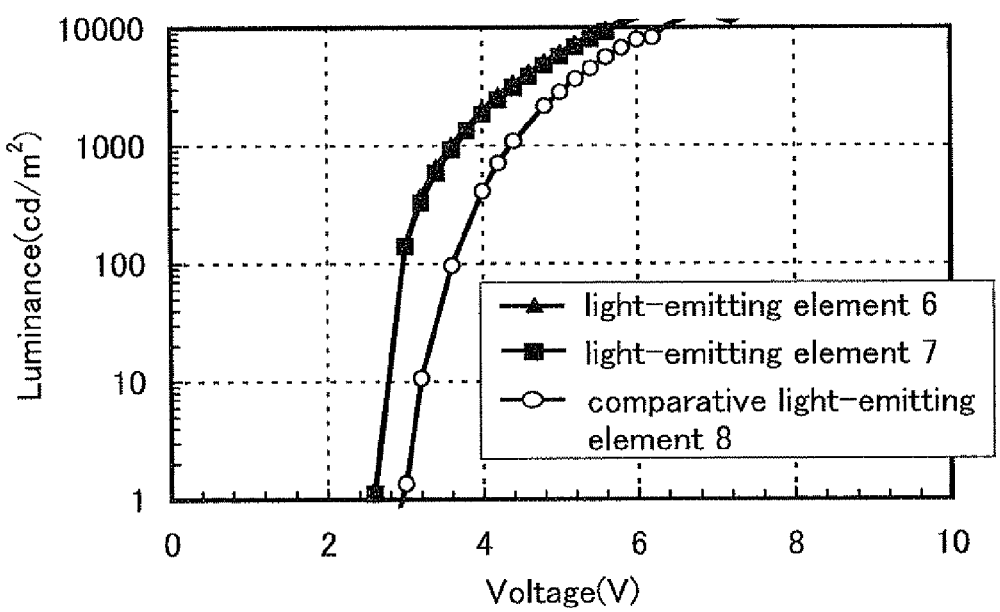
FIG. 43 is a diagram showing voltage-luminance characteristics of the light-emitting elements manufactured in Embodiment 7.
Figure 44:
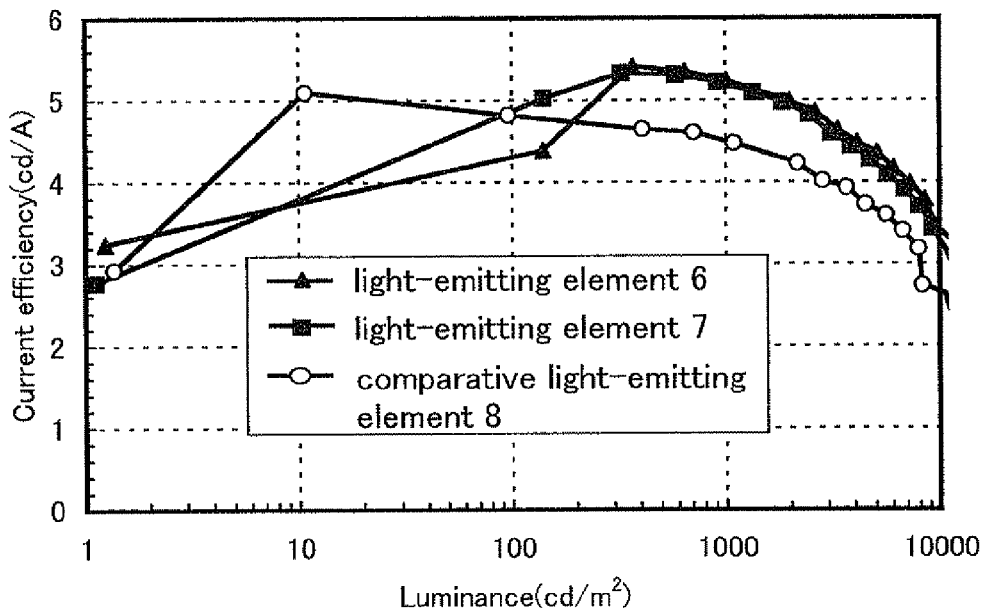
FIG. 44 is a diagram showing luminance-current efficiency characteristics of the light-emitting elements manufactured in Embodiment 7.
Figure 45:
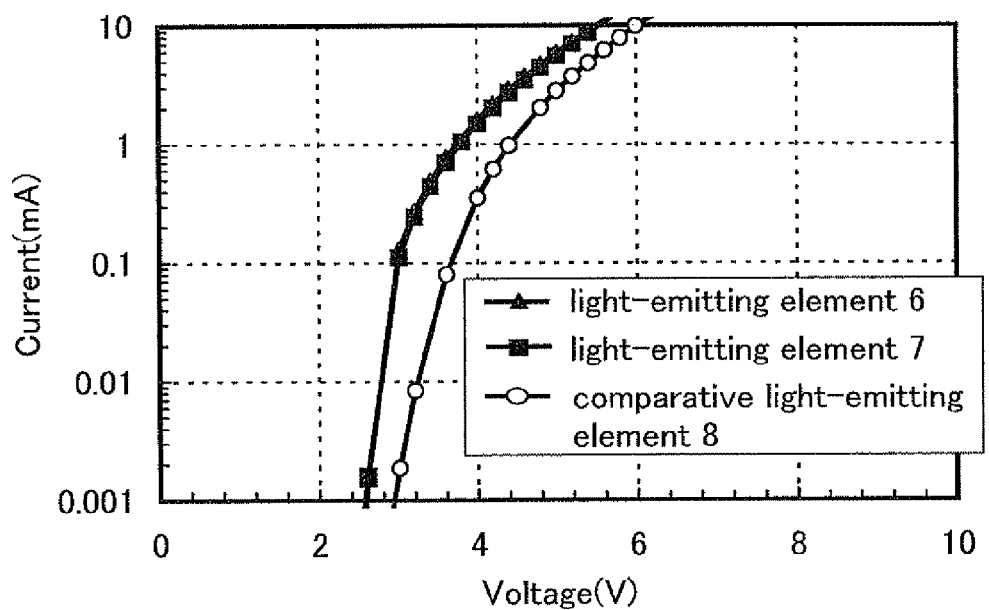
FIG. 45 is a diagram showing voltage-current characteristics of the light-emitting elements manufactured in Embodiment 7.

FIG. 42 shows current density-luminance characteristics of the light-emitting element 6, the light-emitting element 7, and the comparative light-emitting element 8. FIG. 43 shows the voltage-luminance characteristics. FIG. 44 shows the luminance-current efficiency characteristics. FIG. 45 shows the voltage-current characteristics. Note that FIGS. 42 and 43 show raw measurement data and FIGS. 44 and 45 show the results of calculations based on the measurement data.

Figure 46:
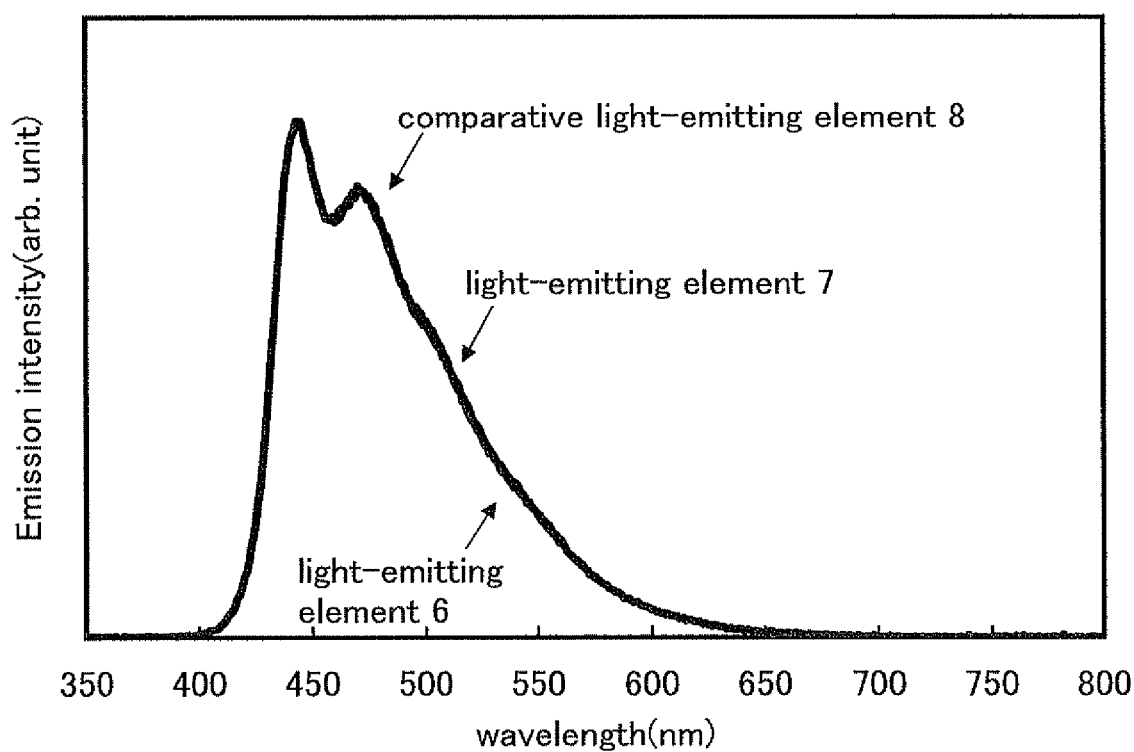
FIG. 46 is a diagram showing emission spectra of the light-emitting elements manufactured in Embodiment 7.

FIG. 46 shows emission spectra when a current of 1 mA flows. It can be seen from FIG. 46 that light emission of each of the light-emitting element 6, the light-emitting element 7, and the comparative light-emitting element 8 results from YGA2S.

The comparative light-emitting element 8 provides blue light emission where the CIE chromaticity coordinates are (x=0.17, y=0.19) when the luminance is 1090 cd/m². The current efficiency is 4.5 cd/A when the luminance is 1090 cd/m². When the luminance is 1090 cd/m², the voltage is 4.4 V; the current density, 24.4 mA/cm²; and the power efficiency, 3.2 lm/W.

On the other hand, the light-emitting element 6 provides blue light emission where the CIE chromaticity coordinates are (x=0.16, y=0.19) when the luminance is 1010 cd/m². The current efficiency is 5.2 cd/A when the luminance is 1010 cd/m². When the luminance is 1010 cd/m², the voltage is 3.6 V; the current density, 19.2 mA/cm²; and the power efficiency, 4.6 lm/W.

The light-emitting element 7 provides blue light emission where the CIE chromaticity coordinates are (x=0.16, y=0.19) when the luminance is 920 cd/m². The current efficiency is 5.2 cd/A when the luminance is 920 cd/m². When the luminance is 920 cd/m², the voltage is 3.6 V; the current density, 17.7 mA/cm²; and the power efficiency, 4.6 lm/W.

It can be seen from FIG. 45 that the light-emitting element 6 and the light-emitting element 7 require lower voltage than the comparative light-emitting element 8 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 44 that the light-emitting element 6 and the light-emitting element 7 have higher current efficiency than the comparative light-emitting element 8. Thus, as shown in FIG. 43, the light-emitting element 6 and the light-emitting element 7 require lower voltage than the comparative light-emitting element 8 to provide the same luminance.

That is, it can be seen that the light-emitting element 6 and the light-emitting element 7 require lower voltage and consume less power than the comparative light-emitting element 8 to provide the same luminance.

By application of the present invention, a light-emitting element with low driving voltage can be obtained. In addition, a light-emitting element which consumes less power can be obtained.

Embodiment 8

In this embodiment, light-emitting elements of the present invention are described with reference to FIG. 41. Methods for manufacturing light-emitting elements of this embodiment are hereinafter described.
(Light-Emitting Element 9)

First, a film of indium tin oxide containing silicon oxide (ITSO) was formed over a glass substrate 2201 by a sputtering method to form a first electrode 2202. Note that the thickness was 110 nm and the electrode area was 2 mm×2 mm.

Next, the substrate provided with the first electrode 2202 was fixed to a substrate holder provided in a vacuum evaporation apparatus such that the side on which the first electrode was formed faced downward. After the pressure in a film formation chamber was lowered to approximately $10^{-4}$ Pa, a layer 2211 containing a composite material of an organic compound and an inorganic compound was formed on the first electrode 2202 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino]biphenyl (abbr.: NPB) was formed to a thickness of 10 nm on the layer 2211 containing a composite material by an evaporation method employing resistance heating to form a hole-transporting layer 2212.

Then, a light-emitting layer 2213 was formed to a thickness of 30 nm on the hole-transporting layer 2212 by co-evaporation of 9-[4-(10-phenyl-9-anthryl)phenyl]-9H-carbazole (abbr.: CzPA) and N,N'-bis[4-(9H-carbazol-9-yl)phenyl]-N,N'-diphenylstilbene-4,4'-diamine (abbr.: YGA2S). Here, the weight ratio of CzPA to YGA2S was adjusted to be 1:0.04 (=CzPA:YGA2S).

After that, a film of 2-phenyl-3-[4'-(3-pyridyl)biphenyl-4-yl]quinoxaline (abbr.: PPy1PQ) represented by the structural formula (195) was formed to a thickness of 20 nm on the light-emitting layer 2213 by an evaporation method employing resistance heating to form an electron-transporting layer (A) 2214. Moreover, a film of bathophenanthroline (abbr.: BPhen) was formed to a thickness of 10 nm on the electron-transporting layer (A) 2214 to form an electron-transporting layer (B) 2215. Thus, the light-emitting elements of this embodiment have a structure in which two electron-transporting layers are stacked.

Furthermore, a film of lithium fluoride was formed to a thickness of 1 nm on the electron-transporting layer (B) 2215 to form an electron-injecting layer 2216.

Lastly, a film of aluminum was formed to a thickness of 200 nm on the electron-injecting layer 2216 by an evaporation method employing resistance heating to form a second electrode 2204. Accordingly, a light-emitting element 9 was manufactured.
(Comparative Light-Emitting Element 10)

A comparative light-emitting element 10 was formed like the light-emitting element 9 by using the same substrate and using tris(8-quinolinolato)aluminum(III) (abbr.: Alq) instead of PPy1PQ. That is, a film of tris(8-quinolinolato)aluminum (III) (abbr.: Alq) was formed to a thickness of 20 nm to form the electron-transporting layer (A). 2214. Except for the electron-transporting layer (A) 2214, the comparative light-emitting element 10 was formed like the light-emitting element 9.

The light-emitting element 9 and the comparative light-emitting element 10 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 47:
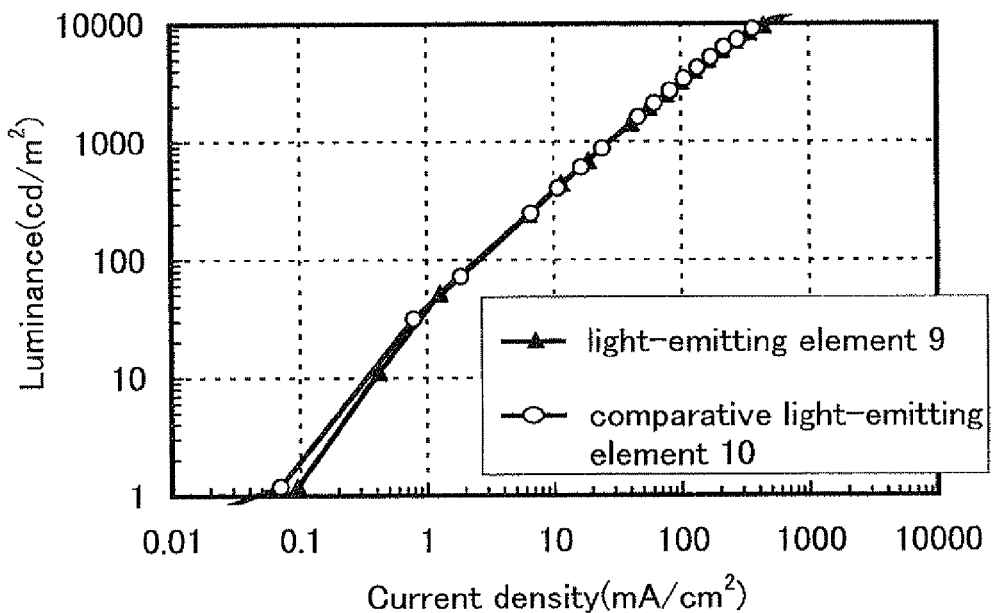
FIG. 47 is a diagram showing current density-luminance characteristics of light-emitting elements manufactured in Embodiment 8.
Figure 48:
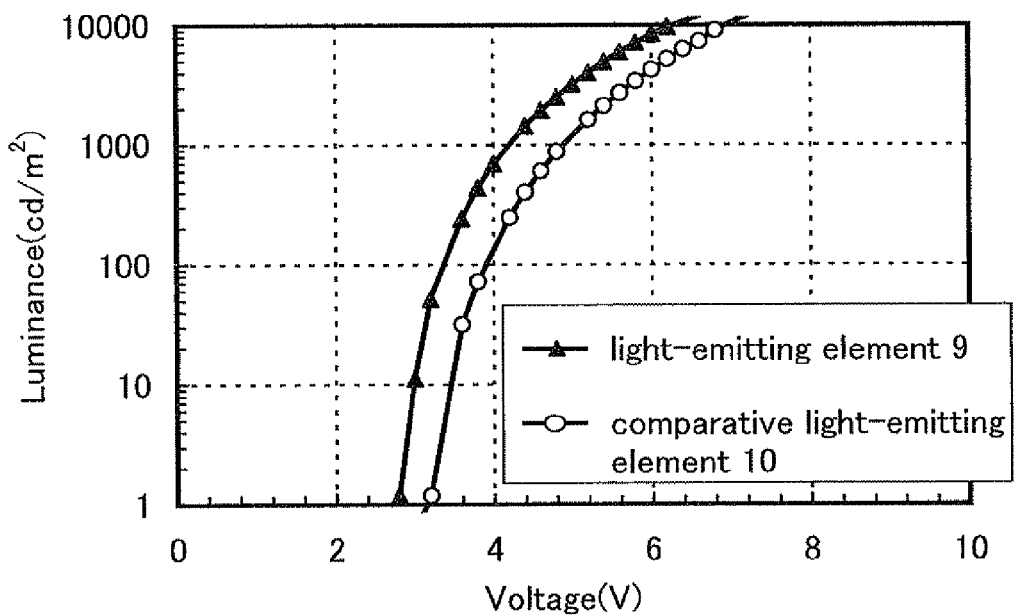
FIG. 48 is a diagram showing voltage-luminance characteristics of the light-emitting elements manufactured in Embodiment 8.
Figure 49:
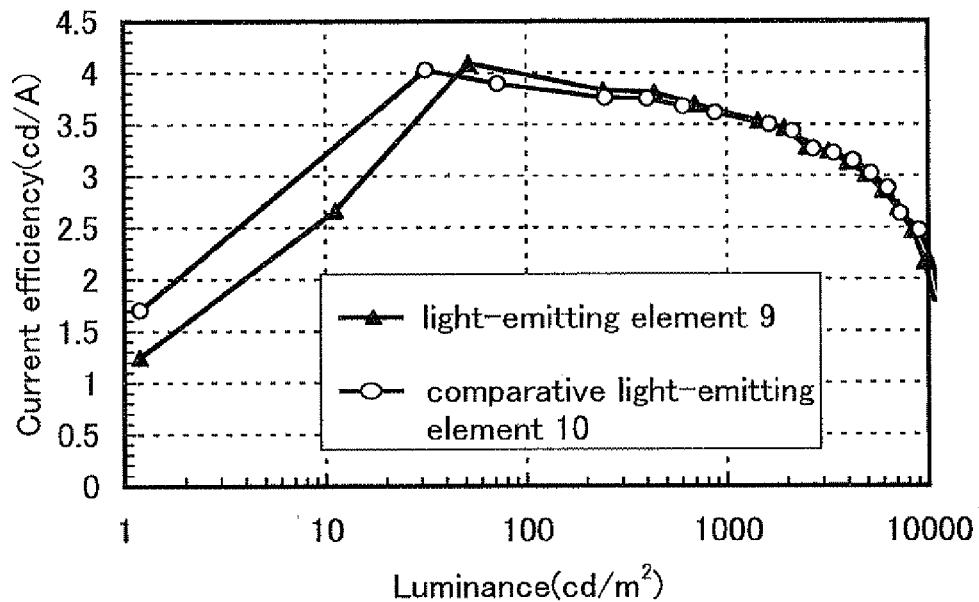
FIG. 49 is a diagram showing luminance-current efficiency characteristics of the light-emitting elements manufactured in Embodiment 8.
Figure 50:
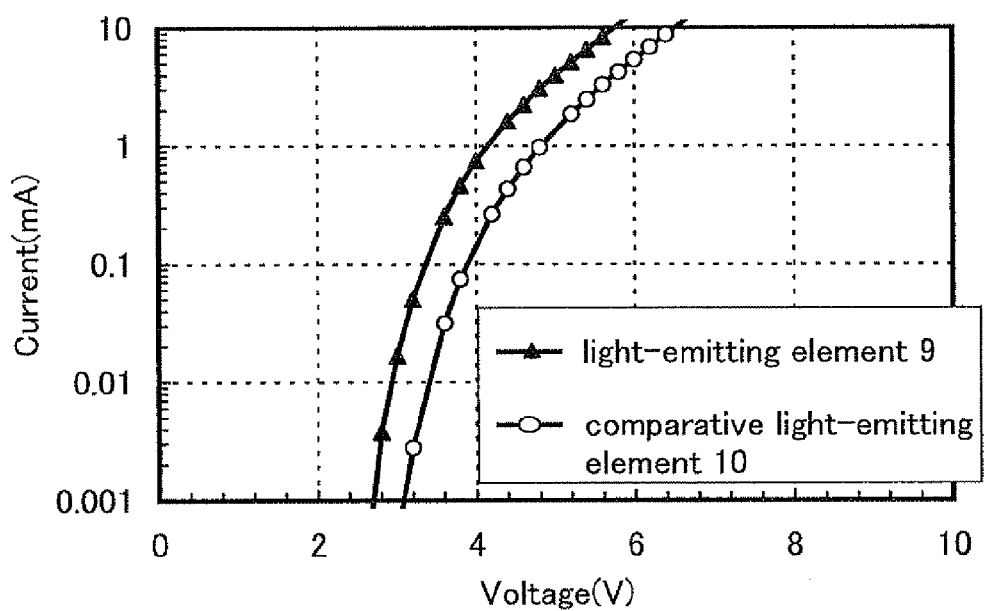
FIG. 50 is a diagram showing voltage-current characteristics of the light-emitting elements manufactured in Embodiment 8.

FIG. 47 shows current density-luminance characteristics of the light-emitting element 9 and the comparative light-emitting element 10. FIG. 48 shows the voltage-luminance characteristics. FIG. 49 shows the luminance-current efficiency characteristics. FIG. 50 shows the voltage-current characteristics. Note that FIGS. 47 and 48 show raw measurement data and FIGS. 49 and 50 show the results of calculations based on the measurement data.

Figure 51:
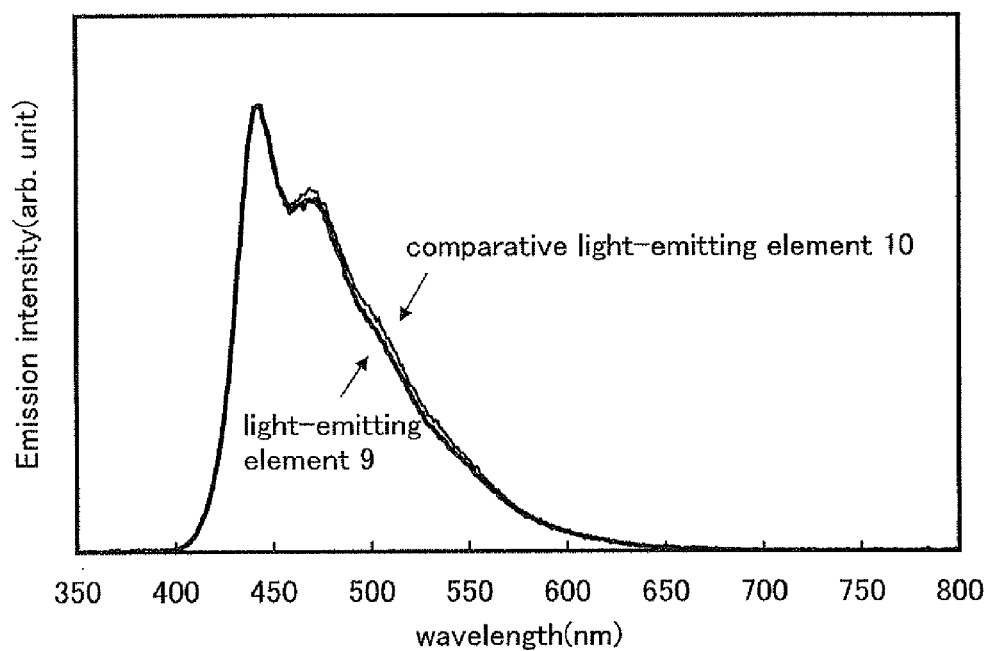
FIG. 51 is a diagram showing emission spectra of the light-emitting elements manufactured in Embodiment 8.

FIG. 51 shows emission spectra when a current of 1 mA flows. It can be seen from FIG. 51 that light emission of each of the light-emitting element 9 and the comparative light-emitting element 10 results from YGA2S.

The comparative light-emitting element 10 provides blue light emission where the CIE chromaticity coordinates are (x=0.16, y=0.17) when the luminance is 880 cd/m$^2$. The current efficiency is 3.6 cd/A when the luminance is 880 cd/m$^2$. When the luminance is 880 cd/m$^2$, the voltage is 4.8 V; the current density, 24.3 mA/cm$^2$; and the power efficiency, 2.4 lm/W.

The light-emitting element 9 provides blue light emission where the CIE chromaticity coordinates are (x=0.16, y=0.17) when the luminance is 690 cd/m$^2$. The current efficiency is 3.7 cd/A when the luminance is 690 cd/m$^2$. When the luminance is 690 cd/m$^2$, the voltage is 4.0 V; the current density, 18.7 mA/cm$^2$; and the power efficiency, 2.9 lm/W.

It can be seen from FIG. 50 that the light-emitting element 9 requires lower voltage than the comparative light-emitting element 10 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 49 that the light-emitting element 9 and the comparative light-emitting element 10 exhibit approximately the same current efficiency. Thus, as shown in FIG. 48, the light-emitting element 9 requires lower voltage than the comparative light-emitting element 10 to provide the same luminance.

That is, it can be seen that the light-emitting element 9 requires lower voltage and consumes less power than the comparative light-emitting element 10 to provide the same luminance.

By application of the present invention, a light-emitting element with low driving voltage can be obtained. In addition, a light-emitting element which consumes less power can be obtained.

Embodiment 9

In this embodiment, light-emitting elements of the present invention are described with reference to FIG. 30. Structural formulas of materials used in this embodiment are given below. Note that the materials, the structural formulas of which have already been shown, are omitted.

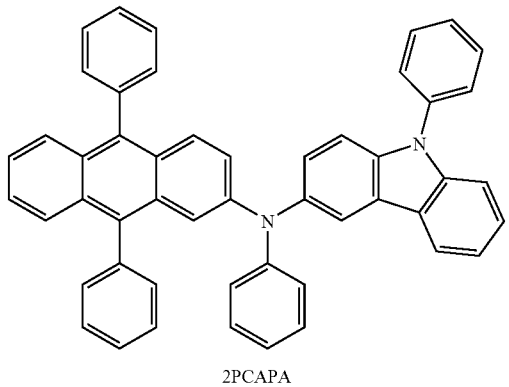

2PCAPA

Methods for manufacturing light-emitting elements of this embodiment are hereinafter described.
(Light-Emitting Element 11)

First, a film of indium tin oxide containing silicon oxide (ITSO) was formed over a glass substrate 2101 by a sputtering method to form a first electrode 2102. Note that the thickness was 110 nm and the electrode area was 2 mm×2 mm.

Next, the substrate provided with the first electrode 2102 was fixed to a substrate holder provided in a vacuum evaporation apparatus such that the side on which the first electrode was formed faced downward. After the pressure in a film formation chamber was lowered to approximately $10^{-4}$ Pa, a layer 2111 containing a composite material of an organic compound and an inorganic compound was formed on the first electrode 2102 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino]biphenyl (abbr.: NPB) was formed to a thickness of 10 nm on the layer 2111 containing a composite material by an evaporation method employing resistance heating to form a hole-transporting layer 2112.

Then, a light-emitting layer 2113 was formed to a thickness of 40 nm on the hole-transporting layer 2112 by co-evaporation of 9-[4-(10-phenyl-9-anthryl)phenyl]-9H-carbazole (abbr.: CzPA) and N-(9,10-diphenyl-2-anthryl)-N,9-diphenyl-9H-carbazol-3-amine (abbr.: 2PCAPA). Here, the weight ratio of CzPA to 2PCAPA was adjusted to be 1:0.05 CzPA:2PCAPA).

After that, a film of 2-phenyl-3-[4-(2-pyridyl)phenyl]quinoxaline (abbr.: 2Py1PQ) represented by the structural formula (101) was formed to a thickness of 30 nm on the light-emitting layer 2113 by an evaporation method employing resistance heating to form an electron-transporting layer 2114.

Furthermore, a film of lithium fluoride was formed to a thickness of 1 nm on the electron-transporting layer 2114 to form an electron-injecting layer 2115.

Lastly, a film of aluminum was formed to a thickness of 200 nm on the electron-injecting layer 2115 by an evaporation method employing resistance heating to form a second electrode 2104. Accordingly, a light-emitting element 11 was manufactured.
(Light-Emitting Element 12)

A light-emitting element 12 was formed like the light-emitting element 11 by using the same substrate and using 2-phenyl-3-[4-(3-pyridyl)phenyl]quinoxaline (abbr.: 3Py1PQ) represented by the structural formula (102) instead of 2Py1PQ. That is, a film of 2-phenyl-3-[4-(3-pyridyl)phenyl]quinoxaline (abbr.: 3Py1PQ) represented by the structural formula (102) was formed to a thickness of 30 nm to form the electron-transporting layer 2114. Except for the electron-transporting layer 2114, the light-emitting element 12 was formed like the light-emitting element 11.
(Comparative Light-Emitting Element 13)

A comparative light-emitting element 13 was formed like the light-emitting element 11 by using the same substrate and using tris(8-quinolinolato)aluminum(III) (abbr.: Alq) instead of 2Py1PQ. That is, a film of tris(8-quinolinolato)aluminum (III) (abbr.: Alq) was formed to a thickness of 30 nm to form the electron-transporting layer 2114. Except for the electron-transporting layer 2114, the comparative light-emitting element 13 was formed like the light-emitting element 11.

The light-emitting element 11, the light-emitting element 12, and the comparative light-emitting element 13 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 52:
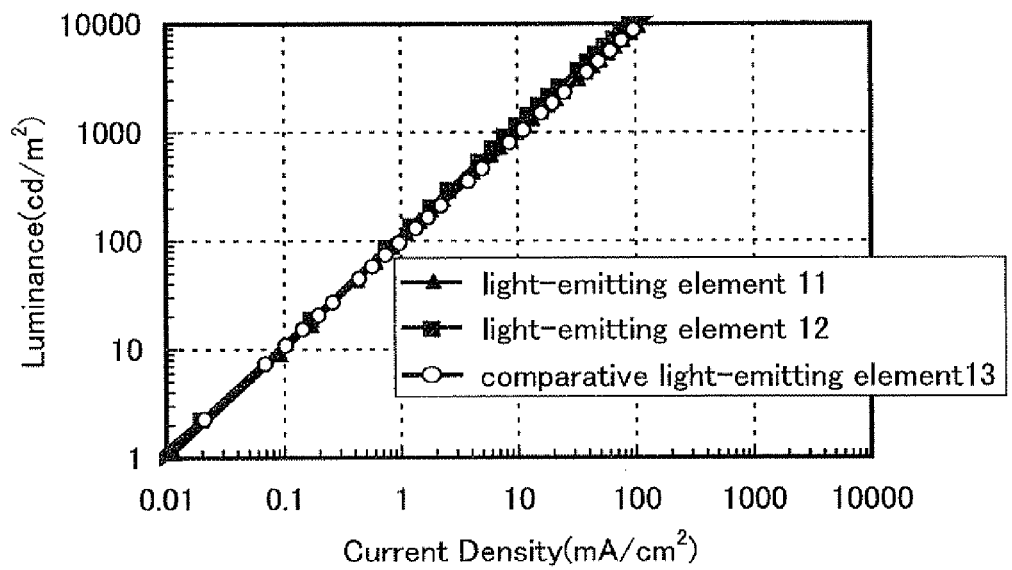
FIG. 52 is a diagram showing current density-luminance characteristics of light-emitting elements manufactured in Embodiment 9.
Figure 53:
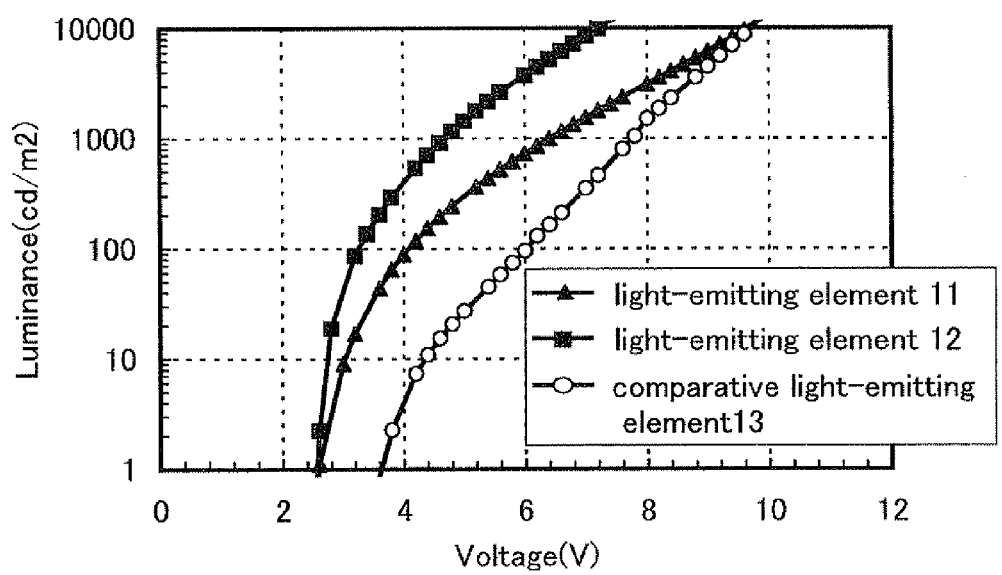
FIG. 53 is a diagram showing voltage-luminance characteristics of the light-emitting elements manufactured in Embodiment 9.
Figure 54:
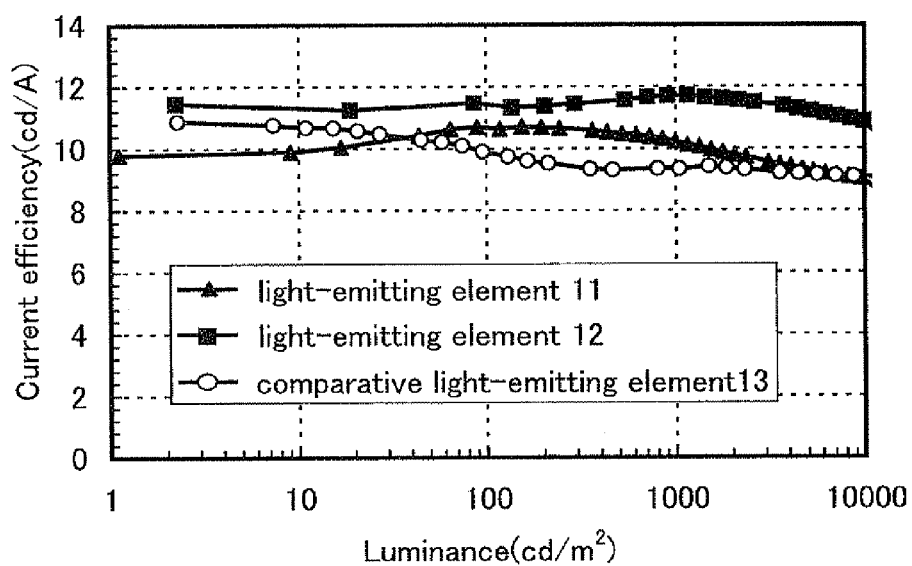
FIG. 54 is a diagram showing luminance-current efficiency characteristics of the light-emitting elements manufactured in Embodiment 9.
Figure 55:
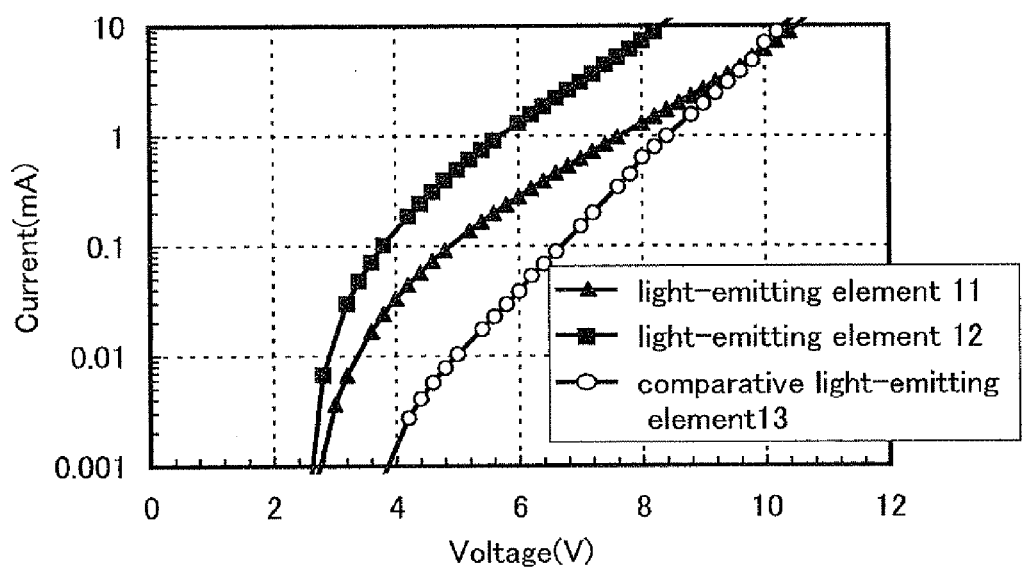
FIG. 55 is a diagram showing voltage-current characteristics of the light-emitting elements manufactured in Embodiment 9.

FIG. 52 shows current density-luminance characteristics of the light-emitting element 11, the light-emitting element 12, and the comparative light-emitting element 13. FIG. 53 shows the voltage-luminance characteristics. FIG. 54 shows the luminance-current efficiency characteristics. FIG. 55 shows the voltage-current characteristics. Note that FIGS. 52 and 53 show raw measurement data and FIGS. 54 and 55 show the results of calculations based on the measurement data.

Figure 56:
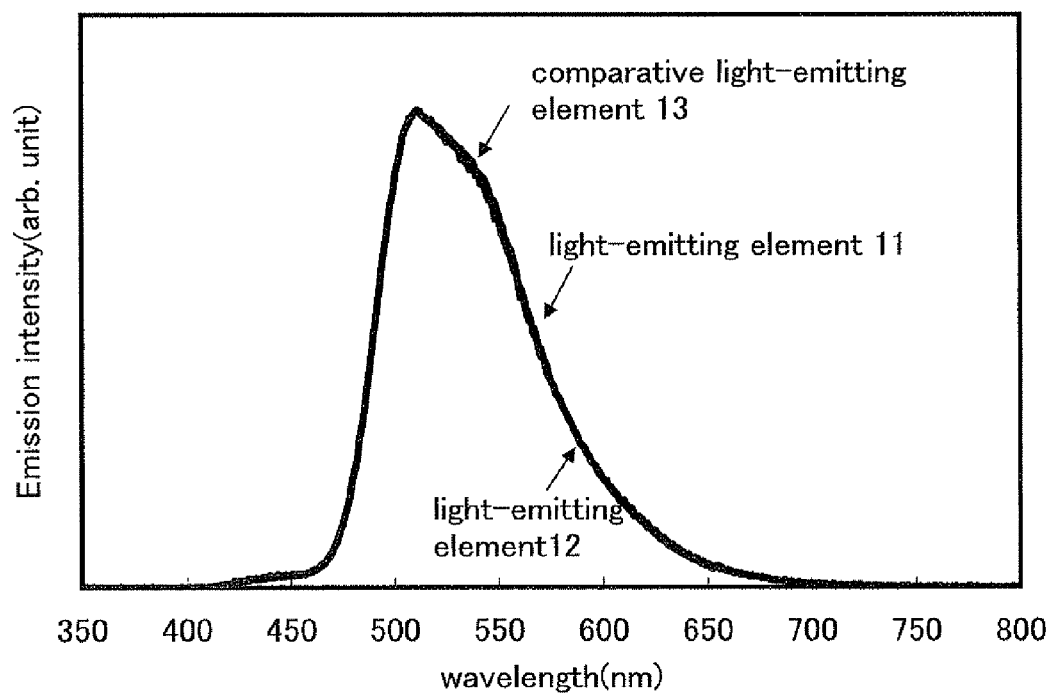
FIG. 56 is a diagram showing emission spectra of the light-emitting elements manufactured in Embodiment 9.

FIG. 56 shows emission spectra when a current of 1 mA flows. It can be seen from FIG. 56 that light emission of each of the light-emitting element 11, the light-emitting element 12, and the comparative light-emitting element 13 results from 2PCAPA.

The comparative light-emitting element 13 provides green light emission where the CIE chromaticity coordinates are (x=0.29, y=0.61) when the luminance is 800 cd/m². The current efficiency is 9.3 cd/A when the luminance is 800 cd/m². When the luminance is 800 cd/m², the voltage is 7.6 V; the current density, 8.6 mA/cm²; and the power efficiency, 3.9 lm/W.

On the other hand, the light-emitting element 11 provides green light emission where the CIE chromaticity coordinates are (x=0.28, y=0.59) when the luminance is 1000 cd/m$^2$. The current efficiency is 10.2 cd/A when the luminance is 1000 cd/m$^2$. When the luminance is 1000 cd/m$^2$, the voltage is 6.4 V; the current density, 9.7 mA/cm$^2$; and the power efficiency, 5.0 lm/W.

It can be seen from FIG. 55 that the light-emitting element 11 requires lower voltage than the comparative light-emitting element 13 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 54 that the light-emitting element 11 has higher current efficiency than the comparative light-emitting element 13. Thus, as shown in FIG. 53, the light-emitting element 11 requires lower voltage than the comparative light-emitting element 13 to provide the same luminance.

That is, it can be seen that the light-emitting element 11 requires lower voltage and consumes less power than the comparative light-emitting element 13 to provide the same luminance.

The light-emitting element 12 provides green light emission where the CIE chromaticity coordinates are (x=0.28, y=0.60) when the luminance is 910 cd/m$^2$. The current efficiency is 11.7 cd/A when the luminance is 910 cd/m$^2$. When the luminance is 910 cd/m$^2$, the voltage is 4.6 V; the current density, 7.8 mA/cm$^2$; and the power efficiency, 8.0 lm/W.

It can be seen from FIG. 55 that the light-emitting element 12 requires lower voltage than the comparative light-emitting element 13 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 54 that the light-emitting element 12 has higher current efficiency than the comparative light-emitting element 13. Thus, as shown in FIG. 53, the light-emitting element 12 requires lower voltage than the comparative light-emitting element 13 to provide the same luminance.

That is, it can be seen that the light-emitting element 12 requires lower voltage and consumes less power than the comparative light-emitting element 13 to provide the same luminance.

By application of the present invention, a light-emitting element with low driving voltage can be obtained. In addition, a light-emitting element which consumes less power can be obtained.

Embodiment 10

In this embodiment, light-emitting elements of the present invention are described with reference to FIG. 30. Methods for manufacturing light-emitting elements of this embodiment are hereinafter described.

(Light-Emitting Element 14)

First, a film of indium tin oxide containing silicon oxide (ITSO) was formed over a glass substrate 2101 by a sputtering method to form a first electrode 2102. Note that the thickness was 110 nm and the electrode area was 2 mm×2 mm.

Next, the substrate provided with the first electrode 2102 was fixed to a substrate holder provided in a vacuum evaporation apparatus such that the side on which the first electrode was formed faced downward. After the pressure in a film formation chamber was lowered to approximately 10$^{-4}$ Pa, a layer 2111 containing a composite material of an organic compound and an inorganic compound was formed on the first electrode 2102 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino]biphenyl (abbr.: NPB) was formed to a thickness of 10 nm on the layer 2111 containing a composite material by an evaporation method employing resistance heating to form a hole-transporting layer 2112.

Then, a light-emitting layer 2113 was formed to a thickness of 40 nm on the hole-transporting layer 2112 by co-evaporation of 9-[4-(10-phenyl-9-anthryl)phenyl]-9H-carbazole (abbr.: CzPA) and N-(9,10-diphenyl-2-anthryl)-N,9-diphenyl-9H-carbazol-3-amine (abbr.: 2PCAPA). Here, the weight ratio of CzPA to 2PCAPA was adjusted to be 1:0.05 (=CzPA: 2PCAPA).

After that, a film of 2-phenyl-3-[4'-(3-pyridyl)biphenyl-4-yl]quinoxaline (abbr.: PPy1PQ) represented by the structural formula (195) was formed to a thickness of 30 nm on the light-emitting layer 2113 by an evaporation method employing resistance heating to form an electron-transporting layer 2114.

Furthermore, a film of lithium fluoride was formed to a thickness of 1 nm on the electron-transporting layer 2114 to form an electron-injecting layer 2115.

Lastly, a film of aluminum was formed to a thickness of 200 nm on the electron-injecting layer 2115 by an evaporation method employing resistance heating to form a second electrode 2104. Accordingly, a light-emitting element 14 was manufactured.

(Comparative Light-Emitting Element 15)

A comparative light-emitting element 15 was formed like the light-emitting element 14 by using the same substrate and using tris(8-quinolinolato)aluminum(III) (abbr.: Alq) instead of PPy1PQ. That is, a film of tris(8-quinolinolato)aluminum (III) (abbr.: Alq) was formed to a thickness of 30 nm to form the electron-transporting layer 2114. Except for the electron-transporting layer 2114, the comparative light-emitting element 15 was formed like the light-emitting element 14.

The light-emitting element 14 and the comparative light-emitting element 15 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 57:
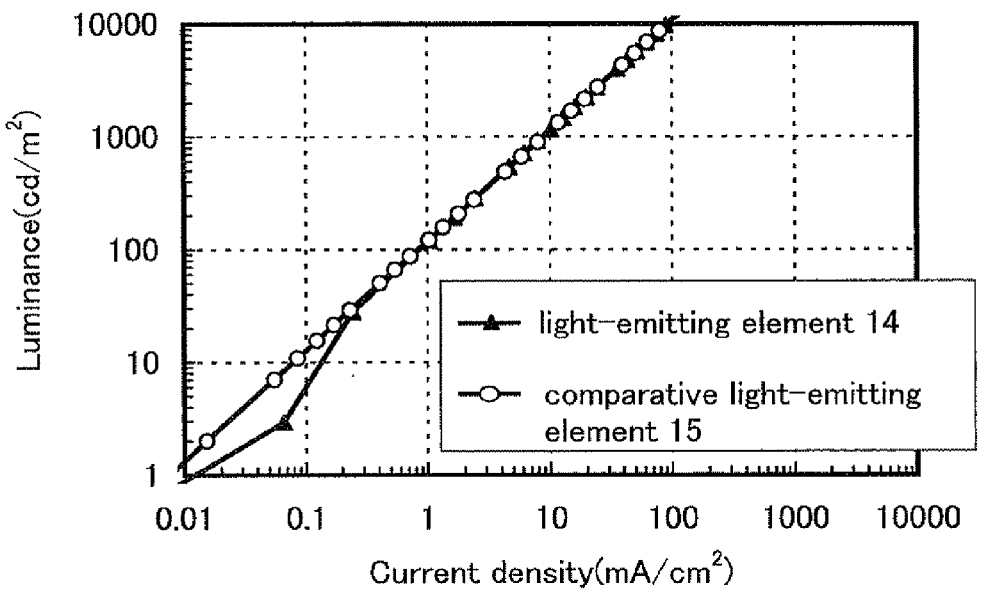
FIG. 57 is a diagram showing current density-luminance characteristics of light-emitting elements manufactured in Embodiment 10.
Figure 58:
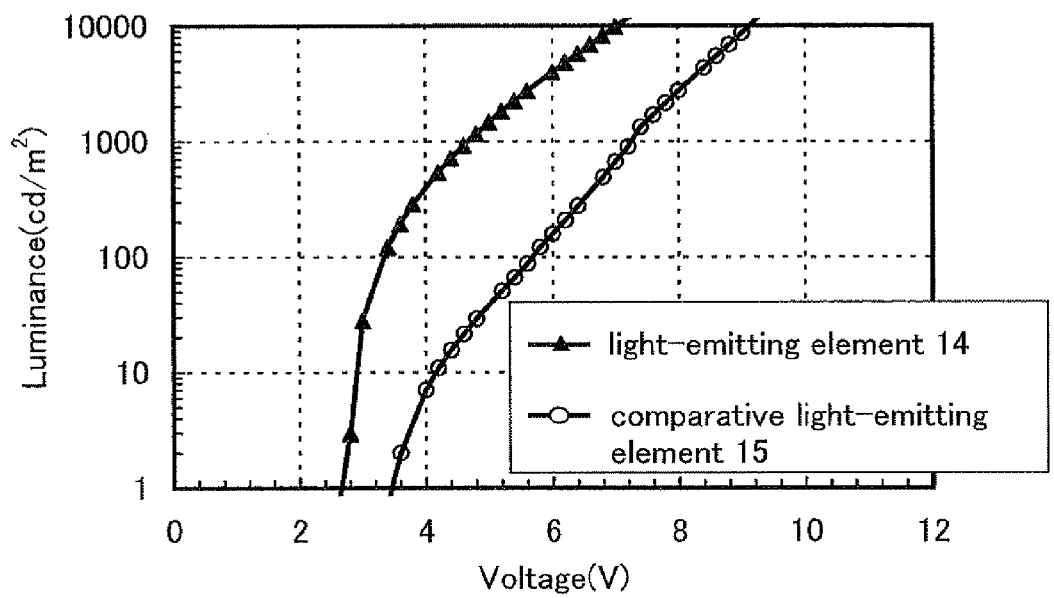
FIG. 58 is a diagram showing voltage-luminance characteristics of the light-emitting elements manufactured in Embodiment 10.
Figure 59:
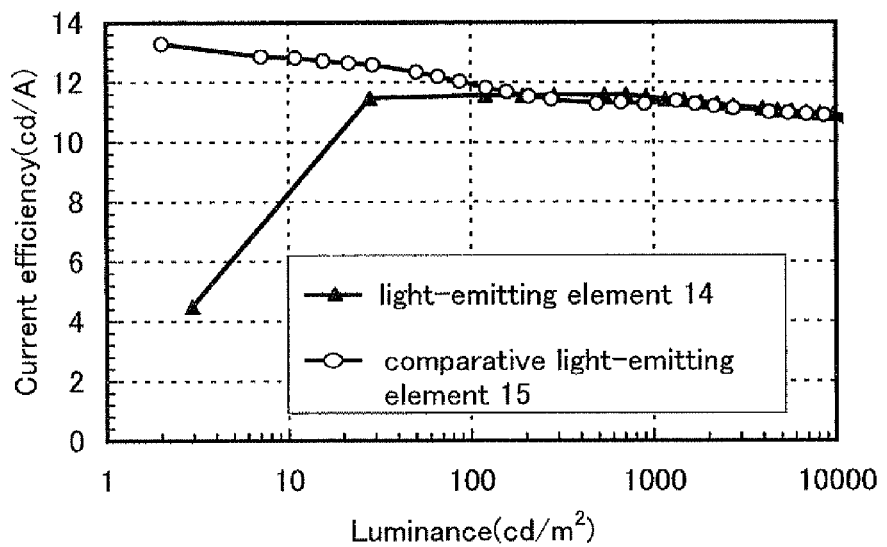
FIG. 59 is a diagram showing luminance-current efficiency characteristics of the light-emitting elements manufactured in Embodiment 10.
Figure 60:
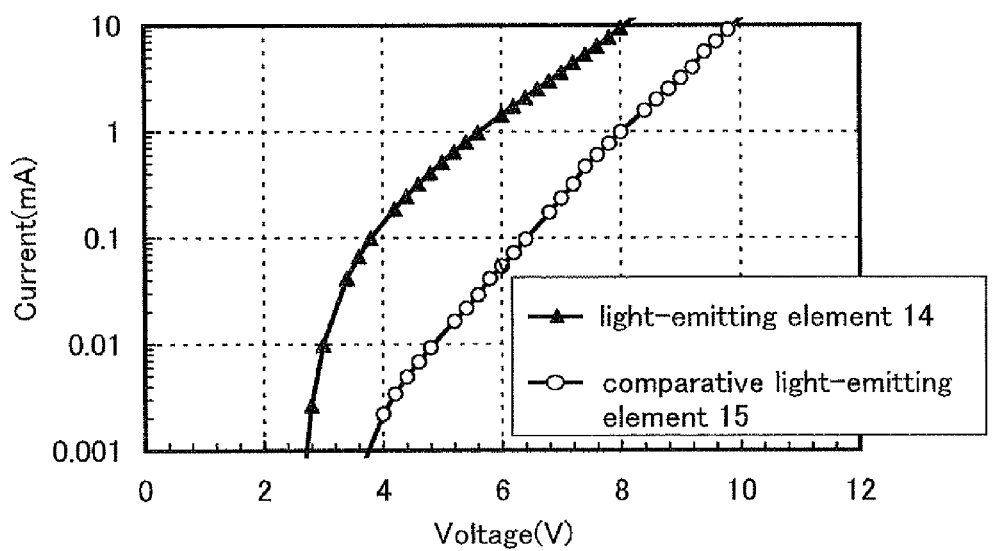
FIG. 60 is a diagram showing voltage-current characteristics of the light-emitting elements manufactured in Embodiment 10.

FIG. 57 shows current density-luminance characteristics of the light-emitting element 14 and the comparative light-emitting element 15. FIG. 58 shows the voltage-luminance characteristics. FIG. 59 shows the luminance-current efficiency characteristics. FIG. 60 shows the voltage-current characteristics. Note that FIGS. 57 and 58 show raw measurement data and FIGS. 59 and 60 show the results of calculations based on the measurement data.

Figure 61:
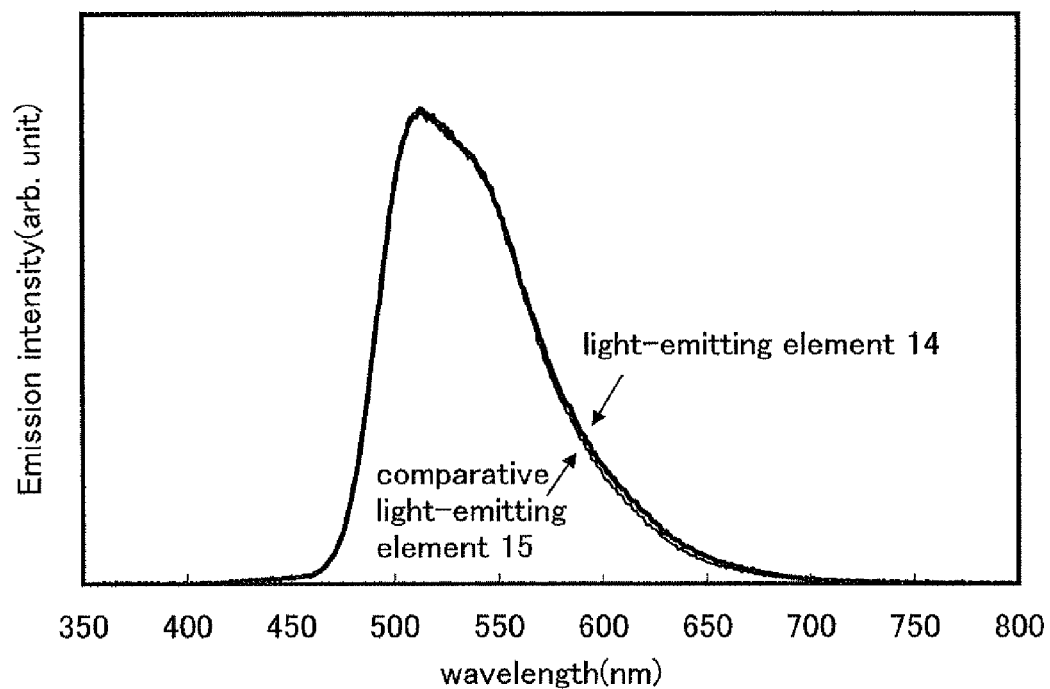
FIG. 61 is a diagram showing emission spectra of the light-emitting elements manufactured in Embodiment 10.

FIG. 61 shows emission spectra when a current of 1 mA flows. It can be seen from FIG. 61 that light emission of each of the light-emitting element 14 and the comparative light-emitting element 15 results from 2PCAPA.

The comparative light-emitting element 15 provides green light emission where the CIE chromaticity coordinates are (x=0.29, y=0.61) when the luminance is 670 cd/m$^2$. The current efficiency is 113 cd/A when the luminance is 670 cd/m$^2$. When the luminance is 670 cd/m$^2$, the voltage is 7.0 V; the current density, 5.9 mA/cm$^2$; and the power efficiency, 5.1 lm/W.

The light-emitting element 14 provides green light emission where the CIE chromaticity coordinates are (x=0.30, y=0.60) when the luminance is 910 cd/m$^2$. The current efficiency is 11.5 cd/A when the luminance is 910 cd/m$^2$. When the luminance is 910 cd/m$^2$, the voltage is 4.6 V; the current density, 7.9 mA/cm$^2$; and the power efficiency, 7.9 lm/W.

It can be seen from FIG. 60 that the light-emitting element 14 requires lower voltage than the comparative light-emitting element 15 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 59 that the light-emitting element 14 and the comparative light-emitting element 15 exhibit approximately the same current efficiency. Thus, as shown in FIG. 58, the light-emitting element 14 requires lower voltage than the comparative light-emitting element 15 to provide the same luminance.

That is, it can be seen that the light-emitting element 14 requires lower voltage and consumes less power than the comparative light-emitting element 15 to provide the same luminance.

By application of the present invention, a light-emitting element with low driving voltage can be obtained. In addition, a light-emitting element which consumes less power can be obtained.

Embodiment 11

In this embodiment, light-emitting elements of the present invention are described with reference to FIG. 41. Methods for manufacturing light-emitting elements of this embodiment are hereinafter described.

(Light-Emitting Element 16)

First, a film of indium tin oxide containing silicon oxide (ITSO) was formed over a glass substrate 2201 by a sputtering method to form a first electrode 2202. Note that the thickness was 110 nm and the electrode area was 2 mm×2 mm.

Next, the substrate provided with the first electrode 2202 was fixed to a substrate holder provided in a vacuum evaporation apparatus such that the side on which the first electrode was formed faced downward. After the pressure in a film formation chamber was lowered to approximately 10$^{-4}$ Pa, a layer 2211 containing a composite material of an organic compound and an inorganic compound was formed on the first electrode 2202 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino]biphenyl (abbr.: NPB) was formed to a thickness of 10 nm on the layer 2211 containing a composite material by an evaporation method employing resistance heating to form a hole-transporting layer 2212.

Then, a light-emitting layer 2213 was formed to a thickness of 40 nm on the hole-transporting layer 2212 by co-evaporation of 9-[4-(10-phenyl-9-anthryl)phenyl]-9H-carbazole (abbr.: CzPA) and N-(9,10-diphenyl-2-anthryl)-N,9-diphenyl-9H-carbazol-3-amine (abbr.: 2PCAPA). Here, the weight ratio of CzPA to 2PCAPA was adjusted to be 1:0.05 CzPA: 2PCAPA).

After that, a film of 2-phenyl-3-[4-(2-pyridyl)phenyl]quinoxaline (abbr.: 2Py1PQ) represented by the structural formula (101) was formed to a thickness of 10 nm on the light-emitting layer 2213 by an evaporation method employing resistance heating to form an electron-transporting layer (A) 2214. Moreover, a film of bathophenanthroline (abbr.: BPhen) was formed to a thickness of 20 nm on the electron-transporting layer (A) 2214 to form an electron-transporting layer (B) 2215. Thus, the light-emitting elements of this embodiment have a structure in which two electron-transporting layers are stacked.

Furthermore, a film of lithium fluoride was formed to a thickness of 1 nm on the electron-transporting layer (B) 2215 to form an electron-injecting layer 2216.

Lastly, a film of aluminum was formed to a thickness of 200 nm on the electron-injecting layer 2216 by an evaporation method employing resistance heating to form a second electrode 2204. Accordingly, a light-emitting element 16 was manufactured.

(Light-Emitting Element 17)

A light-emitting element 17 was formed like the light-emitting element 16 by using the same substrate and using 2-phenyl-3-[4-(3-pyridyl)phenyl]quinoxaline (abbr.: 3Py1PQ) represented by the structural formula (102) instead of 2Py1PQ. That is, a film of 2-phenyl-3-[4-(3-pyridyl)phenyl]quinoxaline (abbr.: 3Py1PQ) represented by the structural formula (102) was formed to a thickness of 10 nm to form the electron-transporting layer (A) 2214. Except for the electron-transporting layer (A) 2214, the light-emitting element 17 was formed like the light-emitting element 16.

(Comparative Light-Emitting Element 18)

A comparative light-emitting element 18 was formed like the light-emitting element 16 by using the same substrate and using tris(8-quinolinolato)aluminum(III) (abbr.: Alq) instead of 2Py1PQ. That is, a film of tris(8-quinolinolato)aluminum (III) (abbr.: Alq) was formed to a thickness of 10 nm to form the electron-transporting layer (A) 2214. Except for the electron-transporting layer (A) 2214, the comparative light-emitting element 18 was formed like the light-emitting element 16.

The light-emitting element 16, the light-emitting element 17, and the comparative light-emitting element 18 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 62:
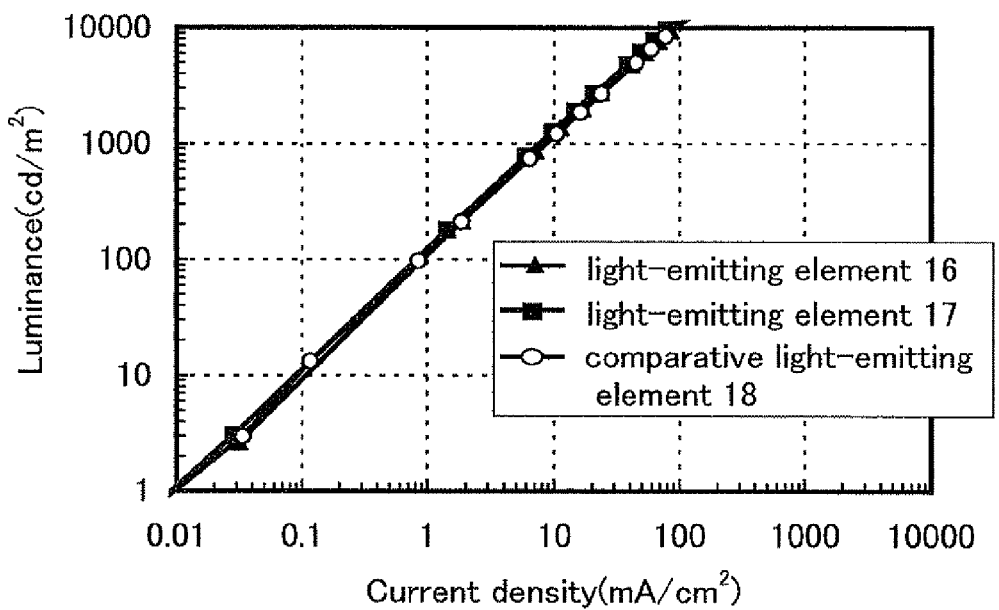
FIG. 62 is a diagram showing current density-luminance characteristics of light-emitting elements manufactured in Embodiment 11.
Figure 63:
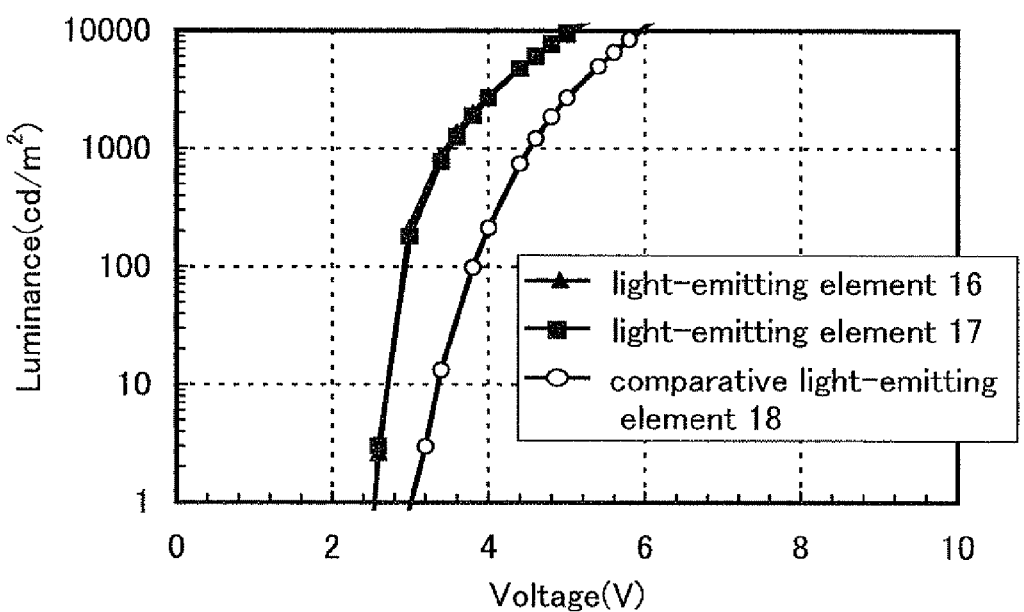
FIG. 63 is a diagram showing voltage-luminance characteristics of the light-emitting elements manufactured in Embodiment 11.
Figure 64:
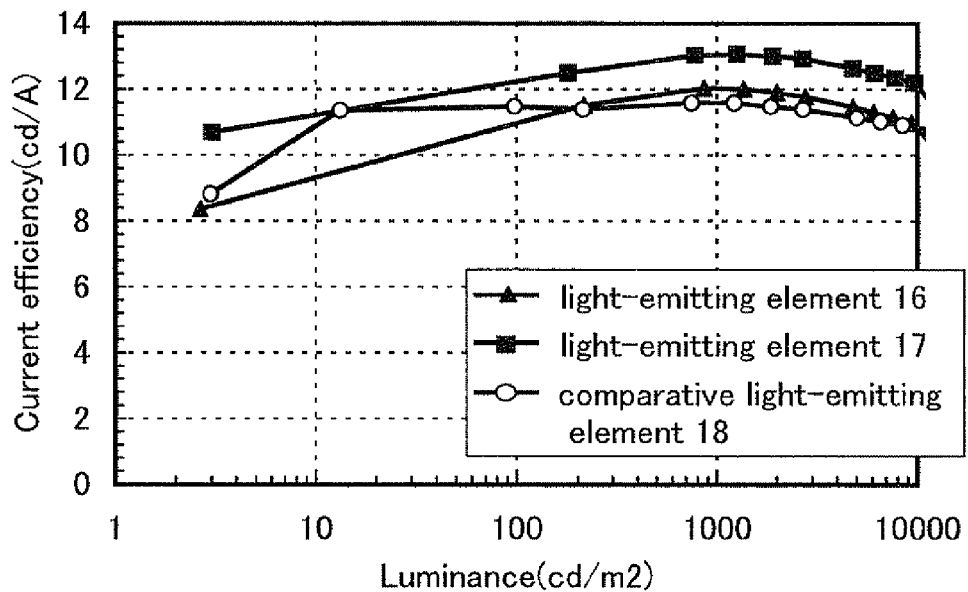
FIG. 64 is a diagram showing luminance-current efficiency characteristics of the light-emitting elements manufactured in Embodiment 11.
Figure 65:
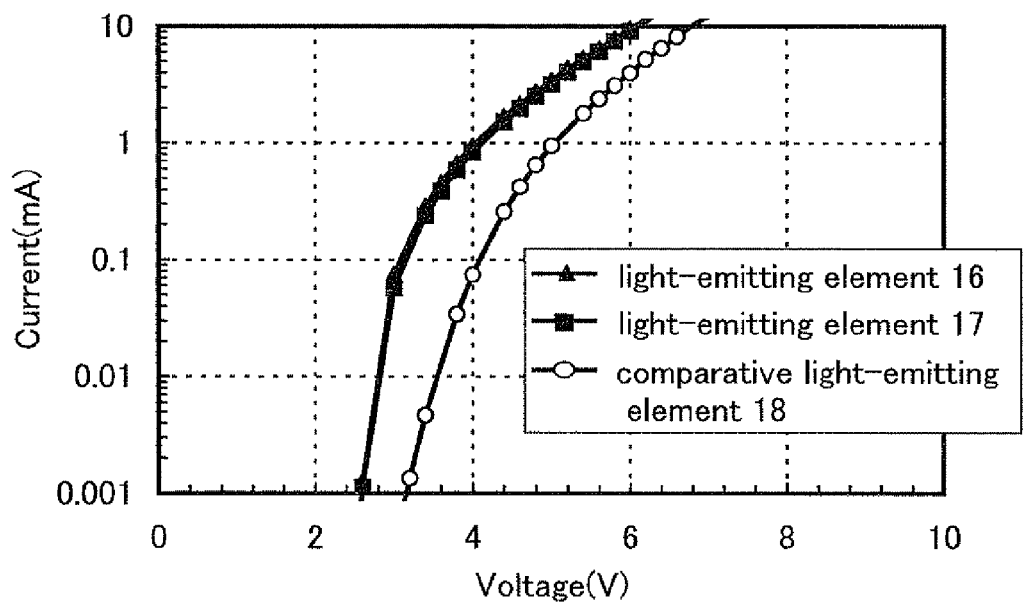
FIG. 65 is a diagram showing voltage-current characteristics of the light-emitting elements manufactured in Embodiment 11.

FIG. 62 shows current density-luminance characteristics of the light-emitting element 16, the light-emitting element 17, and the comparative light-emitting element 18. FIG. 63 shows the voltage-luminance characteristics. FIG. 64 shows the luminance-current efficiency characteristics. FIG. 65 shows the voltage-current characteristics. Note that FIGS. 62 and 63 show raw measurement data and FIGS. 64 and 65 show the results of calculations based on the measurement data.

Figure 66:
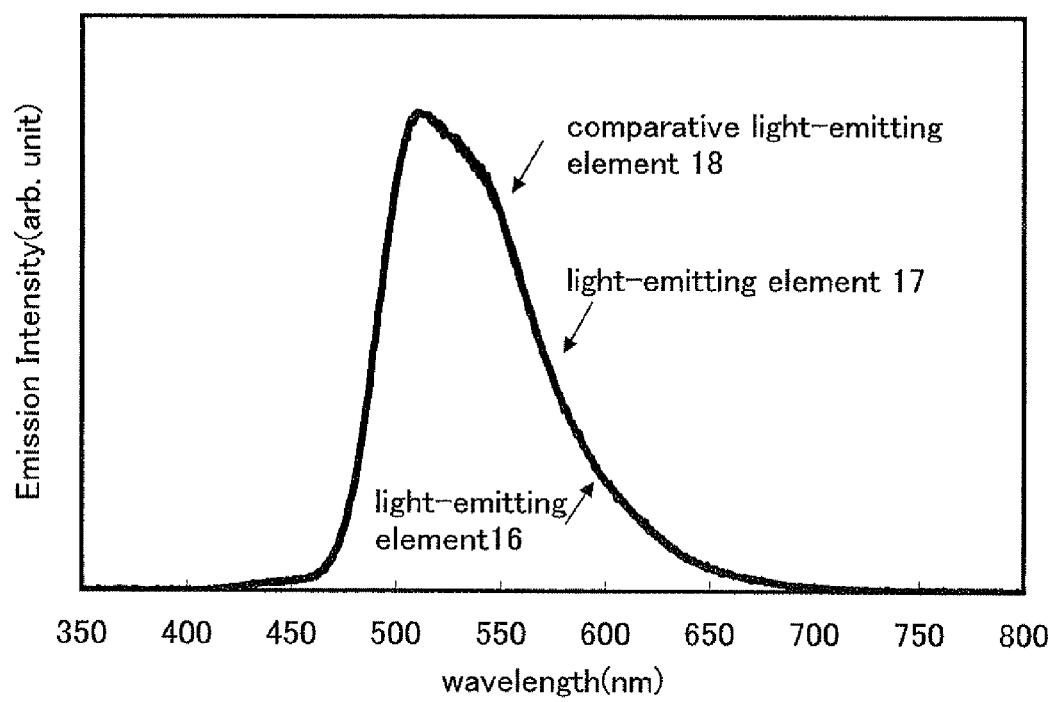
FIG. 66 is a diagram showing emission spectra of the light-emitting elements manufactured in Embodiment 11.

FIG. 66 shows emission spectra when a current of 1 mA flows. It can be seen from FIG. 66 that light emission of each of the light-emitting element 16, the light-emitting element 17, and the comparative light-emitting element 18 results from 2PCAPA.

The comparative light-emitting element 18 provides green light emission where the CIE chromaticity coordinates are (x=0.29, y=0.60) when the luminance is 1220 cd/m$^2$. The current efficiency is 11.6 cd/A when the luminance is 1220 cd/m$^2$. When the luminance is 1220 cd/m$^2$, the voltage is 4.6 V; the current density, 10.5 mA/cm$^2$; and the power efficiency, 7.9 lm/W.

On the other hand, the light-emitting element 16 provides green light emission where the CIE chromaticity coordinates are (x=0.29, y=0.60) when the luminance is 860 cd/m$^2$. The current efficiency is 12.0 cd/A, which is indicative of high efficiency, when the luminance is 860 cd/m$^2$. When the luminance is 860 cd/m$^2$, the voltage is 3.4 V; the current density, 7.2 mA/cm$^2$; and the power efficiency, 11.1 lm/W, which is indicative of high power efficiency.

It can be seen from FIG. 65 that the light-emitting element 16 requires lower voltage than the comparative light-emitting element 18 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 64 that the light-emitting element 16 and the comparative light-emitting element 18 exhibit approximately the same current efficiency. Thus, as shown in FIG. 63, the light-emitting element 16 requires lower voltage than the comparative light-emitting element 18 to provide the same luminance.

That is, it can be seen that the light-emitting element 16 requires lower voltage and consumes less power than the comparative light-emitting element 18 to provide the same luminance.

The light-emitting element 17 provides green light emission where the CIE chromaticity coordinates are (x=0.28, y=0.60) when the luminance is 780 cd/m$^2$. The current efficiency is 13.0 cd/A, which is indicative of high efficiency, when the luminance is 780 cd/m$^2$. When the luminance is 780 cd/m$^2$, the voltage is 3.4 V; the current density, 6.0 mA/cm$^2$; and the power efficiency, 12.0 lm/W, which is indicative of high power efficiency.

It can be seen from FIG. 65 that the light-emitting element 17 requires lower voltage than the comparative light-emitting element 18 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 64 that the light-emitting element 17 has higher current efficiency than the comparative light-emitting element 18. Thus, as shown in FIG. 63, the light-emitting element 17 requires lower voltage than the comparative light-emitting element 18 to provide the same luminance.

That is, it can be seen that the light-emitting element 17 requires lower voltage and consumes less power than the comparative light-emitting element 18 to provide the same luminance.

By application of the present invention, a light-emitting element with low driving voltage can be obtained. In addition, a light-emitting element which consumes less power can be obtained.

Embodiment 12

In this embodiment, light-emitting elements of the present invention are described with reference to FIG. 41. Methods for manufacturing light-emitting elements of this embodiment are hereinafter described.
(Light-Emitting Element 19)

First, a film of indium tin oxide containing silicon oxide (ITSO) was formed over a glass substrate 2201 by a sputtering method to form a first electrode 2202. Note that the thickness was 110 nm and the electrode area was 2 mm×2 mm.

Next, the substrate provided with the first electrode 2202 was fixed to a substrate holder provided in a vacuum evaporation apparatus such that the side on which the first electrode was formed faced downward. After the pressure in a film formation chamber was lowered to approximately 10$^{-4}$ Pa, a layer 2211 containing a composite material of an organic compound and an inorganic compound was formed on the first electrode 2202 by co-evaporation of 4,4'-bis[N-(1-naphthyl)-N-phenylamino]biphenyl (abbr.: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino] biphenyl (abbr.: NPB) was formed to a thickness of 10 nm on the layer 2211 containing a composite material by an evaporation method employing resistance heating to form a hole-transporting layer 2212.

Then, a light-emitting layer 2213 was formed to a thickness of 40 nm on the hole-transporting layer 2212 by co-evaporation of 9-[4-(10-phenyl-9-anthryl)phenyl]-9H-carbazole (abbr.: CzPA) and N-(9,10-diphenyl-2-anthryl)-N,9-diphenyl-9H-carbazol-3-amine (abbr.: 2PCAPA). Here, the weight ratio of CzPA to 2PCAPA was adjusted to be 1:0.05 (=CzPA: 2PCAPA).

After that, a film of 2-phenyl-3-[4'-(3-pyridyl)biphenyl-4-yl]quinoxaline (abbr.: PPy1PQ) represented by the structural formula (195) was formed to a thickness of 20 nm on the light-emitting layer 2213 by an evaporation method employing resistance heating to form an electron-transporting layer (A) 2214. Moreover, a film of bathophenanthroline (abbr.: BPhen) was formed to a thickness of 10 nm on the electron-transporting layer (A) 2214 to form an electron-transporting layer (B) 2215. Thus, the light-emitting elements of this embodiment have a structure in which two electron-transporting layers are stacked.

Furthermore, a film of lithium fluoride was formed to a thickness of 1 nm on the electron-transporting layer (B) 2215 to form an electron-injecting layer 2216.

Lastly, a film of aluminum was formed to a thickness of 200 nm on the electron-injecting layer 2216 by an evaporation method employing resistance heating to form a second electrode 2204. Accordingly, a light-emitting element 19 was manufactured.
(Comparative Light-Emitting Element 20)

A comparative light-emitting element 20 was formed like the light-emitting element 19 by using the same substrate and using tris(8-quinolinolato)aluminum(III) (abbr.: Alq) instead of PPy1PQ. That is, a film of tris(8-quinolinolato)aluminum (III) (abbr.: Alq) was formed to a thickness of 20 nm to form the electron-transporting layer (A) 2214. Except for the electron-transporting layer (A) 2214, the comparative light-emitting element 20 was formed like the light-emitting element 19.

The light-emitting element 19 and the comparative light-emitting element 20 obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 67:
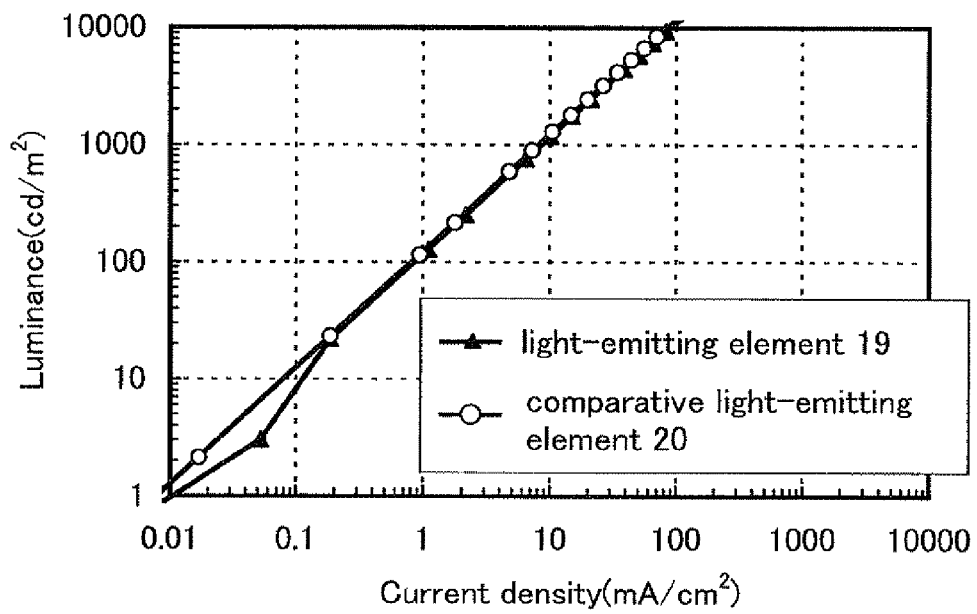
FIG. 67 is a diagram showing current density-luminance characteristics of light-emitting elements manufactured in Embodiment 12.
Figure 68:
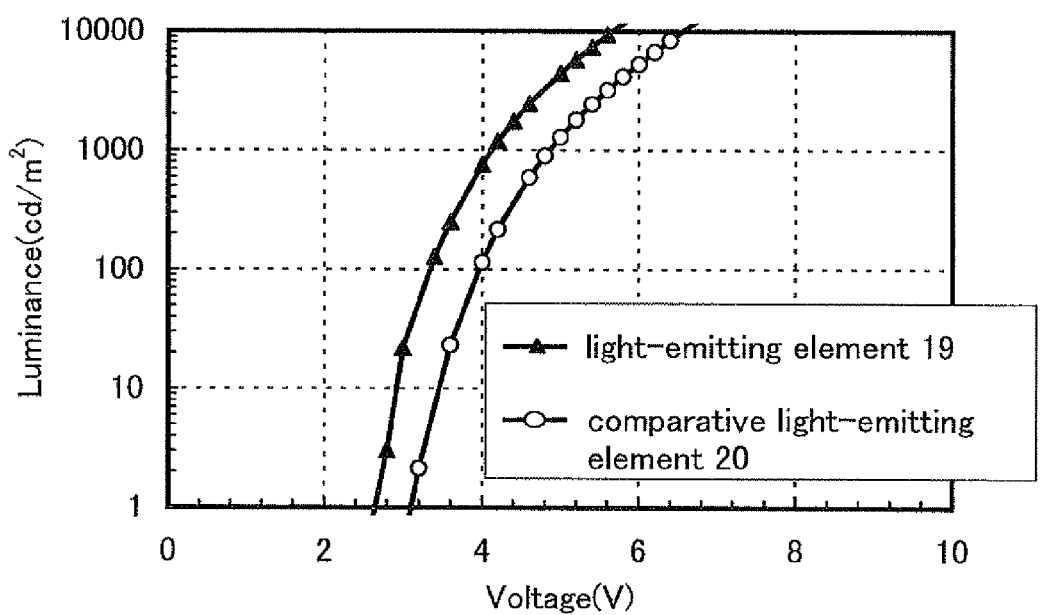
FIG. 68 is a diagram showing voltage-luminance characteristics of the light-emitting elements manufactured in Embodiment 12.
Figure 69:
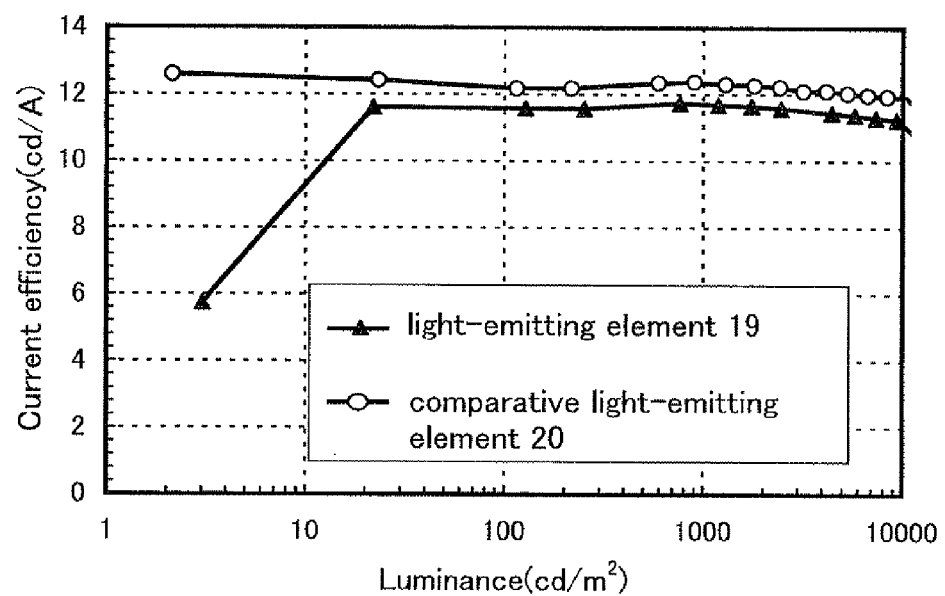
FIG. 69 is a diagram showing luminance-current efficiency characteristics of the light-emitting elements manufactured in Embodiment 12.
Figure 70:
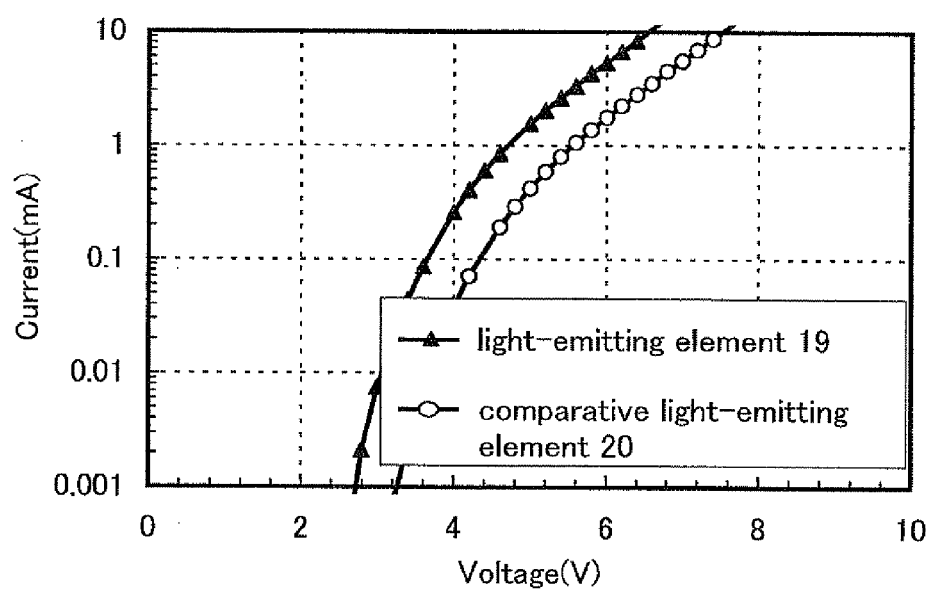
FIG. 70 is a diagram showing voltage-current characteristics of the light-emitting elements manufactured in Embodiment 12.

FIG. 67 shows current density-luminance characteristics of the light-emitting element 19 and the comparative light-emitting element 20. FIG. 68 shows the voltage-luminance characteristics. FIG. 69 shows the luminance-current efficiency characteristics. FIG. 70 shows the voltage-current characteristics. Note that FIGS. 67 and 68 show raw measurement data and FIGS. 69 and 70 show the results of calculations based on the measurement data.

Figure 71:
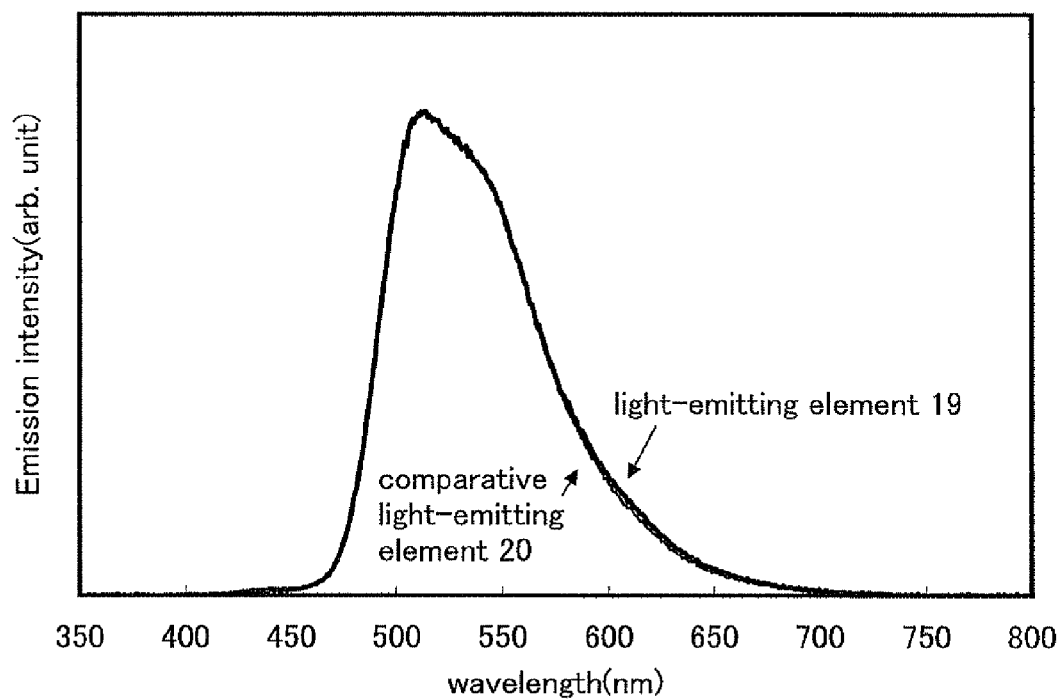
FIG. 71 is a diagram showing emission spectra of the light-emitting elements manufactured in Embodiment 12.

FIG. 71 shows emission spectra when a current of 1 mA flows. It can be seen from FIG. 71 that light emission of each of the light-emitting element 19 and the comparative light-emitting element 20 results from 2PCAPA.

The comparative light-emitting element 20 provides green light emission where the CIE chromaticity coordinates are (x=0.29, y=0.61) when the luminance is 900 cd/m$^2$. The current efficiency is 12.4 cd/A when the luminance is 900 cd/m$^2$. When the luminance is 900 cd/m$^2$, the voltage is 4.8 V; the current density, 7.3 mA/cm$^2$; and the power efficiency, 8.1 lm/W.

The light-emitting element 19 provides green light emission where the CIE chromaticity coordinates are (x=0.30, y=0.60) when the luminance is 1190 cd/m$^2$. The current efficiency is 11.7 cd/A when the luminance is 1190 cd/m$^2$. When the luminance is 1190 cd/m$^2$, the voltage is 4.2 V; the current density, 10.2 mA/cm$^2$; and the power efficiency, 83 lm/W.

It can be seen from FIG. 70 that the light-emitting element 19 requires lower voltage than the comparative light-emitting element 20 to allow the same amount of electric current to flow. That is, by application of the present invention, electric current flows more easily when voltage is applied. Accordingly, it can be considered that a quinoxaline derivative of the present invention has excellent electron-transporting property.

It can also be seen from FIG. 69 that the light-emitting element 19 and the comparative light-emitting element 20 exhibit approximately the same current efficiency. Thus, as shown in FIG. 68, the light-emitting element 19 requires lower voltage than the comparative light-emitting element 20 to provide the same luminance.

That is, it can be seen that the light-emitting element 19 requires lower voltage and consumes less power than the comparative light-emitting element 20 to provide the same luminance.

By application of the present invention, a light-emitting element with low driving voltage can be obtained. In addition, a light-emitting element with low power consumption can be obtained.

This application is based on Japanese Patent Application serial no. 2007-310286 filed with Japan Patent Office on Nov. 30, 2007, the entire contents of which are hereby incorporated by reference.

What is claimed is:

1. A quinoxaline compound represented by a formula (G11),

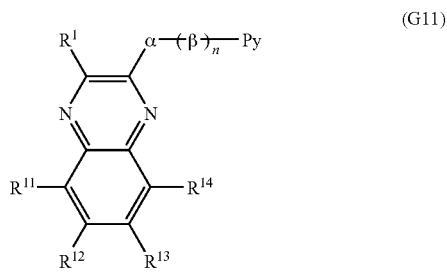

Wherein:

α is represented by any of following formulas (12-1) to (12-10),

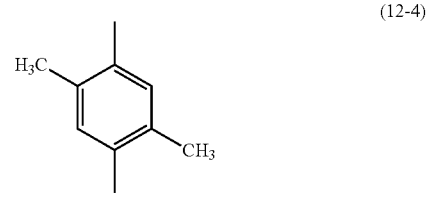

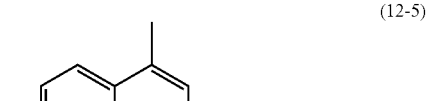

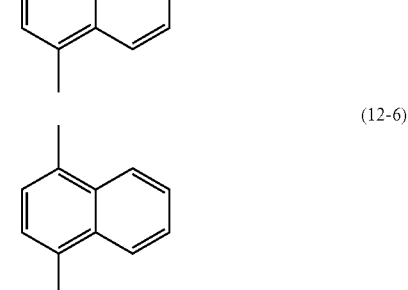

205
-continued
(12-7)
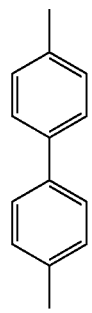
(12-8)
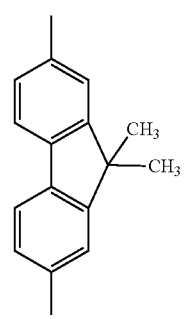
(12-9)
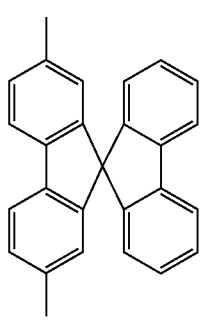
(12-10)
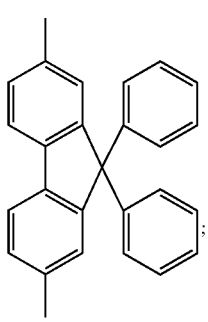
β is represented by any of the formulas (12-1) to (12-10) above;
n represents 1;
Py represents a pyridyl group substituted by methyl or unsubstituted pyridyl group; $R^{11}$ $R^{12}$, $R^{13}$ and $R^{14}$ are the same or different from each other and are represented by the following formulas (14-1) to (14-22),
(14-1)
206
-continued
(14-2)
(14-3)
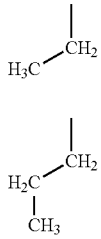
(14-4)
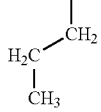
(14-5)
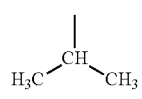
(14-6)
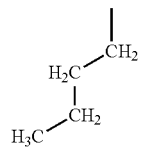
(14-7)
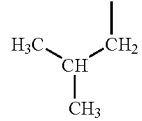
(14-8)
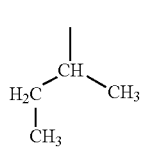
(14-9)
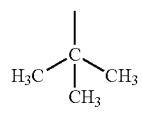
(14-10)
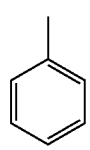
(14-11)
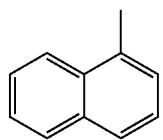
(14-12)
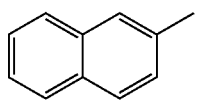

(14-13)
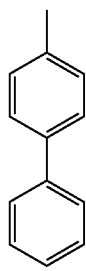

(14-14)
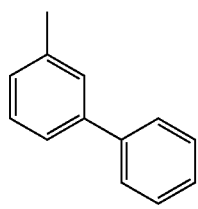

(14-15)
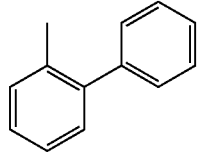

(14-16)
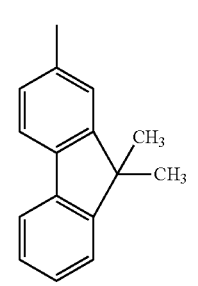

(14-17)
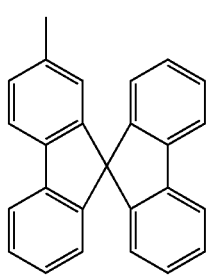

(14-18)
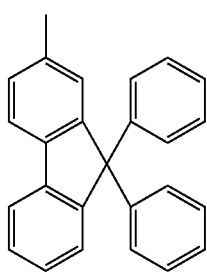

(14-19)
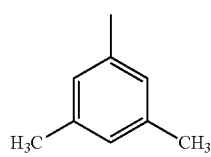

(14-20)
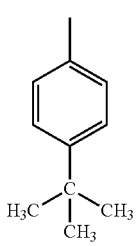

(14-21)
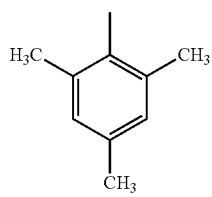

(14-22)
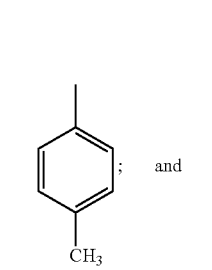 ; and

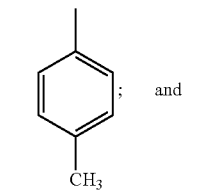

$R^1$ is represented by the formulas (14-2) to (14-22) above.

2. The quinoxaline compound according to claim 1, wherein β is any of formula (12-1), formula (12-2), formula (12-3), formula (12-5), formula (12-6), or formula (12-7).

3. The quinoxaline compound according to claim 1, wherein the quinoxaline compound has the following formula (G12), (G12)
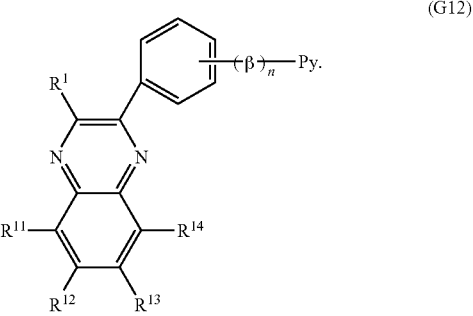

4. The quinoxaline compound according to claim 1, wherein the quinoxaline compound has the following formula (G13),

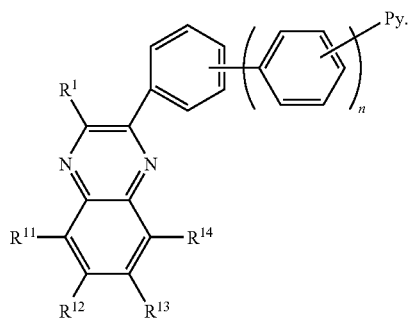
(G13)

5. The quinoxaline compound according to claim 1, wherein the quinoxaline compound has the following formula (G14),

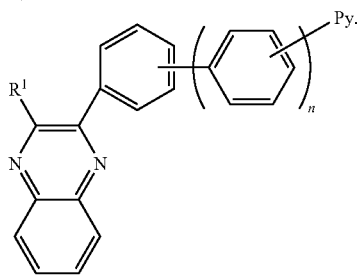
(G14)

6. The quinoxaline compound according to claim 1, wherein the quinoxaline compound has the following formula (G15),

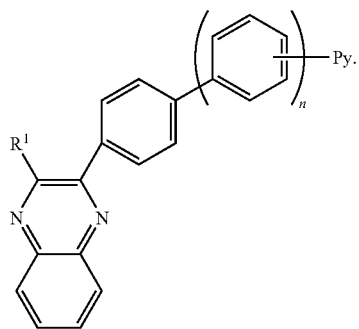
(G15)

7. The quinoxaline compound according to claim 1, wherein the quinoxaline compound has the following formula (G16),

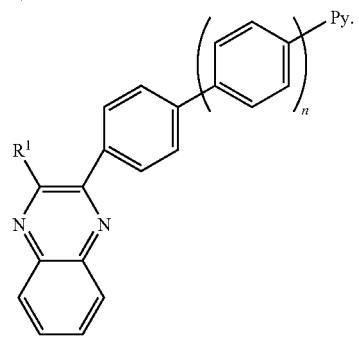
(G16)

8. The quinoxaline compound according to claim 1, wherein $R^1$ is formula (14-10), formula (14-13), formula (14-14) or formula (14-15).

9. A quinoxaline compound represented by a formula (G21),

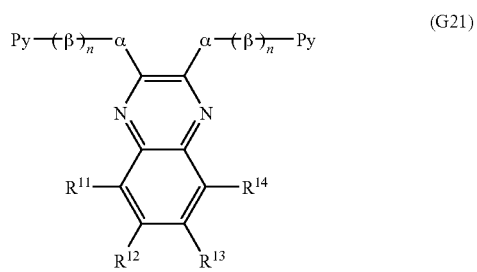
(G21)

Wherein:

α is represented by any of following formulas (12-1) to (12-10),

(12-1)

(12-2)

(12-3)

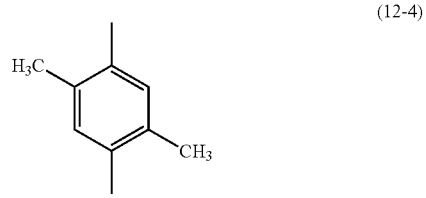
(12-4)

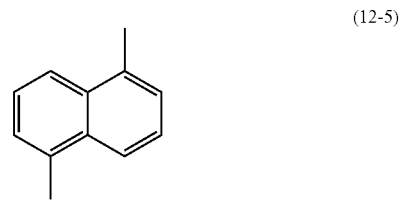
(12-5)

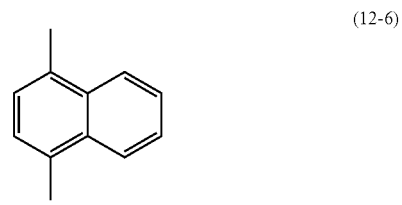
(12-6)

-continued (12-7)

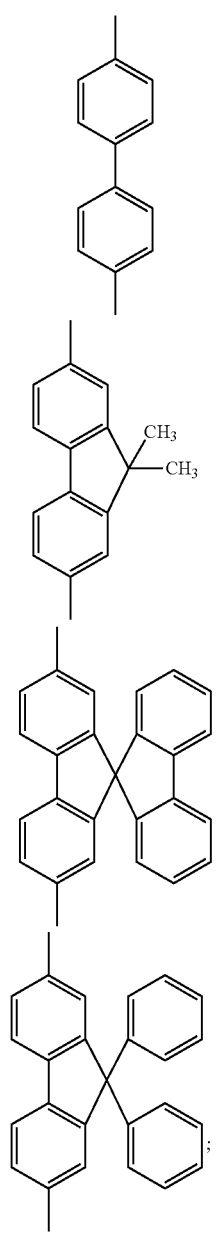

(12-8)

(12-9)

(12-10)

β is represented by any of the formulas (12-1) to (12-10) above;

n represents an integer of 0 or 1;

Py represents a pyridyl group substituted by methyl or unsubstituted pyridyl group; and $R^{11}$ $R^{12}$, $R^{13}$ and $R^{14}$ are the same or different from each other and are represented by the following formulas (14-1) to (14-22), (14-1)

|
H (14-2)

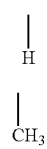

-continued (14-3)

H₃C—CH₂—|

(14-4)

H₂C—CH₂—|
    |
    CH₃

(14-5)

H₃C—CH—CH₃
     |

(14-6)

H₂C—CH₂—|
 |
H₃C—CH₂

(14-7)

H₃C—CH₂—|
    |
   CH—
    |
   CH₃

(14-8)

H₂C—CH—|
 |    |
CH₃  CH₃

(14-9)

|
H₃C—C—CH₃
    |
   CH₃

(14-10)

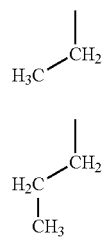

(14-11)

(14-12)

(14-13)

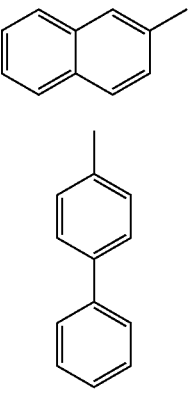

(14-14) 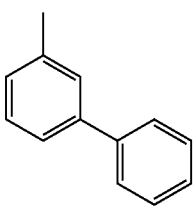

(14-15) 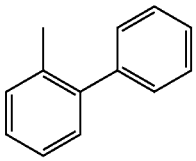

(14-16) 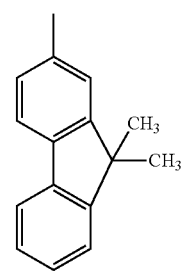

(14-17) 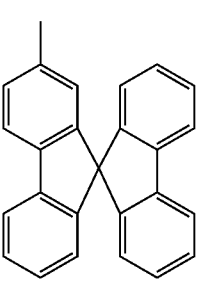

(14-18) 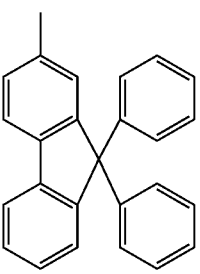

(14-19) 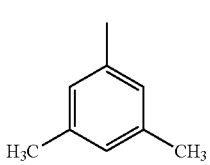

(14-20) 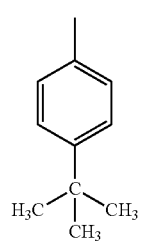

(14-21) 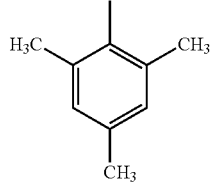

(14-22) 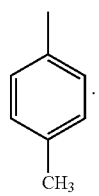

10. The quinoxaline compound according to claim 9, wherein β is any of formula (12-1), formula (12-2), formula (12-3), formula (12-5), formula (12-6), or formula (12-7).

11. The quinoxaline compound according to claim 9, wherein the quinoxaline compound has the following formula (G22), (G22) 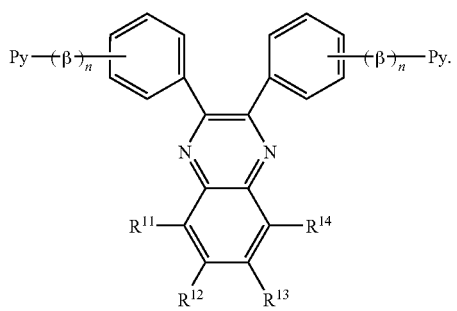

12. The quinoxaline compound according to claim 9, wherein the quinoxaline compound has the following formula (G23), (G23) 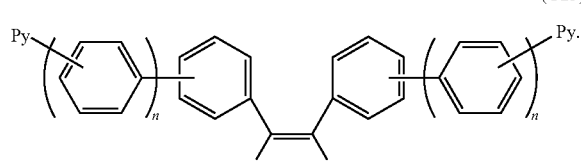

13. The quinoxaline compound according to claim 9, wherein the quinoxaline compound has the following formula (G24),

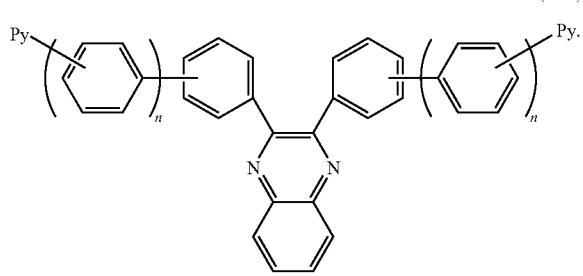
(G24)
14. The quinoxaline compound according to claim 9, wherein the quinoxaline compound has the following formula (G25),
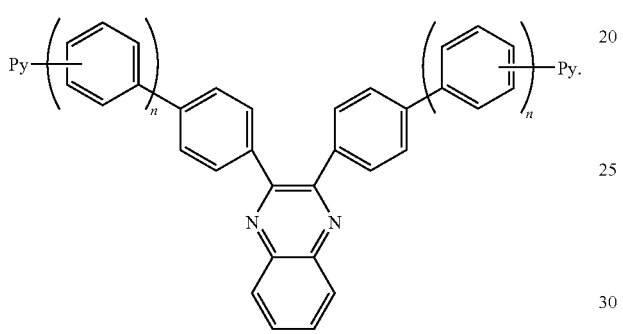
(G25)
15. The quinoxaline compound according to claim 9, wherein the quinoxaline compound has the following formula (G26),
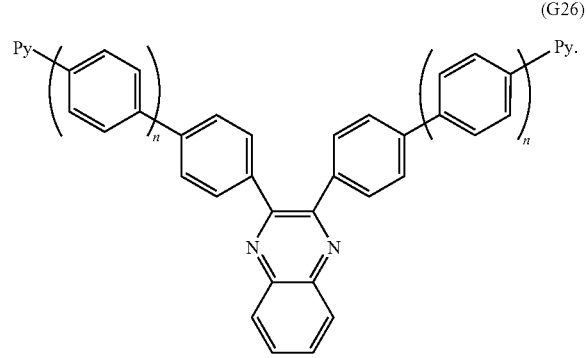
(G26)
* * * * *

UNITED STATES PATENT AND TRADEMARK OFFICE
CERTIFICATE OF CORRECTION

PATENT NO. : 8,314,101 B2
APPLICATION NO. : 12/277421
DATED : November 20, 2012
INVENTOR(S) : Hiroshi Kadoma et al.

It is certified that error appears in the above-identified patent and that said Letters Patent is hereby corrected as shown below:

In the Specification:

Column 24, Line 5; Change "(G21), to $R^{14}$" to --(G21), $R^{11}$ to $R^{14}$--.

Column 145, Line 45; Change "with dial such as" to --with diol such as--.

Column 148, Line 40; Change "a represents" to --α represents--.

Column 150, Line 27; Change "13 represents an" to --β represents an--.

Column 151, Line 35; Change "cc represents" to --α represents--.

Column 156, Line 7; Change "iridium acetylacetonate" to --iridium(III) acetylacetonate--.

Column 156, Line 26; Change "bis[2-(T-" to --bis[2-2'--.

Column 157, Lines 18-19; Change "(abbr.: BAIq)" to --(abbr.: BA1q)--.

Column 157, Lines 41-42; Change "(abbr.: CzAlPA)" to --(abbr.: CzA1PA)--.

Column 158, Line 5; Change "all-co-(benzo[2," to --alt-co-(benzo[2,--.

Column 159, Line 10; Change "thereat" to --thereof--.

Column 159, Line 17; Change "(MgAg, AlLi)" to --(MgAg, AlLi)--.

Column 160, Line 57; Change "PFTs" to --TFTs--.

Column 166, Line 24; Change "(MgAg, AlLi)" to --(MgAg, AlLi)--.

Column 189, Line 14; Change "(MO)" to --(ITSO)--.

Column 203, Line 40; Change "83 lm/W" to --8.7 lm/W--.

Signed and Sealed this
Nineteenth Day of February, 2013

Teresa Stanek Rea
*Acting Director of the United States Patent and Trademark Office*